US009738908B2

(12) United States Patent
Wu

(10) Patent No.: US 9,738,908 B2
(45) **Date of Patent: *Aug. 22, 2017**

(54) CRISPR/CAS SYSTEMS FOR GENOMIC MODIFICATION AND GENE MODULATION

(71) Applicant: System Biosciences, LLC, Mountain View, CA (US)

(72) Inventor: Fangting Wu, Mountain View, CA (US)

(73) Assignee: System Biosciences, LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,655

(22) Filed: Mar. 17, 2014

(65) Prior Publication Data

US 2014/0273226 A1 Sep. 18, 2014

Related U.S. Application Data

(60) Provisional application No. 61/799,586, filed on Mar. 15, 2013.

(51) Int. Cl.

*C12N 9/22* (2006.01)
*C12N 9/14* (2006.01)
*C12N 15/90* (2006.01)
*C12N 15/85* (2006.01)
*C12N 15/10* (2006.01)
*C12N 15/11* (2006.01)

(52) U.S. Cl.

CPC ............. *C12N 15/907* (2013.01); *C12N 9/22* (2013.01); *C12N 15/102* (2013.01); *C12N 15/11* (2013.01); *C12N 15/85* (2013.01); *C12N 2800/22* (2013.01)

(58) Field of Classification Search

CPC .... C12N 15/102; C12N 15/85; C12N 15/907; C12N 9/22; C12N 15/63
USPC ...................... 435/320.1, 325, 455; 536/23.2
See application file for complete search history.

(56) References Cited

U.S. PATENT DOCUMENTS 5,571,690 A 11/1996 Hecht
8,252,535 B2 8/2012 Biekle et al.
8,697,359 B1 4/2014 Zhang
8,771,945 B1 7/2014 Zhang
8,795,965 B2 8/2014 Zhang
8,865,406 B2 10/2014 Zhang et al.
8,871,445 B2 10/2014 Cong et al.
8,889,356 B2 11/2014 Zhang
8,889,418 B2 11/2014 Zhang et al.
8,895,308 B1 11/2014 Zhang et al.
8,906,616 B2 12/2014 Zhang et al.
2010/0076057 A1 3/2010 Sontheimer et al.
2010/0093617 A1 4/2010 Barrangou et al.
2010/0104690 A1 4/2010 Barrangou et al.
2011/0002889 A1 1/2011 Barrangou et al.
2011/0189776 A1 8/2011 Terns et al.
2011/0300538 A1 12/2011 Barrangou et al.
2013/0011828 A1 1/2013 Barrangou et al.
2014/0068797 A1 3/2014 Doudna et al.
2014/0170753 A1 6/2014 Zhang
2014/0179006 A1 6/2014 Zhang
2014/0179770 A1 6/2014 Zhang et al.
2014/0186843 A1 7/2014 Zhang et al.
2014/0186919 A1 7/2014 Zhang et al.
2014/0186958 A1 7/2014 Zhang et al.
2014/0189896 A1 7/2014 Zhang et al.
2014/0227787 A1 8/2014 Zhang
2014/0242664 A1 8/2014 Zhang et al.
2014/0242699 A1 8/2014 Zhang
2014/0248702 A1 9/2014 Cong et al.
2014/0256046 A1 9/2014 Zhang et al.
2014/0310830 A1 10/2014 Zhang et al.
2014/0342456 A1 11/2014 Mali et al.
2014/0342457 A1 11/2014 Mali et al.
2014/0342458 A1 11/2014 Mali et al.
2014/0356956 A1 12/2014 Church et al.
2014/0356958 A1 12/2014 Mali et al.
2014/0356959 A1 12/2014 Church et al.
2014/0357530 A1 12/2014 Zhang et al.
2015/0020223 A1 1/2015 Zhang et al.

FOREIGN PATENT DOCUMENTS

WO 2006/055836 5/2006
WO 2007/025097 3/2007
WO 2008/052101 5/2008
WO 2008/122314 10/2008
WO 2010/011961 1/2010
WO 2010/054154 5/2010
WO 2010/075424 7/2010
WO 2012/054726 4/2012
WO 2012/164565 12/2012
WO 2013/176772 11/2013

(Continued)

OTHER PUBLICATIONS

Sapranauskas et al. Nucleic Acids Research, 2011, 1-8.*
(Cong et al. (2013) Science, 339:819-822, and supplementary materials, published online Jan. 3, 2013).*
Barrangou, "RNA-mediated programmable DNA cleavage." Nature Biotechnology, 30(9), p. 836-838 (Sep. 2012).

(Continued)

*Primary Examiner* — Janet Epps-Smith
(74) *Attorney, Agent, or Firm* — Dergosits & Noah LLP

(57) ABSTRACT

The invention relates to engineered CRISPR/Cas9 systems for genomic modification and regulation of gene expression in mammalian cells. The specification describes the design and validation of polynucleotides encoding the *Streptococcus pyogenes* (*S. pyogenes*) Cas9 gene and protein and variants of that protein, where the nucleotide sequence has been optimized for expression in mammalian cells, and also modified by fused sequences that enhance various aspects of the CRISPR/Cas system. The specification also describes systems for RNA-guided genome engineering and gene regulation in mammalian cells, including human cells.

11 Claims, 41 Drawing Sheets

(56) References Cited

FOREIGN PATENT DOCUMENTS

| | | |
|---|---|---|
| WO | 2014/093595 | 6/2014 |
| WO | 2014/093622 | 6/2014 |
| WO | 2014/093635 | 6/2014 |
| WO | 2014/093655 | 6/2014 |
| WO | 2014/093661 | 6/2014 |
| WO | 2014/093694 | 6/2014 |
| WO | 2014/093701 | 6/2014 |
| WO | 2014/093709 | 6/2014 |
| WO | 2014/093712 | 6/2014 |
| WO | 2014/093718 | 6/2014 |
| WO | 2014/099744 | 6/2014 |
| WO | 2014/099750 | 6/2014 |
| WO | 2014/197568 | 12/2014 |

OTHER PUBLICATIONS

Bassett et al., “Highly Efficient Targeted Mutagenesis of Drosophila with the CRISPR/Cas9 System,” Cell Rep., 4(1):220-228 (Jul. 11, 2013).
Bhaya et al., “CRISPR-Cas systems in bacteria and archaea: versatile small RNAs for adaptive defense and regulation,” Annu. Rev. Genet. 45, 273 (2011).
Brouns, “A Swiss Army Knife of Immunity” Science 337: p. 808-809 (Aug. 17, 2012).
Burgess, “A CRISPR genome-editing tool.” Nature Reviews-Genetics vol. 14 (Feb. 2013), published online Jan. 16, 2013.
Carr and Church, “Genome engineering,” Nat. Biotechnol. 27, 1151 (2009).
Cho et al., “Targeted genome engineering in human cells with the Cas9 RNA-guided endonuclease,” Nature Biotechnology 31:230-232 (epub Jan. 29, 2013).
Cong et al., “Multiplex Genome Engineering Using CRISPR/Cas Systems” Science 339(6121):819-823 (Feb. 15, 2013), epub Science Express (Jan. 3, 2013).
Gilbert et al., “CRISPR-mediated modular RNA-guided regulation of transcription in eukaryotes,” Cell 154(2):442-451 (epub Jul. 11, 2013).
Hale et al., “Essential Features and Rational Design of CRISPR RNAs that Function with the Cas RAMP Module Complex to Cleave RNAs.” Molecular Cell 45, p. 292-302 (print Feb. 10, 2012) [epub: Jan. 5, 2012].
Hwang et al. “Efficient genome editing in zebrafish using a CRISPR-Cas system.” Nat. Biotechnol. advance online publication (Jan. 29, 2013).
Jiang et al, “RNA-guided editing of bacterial genomes using CRISPR-Cas systems,” Nature Biotechnol., 31(3):233-239 (Mar. 2013; epub Jan. 29, 2013).
Jinek et al., (2012) “A Programmable Dual-RNA-Guided DNA Endonuclease in Adaptive Bacterial Immunity” Science 337(6096): p. 816-821 (print edition Aug. 17, 2012; epub Science Express, Jun. 28, 2012).
Jinek et al., RNA-programmed genome editing in human cells. (Jan. 29, 2013) eLife 2:e00471.
Koike-Yusa et al., “Genome-wide recessive genetic screening in mammalian cells with a lentiviral CRISPR-guide RNA library,” Nature Biotechnology 32:267-273 (2014); epub Dec. 23, 2013.
Konermann et al., “Optical control of mammalian endogenous transcription and epigenetic states,” Nature 500 (7463):472-476 (2013); epub Jul. 23, 2013.
Mäkinen et al., “Stable RNA interference: comparison of U6 and H1 promoters in endothelial cells and in mouse brain” J. Gene Med. 8(4):433-441 (2006).
Mali et al., “RNA-Guided Human Genome Engineering via Cas9” Science 339(6121):823-826 (Feb. 15, 2013), epub Science Express (Jan. 3, 2013).
Mali et al., “CAS9 transcriptional activators for target specificity screening and paired nickases for cooperative genome engineering,” Nature Biotechnology 31:833-838 (epub Aug. 1, 2013).
Makarova et al., “Evolution and classification of the CRISPR-Cas systems.” Nat. Rev. Microbiol. 9, 467 (2011).
Perez-Pinera et al, “RNA-guided gene activation by CRISPR-Cas9-based transcription factors,” Nature Methods 10:973-976 (epub Jul. 25, 2013).
Ran et al., “Double Nicking by RNA-Guided CRISPR Cas9 for Enhanced Genome Editing Specificity.” Cell 154 (6):1380-1389 (Sep. 2013).
Segal, “Bacteria herald a new era of gene editing,” eLife, Jan. 29, 2013; 2:e00563.
Shalem et al, “Genome-Scale CRISPR-Cas9 Knockout Screening in Human Cells,” Science (Jan. 3, 2014) p. 84-87, epub Sciencexpress Dec. 12, 2013.
Shen et al., “Generation of gene-modified mice via Cas9/RNA-mediated gene targeting,” Cell Res., 23(5):720-723 (May 2013; epub Apr. 2, 2013).
Sontheimer and Marraffini, “Slicer for DNA” Nature 468:p. 45-46 (in print Nov. 4, 2010; epub Nov. 3, 2010).
Sorek et al., “CRISPR—a widespread system that provides acquired resistance against phages in bacteria and archaea,” Nature Reviews Microbiology 6:181-186 (Mar. 2008).
System Biosciences, Inc., pGreenFire™ Pathway Reporter Lentivectors Cat. # TROXX Series User Manual, 19 pgs, dated Aug. 24, 2012.
System Biosciences, Inc., “PrecisionX Cas9 SmartNuclease™ Vector System, Catalog Nos. CASxxx series User Manual,” ver.1, dated Apr. 22, 2013 (16 pages), retrieved from <http://www.systembio.com/downloads/Cas9-SmartNuclease-user-manual.pdf>.
System Biosciences, Inc., “PrecisionX Cas9 SmartNuclease™RNA System, Catalog Nos. CAS5xxA-1 series User Manual,” ver.2, dated Sep. 3, 2013 17 pages, retrieved from <http://www.systembio.com/downloads/CAS5xxA-1-gRNA_Cas9_mRNA.pdf>.
Terns and Terns, “CRISPR-based adaptive immune systems.” Curr. Opin. Microbiol. 14, 321 (2011).
Wang et al., “One-step generation of mice carrying mutations in multiple genes by CRISPR/Cas-mediated genome engineering,” Cell 153(4):910-918 (May 9, 2013; epub May 2, 2013).
Wiedenheft, Sternberg and Doudna, “RNA-guided genetic silencing systems in bacteria and archaea.” Nature 482; p. 331-338 (print Feb. 15, 2012; epub Feb. 15, 2012).
Sanders “Cheap and easy technique to snip DNA could revolutionize gene therapy.” Media Relations, Univ. of California Berkeley, NewsCenter website (dated Jan. 7, 2013). Retrieved from: <URL: http://newscenter.berkeley.edu/2013/01/07/cheap-and-easy-technique-to-snip-dna-could-revolutionize-gene-therapy/>.
Cain, “CRISPR genome editing,” SciBX Science-Business eXchange 6(4); doi:10.1038/scibx.2013.77 (epub Jan. 31, 2013).
Collins, “Copy-editing the Genome: Extreme Personalized Medicine?” NIH Director’s Blog (Jan. 22, 2013); retrieved from: <URL: http://directorsblog.nih.gov/copy-editing-the-genome-extreme-personalized-medicine/>; [retrieved on xx/xx/xx].
Leuty “QB3 powers new wave of bio startups,” San Francisco Business Times (dated Sep. 14, 2012); retrieved from: <http://www.bizjournals.com/sanfrancisco/print-edition/2012/09/14/qb3-powers-new-wave-of-bio-startups.html?page=all>; [retrieved approximately Feb. 2013].
Addgene, “CRISPR/Cas Plasmids and Protocols,” webpage retrieved from: <https://www.addgene.org/CRISPR/>; [retrieved on May 8, 2014].
Addgene, “CRISPR/Cas Plasmids for use in: Mammals,” webpage retrieved from: <https://www.addgene.org/CRISPR/mammalian/ >; [retrieved on May 8, 2014].
National Center for Biotechnology Information (NCBI), National Institutes of Health, GenBank® Accession No. AAK33936.1.
National Center for Biotechnology Information (NCBI), National Institutes of Health, GenBank® Accession No. NC_002737.
Cong et al., Science 339(6121):819-823 (print publication Feb. 15, 2013) with accompanying Supplemental Materials (34 pages).
Fath et al., “Multiparameter RNA and Codon Optimization: A Standardized Tool to Assess and Enhance Autologous Mammalian Gene Expression,” PLoS ONE 6(3):e17956 (publ Mar. 3, 2011); 14 pages.

(56) References Cited

OTHER PUBLICATIONS

U.S. Appl. No. 14/211,858, by Wu, entitled "Compositions and Methods Directed to CRISPR/Cas Genomic Engineering Systems," filed Mar. 14, 2014; Office Action dated Jun. 2, 2015.

* cited by examiner

EF1-hspCas9-H1-AAVS
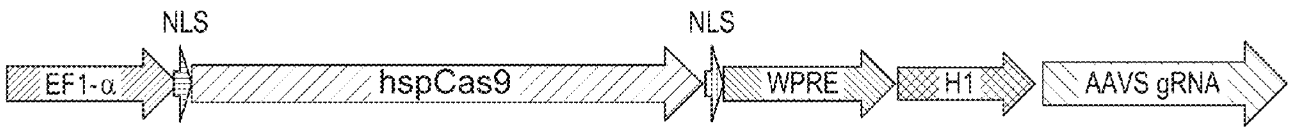
FIG. 3A
EF1-spCas9-mcherry-H1-AAVS
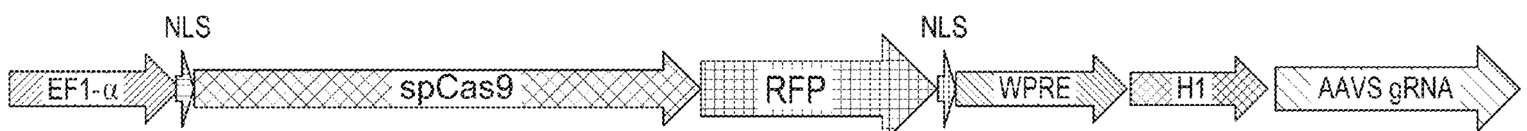
FIG. 3B
AAVS target sequence: GGGGCCACTAGGGACAGGAT (SEQ ID NO: 18)
FIG. 3C

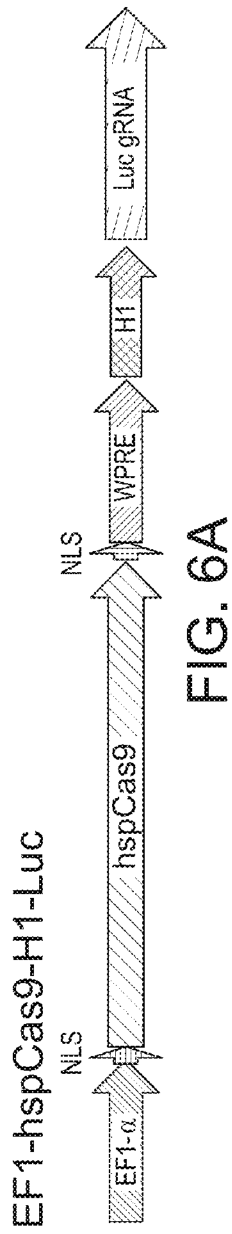
FIG. 6A
Luciferase gRNA sequences:
Luc gRNA1: GGCATGCGAGAATCTGACGC (SEQ ID NO: 20)
Luc gRNA2: CATGCCAGAGATCCTATTTT (SEQ ID NO: 21)
FIG. 6B
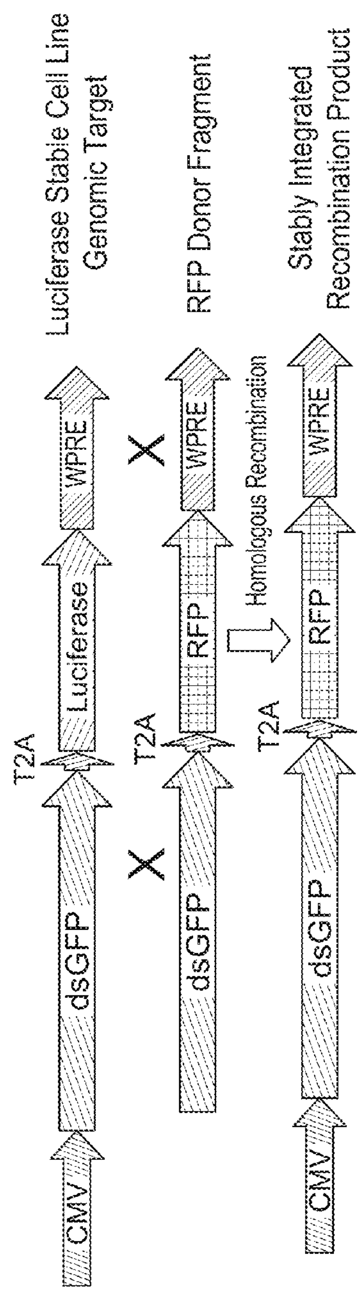
FIG. 6C

| Nuclear Localization Signal | Amino Acid Sequence | Nucleotide Sequence |
|---|---|---|
| NLS1 | MPKKKRKVA (SEQ ID NO: 22) | ATGCCAAAGAAGAAGCGTAAGGTCGCT (SEQ ID NO: 23) |
| NLS2 | SRADPKKKRKV* (SEQ ID NO: 24) | AGCAGAGCCGACCCCAAGAAGAAGCGGAAGGTGTAG (SEQ ID NO: 25) |
| NLS3 | KRPAATKKAGQAKKKK* (SEQ ID NO: 26) | AAGCGGCCTGCCGCCACCAAGAAGGCTGGCCAGGCCAAGAAGAAGAAGTAG (SEQ ID NO: 27) |
| NLS4 | MAPKKKRKVGIHGVPAA (SEQ ID NO: 28) | ATGGCTCCCAAGAAGAAGCGAAAGGTGGGCATCCACGGCGTGCCCGCTGCC (SEQ ID NO: 29) |
| NLS5 | KRPAATKKAGQAKKKK* (SEQ ID NO: 30) | AAACGCCCAGCCGCCACCAAGAAAGCAGGACAGGCAAAGAAGAAGAAGTGA (SEQ ID NO: 31) |

FIG. 9A

| Construct | Relative Fluorescence |
|---|---|
| NLS1-spCas9-mcherry | Detectable expression. Poor nuclear localization. |
| NLS1-spCas9-mcherry-NLS2 | Detectable expression. Improved nuclear localization. |
| NLS1-spCas9-mcherry-NLS3 | Detectable expression. Improved nuclear localization. |
| NLS4-hspCas9-mcherry-NLS5 | Robust expression. Strong nuclear localization. |

FIG. 9B

1. DNA marker
2. EF1-hspCas9-H1-AAVS-gRNA
3. EF1-hspCas9 (D10A)-H1-AAVS-gRNA
4. EF1-hspCas9-DM-H1-AAVS-gRNA
5. Negative control EGIP cell

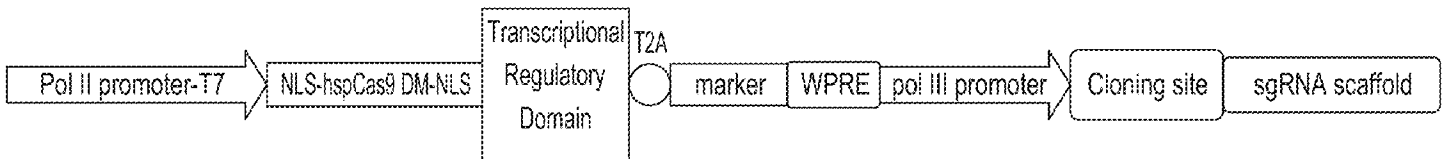

FIG. 16A

KRAB Domain Nucleotide Sequence

GACGGCGGTGGTGCTTTGTCTCCTCAGCACTCTGCTGTCACTCAAGGAAGTATCATCAAGAACAAGGAGGGCATGGATGCTAAGTCACT
AACTGCCTGGTCCCGGACACTGGTGACCTTCAAGGATGTATTTGTGGACTTCACCAGGGAGGAGTGGAAGCTGCTGGACACTGCTCAGC
AGATCGTGTACAGAAATGTGATGCTGGAGAACTATAAGAACCTGGTTTCCTTGGGTTATCAGCTTACTAAGCCAGATGTGATCCTCCGG
TTGGAGAAGGGAGAAGAGCCCTGGCTGGTGGAGAGAGAAATTCACCAAGAGACACATCCTGATTCAGAGACTGCATTTGAAATCAAATC
ATCAGTT
(SEQ ID NO: 38)

KRAB Domain Amino Acid Sequence

DGGGALSPQHSAVTQGSIIKNKEGMDAKSLTAWSRTLVTFKDVFVDFTREEWKLLDTAQQIVYRNVMLENYKNLVSLGYQLTKPDVILR
LEKGEEPWLVEREIHQETHPDSETAFEIKSSV
(SEQ ID NO: 39)

VP64 Domain Nucleotide Sequence

GGTTCCGGACGGGCTGACGCATTGGACGATTTTGATCTGGATATGCTGGGAAGTGACGCCCTCGATGATTTTGACCTTGACATGCTTGG
TTCGGATGCCCTTGATGACTTTGACCTCGACATGCTCGGCAGTGACGCCCTTGATGATTTCGACCTGGACATGCTGATTAACTCTAGA
(SEQ ID NO: 40)

VP64 Domain Amino Acid Sequence

GSGRADALDDFDLDMLGSDALDDFDLDMLGSDALDDFDLDMLGSDALDDFDLDMLINSR
(SEQ ID NO: 41)

FIG. 16B

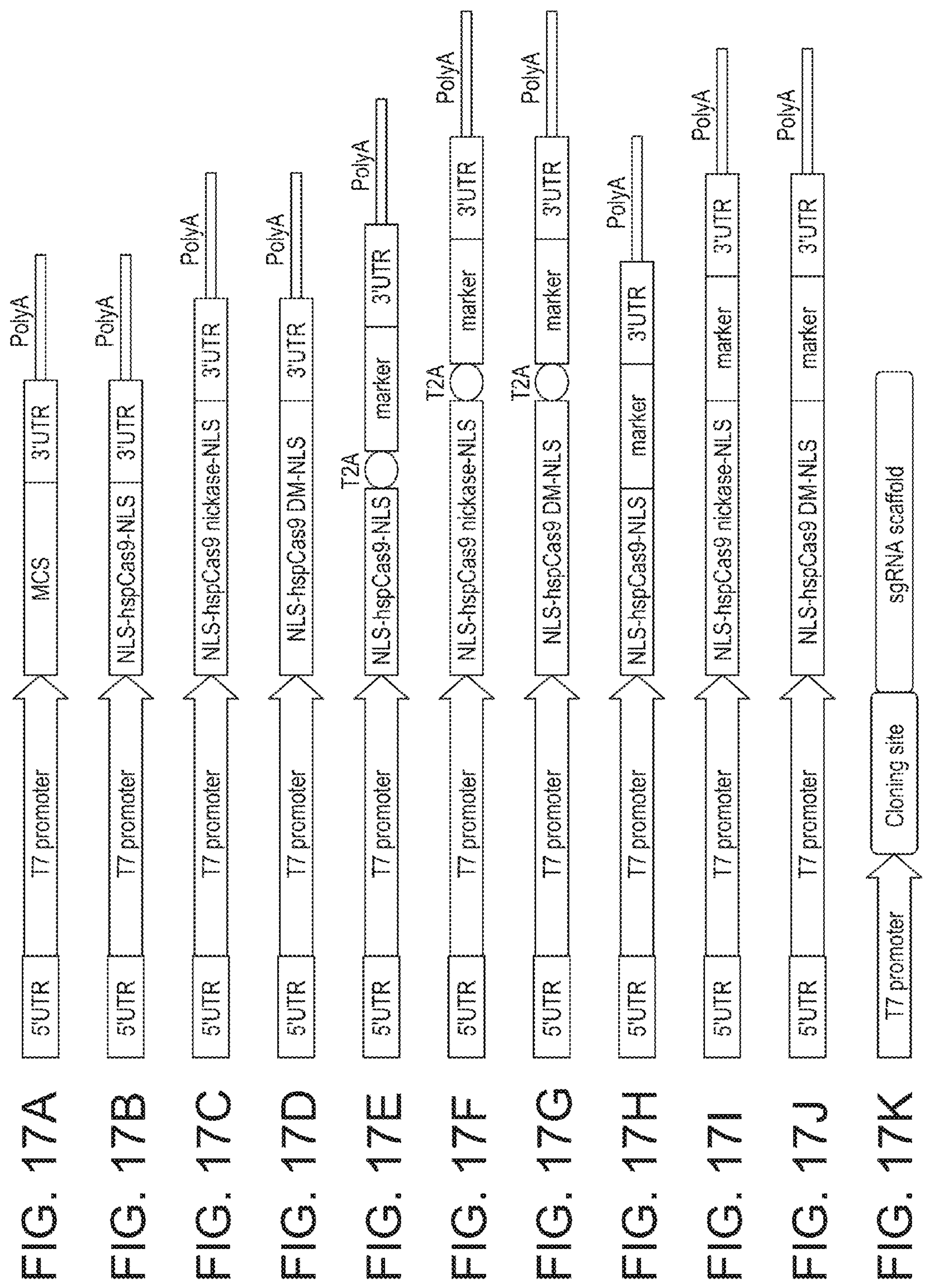
FIG. 17A
5'UTR
T7 promoter
MCS
3'UTR
PolyA
FIG. 17B
5'UTR
T7 promoter
NLS-hspCas9-NLS
3'UTR
PolyA
FIG. 17C
5'UTR
T7 promoter
NLS-hspCas9 nickase-NLS
3'UTR
PolyA
FIG. 17D
5'UTR
T7 promoter
NLS-hspCas9 DM-NLS
3'UTR
PolyA
FIG. 17E
5'UTR
T7 promoter
NLS-hspCas9-NLS
T2A
marker
3'UTR
PolyA
FIG. 17F
5'UTR
T7 promoter
NLS-hspCas9 nickase-NLS
T2A
marker
3'UTR
PolyA
FIG. 17G
5'UTR
T7 promoter
NLS-hspCas9 DM-NLS
T2A
marker
3'UTR
PolyA
FIG. 17H
5'UTR
T7 promoter
NLS-hspCas9-NLS
marker
3'UTR
PolyA
FIG. 17I
5'UTR
T7 promoter
NLS-hspCas9 nickase-NLS
marker
3'UTR
PolyA
FIG. 17J
5'UTR
T7 promoter
NLS-hspCas9 DM-NLS
marker
3'UTR
PolyA
FIG. 17K
T7 promoter
Cloning site
sgRNA scaffold

**Native *Streptococcus pyogenes (S. pyogenes)* Wild Type Cas9 Protein Amino Acid Sequence**

MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKVVDELVKVMGRHKPENIVIEMARENQ
TTQKGQKNSRERMKRIEEGIKELGSQILKEHPVENTQLQNEKLYLYYLQNGRDMYVDQELDINR
LSDYDVDHIVPQSFLKDDSIDNKVLTRSDKNRGKSDNVPSEEVVKKMKNYWRQLLNAKLITQRK
FDNLTKAERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVYDVRKMIAK
SEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLAS
AGELQKGNELALPSKYVNFLYLASHYEKLKGSPEDNEQKQLFVEQHKHYLDEIIEQISEFSKRV
ILADANLDKVLSAYNKHRDKPIREQAENIIHLFTLTNLGAPAAFKYFDTTIDRKRYTSTKEVLD
ATLIHQSITGLYETRIDLSQLGGD*

(SEQ ID NO: 1)

FIG. 18

Native *Streptococcus pyogenes* Wild Type cas9 Gene
Open Reading Frame Nucleotide Sequence

```
ATGGATAAGAAATACTCAATAGGCTTAGATATCGGCACAAATAGCGTCGGATGGGCGGTGATCA
CTGATGAATATAAGGTTCCGTCTAAAAAGTTCAAGGTTCTGGGAAATACAGACCGCCACAGTAT
CAAAAAAAATCTTATAGGGGCTCTTTTATTTGACAGTGGAGAGACAGCGGAAGCGACTCGTCTC
AAACGGACAGCTCGTAGAAGGTATACACGTCGGAAGAATCGTATTTGTTATCTACAGGAGATTT
TTTCAAATGAGATGGCGAAAGTAGATGATAGTTTCTTTCATCGACTTGAAGAGTCTTTTTTGGT
GGAAGAAGACAAGAAGCATGAACGTCATCCTATTTTTGGAAATATAGTAGATGAAGTTGCTTAT
CATGAGAAATATCCAACTATCTATCATCTGCGAAAAAAATTGGTAGATTCTACTGATAAAGCGG
ATTTGCGCTTAATCTATTTGGCCTTAGCGCATATGATTAAGTTTCGTGGTCATTTTTTGATTGA
GGGAGATTTAAATCCTGATAATAGTGATGTGGACAAACTATTTATCCAGTTGGTACAAACCTAC
AATCAATTATTTGAAGAAAACCCTATTAACGCAAGTGGAGTAGATGCTAAAGCGATTCTTTCTG
CACGATTGAGTAAATCAAGACGATTAGAAAATCTCATTGCTCAGCTCCCCGGTGAGAAGAAAAA
TGGCTTATTTGGGAATCTCATTGCTTTGTCATTGGGTTTGACCCCTAATTTTAAATCAAATTTT
GATTTGGCAGAAGATGCTAAATTACAGCTTTCAAAAGATACTTACGATGATGATTTAGATAATT
TATTGGCGCAAATTGGAGATCAATATGCTGATTTGTTTTTGGCAGCTAAGAATTTATCAGATGC
TATTTTACTTTCAGATATCCTAAGAGTAAATACTGAAATAACTAAGGCTCCCCTATCAGCTTCA
ATGATTAAACGCTACGATGAACATCATCAAGACTTGACTCTTTTAAAAGCTTTAGTTCGACAAC
AACTTCCAGAAAAGTATAAAGAAATCTTTTTTGATCAATCAAAAAACGGATATGCAGGTTATAT
TGATGGGGGAGCTAGCCAAGAAGAATTTTATAAATTTATCAAACCAATTTTAGAAAAAATGGAT
GGTACTGAGGAATTATTGGTGAAACTAAATCGTGAAGATTTGCTGCGCAAGCAACGGACCTTTG
ACAACGGCTCTATTCCCCATCAAATTCACTTGGGTGAGCTGCATGCTATTTTGAGAAGACAAGA
AGACTTTTATCCATTTTTAAAAGACAATCGTGAGAAGATTGAAAAAATCTTGACTTTTCGAATT
CCTTATTATGTTGGTCCATTGGCGCGTGGCAATAGTCGTTTTGCATGGATGACTCGGAAGTCTG
AAGAAACAATTACCCCATGGAATTTTGAAGAAGTTGTCGATAAAGGTGCTTCAGCTCAATCATT
TATTGAACGCATGACAAACTTTGATAAAAATCTTCCAAATGAAAAAGTACTACCAAAACATAGT
TTGCTTTATGAGTATTTTACGGTTTATAACGAATTGACAAAGGTCAAATATGTTACTGAAGGAA
TGCGAAAACCAGCATTTCTTTCAGGTGAACAGAAGAAAGCCATTGTTGATTTACTCTTCAAAAC
AAATCGAAAAGTAACCGTTAAGCAATTAAAAGAAGATTATTTCAAAAAAATAGAATGTTTTGAT
AGTGTTGAAATTTCAGGAGTTGAAGATAGATTTAATGCTTCATTAGGTACCTACCATGATTTGC
TAAAAATTATTAAAGATAAAGATTTTTTGGATAATGAAGAAAATGAAGATATCTTAGAGGATAT
TGTTTTAACATTGACCTTATTTGAAGATAGGGAGATGATTGAGGAAAGACTTAAAACATATGCT
CACCTCTTTGATGATAAGGTGATGAAACAGCTTAAACGTCGCCGTTATACTGGTTGGGGACGTT
TGTCTCGAAAATTGATTAATGGTATTAGGGATAAGCAATCTGGCAAAACAATATTAGATTTTTT
GAAATCAGATGGTTTTGCCAATCGCAATTTTATGCAGCTGATCCATGATGATAGTTTGACATTT
AAAGAAGACATTCAAAAAGCACAAGTGTCTGGACAAGGCGATAGTTTACATGAACATATTGCAA
ATTTAGCTGGTAGCCCTGCTATTAAAAAAGGTATTTTACAGACTGTAAAAGTTGTTGATGAATT
```

FIG. 19 (part 1 of 2, continued next page)

GGTCAAAGTAATGGGGCGGCATAAGCCAGAAAATATCGTTATTGAAATGGCACGTGAAAATCAG
ACAACTCAAAAGGGCCAGAAAAATTCGCGAGAGCGTATGAAACGAATCGAAGAAGGTATCAAAG
AATTAGGAAGTCAGATTCTTAAAGAGCATCCTGTTGAAAATACTCAATTGCAAAATGAAAAGCT
CTATCTCTATTATCTCCAAAATGGAAGAGACATGTATGTGGACCAAGAATTAGATATTAATCGT
TTAAGTGATTATGATGTCGATCACATTGTTCCACAAAGTTTCCTTAAAGACGATTCAATAGACA
ATAAGGTCTTAACGCGTTCTGATAAAAATCGTGGTAAATCGGATAACGTTCCAAGTGAAGAAGT
AGTCAAAAAGATGAAAAACTATTGGAGACAACTTCTAAACGCCAAGTTAATCACTCAACGTAAG
TTTGATAATTTAACGAAAGCTGAACGTGGAGGTTTGAGTGAACTTGATAAAGCTGGTTTTATCA
AACGCCAATTGGTTGAAACTCGCCAAATCACTAAGCATGTGGCACAAATTTTGGATAGTCGCAT
GAATACTAAATACGATGAAAATGATAAACTTATTCGAGAGGTTAAAGTGATTACCTTAAAATCT
AAATTAGTTTCTGACTTCCGAAAAGATTTCCAATTCTATAAAGTACGTGAGATTAACAATTACC
ATCATGCCCATGATGCGTATCTAAATGCCGTCGTTGGAACTGCTTTGATTAAGAAATATCCAAA
ACTTGAATCGGAGTTTGTCTATGGTGATTATAAAGTTTATGATGTTCGTAAAATGATTGCTAAG
TCTGAGCAAGAAATAGGCAAAGCAACCGCAAAATATTTCTTTTACTCTAATATCATGAACTTCT
TCAAAACAGAAATTACACTTGCAAATGGAGAGATTCGCAAACGCCCTCTAATCGAAACTAATGG
GGAAACTGGAGAAATTGTCTGGGATAAAGGGCGAGATTTTGCCACAGTGCGCAAAGTATTGTCC
ATGCCCCAAGTCAATATTGTCAAGAAAACAGAAGTACAGACAGGCGGATTCTCCAAGGAGTCAA
TTTTACCAAAAAGAAATTCGGACAAGCTTATTGCTCGTAAAAAAGACTGGGATCCAAAAAAATA
TGGTGGTTTTGATAGTCCAACGGTAGCTTATTCAGTCCTAGTGGTTGCTAAGGTGGAAAAAGGG
AAATCGAAGAAGTTAAAATCCGTTAAAGAGTTACTAGGGATCACAATTATGGAAAGAAGTTCCT
TTGAAAAAAATCCGATTGACTTTTTAGAAGCTAAAGGATATAAGGAAGTTAAAAAAGACTTAAT
CATTAAACTACCTAAATATAGTCTTTTTGAGTTAGAAAACGGTCGTAAACGGATGCTGGCTAGT
GCCGGAGAATTACAAAAAGGAAATGAGCTGGCTCTGCCAAGCAAATATGTGAATTTTTTATATT
TAGCTAGTCATTATGAAAAGTTGAAGGGTAGTCCAGAAGATAACGAACAAAAACAATTGTTTGT
GGAGCAGCATAAGCATTATTTAGATGAGATTATTGAGCAAATCAGTGAATTTTCTAAGCGTGTT
ATTTTAGCAGATGCCAATTTAGATAAAGTTCTTAGTGCATATAACAAACATAGAGACAAACCAA
TACGTGAACAAGCAGAAAATATTATTCATTTATTTACGTTGACGAATCTTGGAGCTCCCGCTGC
TTTTAAATATTTTGATACAACAATTGATCGTAAACGATATACGTCTACAAAAGAAGTTTTAGAT
GCCACTCTTATCCATCAATCCATCACTGGTCTTTATGAAACACGCATTGATTTGAGTCAGCTAG
GAGGTGACTGA (SEQ ID NO: 2)

FIG. 19 (continued, part 2 of 2)

Mammalian Codon-Optimized *Streptococcus pyogenes* Wild Type cas9 Gene Open Reading Frame Nucleotide Sequence

ATGGACAAAAAGTATAGTATCGGACTGGATATTGGCACTAACAGCGTGGGATGGGCCGTCATCA
CCGACGAGTACAAAGTGCCAAGCAAGAAGTTCAAGGTCCTGGGAAACACCGATAGACACAGTAT
CAAGAAAAATCTGATTGGAGCCCTGCTGTTCGACTCAGGGGAGACAGCTGAAGCAACTAGGCTG
AAAAGAACAGCTAGGAGACGGTATACTCGCCGAAAGAATCGGATCTGCTACCTCCAGGAGATTT
TCTCCAACGAAATGGCCAAGGTGGACGATAGTTTCTTTCATCGCCTGGAGGAATCATTCCTGGT
CGAGGAAGATAAGAAACACGAGAGGCATCCCATCTTTGGCAACATTGTGGACGAGGTCGCTTAT
CACGAAAAGTACCCTACAATCTATCATCTGCGGAAGAAACTGGTGGACAGCACTGATAAGGCAG
ACCTGCGCCTGATCTATCTGGCCCTGGCTCACATGATTAAGTTCAGGGGGCATTTTCTGATCGA
GGGCGATCTGAACCCAGACAATTCCGATGTGGACAAGCTGTTCATCCAGCTGGTCCAGACATAC
AATCAGCTGTTTGAGGAAAACCCCATTAATGCATCTGGGGTGGACGCAAAAGCCATCCTGAGTG
CCAGACTGTCTAAGAGTAGGAGACTGGAGAACCTGATCGCTCAGCTGCCAGGCGAAAAGAAAAA
CGGCCTGTTTGGAAATCTGATTGCACTGTCACTGGGACTGACCCCCAACTTCAAGAGCAATTTT
GATCTGGCCGAGGACGCTAAGCTCCAGCTGAGCAAGGACACCTACGACGATGACCTGGATAACC
TGCTGGCTCAGATCGGCGATCAGTACGCAGACCTGTTCCTGGCCGCTAAGAATCTGTCTGACGC
CATCCTGCTGAGTGATATTCTGAGAGTGAACACCGAGATTACAAAAGCCCCCCTGTCAGCTAGC
ATGATCAAGAGATATGACGAGCACCATCAGGATCTGACCCTGCTGAAGGCTCTGGTGCGGCAGC
AGCTGCCTGAGAAGTACAAAGAAATCTTCTTTGATCAGAGCAAGAATGGGTACGCCGGCTATAT
TGACGGCGGAGCTTCCCAGGAGGAGTTCTACAAGTTTATCAAACCTATTCTGGAGAAGATGGAC
GGCACTGAGGAACTGCTGGTGAAACTGAATCGGGAAGACCTGCTGCGGAAGCAGCGCACCTTCG
ATAACGGCAGCATCCCTCACCAGATTCATCTGGGAGAGCTGCACGCAATCCTGCGGCGCCAGGA
AGACTTCTACCCATTTCTGAAGGATAACCGGGAGAAGATCGAAAAAATTCTGACTTTCCGCATC
CCCTACTATGTGGGGCCTCTGGCAAGAGGCAATTCCCGGTTTGCCTGGATGACCCGCAAGTCTG
AGGAAACAATCACTCCCTGGAACTTCGAGGAAGTGGTCGATAAGGGCGCTTCCGCACAGTCTTT
CATTGAGAGGATGACAAATTTTGACAAGAACCTGCCAAATGAAAAAGTGCTGCCCAAGCACAGC
CTGCTGTACGAGTATTTCACCGTCTATAACGAACTGACAAAGGTGAAATACGTCACTGAGGGCA
TGAGAAAGCCTGCCTTCCTGTCCGGAGAACAGAAGAAAGCTATCGTGGACCTGCTGTTTAAAAC
CAATCGGAAGGTGACAGTCAAGCAGCTGAAAGAGGACTACTTCAAGAAAATTGAATGTTTCGAT
TCTGTGGAGATCAGTGGGGTCGAAGACAGGTTTAACGCCTCTCTGGGCACCTACCACGATCTGC
TGAAGATCATTAAGGATAAAGACTTCCTGGACAACGAGGAAAATGAGGACATCCTGGAGGACAT
TGTGCTGACCCTGACACTGTTTGAGGATCGGGAAATGATCGAGGAACGCCTGAAGACCTACGCC
CATCTGTTCGATGACAAAGTGATGAAACAGCTGAAGCGAAGGAGATACACTGGGTGGGGCCGAC
TGAGCAGGAAGCTGATCAATGGCATTCGCGACAAACAGAGTGGAAAGACAATCCTGGACTTTCT
GAAGTCAGATGGCTTCGCTAACAGGAATTTTATGCAGCTGATTCACGATGACTCTCTGACTTTC
AAAGAGGACATCCAGAAGGCACAGGTGTCCGGACAGGGGGACTCTCTGCACGAGCATATCGCAA
ACCTGGCCGGGAGCCCTGCCATCAAGAAAGGCATCCTCCAGACCGTGAAGGTGGTGGACGAGCT

FIG. 20 (part 1 of 2, continued next page)

GGTGAAAGTCATGGGAAGACATAAGCCAGAAAACATCGTGATTGAGATGGCCAGGGAGAATCAG
ACCACACAGAAAGGGCAGAAGAACTCTCGGGAGCGCATGAAACGCATCGAGGAAGGAATTAAGG
AACTGGGGAGTCAGATCCTGAAAGAGCACCCCGTGGAAAACACACAGCTCCAGAATGAGAAGCT
GTATCTGTACTACCTCCAGAATGGCCGCGATATGTACGTGGACCAGGAGCTGGATATTAACCGA
CTGTCAGATTATGACGTGGATCATATCGTCCCACAGTCATTCCTGAAAGATGACAGCATTGACA
ATAAGGTGCTGACCCGCAGCGACAAAAACCGAGGAAAGAGTGATAATGTCCCCTCAGAGGAAGT
GGTCAAGAAAATGAAGAACTACTGGAGGCAGCTGCTGAATGCCAAACTGATCACCCAGCGAAAG
TTTGATAACCTGACAAAAGCTGAGAGGGGGGGCCTGTCCGAACTGGACAAAGCAGGCTTCATCA
AGCGACAGCTGGTGGAGACAAGGCAGATCACAAAGCACGTCGCTCAGATCCTGGACAGCAGGAT
GAACACCAAGTACGATGAGAATGACAAACTGATCCGGGAAGTGAAGGTCATTACACTGAAGTCA
AAACTGGTGAGCGACTTTAGGAAAGATTTCCAGTTCTACAAGGTCAGAGAGATCAACAACTACC
ACCATGCTCATGACGCATACCTGAACGCAGTGGTCGGGACTGCCCTGATTAAGAAATACCCTAA
ACTGGAGTCTGAGTTCGTGTACGGCGACTATAAGGTGTACGATGTCAGAAAAATGATCGCCAAG
AGCGAGCAGGAAATTGGCAAAGCCACCGCTAAGTATTTCTTTTACTCCAACATCATGAATTTCT
TTAAGACTGAGATCACCCTGGCAAATGGCGAAATCCGAAAGAGGCCACTGATTGAGACTAACGG
AGAGACAGGGGAAATCGTGTGGGACAAAGGAAGAGATTTTGCTACCGTGCGGAAGGTCCTGAGT
ATGCCCCAAGTGAATATTGTCAAGAAAACAGAGGTGCAGACTGGAGGGTTCAGTAAGGAATCAA
TTCTGCCTAAACGCAACAGCGATAAGCTGATCGCCCGAAAGAAAGACTGGGACCCCAAGAAGTA
TGGCGGATTCGACTCCCCAACCGTGGCTTACTCTGTCCTGGTGGTCGCAAAGGTGGAGAAGGGA
AAAAGCAAGAAACTGAAATCCGTCAAGGAACTGCTGGGGATCACAATTATGGAGAGGAGCAGCT
TCGAAAAGAATCCTATCGATTTTCTGGAGGCCAAAGGGTATAAGGAAGTGAAGAAAGACCTGAT
CATCAAGCTGCCAAAGTACTCTCTGTTTGAGCTGGAAAACGGCAGAAAGCGGATGCTGGCAAGT
GCCGGCGAGCTGCAAAAAGGAAATGAACTGGCCCTGCCCTCAAAGTACGTGAACTTCCTGTATC
TGGCTAGCCACTACGAGAAGCTGAAAGGCTCCCCTGAGGATAACGAACAGAAACAGCTGTTTGT
GGAGCAGCACAAGCATTATCTGGACGAGATCATTGAACAGATTAGCGAGTTCTCCAAACGCGTG
ATCCTGGCTGACGCAAATCTGGATAAGGTCCTGTCTGCATACAACAAACACAGGGACAAGCCAA
TCAGAGAGCAGGCCGAAAATATCATTCATCTGTTCACTCTGACCAACCTGGGAGCCCCCGCAGC
CTTCAAGTATTTTGACACTACCATCGATCGCAAACGATACACAAGCACTAAGGAGGTGCTGGAT
GCTACCCTGATCCACCAGAGCATTACTGGGCTGTACGAGACAAGGATCGACCTGTCCCAGCTGG
GGGGAGAC (SEQ ID NO: 3)

FIG. 20 (continued, part 2 of 2)

**Mammalian Codon-Optimized *Streptococcus pyogenes* Wild Type cas9 Gene Open Reading Frame Encoding N- and C-Terminal Nuclear Localization Signals**

<u>ATGGCTCCCAAGAAGAAGCGAAAGGTGGGCATCCACGGCGTGCCCGCTGCC</u>GACAAAAAGTATA
GTATCGGACTGGATATTGGCACTAACAGCGTGGGATGGGCCGTCATCACCGACGAGTACAAAGT
GCCAAGCAAGAAGTTCAAGGTCCTGGGAAACACCGATAGACACAGTATCAAGAAAAATCTGATT
GGAGCCCTGCTGTTCGACTCAGGGGAGACAGCTGAAGCAACTAGGCTGAAAAGAACAGCTAGGA
GACGGTATACTCGCCGAAAGAATCGGATCTGCTACCTCCAGGAGATTTTCTCCAACGAAATGGC
CAAGGTGGACGATAGTTTCTTTCATCGCCTGGAGGAATCATTCCTGGTCGAGGAAGATAAGAAA
CACGAGAGGCATCCCATCTTTGGCAACATTGTGGACGAGGTCGCTTATCACGAAAAGTACCCTA
CAATCTATCATCTGCGGAAGAAACTGGTGGACAGCACTGATAAGGCAGACCTGCGCCTGATCTA
TCTGGCCCTGGCTCACATGATTAAGTTCAGGGGGCATTTTCTGATCGAGGGCGATCTGAACCCA
GACAATTCCGATGTGGACAAGCTGTTCATCCAGCTGGTCCAGACATACAATCAGCTGTTTGAGG
AAAACCCCATTAATGCATCTGGGGTGGACGCAAAAGCCATCCTGAGTGCCAGACTGTCTAAGAG
TAGGAGACTGGAGAACCTGATCGCTCAGCTGCCAGGCGAAAAGAAAAACGGCCTGTTTGGAAAT
CTGATTGCACTGTCACTGGGACTGACCCCCAACTTCAAGAGCAATTTTGATCTGGCCGAGGACG
CTAAGCTCCAGCTGAGCAAGGACACCTACGACGATGACCTGGATAACCTGCTGGCTCAGATCGG
CGATCAGTACGCAGACCTGTTCCTGGCCGCTAAGAATCTGTCTGACGCCATCCTGCTGAGTGAT
ATTCTGAGAGTGAACACCGAGATTACAAAAGCCCCCCTGTCAGCTAGCATGATCAAGAGATATG
ACGAGCACCATCAGGATCTGACCCTGCTGAAGGCTCTGGTGCGGCAGCAGCTGCCTGAGAAGTA
CAAAGAAATCTTCTTTGATCAGAGCAAGAATGGGTACGCCGGCTATATTGACGGCGGAGCTTCC
CAGGAGGAGTTCTACAAGTTTATCAAACCTATTCTGGAGAAGATGGACGGCACTGAGGAACTGC
TGGTGAAACTGAATCGGGAAGACCTGCTGCGGAAGCAGCGCACCTTCGATAACGGCAGCATCCC
TCACCAGATTCATCTGGGAGAGCTGCACGCAATCCTGCGGCGCCAGGAAGACTTCTACCCATTT
CTGAAGGATAACCGGGAGAAGATCGAAAAAATTCTGACTTTCCGCATCCCCTACTATGTGGGGC
CTCTGGCAAGAGGCAATTCCCGGTTTGCCTGGATGACCCGCAAGTCTGAGGAAACAATCACTCC
CTGGAACTTCGAGGAAGTGGTCGATAAGGGCGCTTCCGCACAGTCTTTCATTGAGAGGATGACA
AATTTTGACAAGAACCTGCCAAATGAAAAGGTGCTGCCCAAGCACAGCCTGCTGTACGAGTATT
TCACCGTCTATAACGAACTGACAAAGGTGAAATACGTCACTGAGGGCATGAGAAAGCCTGCCTT
CCTGTCCGGAGAACAGAAGAAAGCTATCGTGGACCTGCTGTTTAAAACCAATCGGAAGGTGACA
GTCAAGCAGCTGAAAGAGGACTACTTCAAGAAAATTGAATGTTTCGATTCTGTGGAGATCAGTG
GGGTCGAAGACAGGTTTAACGCCTCTCTGGGCACCTACCACGATCTGCTGAAGATCATTAAGGA
TAAAGACTTCCTGGACAACGAGGAAAATGAGGACATCCTGGAGGACATTGTGCTGACCCTGACA
CTGTTTGAGGATCGGGAAATGATCGAGGAACGCCTGAAGACCTACGCCCATCTGTTCGATGACA
AAGTGATGAAACAGCTGAAGCGAAGGAGATACACTGGGTGGGGCCGACTGAGCAGGAAGCTGAT
CAATGGCATTCGCGACAAACAGAGTGGAAAGACAATCCTGGACTTTCTGAAGTCAGATGGCTTC
GCTAACAGGAATTTTATGCAGCTGATTCACGATGACTCTCTGACTTTCAAAGAGGACATCCAGA
AGGCACAGGTGTCCGGACAGGGGGACTCTCTGCACGAGCATATCGCAAACCTGGCCGGGAGCCC

FIG. 21 (part 1 of 2, continued next page)

TGCCATCAAGAAAGGCATCCTCCAGACCGTGAAGGTGGTGGACGAGCTGGTGAAAGTCATGGGA
AGACATAAGCCAGAAAACATCGTGATTGAGATGGCCAGGGAGAATCAGACCACACAGAAAGGGC
AGAAGAACTCTCGGGAGCGCATGAAACGCATCGAGGAAGGAATTAAGGAACTGGGGAGTCAGAT
CCTGAAAGAGCACCCCGTGGAAAACACACAGCTCCAGAATGAGAAGCTGTATCTGTACTACCTC
CAGAATGGCCGCGATATGTACGTGGACCAGGAGCTGGATATTAACCGACTGTCAGATTATGACG
TGGATCATATCGTCCCACAGTCATTCCTGAAAGATGACAGCATTGACAATAAGGTGCTGACCCG
CAGCGACAAAAACCGAGGAAAGAGTGATAATGTCCCCTCAGAGGAAGTGGTCAAGAAAATGAAG
AACTACTGGAGGCAGCTGCTGAATGCCAAACTGATCACCCAGCGAAAGTTTGATAACCTGACAA
AAGCTGAGAGGGGGGGCCTGTCCGAACTGGACAAAGCAGGCTTCATCAAGCGACAGCTGGTGGA
GACAAGGCAGATCACAAAGCACGTCGCTCAGATCCTGGACAGCAGGATGAACACCAAGTACGAT
GAGAATGACAAACTGATCCGGGAAGTGAAGGTCATTACACTGAAGTCAAAACTGGTGAGCGACT
TTAGGAAAGATTTCCAGTTCTACAAGGTCAGAGAGATCAACAACTACCACCATGCTCATGACGC
ATACCTGAACGCAGTGGTCGGGACTGCCCTGATTAAGAAATACCCTAAACTGGAGTCTGAGTTC
GTGTACGGCGACTATAAGGTGTACGATGTCAGAAAAATGATCGCCAAGAGCGAGCAGGAAATTG
GCAAAGCCACCGCTAAGTATTTCTTTTACTCCAACATCATGAATTTCTTTAAGACTGAGATCAC
CCTGGCAAATGGCGAAATCCGAAAGAGGCCACTGATTGAGACTAACGGAGAGACAGGGGAAATC
GTGTGGGACAAAGGAAGAGATTTTGCTACCGTGCGGAAGGTCCTGAGTATGCCCCAAGTGAATA
TTGTCAAGAAAACAGAGGTGCAGACTGGAGGGTTCAGTAAGGAATCAATTCTGCCTAAACGCAA
CAGCGATAAGCTGATCGCCCGAAAGAAAGACTGGGACCCCAAGAAGTATGGCGGATTCGACTCC
CCAACCGTGGCTTACTCTGTCCTGGTGGTCGCAAAGGTGGAGAAGGGAAAAAGCAAGAAACTGA
AATCCGTCAAGGAACTGCTGGGGATCACAATTATGGAGAGGAGCAGCTTCGAAAAGAATCCTAT
CGATTTTCTGGAGGCCAAAGGGTATAAGGAAGTGAAGAAAGACCTGATCATCAAGCTGCCAAAG
TACTCTCTGTTTGAGCTGGAAAACGGCAGAAAGCGGATGCTGGCAAGTGCCGGCGAGCTGCAAA
AAGGAAATGAACTGGCCCTGCCCTCAAAGTACGTGAACTTCCTGTATCTGGCTAGCCACTACGA
GAAGCTGAAAGGCTCCCCTGAGGATAACGAACAGAAACAGCTGTTTGTGGAGCAGCACAAGCAT
TATCTGGACGAGATCATTGAACAGATTAGCGAGTTCTCCAAACGCGTGATCCTGGCTGACGCAA
ATCTGGATAAGGTCCTGTCTGCATACAACAAACACAGGGACAAGCCAATCAGAGAGCAGGCCGA
AAATATCATTCATCTGTTCACTCTGACCAACCTGGGAGCCCCCGCAGCCTTCAAGTATTTTGAC
ACTACCATCGATCGCAAACGATACACAAGCACTAAGGAGGTGCTGGATGCTACCCTGATCCACC
AGAGCATTACTGGGCTGTACGAGACAAGGATCGACCTGTCCCAGCTGGGGGGAGACAAACGCCC
AGCCGCCACCAAGAAAGCAGGACAGGCAAAGAAGAAGAAGTGA (SEQ ID NO: 4)

FIG. 21 (continued, part 2 of 2)

*Streptococcus pyogenes* Wild Type cas9 Protein Fused with N-terminal myc-tag and N- and C-Terminal Nuclear Localization Signals

MASMQKLISEEDLMAPKKKRKVGIHGVPAADKKYSIGLDIGTNSVGWAVITDEYKVPSKKFKVL
GNTDRHSIKKNLIGALLFDSGETAEATRLKRTARRRYTRRKNRICYLQEIFSNEMAKVDDSFFH
RLEESFLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRLENLIA
QLPGEKKNGLFGNLIALSLGLTPNFKSNFDLAEDAKLQLSKDTYDDDLDNLLAQIGDQYADLFL
AAKNLSDAILLSDILRVNTEITKAPLSASMIKRYDEHHQDLTLLKALVRQQLPEKYKEIFFDQS
KNGYAGYIDGGASQEEFYKFIKPILEKMDGTEELLVKLNREDLLRKQRTFDNGSIPHQIHLGEL
HAILRRQEDFYPFLKDNREKIEKILTFRIPYYVGPLARGNSRFAWMTRKSEETITPWNFEEVVD
KGASAQSFIERMTNFDKNLPNEKVLPKHSLLYEYFTVYNELTKVKYVTEGMRKPAFLSGEQKKA
IVDLLFKTNRKVTVKQLKEDYFKKIECFDSVEISGVEDRFNASLGTYHDLLKIIKDKDFLDNEE
NEDILEDIVLTLTLFEDREMIEERLKTYAHLFDDKVMKQLKRRRYTGWGRLSRKLINGIRDKQS
GKTILDFLKSDGFANRNFMQLIHDDSLTFKEDIQKAQVSGQGDSLHEHIANLAGSPAIKKGILQ
TVKVVDELVKVMGRHKPENIVIEMARENQTTQKGQKNSRERMKRIEEGIKELGSQILKEHPVEN
TQLQNEKLYLYYLQNGRDMYVDQELDINRLSDYDVDHIVPQSFLKDDSIDNKVLTRSDKNRGKS
DNVPSEEVVKKMKNYWRQLLNAKLITQRKFDNLTKAERGGLSELDKAGFIKRQLVETRQITKHV
AQILDSRMNTKYDENDKLIREVKVITLKSKLVSDFRKDFQFYKVREINNYHHAHDAYLNAVVGT
ALIKKYPKLESEFVYGDYKVYDVRKMIAKSEQEIGKATAKYFFYSNIMNFFKTEITLANGEIRK
RPLIETNGETGEIVWDKGRDFATVRKVLSMPQVNIVKKTEVQTGGFSKESILPKRNSDKLIARK
KDWDPKKYGGFDSPTVAYSVLVVAKVEKGKSKKLKSVKELLGITIMERSSFEKNPIDFLEAKGY
KEVKKDLIIKLPKYSLFELENGRKRMLASAGELQKGNELALPSKYVNFLYLASHYEKLKGSPED
NEQKQLFVEQHKHYLDEIIEQISEFSKRVILADANLDKVLSAYNKHRDKPIREQAENIIHLFTL
TNLGAPAAFKYFDTTIDRKRYTSTKEVLDATLIHQSITGLYETRIDLSQLGGDKRPAATKKAGQ
AKKKK*

(SEQ ID NO: 5)

FIG. 22

**Mammalian Codon-Optimized *Streptococcus pyogenes* Wild Type cas9 Gene Open Reading Frame Encoding Fused N-terminal myc-tag and N- and C-Terminal Nuclear Localization Signals**

```
atggctagtatgcagaaactgattagtgaagaggacctgATGGCTCCCAAGAAGAAGCGAAAGG
TGGGCATCCACGGCGTGCCCGCTGCCGACAAAAAGTATAGTATCGGACTGGATATTGGCACTAA
CAGCGTGGGATGGGCCGTCATCACCGACGAGTACAAAGTGCCAAGCAAGAAGTTCAAGGTCCTG
GGAAACACCGATAGACACAGTATCAAGAAAAATCTGATTGGAGCCCTGCTGTTCGACTCAGGGG
AGACAGCTGAAGCAACTAGGCTGAAAAGAACAGCTAGGAGACGGTATACTCGCCGAAAGAATCG
GATCTGCTACCTCCAGGAGATTTTCTCCAACGAAATGGCCAAGGTGGACGATAGTTTCTTTCAT
CGCCTGGAGGAATCATTCCTGGTCGAGGAAGATAAGAAACACGAGAGGCATCCCATCTTTGGCA
ACATTGTGGACGAGGTCGCTTATCACGAAAAGTACCCTACAATCTATCATCTGCGGAAGAAACT
GGTGGACAGCACTGATAAGGCAGACCTGCGCCTGATCTATCTGGCCCTGGCTCACATGATTAAG
TTCAGGGGGCATTTTCTGATCGAGGGCGATCTGAACCCAGACAATTCCGATGTGGACAAGCTGT
TCATCCAGCTGGTCCAGACATACAATCAGCTGTTTGAGGAAAACCCCATTAATGCATCTGGGGT
GGACGCAAAAGCCATCCTGAGTGCCAGACTGTCTAAGAGTAGGAGACTGGAGAACCTGATCGCT
CAGCTGCCAGGCGAAAAGAAAAACGGCCTGTTTGGAAATCTGATTGCACTGTCACTGGGACTGA
CCCCCAACTTCAAGAGCAATTTTGATCTGGCCGAGGACGCTAAGCTCCAGCTGAGCAAGGACAC
CTACGACGATGACCTGGATAACCTGCTGGCTCAGATCGGCGATCAGTACGCAGACCTGTTCCTG
GCCGCTAAGAATCTGTCTGACGCCATCCTGCTGAGTGATATTCTGAGAGTGAACACCGAGATTA
CAAAAGCCCCCCTGTCAGCTAGCATGATCAAGAGATATGACGAGCACCATCAGGATCTGACCCT
GCTGAAGGCTCTGGTGCGGCAGCAGCTGCCTGAGAAGTACAAAGAAATCTTCTTTGATCAGAGC
AAGAATGGGTACGCCGGCTATATTGACGGCGGAGCTTCCCAGGAGGAGTTCTACAAGTTTATCA
AACCTATTCTGGAGAAGATGGACGGCACTGAGGAACTGCTGGTGAAACTGAATCGGGAAGACCT
GCTGCGGAAGCAGCGCACCTTCGATAACGGCAGCATCCCTCACCAGATTCATCTGGGAGAGCTG
CACGCAATCCTGCGGCGCCAGGAAGACTTCTACCCATTTCTGAAGGATAACCGGGAGAAGATCG
AAAAAATTCTGACTTTCCGCATCCCCTACTATGTGGGGCCTCTGGCAAGAGGCAATTCCCGGTT
TGCCTGGATGACCCGCAAGTCTGAGGAAACAATCACTCCCTGGAACTTCGAGGAAGTGGTCGAT
AAGGGCGCTTCCGCACAGTCTTTCATTGAGAGGATGACAAATTTTGACAAGAACCTGCCAAATG
AAAAAGTGCTGCCCAAGCACAGCCTGCTGTACGAGTATTTCACCGTCTATAACGAACTGACAAA
GGTGAAATACGTCACTGAGGGCATGAGAAAGCCTGCCTTCCTGTCCGGAGAACAGAAGAAAGCT
ATCGTGGACCTGCTGTTTAAAACCAATCGGAAGGTGACAGTCAAGCAGCTGAAAGAGGACTACT
TCAAGAAAATTGAATGTTTCGATTCTGTGGAGATCAGTGGGGTCGAAGACAGGTTTAACGCCTC
TCTGGGCACCTACCACGATCTGCTGAAGATCATTAAGGATAAAGACTTCCTGGACAACGAGGAA
AATGAGGACATCCTGGAGGACATTGTGCTGACCCTGACACTGTTTGAGGATCGGGAAATGATCG
AGGAACGCCTGAAGACCTACGCCCATCTGTTCGATGACAAAGTGATGAAACAGCTGAAGCGAAG
GAGATACACTGGGTGGGGCCGACTGAGCAGGAAGCTGATCAATGGCATTCGCGACAAACAGAGT
GGAAAGACAATCCTGGACTTTCTGAAGTCAGATGGCTTCGCTAACAGGAATTTTATGCAGCTGA
TTCACGATGACTCTCTGACTTTCAAAGAGGACATCCAGAAGGCACAGGTGTCCGGACAGGGGGA
```

FIG. 23 (part 1 of 2, continued next page)

CTCTCTGCACGAGCATATCGCAAACCTGGCCGGGAGCCCTGCCATCAAGAAAGGCATCCTCCAG
ACCGTGAAGGTGGTGGACGAGCTGGTGAAAGTCATGGGAAGACATAAGCCAGAAAACATCGTGA
TTGAGATGGCCAGGGAGAATCAGACCACACAGAAAGGGCAGAAGAACTCTCGGGAGCGCATGAA
ACGCATCGAGGAAGGAATTAAGGAACTGGGGAGTCAGATCCTGAAAGAGCACCCCGTGGAAAAC
ACACAGCTCCAGAATGAGAAGCTGTATCTGTACTACCTCCAGAATGGCCGCGATATGTACGTGG
ACCAGGAGCTGGATATTAACCGACTGTCAGATTATGACGTGGATCATATCGTCCCACAGTCATT
CCTGAAAGATGACAGCATTGACAATAAGGTGCTGACCCGCAGCGACAAAAACCGAGGAAAGAGT
GATAATGTCCCCTCAGAGGAAGTGGTCAAGAAAATGAAGAACTACTGGAGGCAGCTGCTGAATG
CCAAACTGATCACCCAGCGAAAGTTTGATAACCTGACAAAAGCTGAGAGGGGGGGCCTGTCCGA
ACTGGACAAAGCAGGCTTCATCAAGCGACAGCTGGTGGAGACAAGGCAGATCACAAAGCACGTC
GCTCAGATCCTGGACAGCAGGATGAACACCAAGTACGATGAGAATGACAAACTGATCCGGGAAG
TGAAGGTCATTACACTGAAGTCAAAACTGGTGAGCGACTTTAGGAAAGATTTCCAGTTCTACAA
GGTCAGAGAGATCAACAACTACCACCATGCTCATGACGCATACCTGAACGCAGTGGTCGGACT
GCCCTGATTAAGAAATACCCTAAACTGGAGTCTGAGTTCGTGTACGGCGACTATAAGGTGTACG
ATGTCAGAAAAATGATCGCCAAGAGCGAGCAGGAAATTGGCAAAGCCACCGCTAAGTATTTCTT
TTACTCCAACATCATGAATTTCTTTAAGACTGAGATCACCCTGGCAAATGGCGAAATCCGAAAG
AGGCCACTGATTGAGACTAACGGAGAGACaGGGGAAATCGTGTGGGACAAAGGAAGAGATTTTG
CTACCGTGCGGAAGGTCCTGAGTATGCCCCAAGTGAATATTGTCAAGAAAACAGAGGTGCAGAC
TGGAGGGTTCAGTAAGGAATCAATTCTGCCTAAACGCAACAGCGATAAGCTGATCGCCCGAAAG
AAAGACTGGGACCCCAAGAAGTATGGCGGATTCGACTCCCCAACCGTGGCTTACTCTGTCCTGG
TGGTCGCAAAGGTGGAGAAGGGAAAAAGCAAGAAACTGAAATCCGTCAAGGAACTGCTGGGGAT
CACAATTATGGAGAGGAGCAGCTTCGAAAAGAATCCTATCGATTTTCTGGAGGCCAAAGGGTAT
AAGGAAGTGAAGAAAGACCTGATCATCAAGCTGCCAAAGTACTCTCTGTTTGAGCTGGAAAACG
GCAGAAAGCGGATGCTGGCAAGTGCCGGCGAGCTGCAAAAAGGAAATGAACTGGCCCTGCCCTC
AAAGTACGTGAACTTCCTGTATCTGGCTAGCCACTACGAGAAGCTGAAAGGCTCCCCTGAGGAT
AACGAACAGAAACAGCTGTTTGTGGAGCAGCACAAGCATTATCTGGACGAGATCATTGAACAGA
TTAGCGAGTTCTCCAAACGCGTGATCCTGGCTGACGCAAATCTGGATAAGGTCCTGTCTGCATA
CAACAAACACAGGGACAAGCCAATCAGAGAGCAGGCCGAAAATATCATTCATCTGTTCACTCTG
ACCAACCTGGGAGCCCCCGCAGCCTTCAAGTATTTTGACACTACCATCGATCGCAAACGATACA
CAAGCACTAAGGAGGTGCTGGATGCTACCCTGATCCACCAGAGCATTACTGGGCTGTACGAGAC
AAGGATCGACCTGTCCCAGCTGGGGGGAGACAAACGCCCAGCCGCCACCAAGAAAGCAGGACAG
GCAAAGAAGAAGAAGTGA (SEQ ID NO: 6)

FIG. 23 (continued, part 2 of 2)

**Mammalian Codon-Optimized *Streptococcus pyogenes* Mutant cas9 Gene Open Reading Frame Encoding Single Mutation (D10A) Nickase**

```
GACAAAAAGTATAGTATCGGACTGGCTATTGGCACTAACAGCGTGGGATGGGCCGTCATCACCG
ACGAGTACAAAGTGCCAAGCAAGAAGTTCAAGGTCCTGGGAAACACCGATAGACACAGTATCAA
GAAAAATCTGATTGGAGCCCTGCTGTTCGACTCAGGGGAGACAGCTGAAGCAACTAGGCTGAAA
AGAACAGCTAGGAGACGGTATACTCGCCGAAAGAATCGGATCTGCTACCTCCAGGAGATTTTCT
CCAACGAAATGGCCAAGGTGGACGATAGTTTCTTTCATCGCCTGGAGGAATCATTCCTGGTCGA
GGAAGATAAGAAACACGAGAGGCATCCCATCTTTGGCAACATTGTGGACGAGGTCGCTTATCAC
GAAAAGTACCCTACAATCTATCATCTGCGGAAGAAACTGGTGGACAGCACTGATAAGGCAGACC
TGCGCCTGATCTATCTGGCCCTGGCTCACATGATTAAGTTCAGGGGGCATTTTCTGATCGAGGG
CGATCTGAACCCAGACAATTCCGATGTGGACAAGCTGTTCATCCAGCTGGTCCAGACATACAAT
CAGCTGTTTGAGGAAAACCCCATTAATGCATCTGGGGTGGACGCAAAAGCCATCCTGAGTGCCA
GACTGTCTAAGAGTAGGAGACTGGAGAACCTGATCGCTCAGCTGCCAGGCGAAAAGAAAAACGG
CCTGTTTGGAAATCTGATTGCACTGTCACTGGGACTGACCCCCAACTTCAAGAGCAATTTTGAT
CTGGCCGAGGACGCTAAGCTCCAGCTGAGCAAGGACACCTACGACGATGACCTGGATAACCTGC
TGGCTCAGATCGGCGATCAGTACGCAGACCTGTTCCTGGCCGCTAAGAATCTGTCTGACGCCAT
CCTGCTGAGTGATATTCTGAGAGTGAACACCGAGATTACAAAAGCCCCCCTGTCAGCTAGCATG
ATCAAGAGATATGACGAGCACCATCAGGATCTGACCCTGCTGAAGGCTCTGGTGCGGCAGCAGC
TGCCTGAGAAGTACAAAGAAATCTTCTTTGATCAGAGCAAGAATGGGTACGCCGGCTATATTGA
CGGCGGAGCTTCCCAGGAGGAGTTCTACAAGTTTATCAAACCTATTCTGGAGAAGATGGACGGC
ACTGAGGAACTGCTGGTGAAACTGAATCGGGAAGACCTGCTGCGGAAGCAGCGCACCTTCGATA
ACGGCAGCATCCCTCACCAGATTCATCTGGGAGAGCTGCACGCAATCCTGCGGCGCCAGGAAGA
CTTCTACCCATTTCTGAAGGATAACCGGGAGAAGATCGAAAAAATTCTGACTTTCCGCATCCCC
TACTATGTGGGGCCTCTGGCAAGAGGCAATTCCCGGTTTGCCTGGATGACCCGCAAGTCTGAGG
AAACAATCACTCCCTGGAACTTCGAGGAAGTGGTCGATAAGGGCGCTTCCGCACAGTCTTTCAT
TGAGAGGATGACAAATTTTGACAAGAACCTGCCAAATGAAAAAGTGCTGCCCAAGCACAGCCTG
CTGTACGAGTATTTCACCGTCTATAACGAACTGACAAAGGTGAAATACGTCACTGAGGGCATGA
GAAAGCCTGCCTTCCTGTCCGGAGAACAGAAGAAAGCTATCGTGGACCTGCTGTTTAAAACCAA
TCGGAAGGTGACAGTCAAGCAGCTGAAAGAGGACTACTTCAAGAAAATTGAATGTTTCGATTCT
GTGGAGATCAGTGGGGTCGAAGACAGGTTTAACGCCTCTCTGGGCACCTACCACGATCTGCTGA
AGATCATTAAGGATAAAGACTTCCTGGACAACGAGGAAAATGAGGACATCCTGGAGGACATTGT
GCTGACCCTGACACTGTTTGAGGATCGGGAAATGATCGAGGAACGCCTGAAGACCTACGCCCAT
CTGTTCGATGACAAAGTGATGAAACAGCTGAAGCGAAGGAGATACACTGGGTGGGGCCGACTGA
GCAGGAAGCTGATCAATGGCATTCGCGACAAACAGAGTGGAAAGACAATCCTGGACTTTCTGAA
GTCAGATGGCTTCGCTAACAGGAATTTTATGCAGCTGATTCACGATGACTCTCTGACTTTCAAA
GAGGACATCCAGAAGGCACAGGTGTCCGGACAGGGGGACTCTCTGCACGAGCATATCGCAAACC
TGGCCGGGAGCCCTGCCATCAAGAAAGGCATCCTCCAGACCGTGAAGGTGGTGGACGAGCTGGT
```

FIG. 24 (part 1 of 2, continued next page)

GAAAGTCATGGGAAGACATAAGCCAGAAAACATCGTGATTGAGATGGCCAGGGAGAATCAGACC
ACACAGAAAGGGCAGAAGAACTCTCGGGAGCGCATGAAACGCATCGAGGAAGGAATTAAGGAAC
TGGGGAGTCAGATCCTGAAAGAGCACCCCGTGGAAAACACACAGCTCCAGAATGAGAAGCTGTA
TCTGTACTACCTCCAGAATGGCCGCGATATGTACGTGGACCAGGAGCTGGATATTAACCGACTG
TCAGATTATGACGTGGATCATATCGTCCCACAGTCATTCCTGAAAGATGACAGCATTGACAATA
AGGTGCTGACCCGCAGCGACAAAAACCGAGGAAAGAGTGATAATGTCCCCTCAGAGGAAGTGGT
CAAGAAAATGAAGAACTACTGGAGGCAGCTGCTGAATGCCAAACTGATCACCCAGCGAAAGTTT
GATAACCTGACAAAAGCTGAGAGGGGGGGCCTGTCCGAACTGGACAAAGCAGGCTTCATCAAGC
GACAGCTGGTGGAGACAAGGCAGATCACAAAGCACGTCGCTCAGATCCTGGACAGCAGGATGAA
CACCAAGTACGATGAGAATGACAAACTGATCCGGGAAGTGAAGGTCATTACACTGAAGTCAAAA
CTGGTGAGCGACTTTAGGAAAGATTTCCAGTTCTACAAGGTCAGAGAGATCAACAACTACCACC
ATGCTCATGACGCATACCTGAACGCAGTGGTCGGGACTGCCCTGATTAAGAAATACCCTAAACT
GGAGTCTGAGTTCGTGTACGGCGACTATAAGGTGTACGATGTCAGAAAAATGATCGCCAAGAGC
GAGCAGGAAATTGGCAAAGCCACCGCTAAGTATTTCTTTTACTCCAACATCATGAATTTCTTTA
AGACTGAGATCACCCTGGCAAATGGCGAAATCCGAAAGAGGCCACTGATTGAGACTAACGGAGA
GACaGGGGAAATCGTGTGGGACAAAGGAAGAGATTTTGCTACCGTGCGGAAGGTCCTGAGTATG
CCCCAAGTGAATATTGTCAAGAAAACAGAGGTGCAGACTGGAGGGTTCAGTAAGGAATCAATTC
TGCCTAAACGCAACAGCGATAAGCTGATCGCCCGAAAGAAAGACTGGGACCCCAAGAAGTATGG
CGGATTCGACTCCCCAACCGTGGCTTACTCTGTCCTGGTGGTCGCAAAGGTGGAGAAGGGAAAA
AGCAAGAAACTGAAATCCGTCAAGGAACTGCTGGGGATCACAATTATGGAGAGGAGCAGCTTCG
AAAAGAATCCTATCGATTTTCTGGAGGCCAAAGGGTATAAGGAAGTGAAGAAAGACCTGATCAT
CAAGCTGCCAAAGTACTCTCTGTTTGAGCTGGAAAACGGCAGAAAGCGGATGCTGGCAAGTGCC
GGCGAGCTGCAAAAAGGAAATGAACTGGCCCTGCCCTCAAAGTACGTGAACTTCCTGTATCTGG
CTAGCCACTACGAGAAGCTGAAAGGCTCCCCTGAGGATAACGAACAGAAACAGCTGTTTGTGGA
GCAGCACAAGCATTATCTGGACGAGATCATTGAACAGATTAGCGAGTTCTCCAAACGCGTGATC
CTGGCTGACGCAAATCTGGATAAGGTCCTGTCTGCATACAACAAACACAGGGACAAGCCAATCA
GAGAGCAGGCCGAAAATATCATTCATCTGTTCACTCTGACCAACCTGGGAGCCCCCGCAGCCTT
CAAGTATTTTGACACTACCATCGATCGCAAACGATACACAAGCACTAAGGAGGTGCTGGATGCT
ACCCTGATCCACCAGAGCATTACTGGGCTGTACGAGACaAGGATCGACCTGTCCCAGCTGGGGG
GAGAC (SEQ ID NO: 7)

FIG. 24 (continued, part 2 of 2)

**Mammalian Codon-Optimized *Streptococcus pyogenes* Mutant cas9 Gene Open Reading Frame Encoding Single Mutation (D10A) Nickase with Fused N-terminal myc-tag and N- and C-Terminal Nuclear Localization Signals** atggctagtatgcagaaactgattagtgaagaggacctgATGGCTCCCAAGAAGAAGCGAAAGG
TGGGCATCCACGGCGTGCCCGCTGCCGACAAAAAGTATAGTATCGGACTGGCTATTGGCACTAA
CAGCGTGGGATGGGCCGTCATCACCGACGAGTACAAAGTGCCAAGCAAGAAGTTCAAGGTCCTG
GGAAACACCGATAGACACAGTATCAAGAAAAATCTGATTGGAGCCCTGCTGTTCGACTCAGGGG
AGACAGCTGAAGCAACTAGGCTGAAAAGAACAGCTAGGAGACGGTATACTCGCCGAAAGAATCG
GATCTGCTACCTCCAGGAGATTTTCTCCAACGAAATGGCCAAGGTGGACGATAGTTTCTTTCAT
CGCCTGGAGGAATCATTCCTGGTCGAGGAAGATAAGAAACACGAGAGGCATCCCATCTTTGGCA
ACATTGTGGACGAGGTCGCTTATCACGAAAAGTACCCTACAATCTATCATCTGCGGAAGAAACT
GGTGGACAGCACTGATAAGGCAGACCTGCGCCTGATCTATCTGGCCCTGGCTCACATGATTAAG
TTCAGGGGGCATTTTCTGATCGAGGGCGATCTGAACCCAGACAATTCCGATGTGGACAAGCTGT
TCATCCAGCTGGTCCAGACATACAATCAGCTGTTTGAGGAAAACCCCATTAATGCATCTGGGGT
GGACGCAAAAGCCATCCTGAGTGCCAGACTGTCTAAGAGTAGGAGACTGGAGAACCTGATCGCT
CAGCTGCCAGGCGAAAAGAAAAACGGCCTGTTTGGAAATCTGATTGCACTGTCACTGGGACTGA
CCCCCAACTTCAAGAGCAATTTTGATCTGGCCGAGGACGCTAAGCTCCAGCTGAGCAAGGACAC
CTACGACGATGACCTGGATAACCTGCTGGCTCAGATCGGCGATCAGTACGCAGACCTGTTCCTG
GCCGCTAAGAATCTGTCTGACGCCATCCTGCTGAGTGATATTCTGAGAGTGAACACCGAGATTA
CAAAAGCCCCCCTGTCAGCTAGCATGATCAAGAGATATGACGAGCACCATCAGGATCTGACCCT
GCTGAAGGCTCTGGTGCGGCAGCAGCTGCCTGAGAAGTACAAAGAAATCTTCTTTGATCAGAGC
AAGAATGGGTACGCCGGCTATATTGACGGCGGAGCTTCCCAGGAGGAGTTCTACAAGTTTATCA
AACCTATTCTGGAGAAGATGGACGGCACTGAGGAACTGCTGGTGAAACTGAATCGGGAAGACCT
GCTGCGGAAGCAGCGCACCTTCGATAACGGCAGCATCCCTCACCAGATTCATCTGGGAGAGCTG
CACGCAATCCTGCGGCGCCAGGAAGACTTCTACCCATTTCTGAAGGATAACCGGGAGAAGATCG
AAAAAATTCTGACTTTCCGCATCCCCTACTATGTGGGGCCTCTGGCAAGAGGCAATTCCCGGTT
TGCCTGGATGACCCGCAAGTCTGAGGAAACAATCACTCCCTGGAACTTCGAGGAAGTGGTCGAT
AAGGGCGCTTCCGCACAGTCTTTCATTGAGAGGATGACAAATTTTGACAAGAACCTGCCAAATG
AAAAAGTGCTGCCCAAGCACAGCCTGCTGTACGAGTATTTCACCGTCTATAACGAACTGACAAA
GGTGAAATACGTCACTGAGGGCATGAGAAAGCCTGCCTTCCTGTCCGGAGAACAGAAGAAAGCT
ATCGTGGACCTGCTGTTTAAAACCAATCGGAAGGTGACAGTCAAGCAGCTGAAAGAGGACTACT
TCAAGAAAATTGAATGTTTCGATTCTGTGGAGATCAGTGGGGTCGAAGACAGGTTTAACGCCTC
TCTGGGCACCTACCACGATCTGCTGAAGATCATTAAGGATAAAGACTTCCTGGACAACGAGGAA
AATGAGGACATCCTGGAGGACATTGTGCTGACCCTGACACTGTTTGAGGATCGGGAAATGATCG
AGGAACGCCTGAAGACCTACGCCCATCTGTTCGATGACAAAGTGATGAAACAGCTGAAGCGAAG
GAGATACACTGGGTGGGGCCGACTGAGCAGGAAGCTGATCAATGGCATTCGCGACAAACAGAGT
GGAAAGACAATCCTGGACTTTCTGAAGTCAGATGGCTTCGCTAACAGGAATTTTATGCAGCTGA FIG. 25 (part 1 of 2, continued next page)

TTCACGATGACTCTCTGACTTTCAAAGAGGACATCCAGAAGGCACAGGTGTCCGGACAGGGGA
CTCTCTGCACGAGCATATCGCAAACCTGGCCGGGAGCCCTGCCATCAAGAAAGGCATCCTCCAG
ACCGTGAAGGTGGTGGACGAGCTGGTGAAAGTCATGGGAAGACATAAGCCAGAAAACATCGTGA
TTGAGATGGCCAGGGAGAATCAGACCACACAGAAAGGGCAGAAGAACTCTCGGGAGCGCATGAA
ACGCATCGAGGAAGGAATTAAGGAACTGGGGAGTCAGATCCTGAAAGAGCACCCCGTGGAAAAC
ACACAGCTCCAGAATGAGAAGCTGTATCTGTACTACCTCCAGAATGGCCGCGATATGTACGTGG
ACCAGGAGCTGGATATTAACCGACTGTCAGATTATGACGTGGATCATATCGTCCCACAGTCATT
CCTGAAAGATGACAGCATTGACAATAAGGTGCTGACCCGCAGCGACAAAAACCGAGGAAAGAGT
GATAATGTCCCCTCAGAGGAAGTGGTCAAGAAAATGAAGAACTACTGGAGGCAGCTGCTGAATG
CCAAACTGATCACCCAGCGAAAGTTTGATAACCTGACAAAAGCTGAGAGGGGGGCCTGTCCGA
ACTGGACAAAGCAGGCTTCATCAAGCGACAGCTGGTGGAGACAAGGCAGATCACAAAGCACGTC
GCTCAGATCCTGGACAGCAGGATGAACACCAAGTACGATGAGAATGACAAACTGATCCGGGAAG
TGAAGGTCATTACACTGAAGTCAAAACTGGTGAGCGACTTTAGGAAAGATTTCCAGTTCTACAA
GGTCAGAGAGATCAACAACTACCACCATGCTCATGACGCATACCTGAACGCAGTGGTCGGGACT
GCCCTGATTAAGAAATACCCTAAACTGGAGTCTGAGTTCGTGTACGGCGACTATAAGGTGTACG
ATGTCAGAAAAATGATCGCCAAGAGCGAGCAGGAAATTGGCAAAGCCACCGCTAAGTATTTCTT
TTACTCCAACATCATGAATTTCTTTAAGACTGAGATCACCCTGGCAAATGGCGAAATCCGAAAG
AGGCCACTGATTGAGACTAACGGAGAGACaGGGGAAATCGTGTGGGACAAAGGAAGAGATTTTG
CTACCGTGCGGAAGGTCCTGAGTATGCCCCAAGTGAATATTGTCAAGAAAACAGAGGTGCAGAC
TGGAGGGTTCAGTAAGGAATCAATTCTGCCTAAACGCAACAGCGATAAGCTGATCGCCCGAAAG
AAAGACTGGGACCCCAAGAAGTATGGCGGATTCGACTCCCCAACCGTGGCTTACTCTGTCCTGG
TGGTCGCAAAGGTGGAGAAGGGAAAAAGCAAGAAACTGAAATCCGTCAAGGAACTGCTGGGGAT
CACAATTATGGAGAGGAGCAGCTTCGAAAAGAATCCTATCGATTTTCTGGAGGCCAAAGGGTAT
AAGGAAGTGAAGAAAGACCTGATCATCAAGCTGCCAAAGTACTCTCTGTTTGAGCTGGAAAACG
GCAGAAAGCGGATGCTGGCAAGTGCCGGCGAGCTGCAAAAAGGAAATGAACTGGCCCTGCCCTC
AAAGTACGTGAACTTCCTGTATCTGGCTAGCCACTACGAGAAGCTGAAAGGCTCCCCTGAGGAT
AACGAACAGAAACAGCTGTTTGTGGAGCAGCACAAGCATTATCTGGACGAGATCATTGAACAGA
TTAGCGAGTTCTCCAAACGCGTGATCCTGGCTGACGCAAATCTGGATAAGGTCCTGTCTGCATA
CAACAAACACAGGGACAAGCCAATCAGAGAGCAGGCCGAAAATATCATTCATCTGTTCACTCTG
ACCAACCTGGGAGCCCCCGCAGCCTTCAAGTATTTTGACACTACCATCGATCGCAAACGATACA
CAAGCACTAAGGAGGTGCTGGATGCTACCCTGATCCACCAGAGCATTACTGGGCTGTACGAGAC
aAGGATCGACCTGTCCCAGCTGGGGGGAGACAAACGCCCAGCCGCCACCAAGAAAGCAGGACAG
GCAAAGAAGAAGAAGTGA (SEQ ID NO: 8)

FIG. 25 (continued, part 2 of 2)

Mammalian Codon-Optimized *Streptococcus pyogenes* Mutant cas9 Gene Open Reading Frame Encoding Double Mutation (D10A and H840A) Null Nuclease ATGGACAAAAAGTATAGTATCGGACTGGCTATTGGCACTAACAGCGTGGGATGGGCCGTCATCA
CCGACGAGTACAAAGTGCCAAGCAAGAAGTTCAAGGTCCTGGGAAACACCGATAGACACAGTAT
CAAGAAAAATCTGATTGGAGCCCTGCTGTTCGACTCAGGGGAGACAGCTGAAGCAACTAGGCTG
AAAAGAACAGCTAGGAGACGGTATACTCGCCGAAAGAATCGGATCTGCTACCTCCAGGAGATTT
TCTCCAACGAAATGGCCAAGGTGGACGATAGTTTCTTTCATCGCCTGGAGGAATCATTCCTGGT
CGAGGAAGATAAGAAACACGAGAGGCATCCCATCTTTGGCAACATTGTGGACGAGGTCGCTTAT
CACGAAAAGTACCCTACAATCTATCATCTGCGGAAGAAACTGGTGGACAGCACTGATAAGGCAG
ACCTGCGCCTGATCTATCTGGCCCTGGCTCACATGATTAAGTTCAGGGGGCATTTTCTGATCGA
GGGCGATCTGAACCCAGACAATTCCGATGTGGACAAGCTGTTCATCCAGCTGGTCCAGACATAC
AATCAGCTGTTTGAGGAAAACCCCATTAATGCATCTGGGGTGGACGCAAAAGCCATCCTGAGTG
CCAGACTGTCTAAGAGTAGGAGACTGGAGAACCTGATCGCTCAGCTGCCAGGCGAAAAGAAAAA
CGGCCTGTTTGGAAATCTGATTGCACTGTCACTGGGACTGACCCCCAACTTCAAGAGCAATTTT
GATCTGGCCGAGGACGCTAAGCTCCAGCTGAGCAAGGACACCTACGACGATGACCTGGATAACC
TGCTGGCTCAGATCGGCGATCAGTACGCAGACCTGTTCCTGGCCGCTAAGAATCTGTCTGACGC
CATCCTGCTGAGTGATATTCTGAGAGTGAACACCGAGATTACAAAAGCCCCCCTGTCAGCTAGC
ATGATCAAGAGATATGACGAGCACCATCAGGATCTGACCCTGCTGAAGGCTCTGGTGCGGCAGC
AGCTGCCTGAGAAGTACAAAGAAATCTTCTTTGATCAGAGCAAGAATGGGTACGCCGGCTATAT
TGACGGCGGAGCTTCCCAGGAGGAGTTCTACAAGTTTATCAAACCTATTCTGGAGAAGATGGAC
GGCACTGAGGAACTGCTGGTGAAACTGAATCGGGAAGACCTGCTGCGGAAGCAGCGCACCTTCG
ATAACGGCAGCATCCCTCACCAGATTCATCTGGGAGAGCTGCACGCAATCCTGCGGCGCCAGGA
AGACTTCTACCCATTTCTGAAGGATAACCGGGAGAAGATCGAAAAAATTCTGACTTTCCGCATC
CCCTACTATGTGGGGCCTCTGGCAAGAGGCAATTCCCGGTTTGCCTGGATGACCCGCAAGTCTG
AGGAAACAATCACTCCCTGGAACTTCGAGGAAGTGGTCGATAAGGGCGCTTCCGCACAGTCTTT
CATTGAGAGGATGACAAATTTTGACAAGAACCTGCCAAATGAAAAAGTGCTGCCCAAGCACAGC
CTGCTGTACGAGTATTTCACCGTCTATAACGAACTGACAAAGGTGAAATACGTCACTGAGGGCA
TGAGAAAGCCTGCCTTCCTGTCCGGAGAACAGAAGAAAGCTATCGTGGACCTGCTGTTTAAAAC
CAATCGGAAGGTGACAGTCAAGCAGCTGAAAGAGGACTACTTCAAGAAAATTGAATGTTTCGAT
TCTGTGGAGATCAGTGGGGTCGAAGACAGGTTTAACGCCTCTCTGGGCACCTACCACGATCTGC
TGAAGATCATTAAGGATAAAGACTTCCTGGACAACGAGGAAAATGAGGACATCCTGGAGGACAT
TGTGCTGACCCTGACACTGTTTGAGGATCGGGAAATGATCGAGGAACGCCTGAAGACCTACGCC
CATCTGTTCGATGACAAAGTGATGAAACAGCTGAAGCGAAGGAGATACACTGGGTGGGGCCGAC
TGAGCAGGAAGCTGATCAATGGCATTCGCGACAAACAGAGTGGAAAGACAATCCTGGACTTTCT
GAAGTCAGATGGCTTCGCTAACAGGAATTTTATGCAGCTGATTCACGATGACTCTCTGACTTTC
AAAGAGGACATCCAGAAGGCACAGGTGTCCGGACAGGGGGACTCTCTGCACGAGCATATCGCAA
ACCTGGCCGGGAGCCCTGCCATCAAGAAAGGCATCCTCCAGACCGTGAAGGTGGTGGACGAGCT FIG. 26 (part 1 of 2, continued next page)

GGTGAAAGTCATGGGAAGACATAAGCCAGAAAACATCGTGATTGAGATGGCCAGGGAGAATCAG
ACCACACAGAAAGGGCAGAAGAACTCTCGGGAGCGCATGAAACGCATCGAGGAAGGAATTAAGG
AACTGGGGAGTCAGATCCTGAAAGAGCACCCCGTGGAAAACACACAGCTCCAGAATGAGAAGCT
GTATCTGTACTACCTCCAGAATGGCCGCGATATGTACGTGGACCAGGAGCTGGATATTAACCGA
CTGTCAGATTATGACGTGGATGCCATCGTCCCACAGTCATTCCTGAAAGATGACAGCATTGACA
ATAAGGTGCTGACCCGCAGCGACAAAAACCGAGGAAAGAGTGATAATGTCCCCTCAGAGGAAGT
GGTCAAGAAAATGAAGAACTACTGGAGGCAGCTGCTGAATGCCAAACTGATCACCCAGCGAAAG
TTTGATAACCTGACAAAAGCTGAGAGGGGGGCCTGTCCGAACTGGACAAAGCAGGCTTCATCA
AGCGACAGCTGGTGGAGACAAGGCAGATCACAAAGCACGTCGCTCAGATCCTGGACAGCAGGAT
GAACACCAAGTACGATGAGAATGACAAACTGATCCGGGAAGTGAAGGTCATTACACTGAAGTCA
AAACTGGTGAGCGACTTTAGGAAAGATTTCCAGTTCTACAAGGTCAGAGAGATCAACAACTACC
ACCATGCTCATGACGCATACCTGAACGCAGTGGTCGGGACTGCCCTGATTAAGAAATACCCTAA
ACTGGAGTCTGAGTTCGTGTACGGCGACTATAAGGTGTACGATGTCAGAAAAATGATCGCCAAG
AGCGAGCAGGAAATTGGCAAAGCCACCGCTAAGTATTTCTTTTACTCCAACATCATGAATTTCT
TTAAGACTGAGATCACCCTGGCAAATGGCGAAATCCGAAAGAGGCCACTGATTGAGACTAACGG
AGAGACaGGGGAAATCGTGTGGGACAAAGGAAGAGATTTTGCTACCGTGCGGAAGGTCCTGAGT
ATGCCCCAAGTGAATATTGTCAAGAAAACAGAGGTGCAGACTGGAGGGTTCAGTAAGGAATCAA
TTCTGCCTAAACGCAACAGCGATAAGCTGATCGCCCGAAAGAAAGACTGGGACCCCAAGAAGTA
TGGCGGATTCGACTCCCCAACCGTGGCTTACTCTGTCCTGGTGGTCGCAAAGGTGGAGAAGGGA
AAAAGCAAGAAACTGAAATCCGTCAAGGAACTGCTGGGGATCACAATTATGGAGAGGAGCAGCT
TCGAAAAGAATCCTATCGATTTTCTGGAGGCCAAAGGGTATAAGGAAGTGAAGAAAGACCTGAT
CATCAAGCTGCCAAAGTACTCTCTGTTTGAGCTGGAAAACGGCAGAAAGCGGATGCTGGCAAGT
GCCGGCGAGCTGCAAAAAGGAAATGAACTGGCCCTGCCCTCAAAGTACGTGAACTTCCTGTATC
TGGCTAGCCACTACGAGAAGCTGAAAGGCTCCCCTGAGGATAACGAACAGAAACAGCTGTTTGT
GGAGCAGCACAAGCATTATCTGGACGAGATCATTGAACAGATTAGCGAGTTCTCCAAACGCGTG
ATCCTGGCTGACGCAAATCTGGATAAGGTCCTGTCTGCATACAACAAACACAGGGACAAGCCAA
TCAGAGAGCAGGCCGAAAATATCATTCATCTGTTCACTCTGACCAACCTGGGAGCCCCCGCAGC
CTTCAAGTATTTTGACACTACCATCGATCGCAAACGATACACAAGCACTAAGGAGGTGCTGGAT
GCTACCCTGATCCACCAGAGCATTACTGGGCTGTACGAGACaAGGATCGACCTGTCCCAGCTGG
GGGGAGAC (SEQ ID NO: 9)

FIG. 26 (continued, part 2 of 2)

**Mammalian Codon-Optimized *Streptococcus pyogenes* Mutant cas9 Gene Open Reading Frame Encoding Double Mutation (D10A and H840A) Null Nuclease Fused with N-terminal myc-tag and N- and C-Terminal Nuclear Localization Signals** atggctagtatgcagaaactgattagtgaagaggacctgATGGCTCCCAAGAAGAAGCGAAAGG
TGGGCATCCACGGCGTGCCCGCTGCCGACAAAAAGTATAGTATCGGACTGGCTATTGGCACTAA
CAGCGTGGGATGGGCCGTCATCACCGACGAGTACAAAGTGCCAAGCAAGAAGTTCAAGGTCCTG
GGAAACACCGATAGACACAGTATCAAGAAAAATCTGATTGGAGCCCTGCTGTTCGACTCAGGGG
AGACAGCTGAAGCAACTAGGCTGAAAAGAACAGCTAGGAGACGGTATACTCGCCGAAAGAATCG
GATCTGCTACCTCCAGGAGATTTTCTCCAACGAAATGGCCAAGGTGGACGATAGTTTCTTTCAT
CGCCTGGAGGAATCATTCCTGGTCGAGGAAGATAAGAAACACGAGAGGCATCCCATCTTTGGCA
ACATTGTGGACGAGGTCGCTTATCACGAAAAGTACCCTACAATCTATCATCTGCGGAAGAAACT
GGTGGACAGCACTGATAAGGCAGACCTGCGCCTGATCTATCTGGCCCTGGCTCACATGATTAAG
TTCAGGGGGCATTTTCTGATCGAGGGCGATCTGAACCCAGACAATTCCGATGTGGACAAGCTGT
TCATCCAGCTGGTCCAGACATACAATCAGCTGTTTGAGGAAAACCCCATTAATGCATCTGGGGT
GGACGCAAAAGCCATCCTGAGTGCCAGACTGTCTAAGAGTAGGAGACTGGAGAACCTGATCGCT
CAGCTGCCAGGCGAAAAGAAAAACGGCCTGTTTGGAAATCTGATTGCACTGTCACTGGGACTGA
CCCCCAACTTCAAGAGCAATTTTGATCTGGCCGAGGACGCTAAGCTCCAGCTGAGCAAGGACAC
CTACGACGATGACCTGGATAACCTGCTGGCTCAGATCGGCGATCAGTACGCAGACCTGTTCCTG
GCCGCTAAGAATCTGTCTGACGCCATCCTGCTGAGTGATATTCTGAGAGTGAACACCGAGATTA
CAAAAGCCCCCCTGTCAGCTAGCATGATCAAGAGATATGACGAGCACCATCAGGATCTGACCCT
GCTGAAGGCTCTGGTGCGGCAGCAGCTGCCTGAGAAGTACAAAGAAATCTTCTTTGATCAGAGC
AAGAATGGGTACGCCGGCTATATTGACGGCGGAGCTTCCCAGGAGGAGTTCTACAAGTTTATCA
AACCTATTCTGGAGAAGATGGACGGCACTGAGGAACTGCTGGTGAAACTGAATCGGGAAGACCT
GCTGCGGAAGCAGCGCACCTTCGATAACGGCAGCATCCCTCACCAGATTCATCTGGGAGAGCTG
CACGCAATCCTGCGGCGCCAGGAAGACTTCTACCCATTTCTGAAGGATAACCGGGAGAAGATCG
AAAAAATTCTGACTTTCCGCATCCCCTACTATGTGGGGCCTCTGGCAAGAGGCAATTCCCGGTT
TGCCTGGATGACCCGCAAGTCTGAGGAAACAATCACTCCCTGGAACTTCGAGGAAGTGGTCGAT
AAGGGCGCTTCCGCACAGTCTTTCATTGAGAGGATGACAAATTTTGACAAGAACCTGCCAAATG
AAAAAGTGCTGCCCAAGCACAGCCTGCTGTACGAGTATTTCACCGTCTATAACGAACTGACAAA
GGTGAAATACGTCACTGAGGGCATGAGAAAGCCTGCCTTCCTGTCCGGAGAACAGAAGAAAGCT
ATCGTGGACCTGCTGTTTAAAACCAATCGGAAGGTGACAGTCAAGCAGCTGAAAGAGGACTACT
TCAAGAAAATTGAATGTTTCGATTCTGTGGAGATCAGTGGGGTCGAAGACAGGTTTAACGCCTC
TCTGGGCACCTACCACGATCTGCTGAAGATCATTAAGGATAAAGACTTCCTGGACAACGAGGAA
AATGAGGACATCCTGGAGGACATTGTGCTGACCCTGACACTGTTTGAGGATCGGGAAATGATCG
AGGAACGCCTGAAGACCTACGCCCATCTGTTCGATGACAAAGTGATGAAACAGCTGAAGCGAAG
GAGATACACTGGGTGGGGCCGACTGAGCAGGAAGCTGATCAATGGCATTCGCGACAAACAGAGT
GGAAAGACAATCCTGGACTTTCTGAAGTCAGATGGCTTCGCTAACAGGAATTTTATGCAGCTGA FIG. 27 (part 1 of 2, continued next page)

TTCACGATGACTCTCTGACTTTCAAAGAGGACATCCAGAAGGCACAGGTGTCCGGACAGGGGA
CTCTCTGCACGAGCATATCGCAAACCTGGCCGGGAGCCCTGCCATCAAGAAAGGCATCCTCCAG
ACCGTGAAGGTGGTGGACGAGCTGGTGAAAGTCATGGGAAGACATAAGCCAGAAAACATCGTGA
TTGAGATGGCCAGGGAGAATCAGACCACACAGAAAGGGCAGAAGAACTCTCGGGAGCGCATGAA
ACGCATCGAGGAAGGAATTAAGGAACTGGGGAGTCAGATCCTGAAAGAGCACCCCGTGGAAAAC
ACACAGCTCCAGAATGAGAAGCTGTATCTGTACTACCTCCAGAATGGCCGCGATATGTACGTGG
ACCAGGAGCTGGATATTAACCGACTGTCAGATTATGACGTGGATGCCATCGTCCCACAGTCATT
CCTGAAAGATGACAGCATTGACAATAAGGTGCTGACCCGCAGCGACAAAAACCGAGGAAAGAGT
GATAATGTCCCCTCAGAGGAAGTGGTCAAGAAAATGAAGAACTACTGGAGGCAGCTGCTGAATG
CCAAACTGATCACCCAGCGAAAGTTTGATAACCTGACAAAAGCTGAGAGGGGGGGCCTGTCCGA
ACTGGACAAAGCAGGCTTCATCAAGCGACAGCTGGTGGAGACAAGGCAGATCACAAAGCACGTC
GCTCAGATCCTGGACAGCAGGATGAACACCAAGTACGATGAGAATGACAAACTGATCCGGGAAG
TGAAGGTCATTACACTGAAGTCAAAACTGGTGAGCGACTTTAGGAAAGATTTCCAGTTCTACAA
GGTCAGAGAGATCAACAACTACCACCATGCTCATGACGCATACCTGAACGCAGTGGTCGGGACT
GCCCTGATTAAGAAATACCCTAAACTGGAGTCTGAGTTCGTGTACGGCGACTATAAGGTGTACG
ATGTCAGAAAAATGATCGCCAAGAGCGAGCAGGAAATTGGCAAAGCCACCGCTAAGTATTTCTT
TTACTCCAACATCATGAATTTCTTTAAGACTGAGATCACCCTGGCAAATGGCGAAATCCGAAAG
AGGCCACTGATTGAGACTAACGGAGAGACaGGGGAAATCGTGTGGGACAAAGGAAGAGATTTTG
CTACCGTGCGGAAGGTCCTGAGTATGCCCCAAGTGAATATTGTCAAGAAAACAGAGGTGCAGAC
TGGAGGGTTCAGTAAGGAATCAATTCTGCCTAAACGCAACAGCGATAAGCTGATCGCCCGAAAG
AAAGACTGGGACCCCAAGAAGTATGGCGGATTCGACTCCCCAACCGTGGCTTACTCTGTCCTGG
TGGTCGCAAAGGTGGAGAAGGGAAAAAGCAAGAAACTGAAATCCGTCAAGGAACTGCTGGGGAT
CACAATTATGGAGAGGAGCAGCTTCGAAAAGAATCCTATCGATTTTCTGGAGGCCAAAGGGTAT
AAGGAAGTGAAGAAAGACCTGATCATCAAGCTGCCAAAGTACTCTCTGTTTGAGCTGGAAAACG
GCAGAAAGCGGATGCTGGCAAGTGCCGGCGAGCTGCAAAAAGGAAATGAACTGGCCCTGCCCTC
AAAGTACGTGAACTTCCTGTATCTGGCTAGCCACTACGAGAAGCTGAAAGGCTCCCCTGAGGAT
AACGAACAGAAACAGCTGTTTGTGGAGCAGCACAAGCATTATCTGGACGAGATCATTGAACAGA
TTAGCGAGTTCTCCAAACGCGTGATCCTGGCTGACGCAAATCTGGATAAGGTCCTGTCTGCATA
CAACAAACACAGGGACAAGCCAATCAGAGAGCAGGCCGAAAATATCATTCATCTGTTCACTCTG
ACCAACCTGGGAGCCCCCGCAGCCTTCAAGTATTTTGACACTACCATCGATCGCAAACGATACA
CAAGCACTAAGGAGGTGCTGGATGCTACCCTGATCCACCAGAGCATTACTGGGCTGTACGAGAC
aAGGATCGACCTGTCCCAGCTGGGGGGAGACAAACGCCCAGCCGCCACCAAGAAAGCAGGACAG
GCAAAGAAGAAGAAGTGA (SEQ ID NO: 10)

FIG. 27 (continued, part 2 of 2)

***Streptococcus pyogenes* Wild Type cas9 Protein Fused with N- and C-Terminal Nuclear Localization Signals**

MAPKKKRKVGIHGVPAADKKYSIGLDIGTNSVGWAVITDEYKVPSKKFKVLGNTDRHSIKKNLI
GALLFDSGETAEATRLKRTARRRYTRRKNRICYLQEIFSNEMAKVDDSFFHRLEESFLVEEDKK
HERHPIFGNIVDEVAYHEKYPTIYHLRKKLVDSTDKADLRLIYLALAHMIKFRGHFLIEGDLNP
DNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSD
ILRVNTEITKAPLSASMIKRYDEHHQDLTLLKALVRQQLPEKYKEIFFDQSKNGYAGYIDGGAS
QEEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIERMT
NFDKNLPNEKVLPKHSLLYEYFTVYNELTKVKYVTEGMRKPAFLSGEQKKAIVDLLFKTNRKVT
VKQLKEDYFKKIECFDSVEISGVEDRFNASLGTYHDLLKIIKDKDFLDNEENEDILEDIVLTLT
LFEDREMIEERLKTYAHLFDDKVMKQLKRRRYTGWGRLSRKLINGIRDKQSGKTILDFLKSDGF
ANRNFMQLIHDDSLTFKEDIQKAQVSGQGDSLHEHIANLAGSPAIKKGILQTVKVVDELVKVMG
RHKPENIVIEMARENQTTQKGQKNSRERMKRIEEGIKELGSQILKEHPVENTQLQNEKLYLYYL
QNGRDMYVDQELDINRLSDYDVDHIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYD
ENDKLIREVKVITLKSKLVSDFRKDFQFYKVREINNYHHAHDAYLNAVVGTALIKKYPKLESEF
VYGDYKVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDPKKYGGFDS
PTVAYSVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFVEQHKH
YLDEIIEQISEFSKRVILADANLDKVLSAYNKHRDKPIREQAENIIHLFTLTNLGAPAAFKYFD
TTIDRKRYTSTKEVLDATLIHQSITGLYETRIDLSQLGGDKRPAATKKAGQAKKKK*

(SEQ ID NO: 11)

FIG. 28

*Streptococcus pyogenes* Mutant cas9 Protein containing Single Mutation (D10A) Nickase Fused with N- and C-Terminal Nuclear Localization Signals

```
MAPKKKRKVGIHGVPAADKKYSIGLAIGTNSVGWAVITDEYKVPSKKFKVLGNTDRHSIKKNLI
GALLFDSGETAEATRLKRTARRRYTRRKNRICYLQEIFSNEMAKVDDSFFHRLEESFLVEEDKK
HERHPIFGNIVDEVAYHEKYPTIYHLRKKLVDSTDKADLRLIYLALAHMIKFRGHFLIEGDLNP
DNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSD
ILRVNTEITKAPLSASMIKRYDEHHQDLTLLKALVRQQLPEKYKEIFFDQSKNGYAGYIDGGAS
QEEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIERMT
NFDKNLPNEKVLPKHSLLYEYFTVYNELTKVKYVTEGMRKPAFLSGEQKKAIVDLLFKTNRKVT
VKQLKEDYFKKIECFDSVEISGVEDRFNASLGTYHDLLKIIKDKDFLDNEENEDILEDIVLTLT
LFEDREMIEERLKTYAHLFDDKVMKQLKRRRYTGWGRLSRKLINGIRDKQSGKTILDFLKSDGF
ANRNFMQLIHDDSLTFKEDIQKAQVSGQGDSLHEHIANLAGSPAIKKGILQTVKVVDELVKVMG
RHKPENIVIEMARENQTTQKGQKNSRERMKRIEEGIKELGSQILKEHPVENTQLQNEKLYLYYL
QNGRDMYVDQELDINRLSDYDVDHIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYD
ENDKLIREVKVITLKSKLVSDFRKDFQFYKVREINNYHHAHDAYLNAVVGTALIKKYPKLESEF
VYGDYKVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDPKKYGGFDS
PTVAYSVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFVEQHKH
YLDEIIEQISEFSKRVILADANLDKVLSAYNKHRDKPIREQAENIIHLFTLTNLGAPAAFKYFD
TTIDRKRYTSTKEVLDATLIHQSITGLYETRIDLSQLGGDKRPAATKKAGQAKKKK*
```

(SEQ ID NO: 12)

FIG. 29

_Streptococcus pyogenes_ Mutant cas9 Protein containing Double Mutation (D10A and H840A) Null Nuclease with Fused N- and C-Terminal Nuclear Localization Signals

MAPKKKRKVGIHGVPAADKKYSIGIAIGTNSVGWAVITDEYKVPSKKFKVLGNTDRHSIKKNLI
GALLFDSGETAEATRLKRTARRRYTRRKNRICYLQEIFSNEMAKVDDSFFHRLEESFLVEEDKK
HERHPIFGNIVDEVAYHEKYPTIYHLRKKLVDSTDKADLRLIYLALAHMIKFRGHFLIEGDLNP
DNSDVDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAILLSD
ILRVNTEITKAPLSASMIKRYDEHHQDLTLLKALVRQQLPEKYKEIFFDQSKNGYAGYIDGGAS
QEEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIERMT
NFDKNLPNEKVLPKHSLLYEYFTVYNELTKVKYVTEGMRKPAFLSGEQKKAIVDLLFKTNRKVT
VKQLKEDYFKKIECFDSVEISGVEDRFNASLGTYHDLLKIIKDKDFLDNEENEDILEDIVLTLT
LFEDREMIEERLKTYAHLFDDKVMKQLKRRRYTGWGRLSRKLINGIRDKQSGKTILDFLKSDGF
ANRNFMQLIHDDSLTFKEDIQKAQVSGQGDSLHEHIANLAGSPAIKKGILQTVKVVDELVKVMG
RHKPENIVIEMARENQTTQKGQKNSRERMKRIEEGIKELGSQILKEHPVENTQLQNEKLYLYYL
QNGRDMYVDQELDINRLSDYDVDAIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYD
ENDKLIREVKVITLKSKLVSDFRKDFQFYKVREINNYHHAHDAYLNAVVGTALIKKYPKLESEF
VYGDYKVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDPKKYGGFDS
PTVAYSVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFVEQHKH
YLDEIIEQISEFSKRVILADANLDKVLSAYNKHRDKPIREQAENIIHLFTLTNLGAPAAFKYFD
TTIDRKRYTSTKEVLDATLIHQSITGLYETRIDLSQLGGDKRPAATKKAGQAKKKK*

(SEQ ID NO: 13)

FIG. 30

CRISPR/CAS SYSTEMS FOR GENOMIC MODIFICATION AND GENE MODULATION

CROSS-REFERENCE TO RELATED APPLICATIONS

This application claims benefit of U.S. Provisional Application Ser. No. 61/799,586, filed in the United States Patent and Trademark Office on Mar. 15, 2013, which is herein incorporated by reference in its entirety.

SEQUENCE LISTING

The instant application contains a Sequence Listing which has been submitted electronically in ASCII format and is hereby incorporated by reference in its entirety. Said ASCII copy, created on May 8, 2014, is named 1458.03NPR2_SL.txt and is 122,076 bytes in size.

FIELD OF THE INVENTION

The invention relates generally to compositions, methods and systems for targeted genomic modification and targeted regulation of gene expression in mammalian cells, for example, in human cells. These compositions, methods and systems of the invention find a variety of uses, for example, as genome engineering tools for genomic editing and gene modulation in cells. These materials and methods find diverse application in the fields of basic biological sciences research, biotechnology, biomedicine and as therapeutics in the treatment of disease.

BACKGROUND OF THE INVENTION

In the past decade, a great deal of progress has been made in the field of targeted genomic engineering. Technologies such as designer zinc finger nucleases (ZFNs), transcriptional activator-like effector nucleases (TALENs), and homing meganucleases have made possible site-specific genome modifications in many different model organisms, ranging from zebrafish to mammalian cells. Based on the results to date, however, genome editing tools that are efficient, flexible, and cost-effective have remained elusive.

Small RNA-based defense systems that provide adaptive, heritable immunity against viruses, plasmids, and other mobile genetic elements have been identified in archaea and bacteria. The discovery of the prokaryotic type II CRISPR (clustered regularly interspaced short palindromic repeats) system, originally identified in the bacterium *Streptococcus pyogenes* as a mechanism to defend against viruses and foreign DNA, where prokaryotes with CRISPR-Cas immune systems capture short fragments of invader genetic material with the CRISPR loci in the genomes, and small RNAs produced from the CRISPR loci (crRNAs) guide Cas proteins to recognize and degrade the invading nucleic acids. It has been proposed that the bacterial CRISPR-Cas system has the potential to provide a tool for targeted genome engineering. However, the CRISPR system is taken from prokaryotes, and adapting those bacterial components to operate in mammalian host cells in an efficient, rapid, adaptable and cost-effective manner remains unproven.

In a native prokaryotic host, the CRISPR/CRISPR-associated (Cas) system involves (1) integration of short regions of genetic material that are homologous to the foreign invading nucleic acids, called "spacers", in clustered arrays in the host genome, (2) expression of short guiding RNAs (crRNAs) from the spacers, (3) binding of the crRNAs to specific portions of the foreign DNA called protospacers, and (4) degradation of protospacers by CRISPR-associated nucleases (Cas). A Type-II CRISPR system has been previously described in the bacterium *Streptococcus pyogenes*, where four genes (Cas9, Cas1, Cas2, Csn1) and two non-coding small RNAs (pre-crRNA and tracrRNA (trans-activating CRISPR RNA)) act in concert to target and degrade foreign DNA in a sequence-specific manner (Jinek et al., "A Programmable Dual-RNA-Guided DNA Endonuclease in Adaptive Bacterial Immunity," *Science* 337(6096):816-821 (August 2012, epub Jun. 28, 2012)). Cas9, is a double stranded nuclease, with two active cutting sites, one for each strand of the double helix. Cas9 is thought to be the only protein involved in the crRNA/tracrRNA-guided silencing of foreign nucleic acids.

The specificity of binding of the CRISPR components to the foreign DNA is controlled by the non-repetitive spacer elements in the pre-crRNA, which upon transcription along with the tracrRNA, directs the Cas9 nuclease to the protospacer:crRNA heteroduplex and induces double-strand breakage (DSB) formation. Additionally, the Cas9 nuclease cuts the DNA only if a protospacer adjacent motif (PAM) nucleotide sequence is present immediately downstream of the protospacer sequence, whose canonical sequence in *S. pyogenes* is 5'-NGG-3', where N refers to any nucleotide.

The potential for designing a customizable RNA-programmed CRISPR/Cas9 system that would function in mammalian cells has been explored, with the hope that such systems would provide customizable genome-editing applications in mammalian cells. Cong et al., "Multiplex Genome Engineering Using CRISPR/Cas Systems" *Science* 339 (6121):819-823 (Feb. 15, 2013), epub *Science Express* (Jan. 3, 2013); Mali et al., "RNA-Guided Human Genome Engineering via Cas9" *Science* 339(6121):823-826 (Feb. 15, 2013), epub *Science Express* (Jan. 3, 2013); and Cho et al., "Targeted genome engineering in human cells with the Cas9 RNA-guided endonuclease," *Nature Biotechnology* 31:230-232 (epub Jan. 29, 2013). Various groups have introduced double stranded breaks at endogenous genomic loci in human cells and mouse cells using a codon-optimized version of the *S. pyogenes* Cas9 protein. These systems incorporate and express a single engineered chimeric crRNA:tracrRNA transcript (which would normally be expressed as two different RNAs in the native type II CRISPR bacterial system), and where the chimeric transcript further contains targeting sequence to a desired genomic target. These crRNA-tracrRNA fusions are alternatively termed guide RNA, chimeric guide RNA or targeting RNA. These components are sufficient in mammalian host cells to direct the double stranded cleavage of a target genomic DNA in a sequence-specific manner.

Mutant forms of Cas9 nuclease have been developed to take advantage of the Cas9 nuclease activity in genome engineering and transcriptional regulation. One mutant form of Cas9 nuclease containing a single amino acid substitution (D10A) has lost its native double-stranded nuclease activity present in the wild type form, but retains partial function as a single-stranded nickase (Jinek et al., *Science* 337(6096), p. 816-821 [August 2012], epub Jun. 28, 2012), generating a break in the complementary strand of DNA rather than both strands as with the wild-type. This allows repair of the DNA template using a high-fidelity pathway rather than non-homologous end joining (NHEJ). The higher fidelity pathway prevents formation of indels at the targeted locus, and possibly other locations in the genome to reduce possible off-target/toxicity effects while maintaining ability to undergo homologous recombination (Cong et al., *Science*

339(6121):819-823 (Feb. 15, 2013), epub *Science Express* (Jan. 3, 2013)). Paired nicking has been shown to reduce off-target activity by 50- to 1,500 fold in cell lines and to facilitate gene knockouts in mouse zygotes without losing on-target cleavage efficiency (Ran et al., "Double Nicking by RNA-Guided CRISPR Cas9 for Enhanced Genome Editing Specificity." *Cell* 154(6):1380-1389 (September 2013)). A double-mutant (DM) form of Cas9 containing the D10A mutation as well as a H840A mutation shows no single-stranded or double-stranded nuclease activity, and is termed a null nuclease.

Precise editing or replacement of mutant genes and introduction of new gene sequences into cells has remained a goal of gene therapy since its inception. The ability to edit chromosomal DNA and regulate transcription in vivo using customizable gene-specific tools remain a powerful tools in the study of biological systems and holds promise for the study of cellular systems, human physiology and a potential therapeutics in the treatment of human disease. Gene regulatory tools can be used, for example, to study biology by perturbing gene networks, and also for example, can be used to treat genetic diseases by repairing genetic defects or by introducing genes into cells for therapeutic purposes.

This goal looked promising when it was demonstrated that targeted cleavage of chromosomal sequences and enhanced homologous recombination (HR) could be achieved using chimeric molecules composed of a nuclease domain and customizable reprogrammed DNA-recognition domains, including zinc-finger nucleases (ZFNs) and transcription activator-like (TAL) effector nucleases (TALENs). However, these two systems face technical and practical limitations, including off-site cleavage events, cell toxicity, and are time and cost intensive to develop.

The potential for using CRISPR/Cas9 components to construct customizable systems to regulate transcription has been proposed. It has been demonstrated that a catalytically silent Cas-9 mutant (a null nuclease) can be tethered to specified gene promoter regions and has the effect of reducing expression of those genes. These systems are limited in their utility due to the slight gene suppression effects that can be achieved.

The possibility of constructing chimeric transcription factors to regulate gene expression using the DNA targeting ability of CRISPR/Cas9 components combined with tethered transcriptional activation or suppression domains has been suggested. See Gilbert et al., "CRISPR-mediated modular RNA-guided regulation of transcription in eukaryotes," *Cell* 154(2):442-451 (epub Jul. 11, 2013); Perez-Pinera et al, "RNA-guided gene activation by CRISPR-Cas9-based transcription factors," *Nature Methods* 10:973-976 (epub Jul. 25, 2013); Mali et al., "CAS9 transcriptional activators for target specificity screening and paired nickases for cooperative genome engineering," *Nature Biotechnology* 31:833-838 (epub Aug. 1, 2013). Optimized forms of these CRISPR/Cas chimeric transcription factors have yet to be developed.

Genome engineering and genetic modulation by the control of individual gene expression hold great promise for research and potential therapeutics. CRISPR/Cas RNA-guided genome targeting and gene regulation in mammalian cells using modified bacterial CRISPR/Cas components defines a potential new class of tools with broad applicability to diverse fields in biology and medicine. However, the development of such tools must be improved in order to make these modalities more cost effective and less time consuming.

What is needed in the art are rapid, cost-effective and versatile tools and methods for RNA-programmed genome engineering and RNA-programmed control of gene expression. Ideally, these tools will have an ease in designing sequence guide molecules and also show a high efficiency of delivery into host cells such as mammalian cells. The development of systems that use small RNAs as guides (such as CRISPR/Cas systems) to cleave DNA in a sequence-specific manner resulting in directed genomic modification or to synthesize customized transcription factors for a particular gene of interest will find significant utility.

The present invention, in its many embodiments, provides compositions and methods that overcome these challenges in the industry, have a number of advantages over the state of the art and provide many benefits previously unrealized in other types of products. In addition, still further benefits flow from the invention described herein, as will be apparent upon reading the present disclosure.

SUMMARY OF THE INVENTION

The present disclosure provides an engineered CRISPR II system for genomic modification in mammalian cells, generally comprising (i) a polynucleotide encoding a *Streptococcus pyogenes* Cas9 protein, and (ii) at least one guide-RNA for RNA-guided genome engineering in human or mouse cells. The guide RNA molecules comprise a crRNA-tracrRNA scaffold polynucleotide, and a targeting sequence corresponding to a genomic target of interest. The CRISPR system provides tools for highly targeted genomic engineering, such as gene editing and gene replacement, and also tools for gene expression modulation. The present disclosure describes the design, expression and testing of a polynucleotide that has been optimized for expression of *S. pyogenes* Cas9 proteins in mammalian cells, such as human or mouse cells, and describes the design and testing of an all-in-one system for genomic engineering, where the Cas9 protein and the guide RNA are expressed from the same vector construct. The Cas9 tools described herein find widespread use in diverse fields of basic sciences, biotechnology, biomedicine and in the development of human therapeutics, for example, in the development materials for therapeutic transplantation.

In one aspect, the invention provides a variety of polynucleotides that encode Cas9 polypeptides. These polynucleotides can comprise nucleotide sequences that are optimized for expression of the genes in mammalian host cells, for example, human cells or mouse cells, principally by optimizing the open reading frame to reflect preferred mammalian codon utilization. The polypeptides encoded by these polynucleotides can comprise essentially the Cas9 polypeptide amino acid sequence, or the polypeptides can be modified as fusion proteins that may contain additional operably linked sequences, such as, for example but not limited to, any type or quantity of beneficial secondary sequences, such as tags, markers, or one or more nuclear localization signals. The Cas9 polynucleotides of the invention can encode the wild type form of the *S. pyogenes* Cas9 nuclease, or alternatively, can encode mutant forms of the protein, for example, mutants that retain only single stranded nickase activity and mutant forms that have lost all nuclease activity, i.e., a null nuclease. In other embodiments, the invention encompasses variants (such as conservative variants) and subsequences (portions) of these polynucleotides (e.g., subsequences which are at least 100 nucleotides in length), and additional polynucleotides that are derived from polynucleotides specifically recited in the disclosure. In some aspects, the invention encompasses the polypeptides encoded by the polynucleotides.

In some embodiments, the polynucleotides of the invention are in the context of vectors, e.g., expression vectors, which are also features of the invention. The expression vectors can be mammalian expression vectors, such as human expression vectors. In some embodiments, the expression vectors are designed to express both a Cas9 polypeptide and a guide RNA from the same vector, and are termed "all-in-one" vectors. In some embodiments, the vectors of the invention are designed for use with in vitro transcription systems, for example, containing one or more bacteriophage promoter elements such as a T7 promoter, and can be used to produce mRNA encoding a Cas9 polypeptide and/or RNA encoding a CRISPR guide RNA in a cell-free IVT reaction. In some aspects, the Cas9 gene that is used with the invention is a native bacterial cas9 gene.

In some embodiments, the invention provides a method for targeted genomic modification of mammalian cells, the methods having the steps of (a) providing: (i) a mammalian all-in-one expression construct comprising a first polynucleotide encoding a bacterial Cas9 protein, or a variant thereof or a fusion protein therewith, and a second polynucleotide encoding a guide RNA comprising: (I) a crRNA-tracrRNA scaffold polynucleotide, and (II) a targeting sequence operably linked to the crRNA-tracrRNA scaffold polynucleotide, where the targeting sequence corresponds to a genomic locus of interest, (ii) a mammalian host cell comprising the genomic locus of interest, and (b) delivering the mammalian expression construct into the mammalian host cell where the first and second polynucleotides are expressed (transcribed) within the mammalian host cell. This method can optionally further include visualizing, identifying or selecting for host cells having a genomic modification at the genomic locus of interest that is induced by the delivering the mammalian expression construct into the mammalian host cell.

In other methods for targeted genomic modification in mammalian cells, the Cas9 polypeptide and guide RNA are encoded on two separate vectors. In these methods, the steps generally follow the sequence of (a) providing: a cas9 polynucleotide recited in the disclosure, or a conservative variant thereof, and a guide RNA comprising (A) a crRNA-tracrRNA scaffold polynucleotide, and (B) a targeting sequence operably linked to the crRNA-tracrRNA scaffold polynucleotide, said targeting sequence corresponding to a genomic locus of interest, and (iii) a mammalian host cell comprising the genomic locus of interest, and (b) delivering the two polynucleotides into the mammalian host cell. In variations of this method, a donor polynucleotide having homology to the genomic target of interest is included in a cotransfection. In some variations of these methods, the transfected material can be either plasmid DNA, or can be RNA generated by in vitro transcription. In still other variations, the methods for targeted genomic modification are multiplexed, meaning that more than one genomic locus is targeted for modification. In still other variations of these methods, the transformation of the host cells can be followed by visualizing, identifying or selecting for host cells having a genomic modification at the genomic locus of interest.

In still other embodiments, the invention provides complete systems for targeted genomic modification in mammalian cells comprising: (a) an all-in-one mammalian expression construct encoding both a Cas9 polypeptide and a guide RNA, (b) a mammalian host cell comprising a genomic target of interest, and (c) a means for delivering the mammalian expression construct into the host cell, where the Cas9 mRNA and the guide RNA are expressed inside the mammalian host cell after delivery of the mammalian expression construct into the mammalian cell. This system can further contain a donor polynucleotide having homology to the genomic target of interest, where the donor and the genomic target of interest undergo homologous recombination within the host cell. In some embodiments, the expression vector and the host cell are human. This system can optionally be a multiplex system.

In other aspects, the invention provides methods for regulating gene expression in a mammalian host cell using CRISPR reagents. These methods generally follow the steps of: (a) providing a mammalian host cell and a mammalian all-in-one expression construct encoding a Cas9 fusion protein carrying a transcriptional regulatory domain, and a guide RNA directed to a target gene of interest, and (b) delivering the all-in-one expression construct into the mammalian host cell, where the Cas9 fusion protein and the guide RNA are expressed. In other related embodiments, the invention provides methods for regulating gene expression in a mammalian host cell as above, except where the Cas9 fusion protein carrying a transcriptional regulatory domain, and the guide RNA directed to a target gene of interest are encoded by genes on two different vectors, or RNA produced by in vitro transcription reactions are used to transfect the host cells.

BRIEF DESCRIPTION OF THE DRAWINGS

FIG. 1B provides a plasmid map of a mammalian expression construct for use with the all-in-one CRISPR system, where the construct expresses the wild type Cas9 protein, further fused with myc-tag and NLS sequences. The promoter for the expression of the hspCas9 protein can be chosen from any suitable promoter sequences, examples of which are listed in FIG. 1B. FIG. 1C provides a plasmid map of an all-in-one CRISPR vector similar to the vector of FIG. 1B, except that this vector expresses a mutant variant of the hspCas9 that is a DNA nickase. FIG. 1D provides a plasmid map of an all-in-one CRISPR vector similar to the vector of FIG. 1B, except that this vector expresses a mutant variant of the hspCas9 that is a double mutant null nuclease.

FIG. 3A provides a schematic of the all-in-one expression construct EF1-hspCas9-H1-AAVS, indicating the codon-optimized hspCas9 gene and a guide RNA specific for AAVS sequence. FIG. 3B provides a schematic of the all-in-one expression construct EF1-spCas9-mcherry-H1-AAVS expressing a fusion protein encoded by the bacterial spCas9 and mCherry red fluorescent protein sequence. Both of these construct contain N-terminal and C-terminal NLS. FIG. 3C provides the nucleotide sequence of the AAVS target sequence inserted into the gRNA.

FIG. 6A provides a schematic of the expression construct EF1-hspCas9-H1-Luc. FIG. 6B provides the nucleotide sequences of two targeting sequences used to construct gRNAs that target the luciferase gene.

FIG. 6C in the top panel provides a schematic of the recombinant genomic locus in a GFP/luciferase stable HEK 293T reporter cell line. The middle panel shows the configuration of a donor fragment incorporated in a homologous recombination reaction. The bottom panel shows the configuration of the recombinant genomic locus following the homologous recombination event that takes place in the reporter cell line.

FIG. 9A provides a table containing the amino acid and corresponding nucleotide sequences of five different nuclear localization signals tested for their ability to induce nuclear localization of Cas9 proteins in mammalian cells. FIG. 9B provides a table listing the Cas9 expression constructs that were made and tested for ability of the various NLS to drive nuclear import, and provides the results of the testing.

FIG. 16A provides a schematic of a CRISPR/Cas9 all-in-one expression vector encoding a Cas9 fusion polypeptide that includes a Cas9 double mutant null nuclease amino acid sequence and the amino acid sequence of a mammalian transcriptional regulatory domain. The vector shown in this figure has the option to be used either as plasmid in cell transfections, or can be used for in vitro transcription reactions to generate mRNA encoding a Cas9 polypeptide. This Cas9 polypeptide is a fusion polypeptide containing the hspCas9 DM amino acid sequence and a fused transcription regulatory domain, used in target gene regulation. This plasmid generates a bicistronic mRNA encoding the Cas9 polypeptide as well as a marker of choice. The bicistronic message is translationally processed to produce two independent, unlinked proteins. FIG. 16B provides the nucleotide and amino acid sequences of the transcriptional suppression domain KRAB, and the transcriptional activation domain VP64.

FIG. 17A provides a schematic of a generalized CRISPR/Cas9 mRNA expression vector that can be used for in vitro transcription reactions to generate Cas9 mRNA. The vector features with 5'-UTR and 3'UTP and a polyA tail to enhance mRNA stability and translation efficiency. FIGS. 17B through 17J provide schematics of CRISPR/Cas9 mRNA expression vectors that can be used for in vitro transcription reactions to generate Cas9 mRNA. These vectors can express a variety of Cas9 variants, such as the wild type Cas9 polypeptide, or a Cas9 nickase polypeptide or a Cas9 null nuclease polypeptide. These vectors can be configured to produce Cas9 polypeptide that is fused with a desired marker protein, or alternatively, can be configured to simultaneously produce free Cas9 polypeptide and a marker protein. FIG. 17K provides a schematic of a generalized vector that can be used for in vitro transcription reactions to generate guide RNA molecules used in CRISPR systems.

FIG. 18 provides the amino acid sequence of the native *Streptococcus pyogenes* (*S. pyogenes*) wild type Cas9 protein (SEQ ID NO: 1).

FIG. 19 provides the nucleotide sequence of the native *Streptococcus pyogenes* wild type cas9 gene open reading frame (SEQ ID NO: 2), including the 3' stop codon TGA.

FIG. 20 provides the nucleotide sequence of the mammalian codon-optimized *Streptococcus pyogenes* wild type cas9 gene open reading frame (SEQ ID NO: 3).

FIG. 21 provides the nucleotide sequence of the mammalian codon-optimized *Streptococcus pyogenes* wild type cas9 gene open reading frame encoding N- and C-terminal nuclear localization signals (SEQ ID NO: 4). The nuclear localization signals are solid underlined, and the stop codon is indicated with dashed underline.

FIG. 22 provides the amino acid sequence of the *Streptococcus pyogenes* wild type Cas9 protein fused with N-terminal myc-tag and N- and C-terminal nuclear localization signals (SEQ ID NO: 5). The myc-tag is shown with double underlining, and the and N- and C-terminal nuclear localization signals are single underlined. The corresponding position of a stop codon is indicated by an asterisk.

FIG. 23 provides the nucleotide sequence of the mammalian codon-optimized *Streptococcus pyogenes* wild type Cas9 gene open reading frame encoding fused N-terminal myc-tag and N- and C-terminal nuclear localization signals (SEQ ID NO: 6). The nucleotides encoding the myc-tag are shown in lowercase nucleotides, and the and N- and C-terminal nuclear localization signals are single underlined. The stop codon is indicated by dashed underline.

FIG. 24 provides the nucleotide sequence of the mammalian codon-optimized *Streptococcus pyogenes* mutant cas9 gene open reading frame encoding the single mutation (D10A) nickase (SEQ ID NO: 7). The position of the nucleotide change that results in the D10A mutation is indicated by a box.

FIG. 25 provides the nucleotide sequence of the mammalian codon-optimized *Streptococcus pyogenes* mutant cas9 gene open reading frame encoding the single mutation (D10A) nickase with fused N-terminal myc-tag and N- and C-terminal nuclear localization signals (SEQ ID NO: 8). The nucleotides encoding the myc-tag are shown in lowercase nucleotides, and the and N- and C-terminal nuclear localization signals are single underlined. The stop codon is indicated by dashed underline. The position of the nucleotide change that encodes the D10A mutation is indicated by a box.

FIG. 26 provides the nucleotide sequence of the mammalian codon-optimized *Streptococcus pyogenes* mutant cas9 gene open reading frame encoding the double mutation (D10A and H840A) null nuclease (SEQ ID NO: 9). The positions of the nucleotide changes that result in the D10A and H840A mutations are indicated by boxes.

FIG. 27 provides the nucleotide sequence of the mammalian codon-optimized *Streptococcus pyogenes* mutant cas9 gene open reading frame encoding double mutation (D10A and H840A) null nuclease fused with N-terminal myc-tag and N- and C-terminal nuclear localization signals (SEQ ID NO: 10). The nucleotides encoding the myc-tag are shown in lowercase nucleotides, and the N- and C-terminal nuclear localization signals are single underlined. The stop codon is indicated by dashed underline. The positions of the nucleotide changes that result in the D10A and H840A mutations are indicated by boxes.

FIG. 28 provides the amino acid sequence of the *Streptococcus pyogenes* wild type Cas9 protein fused with N- and C-terminal nuclear localization signals (SEQ ID NO: 11). The amino acids comprising the N- and C-terminal nuclear localization signals are underlined. The corresponding position of a stop codon is indicated by an asterisk.

FIG. 29 provides the amino acid sequence of the *Streptococcus pyogenes* mutant Cas9 protein containing the single mutation (D10A) nickase fused with N- and C-terminal nuclear localization signals (SEQ ID NO: 12). The amino acids comprising the N- and C-terminal nuclear localization signals are underlined. The corresponding position of a stop codon is indicated by an asterisk. The position of the D10A mutation is indicated by a box.

FIG. 30 provides the amino acid sequence of the *Streptococcus pyogenes* mutant Cas9 protein containing the double mutation (D10A and H840A) null nuclease with fused N- and C-terminal nuclear localization signals (SEQ ID NO: 13). The positions of the D10A and H840A mutations are indicated by boxes.

DETAILED DESCRIPTION OF THE INVENTION

Figure 1A:
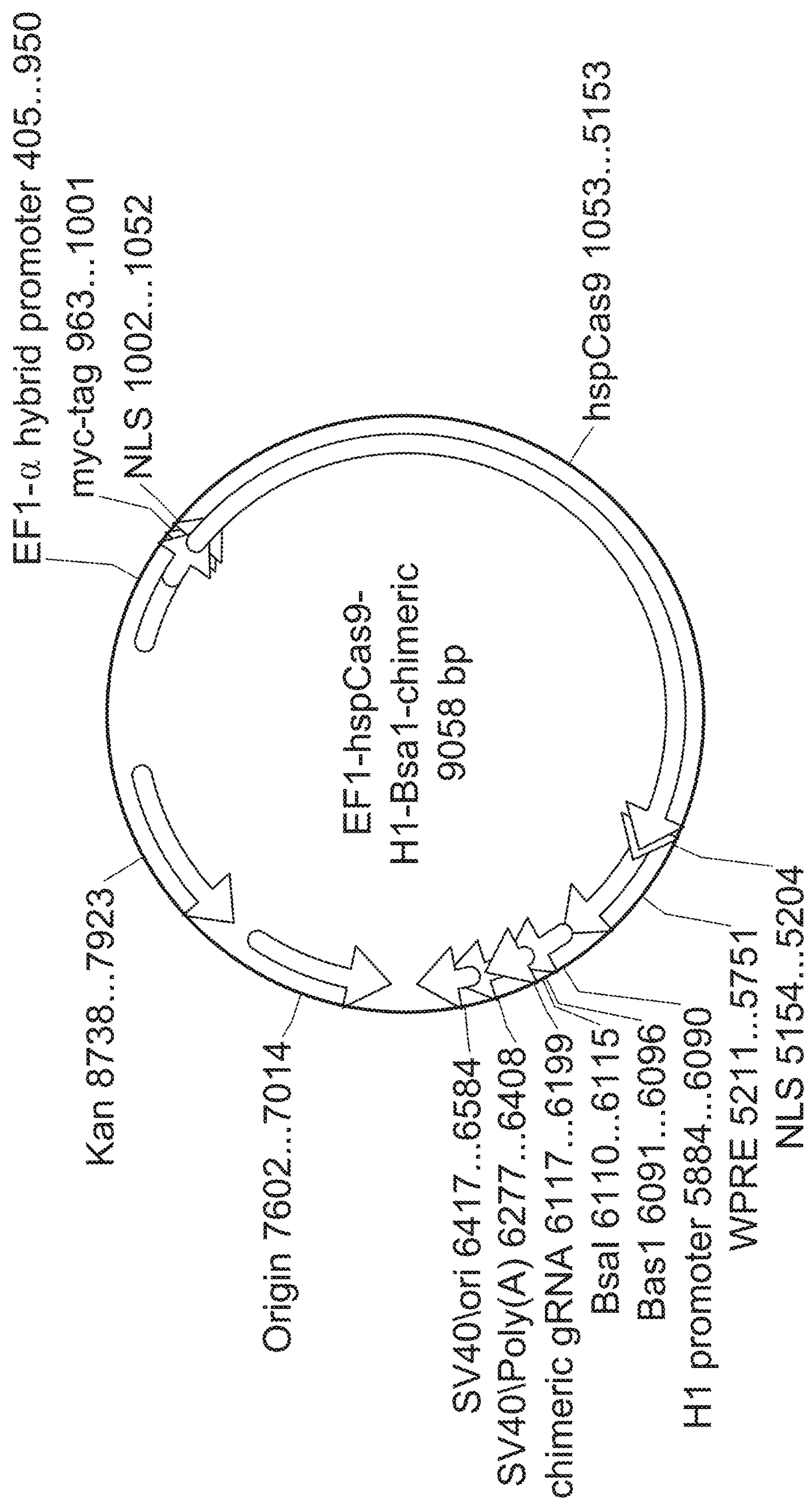
FIG. 1A provides a plasmid map of a mammalian expression construct for use with the all-in-one CRISPR system. The construct expresses the mammalian-codon optimized hspCas9 gene (encoding a wild type Cas9 protein fused with myc-tag and NLS sequences, expression driven by the EF1-α hybrid promoter) and a chimeric guide RNA (expressed from the H1 promoter, both from the single vector. Positions of the major features of the construct are indicated.
Figures 1B, 1C, 1D:
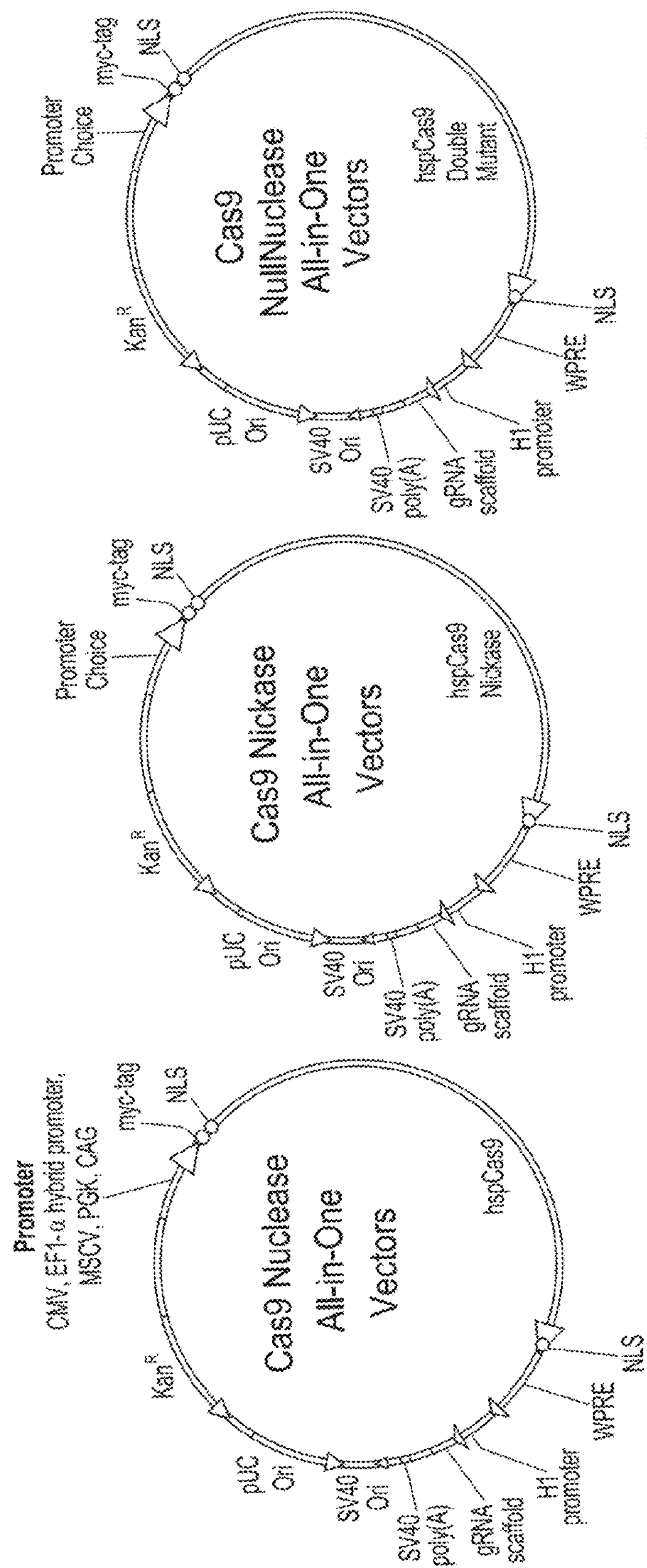
FIGS. 1B, 1C and 1D provide plasmid map schematics of the general form of mammalian all-in-one expression vectors for the expression of CRISPR system components, including mutant variants of the Cas9 protein. Major features of the constructs are indicated.

The type II prokaryotic CRISPR system (Clustered Regularly Interspaced Short Palindromic Repeats), originally identified in the bacterium *Streptococcus pyogenes* (*S. pyogenes*), works as a mechanism to defend bacteria against viruses and other foreign DNA elements. The endogenous bacterial CRISPR-Cas9 system comprises two independently expressed short RNA molecules, namely the crRNA and tracrRNA, and the CRISPR-associated (cas) double-stranded nuclease Cas9. In vivo, the crRNA and tracrRNA molecules are guided to foreign genetic material by homologous sequences on the crRNA. The small RNA molecules recruit the Cas9 protein to the site of sequence homology on the foreign DNA, where the Cas9 protein then cleaves the invading DNA, which results in inactivation of the invading DNA. Cleavage of the DNA is sequence specific, and further requires the presence of an upstream sequence termed the protospacer adjacent motif (PAM) at the target locus.

The native, endogenous prokaryotic CRISPR-Cas9 system components have provided the raw materials to design sequence specific genome editing tools that can function in eukaryotic cells, and more specifically, mammalian cells, including human cells. In these artificially engineered systems, the crRNA and tracrRNA are fused to each other to form a single guide RNA scaffold, and furthermore, also contain short segments (as short as about 20 nucleotides) of targeting sequence. This chimeric molecule, termed a guide RNA or gRNA, can be expressed in mammalian cells, and is able to direct the nuclease activity of Cas9 to the preprogrammed target site, where the enzyme cleaves the DNA.

This DNA cleavage event is a powerful tool in programming site-specific genomic modification at a desired locus. Cleavage by the wild type Cas9, or a Cas9 variant such as mutant forms of Cas9, under appropriate conditions, can trigger programmed genomic editing. The invention disclosed herein provides highly modified CRISPR-Cas9 system components that permit genomic editing, including DNA repair at a single nucleotide position, introduction of single nucleotide changes or indels, and substitution of entire genomic segments by mechanisms of homologous recombination, for example, to produce "knock out" and "knock in" cells, cell lines and transgenic model organisms. The methods provided by the invention described in the present disclosure hold the potential to accomplish gene replacement and gene repair in human therapeutics and in research applications. These genomic DNA modification tools are a valuable asset in a wide variety of applications across basic sciences, biotechnology and biomedicine, including human therapeutics.

The CRISPR/Cas compositions and methods described in the present disclosure are able to achieve genomic targeting and genomic modification in a cost-effective, simple, flexible and highly efficient way. The compositions and methods of the invention provide targeting specificity that is achieved through the construction of a single targeting nucleic acid, in contrast to TALEN genomic modification systems, which require time-consuming protein engineering. The invention also provides for multiplex genome editing.

In other aspects, the invention also provides compositions and methods for targeted regulation of endogenous genes, also by use of the highly modified CRISPR-Cas reagents. Like the compositions and methods for genome editing, the compositions and methods for genome modulation by transcription regulation utilize the highly targeted DNA binding activity of artificial CRISPR-Cas components, where targeting of a modified Cas9 protein to a promoter region of interest can result in either transcriptional activation or transcriptional repression. The invention also provides for multiplex gene regulation, where more than one gene can be simultaneously targeted for transcriptional modulation (either up regulation or down regulation) in a single cell.

The compositions and methods for genomic editing and transcriptional regulation described in the disclosure provide further benefits, such as highly modifiable components, for example, with regard to preferred promoters and other transcriptional regulatory elements that drive the expression of Cas9 and the chimeric guide RNA. The expression vectors of the invention are able to express the wild type Cas9 protein having double-stranded nuclease activity, or express Cas9 variants, such as Cas9 mutants that act as single stranded nickases or other mutants that have lost all nuclease activity (null nucleases). Generally, all that is required to use the compositions and methods of the invention is to subclone a desired targeting sequence into the host vectors described herein. In another beneficial aspect, the invention provides all-in-one CRISPR-Cas9 systems, where both the Cas9 protein and the guide RNA are expressed from a single plasmid, thereby simplifying transfection protocols. In other aspects, the invention provides compositions and methods for in vitro transcription of CRISPR/Cas reagents, thereby generating mRNA encoding Cas9 polypeptides and RNA products that serve as guide RNA molecules. These in vitro transcription products are used in cell transfections for delivery of these components to mammalian host cells.

I. Definitions

Before describing the invention in detail, it is to be understood that this invention is not limited to particular biological systems or cell types. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless defined herein and below in the reminder of the specification, all technical and scientific terms used herein have the same meaning as commonly understood by one of ordinary skill in the art to which the invention pertains.

As used herein, the terms "polynucleotide," "nucleic acid," "oligonucleotide," "oligomer," "oligo" or equivalent terms, refer to molecules that comprises a polymeric arrangement of nucleotide base monomers, where the sequence of monomers defines the polynucleotide. Polynucleotides can include polymers of deoxyribonucleotides to produce deoxyribonucleic acid (DNA), and polymers of ribonucleotides to produce ribonucleic acid (RNA). A polynucleotide can be single- or double-stranded. When single stranded, the [polynucleotide can correspond to the sense or antisense strand of a gene. A single-stranded polynucleotide can hybridize with a complementary portion of a target polynucleotide to form a duplex, which can be a homoduplex or a heteroduplex.

The length of a polynucleotide is not limited in any respect. Linkages between nucleotides can be internucleotide-type phosphodiester linkages, or any other type of linkage. A polynucleotide can be produced by biological means (e.g., enzymatically), either in vivo (in a cell) or in vitro (in a cell-free system). A polynucleotide can be chemically synthesized using enzyme-free systems. A polynucleotide can be enzymatically extendable or enzymatically non-extendable.

By convention, polynucleotides that are formed by 3'-5' phosphodiester linkages (including naturally occurring polynucleotides) are said to have 5'-ends and 3'-ends because the nucleotide monomers that are incorporated into the polymer are joined in such a manner that the 5' phosphate of one mononucleotide pentose ring is attached to the 3' oxygen (hydroxyl) of its neighbor in one direction via the phosphodiester linkage. Thus, the 5'-end of a polynucleotide molecule generally has a free phosphate group at the 5' position of the pentose ring of the nucleotide, while the 3' end of the polynucleotide molecule has a free hydroxyl group at the 3' position of the pentose ring. Within a polynucleotide molecule, a position that is oriented 5' relative to another position is said to be located "upstream," while a position that is 3' to another position is said to be "downstream." This terminology reflects the fact that polymerases proceed and extend a polynucleotide chain in a 5' to 3' fashion along the template strand. Unless denoted otherwise, whenever a polynucleotide sequence is represented, it will be understood that the nucleotides are in 5' to 3' orientation from left to right.

As used herein, it is not intended that the term "polynucleotide" be limited to naturally occurring polynucleotide structures, naturally occurring nucleotides sequences, naturally occurring backbones or naturally occurring internucleotide linkages. One familiar with the art knows well the wide variety of polynucleotide analogues, unnatural nucleotides, non-natural phosphodiester bond linkages and internucleotide analogs that find use with the invention.

As used herein, the expressions "nucleotide sequence," "sequence of a polynucleotide," "nucleic acid sequence," "polynucleotide sequence", and equivalent or similar phrases refer to the order of nucleotide monomers in the nucleotide polymer. By convention, a nucleotide sequence is typically written in the 5' to 3' direction. Unless otherwise indicated, a particular polynucleotide sequence of the invention optionally encompasses complementary sequences, in addition to the sequence explicitly indicated.

As used herein, the term "gene" generally refers to a combination of polynucleotide elements, that when operatively linked in either a native or recombinant manner, provide some product or function. The term "gene" is to be interpreted broadly, and can encompass mRNA, cDNA, cRNA and genomic DNA forms of a gene. In some uses, the term "gene" encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some aspects, genes do not encode a polypeptide, for example, ribosomal RNA genes (rRNA) and transfer RNA (tRNA) genes. In some aspects, the term "gene" includes not only the transcribed sequences, but in addition, also includes non-transcribed regions including upstream and downstream regulatory regions, enhancers and promoters. The term "gene" encompasses mRNA, cDNA and genomic forms of a gene.

In some aspects, the genomic form or genomic clone of a gene includes the sequences of the transcribed mRNA, as well as other non-transcribed sequences which lie outside of the transcript. The regulatory regions which lie outside the mRNA transcription unit are termed 5' or 3' flanking sequences. A functional genomic form of a gene typically contains regulatory elements necessary, and sometimes sufficient, for the regulation of transcription. The term "promoter" is generally used to describe a DNA region, typically but not exclusively 5' of the site of transcription initiation, sufficient to confer accurate transcription initiation. In some aspects, a "promoter" also includes other cis-acting regulatory elements that are necessary for strong or elevated levels of transcription, or confer inducible transcription. In some embodiments, a promoter is constitutively active, while in alternative embodiments, the promoter is conditionally active (e.g., where transcription is initiated only under certain physiological conditions).

Generally, the term "regulatory element" refers to any cis-acting genetic element that controls some aspect of the expression of nucleic acid sequences. In some uses, the term "promoter" comprises essentially the minimal sequences required to initiate transcription. In some uses, the term "promoter" includes the sequences to start transcription, and in addition, also include sequences that can upregulate or downregulate transcription, commonly termed "enhancer elements" and "repressor elements," respectively.

Specific DNA regulatory elements, including promoters and enhancers, generally only function within a class of organisms. For example, regulatory elements from the bacterial genome generally do not function in eukaryotic organisms. However, regulatory elements from more closely related organisms frequently show cross functionality. For example, DNA regulatory elements from a particular mammalian organism, such as human, will most often function in other mammalian species, such as mouse. Furthermore, in designing recombinant genes that will function across many species, there are consensus sequences for many types of regulatory elements that are known to function across species, e.g., in all mammalian cells, including mouse host cells and human host cells.

As used herein, the expressions "in operable combination," "in operable order," "operatively linked," "operatively joined" and similar phrases, when used in reference to nucleic acids, refer to the operational linkage of nucleic acid sequences placed in functional relationships with each other. For example, an operatively linked promoter, enhancer elements, open reading frame, 5' and 3' UTR, and terminator sequences result in the accurate production of an RNA molecule. In some aspects, operatively linked nucleic acid elements result in the transcription of an open reading frame and ultimately the production of a polypeptide (i.e., expression of the open reading frame).

As used herein, the term "genome" refers to the total genetic information or hereditary material possessed by an organism (including viruses), i.e., the entire genetic complement of an organism or virus. The genome generally refers to all of the genetic material in an organism's chromosome(s), and in addition, extra-chromosomal genetic information that is stably transmitted to daughter cells (e.g., the mitochondrial genome). A genome can comprise RNA or DNA. A genome can be linear (mammals) or circular (bacterial). The genomic material typically resides on discrete units such as the chromosomes.

As used herein, a "polypeptide" is any polymer of amino acids (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell, or a polypeptide produced enzymatically in a cell-free system. A polypeptide can also be produced using chemical (non-enzymatic) synthesis methods. A polypeptide is characterized by the amino acid sequence in the polymer. As used herein, the term "protein" is synonymous with polypeptide. The term "peptide" typically refers to a small polypeptide, and typically is smaller than a protein. Unless otherwise stated, it is not intended that a polypeptide be limited by possessing or not possessing any particular biological activity.

As used herein, the expressions "codon utilization" or "codon bias" or "preferred codon utilization" or the like refers, in one aspect, to differences in the frequency of occurrence of any one codon from among the synonymous codons that encode for a single amino acid in protein-coding DNA (where many amino acids have the capacity to be encoded by more than one codon). In another aspect, "codon use bias" can also refer to differences between two species in the codon biases that each species shows. Different organisms often show different codon biases, where preferences for which codons from among the synonymous codons are favored in that organism's coding sequences.

As used herein, the terms "vector," "vehicle," "construct" and "plasmid" are used in reference to any recombinant polynucleotide molecule that can be propagated and used to transfer nucleic acid segment(s) from one organism to another. Vectors generally comprise parts which mediate vector propagation and manipulation (e.g., one or more origin of replication, genes imparting drug or antibiotic resistance, a multiple cloning site, operably linked promoter/enhancer elements which enable the expression of a cloned gene, etc.). Vectors are generally recombinant nucleic acid molecules, often derived from bacteriophages, or plant or animal viruses. Plasmids and cosmids refer to two such recombinant vectors. A "cloning vector" or "shuttle vector" or "subcloning vector" contain operably linked parts that facilitate subcloning steps (e.g., a multiple cloning site containing multiple restriction endonuclease target sequences). A nucleic acid vector can be a linear molecule, or in circular form, depending on type of vector or type of application. Some circular nucleic acid vectors can be intentionally linearized prior to delivery into a cell.

As used herein, the term "expression vector" refers to a recombinant vector comprising operably linked polynucleotide elements that facilitate and optimize expression of a desired gene (e.g., a gene that encodes a protein) in a particular host organism (e.g., a bacterial expression vector or mammalian expression vector). Polynucleotide sequences that facilitate gene expression can include, for example, promoters, enhancers, transcription termination sequences, and ribosome binding sites.

As used herein, the term "host cell" refers to any cell that contains a heterologous nucleic acid. The heterologous nucleic acid can be a vector, such as a shuttle vector or an expression vector. In some aspects, the host cell is able to drive the expression of genes that are encoded on the vector. In some aspects, the host cell supports the replication and propagation of the vector. Host cells can be bacterial cells such as *E. coli*, or mammalian cells (e.g., human cells or mouse cells). When a suitable host cell (such as a suitable mouse cell) is used to create a stably integrated cell line, that cell line can be used to create a complete transgenic organism.

Methods (i.e., means) for delivering vectors/constructs or other nucleic acids (such as in vitro transcribed RNA) into host cells such as bacterial cells and mammalian cells are well known to one of ordinary skill in the art, and are not provided in detail herein. Any method for nucleic acid delivery into a host cell finds use with the invention.

For example, methods for delivering vectors or other nucleic acid molecules into bacterial cells (termed transformation) such as *Escherichia coli* are routine, and include electroporation methods and transformation of *E. coli* cells that have been rendered competent by previous treatment with divalent cations such as $CaCl_2$.

Methods for delivering vectors or other nucleic acid (such as RNA) into mammalian cells in culture (termed transfection) are routine, and a number of transfection methods find use with the invention. These include but are not limited to calcium phosphate precipitation, electroporation, lipid-based methods (liposomes or lipoplexes) such as Transfectamine® (Life Technologies™) and TransFectin™ (Bio-Rad Laboratories), cationic polymer transfections, for example using DEAE-dextran, direct nucleic acid injection, biolistic particle injection, and viral transduction using engineered viral carriers (termed transduction, using e.g., engineered herpes simplex virus, adenovirus, adeno-associated virus, vaccinia virus, Sindbis virus), and sonoporation. Any of these methods find use with the invention.

As used herein, the term "recombinant" in reference to a nucleic acid or polypeptide indicates that the material (e.g., a recombinant nucleic acid, gene, polynucleotide, polypeptide, etc.) has been altered by human intervention. Generally, the arrangement of parts of a recombinant molecule is not a native configuration, or the primary sequence of the recombinant polynucleotide or polypeptide has in some way been manipulated. A naturally occurring nucleotide sequence becomes a recombinant polynucleotide if it is removed from the native location from which it originated (e.g., a chromosome), or if it is transcribed from a recombinant DNA construct. A gene open reading frame is a recombinant molecule if that nucleotide sequence has been removed from it natural context and cloned into any type of nucleic acid vector (even if that ORF has the same nucleotide sequence as the naturally occurring gene). Protocols and reagents to produce recombinant molecules, especially recombinant nucleic acids, are well known to one of ordinary skill in the art. In some embodiments, the term "recombinant cell line" refers to any cell line containing a recombinant nucleic acid, that is to say, a nucleic acid that is not native to that host cell.

As used herein, the terms "heterologous" or "exogenous" as applied to polynucleotides or polypeptides refers to molecules that have been rearranged or artificially supplied to a biological system and are not in a native configuration (e.g., with respect to sequence, genomic position or arrangement of parts) or are not native to that particular biological system. These terms indicate that the relevant material originated from a source other than the naturally occurring source, or refers to molecules having a non-natural configuration, genetic location or arrangement of parts. The terms "exogenous" and "heterologous" are sometimes used interchangeably with "recombinant."

As used herein, the terms "native" or "endogenous" refer to molecules that are found in a naturally occurring biological system, cell, tissue, species or chromosome under study. A "native" or "endogenous" gene is a generally a gene that does not include nucleotide sequences other than nucleotide sequences with which it is normally associated in nature (e.g., a nuclear chromosome, mitochondrial chromosome or chloroplast chromosome). An endogenous gene, transcript or polypeptide is encoded by its natural locus, and is not artificially supplied to the cell.

As used herein, the expression "homologous recombination" refers to a genetic process in which nucleotide sequences are exchanged between two similar molecules of DNA. Homologous recombination (HR) is used by cells to accurately repair harmful breaks that occur on both strands of DNA, known as double-strand breaks or other breaks that generate overhanging sequences. Various molecular events are thought to control HR; however, an understanding of the molecular mechanisms underlying HR are not required to make and use the invention. After some types of DNA damage, various forms of HR repair the damage using the following general steps: (i) resection or excision of the damaged DNA; (ii) strand invasion where an end of the broken DNA molecule "invades" a similar or identical DNA molecule in a region of homology that is not damaged; (iii) finally, either of two pathways is used to effectuate the repair, involving DNA synthesis and relegation. HR requires that there be present some identical or homologous strand of DNA that serves as a template to direct the repair of the damaged DNA.

As used herein, the expressions "donor polynucleotide" or "donor fragment" or "template DNA" refer to the strand of DNA that is the recipient strand during HR strand invasion that is initiated by the damaged DNA. The donor polynucleotide serves as template material to direct the repair of the damaged DNA region.

As used herein, the expression "non-homologous end joining (NHEJ)" refers to a cellular pathway that repairs double-strand breaks in DNA. NHEJ is referred to as "non-homologous" DNA repair because the break ends are directly ligated to each other without the need for a homologous template, in contrast to homologous recombination, which requires a homologous sequence to guide the repair. NHEJ frequently results in imprecise DNA repair, and can introduce errors (including deletions and insertions) in the repaired DNA.

As used herein, the term "marker" most generally refers to a biological feature or trait that, when present in a cell (e.g., is expressed), results in an attribute or phenotype that visualizes or identifies the cell as containing that marker. A variety of marker types are commonly used, and can be for example, visual markers such as color development, e.g., lacZ complementation (β-galactosidase) or fluorescence, e.g., such as expression of green fluorescent protein (GFP) or GFP fusion proteins, RFP, BFP, selectable markers, phenotypic markers (growth rate, cell morphology, colony color or colony morphology, temperature sensitivity), auxotrophic markers (growth requirements), antibiotic sensitivities and resistances, molecular markers such as biomolecules that are distinguishable by antigenic sensitivity (e.g., blood group antigens and histocompatibility markers), cell surface markers (for example H2KK), enzymatic markers, and nucleic acid markers, for example, restriction fragment length polymorphisms (RFLP), single nucleotide polymorphism (SNP) and various other amplifiable genetic polymorphisms.

As used herein, the expressions "selectable marker" or "screening marker" or "positive selection marker" refer to a marker that, when present in a cell, results in an attribute or phenotype that allows selection or segregated of those cells from other cells that do not express the selectable marker trait. A variety of genes are used as selectable markers, e.g., genes encoding drug resistance or auxotrophic rescue are widely known. For example, kanamycin (neomycin) resistance can be used as a trait to select bacteria that have taken up a plasmid carrying a gene encoding for bacterial kanamycin resistance (e.g., the enzyme neomycin phosphotransferase II). Non-transfected cells will eventually die off when the culture is treated with neomycin or similar antibiotic.

A similar mechanism can also be used to select for transfected mammalian cells containing a vector carrying a gene encoding for neomycin resistance (either one of two aminoglycoside phosphotransferase genes; the neo selectable marker). This selection process can be used to establish stably transfected mammalian cell lines. Geneticin (G418) is commonly used to select the mammalian cells that contain stably integrated copies of the transfected genetic material.

As used herein, the expressions "negative selection" or "negative screening marker" refers to a marker that, when present (e.g., expressed, activated, or the like) allows identification of a cell that does not comprise a selected property or trait (e.g., as compared to a cell that does possess the property or trait).

A wide variety of positive and negative selectable markers are known for use in prokaryotes and eukaryotes, and selectable marker tools for plasmid selection in bacteria and mammalian cells are widely available. Bacterial selection systems include, for example but not limited to, ampicillin resistance (β-lactamase), chloramphenicol resistance, kanamycin resistance (aminoglycoside phosphotransferases), and tetracycline resistance. Mammalian selectable marker systems include, for example but not limited to, neomycin/G418 (neomycin phosphotransferase II), methotrexate resistance (dihydropholate reductase; DHFR), hygromycin-B resistance (hygromycin-B phosphotransferase), and blasticidin resistance (blasticidin S deaminase).

As used herein, the term "reporter" refers generally to a moiety, chemical compound or other component that can be used to visualize, quantitate or identify desired components of a system of interest. Reporters are commonly, but not exclusively, genes that encode reporter proteins. For example, a "reporter gene" is a gene that, when expressed in a cell, allows visualization or identification of that cell, or permits quantitation of expression of a recombinant gene. For example, a reporter gene can encode a protein, for example, an enzyme whose activity can be quantitated, for example, chloramphenicol acetyltransferase (CAT) or firefly luciferase protein. Reporters also include fluorescent proteins, for example, green fluorescent protein (GFP) or any of the recombinant variants of GFP, including enhanced GFP (EGFP), blue fluorescent proteins (BFP and derivatives), cyan fluorescent protein (CFP and other derivatives), yellow fluorescent protein (YFP and other derivatives) and red fluorescent protein (RFP and other derivatives).

As used herein, the term "tag" as used in protein tags refers generally to peptide sequences that are genetically fused to other protein open reading frames, thereby producing recombinant fusion proteins. Ideally, the fused tag does not interfere with the native biological activity or function of the larger protein to which it is fused. Protein tags are used for a variety of purposes, for example but not limited to, tags to facilitate purification, detection or visualization of the fusion proteins. Some peptide tags are removable by chemical agents or by enzymatic means, such as by target-specific proteolysis (e.g., by TEV protease, thrombin, Factor Xa or enteropeptidase) or intein splicing.

Affinity tags are appended to proteins to facilitate purification or visualization, and include chitin binding protein (CBP), maltose binding protein (MBP), and glutathione-S-transferase (GST), and the poly(His) tag. Solubilization tags are used to promote the proper folding of proteins, thereby improving solubility and minimizing protein precipitation. Solubilization tags include thioredoxin (TRX) and poly (NANP). Some affinity tags have dual roles as a solubilization agent, such as MBP and GST. Chromatography tags are used to improve the resolution of various separation techniques, such as polyanionic amino acid tags such as FLAG-tag. Epitope tags are short peptide sequences which are incorporated into a fusion protein because the availability of high-affinity antibodies to that peptide sequence. Epitope tags include V5-tag, Myc-tag, and HA-tag. These affinity tags have a variety of uses, including western blotting, immunofluorescence, immunoprecipitation and fusion protein purification. Some epitope tags also find use in the purification of antibodies that are specific for the epitope tag. Fluorescence tags are used to visual fusion protein production and protein subcellular localization, for example, under fluorescence microscopy. GFP and its many variants are commonly used fluorescence tags.

Depending on use, the terms "marker," "reporter" and "tag" may overlap in definition, where the same protein or polypeptide can be used as either a marker, a reporter or a tag in different applications. In some scenarios, a polypeptide may simultaneously function as a reporter and/or a tag and/or a marker, all in the same recombinant gene or protein.

As used herein, the term “prokaryote” refers to organisms belonging to the Kingdom Monera (also termed Procarya), generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, a distinguishing ribosomal structure and other biochemical characteristics. Prokaryotes include subkingdoms Eubacteria (“true bacteria”) and Archaea (sometimes termed “archaebacteria”).

As used herein, the terms “bacteria” or “bacterial” refer to prokaryotic Eubacteria, and are distinguishable from Archaea, based on a number of well-defined morphological and biochemical criteria.

As used herein, the term “eukaryote” refers to organisms (typically multicellular organisms) belonging to the Kingdom Eucarya, generally distinguishable from prokaryotes by the presence of a membrane-bound nucleus and other membrane-bound organelles, linear genetic material (i.e., linear chromosomes), the absence of operons, the presence of introns, message capping and poly-A mRNA, a distinguishing ribosomal structure and other biochemical characteristics.

As used herein, the terms “mammal” or “mammalian” refer to a group of eukaryotic organisms that are endothermic amniotes distinguishable from reptiles and birds by the possession of hair, three middle ear bones, mammary glands in females, a brain neocortex, and most giving birth to live young. The largest group of mammals, the placentals (Eutheria), have a placenta which feeds the offspring during pregnancy. The placentals include the orders Rodentia (including mice and rats) and primates (including humans).

As used herein, the term “encode” refers broadly to any process whereby the information in a polymeric macromolecule is used to direct the production of a second molecule that is different from the first. The second molecule may have a chemical structure that is different from the chemical nature of the first molecule.

For example, in some aspects, the term “encode” describes the process of semi-conservative DNA replication, where one strand of a double-stranded DNA molecule is used as a template to encode a newly synthesized complementary sister strand by a DNA-dependent DNA polymerase. In other aspects, a DNA molecule can encode an RNA molecule (e.g., by the process of transcription that uses a DNA-dependent RNA polymerase enzyme). Also, an RNA molecule can encode a polypeptide, as in the process of translation. When used to describe the process of translation, the term “encode” also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that “encode” as used in that case incorporates both the processes of transcription and translation.

As used herein, the term “derived from” refers to a process whereby a first component (e.g., a first molecule), or information from that first component, is used to isolate, derive or make a different second component (e.g., a second molecule that is different from the first). For example, the mammalian codon-optimized Cas9 polynucleotides of the invention are derived from the wild type Cas9 protein amino acid sequence. Also, the variant mammalian codon-optimized Cas9 polynucleotides of the invention, including the Cas9 single mutant nickase and Cas9 double mutant null-nuclease, are derived from the polynucleotide encoding the wild type mammalian codon-optimized Cas9 protein.

As used herein, the expression “variant” refers to a first composition (e.g., a first molecule), that is related to a second composition (e.g., a second molecule, also termed a “parent” molecule). The variant molecule can be derived from, isolated from, based on or homologous to the parent molecule. For example, the mutant forms of mammalian codon-optimized Cas9 (hspCas9), including the Cas9 single mutant nickase and the Cas9 double mutant null-nuclease, are variants of the mammalian codon-optimized wild type Cas9 (hspCas9). The term variant can be used to describe either polynucleotides or polypeptides.

As applied to polynucleotides, a variant molecule can have entire nucleotide sequence identity with the original parent molecule, or alternatively, can have less than 100% nucleotide sequence identity with the parent molecule. For example, a variant of a gene nucleotide sequence can be a second nucleotide sequence that is at least 50%, 60%, 70%, 80%, 90%, 95%, 98%, 99% or more identical in nucleotide sequence compared to the original nucleotide sequence. Polynucleotide variants also include polynucleotides comprising the entire parent polynucleotide, and further comprising additional fused nucleotide sequences. Polynucleotide variants also includes polynucleotides that are portions or subsequences of the parent polynucleotide, for example, unique subsequences (e.g., as determined by standard sequence comparison and alignment techniques) of the polynucleotides disclosed herein are also encompassed by the invention.

In another aspect, polynucleotide variants includes nucleotide sequences that contain minor, trivial or inconsequential changes to the parent nucleotide sequence. For example, minor, trivial or inconsequential changes include changes to nucleotide sequence that (i) do not change the amino acid sequence of the corresponding polypeptide, (ii) occur outside the protein-coding open reading frame of a polynucleotide, (iii) result in deletions or insertions that may impact the corresponding amino acid sequence, but have little or no impact on the biological activity of the polypeptide, (iv) the nucleotide changes result in the substitution of an amino acid with a chemically similar amino acid. In the case where a polynucleotide does not encode for a protein (for example, a tRNA or a crRNA or a tracrRNA), variants of that polynucleotide can include nucleotide changes that do not result in loss of function of the polynucleotide. In another aspect, conservative variants of the disclosed nucleotide sequences that yield functionally identical nucleotide sequences are encompassed by the invention. One of skill will appreciate that many variants of the disclosed nucleotide sequences are encompassed by the invention.

Variant polypeptides are also disclosed. As applied to proteins, a variant polypeptide can have entire amino acid sequence identity with the original parent polypeptide, or alternatively, can have less than 100% amino acid identity with the parent protein. For example, a variant of an amino acid sequence can be a second amino acid sequence that is at least 50%, 60%, 70%, 80%, 90%, 95%, 98%, 99% or more identical in amino acid sequence compared to the original amino acid sequence.

Polypeptide variants include polypeptides comprising the entire parent polypeptide, and further comprising additional fused amino acid sequences. Polypeptide variants also includes polypeptides that are portions or subsequences of the parent polypeptide, for example, unique subsequences (e.g., as determined by standard sequence comparison and alignment techniques) of the polypeptides disclosed herein are also encompassed by the invention.

In another aspect, polypeptide variants includes polypeptides that contain minor, trivial or inconsequential changes to the parent amino acid sequence. For example, minor, trivial or inconsequential changes include amino acid changes (including substitutions, deletions and insertions) that have little or no impact on the biological activity of the polypeptide, and yield functionally identical polypeptides, including additions of non-functional peptide sequence. In other aspects, the variant polypeptides of the invention change the biological activity of the parent molecule, for example, mutant variants of the Cas9 polypeptide that have modified or lost nuclease activity. One of skill will appreciate that many variants of the disclosed polypeptides are encompassed by the invention.

In some aspects, polynucleotide or polypeptide variants of the invention can include variant molecules that alter, add or delete a small percentage of the nucleotide or amino acid positions, for example, typically less than about 10%, less than about 5%, less than 4%, less than 2% or less than 1%.

As used herein, the term "conservative substitutions" in a nucleotide or amino acid sequence refers to changes in the nucleotide sequence that either (i) do not result in any corresponding change in the amino acid sequence due to the redundancy of the triplet codon code, or (ii) result in a substitution of the original parent amino acid with an amino acid having a chemically similar structure. Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the resulting polypeptide molecule.

The following are groupings of natural amino acids that contain similar chemical properties, where substitutions within a group is a "conservative" amino acid substitution. This grouping indicated below is not rigid, as these natural amino acids can be placed in different grouping when different functional properties are considered. Amino acids having nonpolar and/or aliphatic side chains include: glycine, alanine, valine, leucine, isoleucine and proline. Amino acids having polar, uncharged side chains include: serine, threonine, cysteine, methionine, asparagine and glutamine. Amino acids having aromatic side chains include: phenylalanine, tyrosine and tryptophan. Amino acids having positively charged side chains include: lysine, arginine and histidine. Amino acids having negatively charged side chains include: aspartate and glutamate.

As used herein, the terms "identical" or "percent identity" in the context of two or more nucleic acids or polypeptides refer to two or more sequences or subsequences that are the same ("identical") or have a specified percentage of amino acid residues or nucleotides that are identical ("percent identity") when compared and aligned for maximum correspondence with a second molecule, as measured using a sequence comparison algorithm (e.g., by a BLAST alignment, or any other algorithm known to persons of skill), or alternatively, by visual inspection.

The phrase "substantially identical," in the context of two nucleic acids or polypeptides refers to two or more sequences or subsequences that have at least about 60%, about 80%, about 90%, about 90-95%, about 95%, about 98%, about 99% or more nucleotide or amino acid residue identity, when compared and aligned for maximum correspondence using a sequence comparison algorithm or by visual inspection. Such "substantially identical" sequences are typically considered to be "homologous," without reference to actual ancestry. Preferably, the "substantial identity" between nucleotides exists over a region of the polynucleotide at least about 50 nucleotides in length, at least about 100 nucleotides in length, at least about 200 nucleotides in length, at least about 300 nucleotides in length, or at least about 500 nucleotides in length, most preferably over their entire length of the polynucleotide. Preferably, the "substantial identity" between polypeptides exists over a region of the polypeptide at least about 50 amino acid residues in length, more preferably over a region of at least about 100 amino acid residues, and most preferably, the sequences are substantially identical over their entire length.

The phrase "sequence similarity," in the context of two polypeptides refers to the extent of relatedness between two or more sequences or subsequences. Such sequences will typically have some degree of amino acid sequence identity, and in addition, where there exists amino acid non-identity, there is some percentage of substitutions within groups of functionally related amino acids. For example, substitution (misalignment) of a serine with a threonine in a polypeptide is sequence similarity (but not identity).

As used herein, the term "homologous" refers to two or more amino acid sequences when they are derived, naturally or artificially, from a common ancestral protein or amino acid sequence. Similarly, nucleotide sequences are homologous when they are derived, naturally or artificially, from a common ancestral nucleic acid. Homology in proteins is generally inferred from amino acid sequence identity and sequence similarity between two or more proteins. The precise percentage of identity and/or similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are generally available.

As used herein, the terms "portion," "subsequence," "segment" or "fragment" or similar terms refer to any portion of a larger sequence (e.g., a nucleotide subsequence or an amino acid subsequence) that is smaller than the complete sequence from which it was derived. The minimum length of a subsequence is generally not limited, except that a minimum length may be useful in view of its intended function. The subsequence can be derived from any portion of the parent molecule. In some aspects, the portion or subsequence retains a critical feature or biological activity of the larger molecule, or corresponds to a particular functional domain of the parent molecule, for example, the DNA-binding domain, or the transcriptional activation domain. Portions of polynucleotides can be any length, for example, at least 5, 10, 15, 20, 25, 30, 40, 50, 75, 100, 150, 200, 300 or 500 or more nucleotides in length.

Polynucleotide subsequences of the invention have a variety of uses, for example but not limited to, as hybridization probes to identify polynucleotides of the invention, as PCR primers, or as donor sequences to be incorporated into a targeted homologous recombination event.

As used herein, the term "kit" is used in reference to a combination of articles that facilitate a process, method, assay, analysis or manipulation of a sample. Kits can contain written instructions describing how to use the kit (e.g., instructions describing the methods of the present invention), chemical reagents or enzymes required for the method, primers and probes, as well as any other components.

II. Codon Optimized Cas9 Genes

The invention provides a variety polynucleotides that encode bacterial *Streptococcus pyogenes* Cas9 polypeptides and Cas9 polypeptide variants. In some aspects, these polynucleotides encode the wild type Cas9 polypeptide, but the nucleotide sequence of the polynucleotide has been reengineered in order to optimize expression of that bacterial gene in mammalian host cells. One feature that has been modified in the polynucleotides of the invention is the resequencing of the open reading frames to reflect the differences between bacterial cell and mammalian cell preferred codon usage biases.

In some aspects, the invention provides polynucleotides encoding Cas9 proteins, where the nucleotide sequence of the bacterial wild type ORF has been modified in order to reoptimize for expression in either mouse or human cells. This editing process changed the nucleotide sequence of the ORF, but preserved the amino acid sequence of the Cas9 protein.

This editing process took into account a large number of variables that are known to enhance expression of bacterial-derived ORFs in mammalian host cells. Most significantly, the bacterial Cas9 ORF was edited to account for differences in codon usage bias (i.e., codon preference) between bacterial cells and mammalian cells. However, the editing process also took into account other optimization variables, including but not limited to the removal of features such as mRNA secondary structure, RNA instability motifs, cryptic mRNA splicing sites, premature polyadenylation signal sites, negative CpG islands, internal bacterial Chi sequences, tandem rare codons that may disengage the mammalian translational machinery, and direct repeats, reverse repeats and Dyad repeats. In addition, various features were added during editing of the bacterial wild type ORF sequence, including sequences to program proper mammalian mRNA ribosomal entry, and proper translational termination. Restriction sites that might interfere with downstream applications such as subcloning were also removed.

In some aspects, the invention provides polynucleotides that encode variant Cas9 proteins, including mutant Cas9 proteins, e.g., Cas9 proteins containing a single amino acid substitution (D10A) that has lost its native double-stranded nuclease activity, but retains partial function as a single-stranded nickase that cleaves only the complementary strand of DNA. In other aspects, the invention provides polynucleotides that encode a double-mutant (DM) form of the Cas9 protein containing both the D10A mutation as well as a H840A mutation; this mutant form shows no nuclease activity, and is termed a null nuclease.

In some aspects, the invention provides polynucleotides that encode only the open reading frame (ORF) of a Cas9 gene or a Cas9 gene variant, with no other appended sequences. That is to say, the polynucleotide contains only those nucleotides that encode for the amino acids in the Cas9 polypeptide. That ORF can be operably combined with additional sequences to construct functional recombinant genes.

In other aspects, a Cas9 open reading frame can further comprise operably fused nucleotide sequences that encode any number and any type of beneficial amino acid sequences, for example, any type of fused polypeptide marker or tag of any desired sequence, or fused peptide sequences that mark the fusion protein for a particular post-translational modification, e.g., phosphorylaton, glycosylation, acetylation or lipidation such as myristoylation. The disclosure provides numerous examples of protein markers and protein tags, any of which find use with the invention. The invention is not to be limited to polypeptide markers or tags recited herein, as one of ordinary skill recognizes the diversity of markers and tags known in the art that readily find use with the invention.

In other aspects, the invention provides mammalian codon-optimized polynucleotides encoding Cas9 proteins, and further where the codon optimized open reading frames have been operably fused in frame with nucleotide sequences that encode one or more nuclear localization signal, required for transport of expressed proteins into the mammalian cell nucleus. The invention is not to be limited to any particular nuclear localization signal peptide sequence recited herein, as many different NLS sequences can find use with the invention. The amino acid and corresponding polynucleotide sequences provided in the present disclosure are meant merely to illustrate examples of NLS sequences that can be used, and are not intended to limit the invention. Many suitable NLS sequences are known in the art that find use with the invention, as recognized by one of ordinary skill in the art.

In one aspect, a Cas9 nucleotide sequence of the invention includes a Cas9 ORF (and the encoded polypeptide) without any additional fused nucleotide sequences, thereby encoding only the Cas9 protein without any fused amino acid sequence. In other aspects, any combination, any type and any quantity of appended nucleotide sequences can be used to produce Cas9 fusion genes of the invention. For example, a Cas9 fusion gene and protein of the invention can include one or any number of operably linked nuclear localization signals, one or any number of fused polypeptide tags, for example, the myc-tag for ease of detection and purification of the recombinant Cas9 protein, one or any number of fused marker protein, for example, a red fluorescent protein, green fluorescent protein, blue fluorescent protein, or any other kind of fluorescent protein marker. If multiple constructs and/or proteins are to be expressed in the same cell, each can be associated with a unique tag or maker to allow independent monitoring of protein expression or genomic integration. For example, green fluorescent protein, red fluorescent protein, luciferase and/or chloramphenicol acetyltransferase (CAT) can all be independently detected in the same cell.

Other types of beneficial nucleotide sequences that encode polypeptides, or even singe amino acids, can also be operably linked to the Cas9 ORF to produce Cas9 fusion proteins with additional functionalities. For example, these include but are not limited to, protease recognition sites, signal sequences for post-translational modification, and unnatural amino acids that have beneficial functionalities such as resistance to degradation (improved half life of the fusion protein) and chemically reactive side chains.

In other aspects, a polynucleotide of the invention encoding a Cas9 polypeptide can optionally include operably linked nucleotide regulatory sequences (i.e., non-coding sequences) that produce a functional gene. That is to say, a Cas9 ORF polynucleotide of the invention can be operably linked to regulatory sequences that lead to accurate and efficient transcription and translation of a Cas9 ORF. These regulatory sequences can include, but are not limited to, enhancer elements, promoter elements, termination sequences (for either transcription or translation), polyadenylation signal sequences and intron/exon splicing sequences. In some embodiments, a Cas9 gene of the invention is contained in an expression vector, which may have other nucleotide sequences including an origin of replication, one or more selectable marker, a visual marker, and/or a site that facilitates manipulation of the vector and insertion or subcloning of additional gene sequences, such as one or more restriction site or a multiple cloning site (MCS).

In other aspects, a Cas9 nucleotide sequence of the invention can optionally include operably linked untranslated regions (UTR) that are present on the mRNA, but do not typically encode for protein. UTR have a regulatory function, and can regulate processing of the primary transcript to produce mRNA, stabilize the mRNA, or contribute to translational control in the mammalian host cells. Five prime untranslated regions (5' UTR; also known as a leader sequence) directly upstream from the initiation codon is typically important for the regulation of translation of the transcript. The three prime untranslated region (3'-UTR) immediately following the translation termination codon also has regulatory function.

The present disclosure provides, in part, the following polynucleotides encoding Cas9 polypeptides and variant Cas9 polypeptides, which are a feature of the invention. These nucleotide sequences comprise mammalian codon-optimized open reading frames.

| SEQ ID NO: | FIG. number | Polynucleotide Description |
|---|---|---|
| 3 | 20 | Mammalian Codon-Optimized *Streptococcus pyogenes* Wild Type cas9 Gene Open Reading Frame Nucleotide Sequence |
| 4 | 21 | Mammalian Codon-Optimized *Streptococcus pyogenes* Wild Type cas9 Gene Open Reading Frame Encoding N- and C-Terminal Nuclear Localization Signals |
| 6 | 23 | Mammalian Codon-Optimized *Streptococcus pyogenes* Wild Type cas9 Gene Open Reading Frame Encoding Fused N-terminal myc-tag and N- and C-Terminal Nuclear Localization Signals |
| 7 | 24 | Mammalian Codon-Optimized *Streptococcus pyogenes* Mutant cas9 Gene Open Reading Frame Encoding Single Mutation (D10A) Nickase |
| 8 | 25 | Mammalian Codon-Optimized *Streptococcus pyogenes* Mutant cas9 Gene Open Reading Frame Encoding Single Mutation (D10A) Nickase with Fused N-terminal myc-tag and N- and C-Terminal Nuclear Localization Signals |
| 9 | 26 | Mammalian Codon-Optimized *Streptococcus pyogenes* Mutant cas9 Gene Open Reading Frame Encoding Double Mutation (D10A and H840A) Null Nuclease |
| 10 | 27 | Mammalian Codon-Optimized *Streptococcus pyogenes* Mutant cas9 Gene Open Reading Frame Encoding Double Mutation (D10A and H840A) Null Nuclease Fused with N-terminal myc-tag and N- and C-Terminal Nuclear Localization Signals |

When protein-coding nucleotide sequences are provided, one of skill in the art recognizes that the last codon that is provided may or may not be a stop codon (e.g., TGA). When a protein-coding nucleotide sequence is manipulated, for example to construct fusion genes encoding fusion proteins), any stop codon at the 3'-terminus of the polynucleotide needs to be removed and reengineered in order to produce C-terminal fusions with that corresponding polypeptide.

The present disclosure provides, in part, the following Cas9 polypeptides and variant Cas9 polypeptides, which are also a feature of the invention.

| SEQ ID NO: | FIG. number | Polypeptide Description |
|---|---|---|
| 5 | 22 | *Streptococcus pyogenes* Wild Type cas9 Protein Fused with N-terminal myc-tag and N- and C-Terminal Nuclear Localization Signals |
| 11 | 28 | *Streptococcus pyogenes* Wild Type cas9 Protein Fused with N- and C-Terminal Nuclear Localization Signals |
| 12 | 29 | *Streptococcus pyogenes* Mutant cas9 Protein containing Single Mutation (D10A) Nickase Fused with N- and C-Terminal Nuclear Localization Signals |
| 13 | 30 | *Streptococcus pyogenes* Mutant cas9 Protein containing Double Mutation (D10A and H840A) Null Nuclease with Fused N- and C-Terminal Nuclear Localization Signals |

One of skill in the art will appreciate that the invention is not limited to the polynucleotide or polypeptide sequences disclosed and recited by sequence herein. One of skill will appreciate that the invention also provides many related variant sequences, which are also within the scope of the invention, including variant polypeptides and variant polynucleotides.

Variant polypeptide sequences are polypeptides having conservative amino acid substitutions in the amino acid sequences provided herein, and the polynucleotides that encode those variants, are within the scope of the invention. Conservative amino acid substitutions are changes in the amino acid sequence that result in the substitution of one or more amino acid with a different amino acid having similar chemical properties. Variant polypeptides also includes mutant versions of the polypeptides of the invention (and the polynucleotides that encode them), and are also within the scope of the invention. For example, mutant versions of the wild type Cas9 polypeptide include the single mutant nickase polypeptide, and the double mutant null nuclease polypeptide.

Variant polynucleotides of the invention include polynucleotides that encode for any variant Cas9 polypeptide of the invention. Also for example, variant polynucleotides of the invention include Cas9 polynucleotides of the invention that are modified to contain some trivial or inconsequential change in nucleotide sequence, where the function or activity of the variant polynucleotide remains essentially the same as the disclosed polynucleotide. For example, a Cas9 polynucleotide of the invention that has been modified to contain a nucleotide substitution that does not change the amino acid sequence is a variant polynucleotide of the invention.

In other aspects, subsequences (e.g., portions or fragments) of the polynucleotides of the invention are also within the scope of the invention. For example, subsequences of mammalian codon optimized polynucleotides encoding Cas9 polypeptides are within the scope of the invention. For example, subsequences of these Cas9 polynucleotides that are at least 50 base pairs in length, at least 100 base pairs in length, at least 200 base pairs in length, at least 300 base pairs in length, at least 500 base pairs in length, or at least 1,000 base pairs in length are within the scope of the invention.

III. Vectors

Vectors comprising a polynucleotide of the invention are also a feature of the invention. Polynucleotides of the invention can be incorporated into any desired DNA or RNA based vector, without limitation. For example, a Cas9 open reading frame of the invention can be cloned into an expression vector (for example, an expression vector optimized for RNA expression in mammalian cells, human cells, or mouse cells), a subcloning vector, a shuttle vector, a vector designed for use with in vitro transcription reactions, cosmids, phagemids, and vectors derived from mammalian viruses, including retroviruses (for example, lentiviruses), adenoviruses, and adeno-associated viruses (AAV).

Episomal EBNA-based vectors are also a feature of the invention, which include the Epstein-Barr virus origin of replication OriP and the EBNA-1 protein for relatively long term vector maintenance. The EBNA protein can be delivered in two formats: (i) the Cas9 all-in-one cassette contains an OriP only and the delivery of EBNA is by mRNA transfection, or (ii) the all-in-one cassette contains both Orip and the EBNA gene open reading frame in the single all-in-one construct.

In some applications, vectors of the invention can be conveniently supplied and used in their circular form, or in a linearized form. The linearized form finds use in subcloning steps such as in cloning the guide RNA target sequence into the host vector. Linearized vectors are also used in in vitro transcription reactions.

A) Expression Vectors

In some aspects, the invention provides a wide variety of expression vectors for expression of various products. An expression vector of the invention can be optimally designed to express a protein, e.g., a Cas9 protein or a variant Cas9 protein, in a mammalian host cell. In that embodiment, a vector comprising protein-coding open reading frame and suitable regulatory elements can be delivered into the host cell by any suitable method of transfection or transduction. Within the cell, that ORF is transcribed by endogenous RNA polymerases (RNA pol II in the case where a protein coding gene is expressed) to produce mRNA, and that in turn is translated to produce the encoded protein.

In other aspects, the invention provides expression vectors optimally designed to express a functional RNA molecule, e.g., a chimeric crRNA-tracrRNA molecule that serves as a guide RNA for Cas9 tethering to a target sequence, in mammalian cells. In those embodiments, a vector encoding the guide RNA sequence can be delivered into the host cell by any suitable method of transfection or transduction. Within the cell, those sequences are transcribed by endogenous RNA polymerases (RNA pol III in the case where a CRISPR-type RNA will be expressed) to produce a functional guide RNA molecule.

In other aspects, the invention provides expression vectors that are designed to express either a Cas9 mRNA or a guide RNA in a mammalian host cell, where these two sequences are expressed from two separate expression vectors. In other aspects, the invention provides expression vectors that are designed to express both a Cas9 mRNA and a guide RNA from the same vector in a mammalian host cell, where that vector carries the necessary regulatory elements to express both products. As used herein, these vectors are termed "all-in-one vectors."

B) Promoters and Regulatory Elements

Polynucleotides of the invention are most typically in the context of a vector, such as an expression vector. The expression vector can be associated with any type and any quantity of regulatory elements. Such elements can promote the strong and accurate transcription of the polynucleotide of the invention, for example, to generate mRNA, either in a cell, or in an in vitro transcription reaction. Regulatory elements can refer to DNA elements that regulate transcription or regulate translation. Regulatory elements can reside upstream of an open reading frame, or downstream of an open reading frame. It is not intended that the invention be limited to any particular type or sequence of regulatory elements.

In various aspects, the polynucleotides of the invention, e.g., a Cas9 ORF, are transcribed within mammalian cells to produce mRNA. When mRNA is to be produced (such as when Cas9 encoding genes are transcribed), transcription is directed by an RNA type II polymerase (RNA pol II), which requires a mammalian pol II promoter sequence. The pol II promoter that is used is not limited in any respect. Promoters that function constitutively and promoters that are regulated by induction or repression all find use with the invention. It is not intended that the invention be limited to any of the promoters disclosed herein, as one of ordinary skill in the art recognizes that a wide variety of promoters find use with the invention, for example, constitutively active promoters, inducible promoters, repressible promoters, tissue specific promoters and cell-type specific promoters.

When Cas9 protein is to be expressed, RNA pol II promoters that can drive high levels of protein expression in mammalian cells are generally preferred, and most preferably, are active in a wide range of cell types and species. Constitutively active promoters commonly used in mammalian systems include the simian virus 40 early promoter (SV40), cytomegalovirus immediate-early promoter (CMV), human ubiquitin C promoter (UBC), human elongation factor 1 alpha promoter and hybrid promoter (EF1-α), mouse phosphoglycerate kinase 1 promoter (PGK), and chicken β-actin promoter coupled with CMV early enhancer (CAG) promoter and murine stem cell virus (MSCV) promoter.

In some embodiments, it is desirable to express Cas9 polypeptides only in certain cell types. In those embodiments, the use of tissue specific or cell type specific mammalian promoters can be used. Examples of tissue specific or cell type specific mammalian promoters finding use with the invention include, for example, the human apolipoprotein E promoter and human alpha-1-antitrypsin (AAT) promoter, the human interleukin-2 (IL-2) gene promoter and the estrogen receptor (ER) gene promoter. Other cell type specific promoters include a variety of neuron-specific promoters, muscle-specific promoters and hematopoietic-specific promoters. Tumor specific promoters also find use in the construction of expression vectors of the invention.

An expression vector of the invention can include translation regulatory elements that control accurate translation of the mRNA to produce protein. For example, a Cas9 ORF can be linked to translation initiation sequences, translation termination sequences and/or other post-transcriptional regulatory sequences, such as the woodchuck virus post-transcriptional regulatory element (WPRE) to boost gene expression and stabilize the mRNA transcript.

When guide RNA transcript is to be expressed in a mammalian host cell, transcription is directed by an endogenous RNA type III polymerase (RNA pol III), which requires a mammalian pol III promoter sequence that is operably linked to the guide RNA sequence. In these embodiments, a vector comprising gRNA sequence (including the targeting sequence) driven by an RNA pol III promoter is delivered into the mammalian host cell using any suitable transfection or transduction method. Within the cell, the host RNA pol III enzyme generates a transcript to produce the guide RNA molecule. The disclosure provides examples of pol III promoters that find use with the invention, including the H1 RNA gene promoter. However, it is not intended that the invention be limited to these pol III promoters, as one of ordinary skill in the art recognizes that a wide variety of pol III promoters find use with the invention, for example, the U6 promoter and the 7SK promoter.

C) In Vitro Transcription Vectors

In some aspects, the vectors of the invention are designed to function as template for use with in vitro transcription (IVT) reactions. In those embodiments, the vector will contain at least one suitable bacteriophage promoter that can be utilized by a purified bacteriophage RNA polymerase in the IVT reaction, thereby generating transcription products of the downstream sequences. Preferably, linearized vectors are used in an IVT reaction. A variety of IVT systems can be used, for example, T7, SP6 or T3 promoter/polymerase IVT systems.

The IVT reaction will generate RNA molecules that can then be used in the transfection of mammalian host cells. The IVT RNA products are preferably purified before use in the mammalian cell transfections.

In some embodiments, vectors of the invention are used as template in PCR reactions to generate double stranded amplicons that can then be used in IVT reactions. When PCR amplicons containing suitable IVT promoter sequences are generated, the promoter sequences can be encoded by either the original vector, or they can be generated in the amplicon by use of PCR primers designed to encode and fuse the IVT promoter sequences to the amplicon.

In some aspects, bifunctional vectors can be produced that can function in either vector DNA transfections into mammalian host cells, or alternatively, can be used in IVT reactions to generate transfectable RNA products. In these aspects, a mammalian promoter capable of driving Cas9 mRNA transcription in a host cell can optionally be fused to a suitable bacteriophage promoter sequence (e.g., T7, SP6 or T3 systems) capable of driving the production of RNA in an IVT reaction. These vectors can then be used in either DNA transfections into mammalian host cells (where mRNA is produced in the mammalian host cell by native RNA polymerases using an RNA pol II promoter) or in cell-free IVT reactions to produce transfectable RNA. The IVT reactions can be used to produce either or both the mRNA that encodes the Cas9 protein, and the guide RNA targeting molecule, which are then used in transfections into a mammalian host cell.

In some embodiments, host cells of the invention can be cotransfected with a combination of one or more vectors of the invention (e.g., a Cas9 expression vector) and simultaneously with in vitro transcribed RNA (e.g., an in vitro transcribed guide RNA molecule), or vice versa.

D) Host Cells

In some aspects, vectors of the invention are located within host cells. Host cells comprising a polynucleotide or a vector of the invention is also a feature of the invention. The polynucleotide of the invention that is contained in the host cell can be of any type, for example, an expression vector of the invention, or a mRNA molecule that was produced by in vitro transcription, or an mRNA molecule that was produced by in vivo transcription within the host cell using endogenous RNA polymerases. The type of host cells finding use with the invention are not limited, as many types of host cells can be used.

In some aspects of the invention, bacterial host cells find use, for example, in propagating and producing plasmid DNA. Mammalian host cells such as mouse or human cells find use with the invention as containing targets for genomic editing, and targets for gene regulation. It is not intended that the invention be limited to the human host cells described herein, as the invention is widely applicable to cells derived from many species, including all primates, mouse, rat, and any other mammalian species. Similarly, the invention is widely applicable to use in many cell types, e.g., neuronal cells, muscle cells, cardiac cells and cells derived from connective tissue.

Mammalian cell lines created using the host cells of the invention find widespread use in disease modeling, proof-of-concept research in the development of genetic-based therapeutics, and in generating genomically engineered cell lines, for example stem cells, for use in therapeutic transplantation in the treatment of disease, both in humans and other mammals. Some cell types derived from host cells of the invention find particular use for the purpose of creating transgenic animals (such as transgenic mice) for use in disease modeling and development of gene-based therapeutics.

IV. All-in-One CRISPR Vectors Expressing Cas9 and Guide RNA

The recombinant CRISPR systems for directed genomic modification or gene regulation utilize two components, which are (i) a Cas9 polypeptide, and (ii) a guide RNA consisting of a chimeric crRNA-tracrRNA scaffold and a target sequence that directs the nuclease activity of the Cas9 polypeptide to a desired genomic locus. The guide RNA is customized in order to bind a genomic target of interest.

In some embodiments of the invention, the nucleotide sequences encoding the Cas9 polypeptide and the guide RNA are provided to a mammalian host cell on two separate nucleic acids, for example, two separate vectors, or two separate RNA molecules generated by in vitro transcription.

In some embodiments of the invention, the nucleotide sequences encoding the Cas9 polypeptide and the guide RNA are provided to a mammalian host cell on a single vector, requiring the transfection of only one vector into the mammalian host cell. This configuration is termed an "all-in-one" vector. See, for example, FIGS. 1A-1D, 3A, 3B, 6A, 15A-15C and 16A.

The Cas9 gene that is delivered to a host cell (either in a stand-alone vector or in an all-in-one vector) can comprise any suitable Cas9 nucleotide sequence. For example, when a targeted double stranded cleavage event is desired at the genomic target sequence, then a Cas9 polypeptide having wild type nuclease activity (double stranded nuclease) is used, e.g., as shown generally in FIG. 1B. If a single strand nicking event is desired at the genomic target, then a Cas9 mutant have single strand cutting activity (a nickase) is used, e.g., as shown generally in FIG. 1C. If the CRISPR system is used to deliver transcriptional regulatory motifs to a genomic target in order to modulate transcription of a target gene, then a Cas9 mutant having no DNA nuclease activity (a null nuclease having neither single stranded nor double stranded nuclease activity) can be used, e.g., as shown generally in FIG. 1D. In that case, a gene encoding a Cas9 double mutant (DM) null nuclease can be used to construct the delivery vector.

The Cas9 polypeptide that is encoded can be the wild type polypeptide, or a variant polypeptide (e.g., a mutant form of the Cas9 protein, or a conservative variant or fusion protein thereof), depending on the intended use of the CRISPR system. In one aspect, the invention provides a large number of polynucleotides encoding Cas9 proteins that can be used with the CRISPR system. These polynucleotides encode for the Cas9 polypeptides using nucleotide sequences that are optimized for expression in mammalian host cells. The invention provides codon-optimized nucleotide sequences that encode for wild type and mutant forms of Cas9 polypeptides that comprise essentially only the open reading frame of the protein (e.g., the nucleotide sequences of SEQ ID NOS: 3, 7, 9), or the wild type or mutant forms of the Cas9 ORF that have been fused to one or more nuclear localization signal (e.g., the nucleotide sequences of SEQ ID NO: 4, and a nucleotide sequence encoding a polypeptide of SEQ ID NOS: 11, 12 and 13), or a Cas9 ORF that has been fused to both a tag and one or more NLS (e.g., the nucleotide sequences of SEQ ID NOS: 6, 8, 10). In some aspects, the invention includes polynucleotides encoding a Cas9 polypeptide comprising essentially the native *Streptococcus pyogenes* Cas9 ORF (SEQ ID NO: 2).

The invention also includes variants of these polynucleotides, including variants that encode mutant forms of the Cas9 polypeptide. Other types of variant nucleotide sequences are also a feature of the invention, including any cas9 nucleotide sequence not recited herein but is based on or derived from a Cas9 nucleotide sequence specifically recited herein, for example, derived from SEQ ID NO: 3. Other types of variant nucleotide sequences that are a feature of the invention include nucleotide sequences that contain nucleotide substitutions that encode conservative amino acid substitutions in the corresponding Cas9 polypeptide, and nucleotide substitutions, deletions or insertions that amount to trivial or non-consequential changes in either the mRNA or corresponding encoded protein.

To make the RNA-directed Cas9 system more efficient, affordable, and convenient, a programmable all-in-one vector system was developed. This single vector system expresses both a Cas9 nuclease and a guide RNA, thereby simplifying transfection protocols by requiring the transfection of only a single plasmid. The workflow for the cloning, validation and transfection of the Cas9/gRNA all-in-one expression construct is a follows.

A) Construction of all-in-One Vectors

In some embodiments, the all-in-one vectors can be configured with a mammalian codon-optimized gene encoding the wild type Cas9 double stranded nuclease protein, e.g., the hspCas9 gene. Alternatively, in other embodiments, the vector can comprise a mammalian codon-optimized gene encoding a mutant form of Cas9 having single strand nickase activity, hspCas9 (D10A) nickase, which is used to enhance genome editing specificity when used in conjunction with two gRNAs flanking the target of interest to generate double nicking with a 5'-overhang. In still other embodiments, the CRISPR all-in-one vectors can comprise a mammalian codon-optimized gene encoding a mutant form of Cas9 having no nuclease activity, for example, a Cas9 double mutant (D10A and H840A) null nuclease, encoded by, for example, hspCas9 DM.

Suitable CRISPR guide sequence is also encoded on the all-in-one vectors. Target sequence is inserted into the all-in-one vector adjacent to the chimeric tracrRNA-crRNA gRNA scaffold. This scaffold is a single engineered nucleotide sequence that functionally replaces individual crRNA and tracrRNA molecules that are present in the native bacterial CRISPR systems. In some aspects, the scaffold can have the nucleotide sequence: GTTTTAGAGCTAGAAATAGCAAGTTAAAATAAGGCTAGTCCGTTATCAACTTGAAAAAGTGGCACCGAGT CGGTGCTTTTTTT (SEQ ID NO: 42). See FIGS. 1E and 1F.

Alternatively, other guide RNA scaffolds can be used. For example, a modified chimeric scaffold can be used having the nucleotide sequence: GTTTAAGAGCTATGCTGGAAACAGCATAGCAAGTTAAAATAAGGCTAGTCCGTTATCAACTTGAAAAAGT GGCACCGAGTCGGTGCTTTTTTT (SEQ ID NO: 43). It is not intended that the invention be limited to any particular guide RNA scaffold sequence or scaffold architecture.

In order to create an all-in-one vector containing a target specific CRISPR guide RNA, generally the following steps are used. First, two DNA single stranded oligonucleotides are designed that are sense and antisense sequences of the desired DNA target, where the target is about 20 base pairs upstream of the protospacer adaptor motif (PAM; 5'-NGG-3', where N=any nucleotide). The selection of the target DNA sequence is not limited by any constraints, with the exception of the PAM sequence immediately following the target sequence. The typical length of the target sequence is about 20 base pairs (as shown in FIG. 1F), although target sequences that are longer or shorter can be used.

For example, two DNA oligonucleotides (a top strand and a bottom strand) can be designed according to the following structure shown below.

```
                                        (SEQ ID NO: 16)
5'-TGTATGAGACCACTTNNNNNNNNNNNNNNNNNNNN-3'

                                        (SEQ ID NO: 44)
3'-ACTCTGGTGAANNNNNNNNNNNNNNNNNNNNNCAAA-5'
```

The top strand has an overhang at its 5'-end, which is TGTATGAGACCACTT (SEQ ID NO: 45), followed by the selected target sequence. The bottom strand has an AAAC overhang at its 5'-end followed by a target sequence complementary to the top strand and an AAGTGGTCTCA (SEQ ID NO: 46) overhang at its 3'-end. For example, if the target sequence is:

```
                                        (SEQ ID NO: 47)
AGCGAGGCTAGCGACAGCATAGG
(AGG = PAM sequence),
```

then the two single stranded oligonucleotides sequences would be:

```
top strand:
                                        (SEQ ID NO: 48)
5'-TGTATGAGACCACTTAGCGAGGCTAGCGACAGCAT-3'

bottom strand:
                                        (SEQ ID NO: 49)
5'-AAACATGCTGTCGCTAGCCTCGCTAAGTGGTCTCA-3'
```

Second, the two single stranded oligonucleotides are annealed to generate a sticky ended duplex oligonucleotide for cloning into a linearized expression vector by ligation. Two BsaI restriction sites placed adjacent to the guide RNA scaffold sequence facilitate the cloning of the oligonucleotide duplex target sequence into the vector backbone. The BsaI restriction sites are cut, then used to receive the synthetic oligonucleotide into the guide scaffold architecture. See FIG. 1E.

Third, transform the ligation products into competent *E. coli* cells, grow and select positive clones using LB/kanamycin. Confirm the correct clones by plasmid construct sequencing.

B) Transfection of all-in-One Vectors into Host Cells

Once the vector is prepared, cultured cells are transfected with the construct(s). The protocol below is a general method for transfecting HEK 293T cells, but the method is applicable to many cultured, adherent mammalian cells. The invention is not limited to the use of this host target cell, as a variety of other host cells can be used depending on the application.

Approximately 100,000 to 200,000 target cells (e.g., 293T cells) are plated into a single well of a 12-well plate in one mL of appropriate growth medium. A single well of cells are used as a negative control (which can be a transfection of non-relevant plasmid DNA or linearized Cas9 nuclease plasmid DNA, or untransfected cells).

The next day, or when cells are 50-60% confluent, target cells are transfected with an all-in-one Cas9 vector (and donor vector if homology directed recombination (HDR) is desired) using a suitable transfection protocol following the manufacturer's recommendation for 6-well plates. The use of reduced serum or serum-free media containing no antibiotics to dilute the vector/transfection complex is recommended. For 293T cells, 0.5 μg of the Cas9 vector has been successfully transfected into cells for cleavage of a target luciferase gene and used in a 1:1 ratio of Cas9 vector (0.5 μg) with the homologous recombination donor vector (0.5 μg) for HDR applications. A plasmid ratio of 1:1.5 of Cas9 vector to donor vector has also been successfully used in 293T cells. It is best to optimize the amounts and ratios of Cas9 vector and donor vectors for optimal results in a particular target cell line. Allow at least 12 hours before changing transfection media to complete growth media.

C) Methods for Verifying Guide RNA Specificity

Cultured cells can be assayed for site specific genomic cleavage activity using either a SURVEYOR® Mutation Detection assay (Transgenomic®, Inc.) or other suitable mismatch cleavage assays, mutation characterization by genotyping analysis, or by assessing HDR activity (if donor vector is also supplied to the transfection system in parallel) at about 48-72 hours following transfection. If assaying for HDR of donor vector sequences, cells that contain the desired integrated sequences from the donor vector can be selected using either FACS-based sorting of a fluorescent marker or by antibiotic selection (e.g., Puro/Neo) using a suitable concentration of antibiotics to culture the targeted cell line.

V. Methods for Genomic Editing

The Cas9 Nuclease system for genomic targeting can be used in two ways. The wild-type hspCas9 vectors retain their nuclease domains and will produce double-stranded breaks in the target as guided by the gRNA. This system can be used with HR vectors or applied to mutating a targeted site because it elicits nonhomologous end joining (NHEJ) and insertions/deletions at the site of DNA cleavage.

One amino acid mutation at position D10A in Cas9 results in the inactivation of the nuclease catalytic activity and converts Cas9 to a "nickase" enzyme that makes single-stranded breaks at the target site. This Cas9 Nickase can be used at a targeted site to favor homologous recombination at the site with HR vectors and lowers the rate of NHEJ. The Cas9 double mutant (DM) with changes at amino acid positions D10A and H840A completely inactivates both the nuclease and nickase activities.

Both these variant forms of Cas9 are provided by present disclosure, and can be expressed from the all-in-one CRISPR vector system. These Cas9 vectors were tested and validated for the nickase and loss of activity in assays comparing to the wild-type hspCas9 vector with the AAVS1 gRNA in combination with an AAVS1 HR vector harboring a GFP marker.

In one aspect, the invention provides methods and entire systems for genomic modification that utilize the codon optimized Cas9 polynucleotide. For example, an all-in-one CRISPR system for genomic modification is provided, comprising (i) an polynucleotide encoding an *S. pyogenes* Cas9 protein or variant thereof, and (ii) guide-RNAs for RNA-guided genome engineering in human or mouse cells.

To accommodate the wide variety of potential applications, several features of all-in-one CRISPR II system are customizable. Although the EF1-α hybrid promoter is utilized herein to drive the expression of Cas9 in the all-in-one CRISPR II systems, the design of all-in-one constructs allows easy swapping of the EF1-α hybrid promoter with any kind of pol II promoter. This feature allows all-in-one CRISPR systems to be easily adopted by researchers in different fields. The all-in-one systems described herein also simplify the cloning of gRNA by simply annealing oligos without PCR, and the transformation efficiency of this system achieves 99%. This allows the systems to be easily and cost effectively used by researchers without molecular cloning experience.

The present disclosure provides discussion of mechanistic theories explaining in vivo phenomena, including transcriptional regulation and genomic modification, e.g., by homologous recombination. However, it is not intended that the invention be limited in any regard to the molecular mechanism of action, and knowledge of such mechanisms is not required to make or used the invention. It is not intended that the term "homologous recombination" as used herein be limited in any way with regard to the in vivo mechanism of such genomic modification.

It is not intended that the invention be limited to the generation of any one type of all-in-one CRISPR vector. For example, various Cas9 polypeptides can be incorporated, and wide variety of vector configurations can be used, without departing from the scope of the invention.

A) Validation Data for the Wild Type Cas9 System Targeting the Human AAVS1 Sequence The disclosure provides various examples of proof-of-principle and validation studies using the CRISPR systems of the invention. These studies are intended to illustrate the invention, but not limit the invention.

In one initial validation experiment, the CRISPR-Cas9 nuclease system was compared head-to-head against a TALEN gene-targeting system directed to the well established human AAVS1 locus in the enhanced green fluorescent inhibited protein (EGIP) cell line. See Example 4, and FIG. 3D. The TALEN pair (pZT-AAVS1 L1/R1) has been previously validated for cleavage activity and HDR efficiency, with rates of ~25% for cleavage efficiency and 8.1% efficiency for homology directed recombination in 293T cells (Jizhong Zou, the National Institutes of Health, Center for Regenerative Medicine).

A vector containing a humanized gene sequence (hspCas9 gene; FIG. 23) encoding and expressing the wild type Cas9 protein fused with myc-tag and two nuclear localization signals (FIG. 22) was constructed. Using the Cas9 nuclease expression system (FIG. 3A), a known guide RNA target sequence (FIG. 3C) was cloned into the guide RNA scaffold. The constructions were transfected into the EGIP cell line, along with EGFP donor sequence. The TALEN pair and the CRISPR system were compared in their efficacies to induce cleavage and HDR in the host cell line. Successful homology-directed recombination was assessed by observing the appearance of rescued green fluorescence in the host cells. It was observed that this combination of CRISPR reagents could clearly rescue EGFP signal in the host cells, indicating an accurate HR event (FIG. 4). This verification system also showed that a bacterially encoded Cas9 (spCas9) fused with an mCherry RFP marker to produce a fusion protein (FIG. 3B) also has the ability to direct accurate HDR.

This same experimental system using the same transfected materials and same host cells was also verified using a SURVEYOR® Mutation Detection assay. See Example 5. That assay confirmed that the hspCas9 and the spCas9-mCherry fusion are both able to target and cleave the genomic AAVS target sequence in a predicted manner, generating double stranded breaks at the same position, corresponding to the AAVS sequence.

B) Validation Data for the Wild Type Cas9 System Targeting a Luciferase Gene

To further validate the RNA-directed Cas9 nuclease system, it was tested whether a codon optimized WT cas9 gene and a pair of programmed guide RNAs could direct cleavage and HDR at a second genomic target sequence. See Example 6 and FIG. 6C. A cell line containing an integrated vector expressing GFP and luciferase from the CMV promoter was used as the host cell. Two gRNAs which target genomic sequence flanking the luciferase gene were designed and cloned. FIGS. 6A and 6B. A donor vector was constructed containing a red fluorescent protein (RFP) sequence and homology sequences flanking the luciferase gene. This experimental system provided a powerful cross-validation experiment which can assess HDR by monitoring four different characteristics. If HDR proceeds as predicted, then HDR can be monitored by (i) loss of luciferase activity, (ii) accurate DNA cleavage at the targeted sites using the SURVEYOR® Nuclease Mutation Detection assay, (iii) the appearance of red fluorescent cells in the transfected cultures, and (iv) a sorted population of RFP positive cells would be expected to contain no green fluorescence.

All four of these features were confirmed following transfection of the cells. This system showed (i) a reduction up to 40% of luciferase activity using one of the gRNAs targeting the luciferase locus (Luc-gRNA1), (ii) approximately 30% DNA cleavage efficiency as measured using the SURVEYOR® assay, (iii) the appearance of red fluorescent cells following transfection, and (iii) the loss of green fluorescence correlating with the appearance of red fluorescence in a red-sorted cell population. This data strongly indicates effective targeting of the CRISPR system for the induction of targeted genomic editing.

C) Validation Data for Paired Guide RNA Nickase Gene Targeting

In some aspects, the invention provides CRISPR systems that incorporate Cas9 nickase mutants to direct accurate DNA nicking (without non-homologous end joining), and where the accurate nickase activity is used advantageously in methods for genomic editing incorporating two paired guide RNAs to produce a 5' overhang structure that triggers HDR in the presence of donor DNA. See FIG. 10A.

Figure 3D:
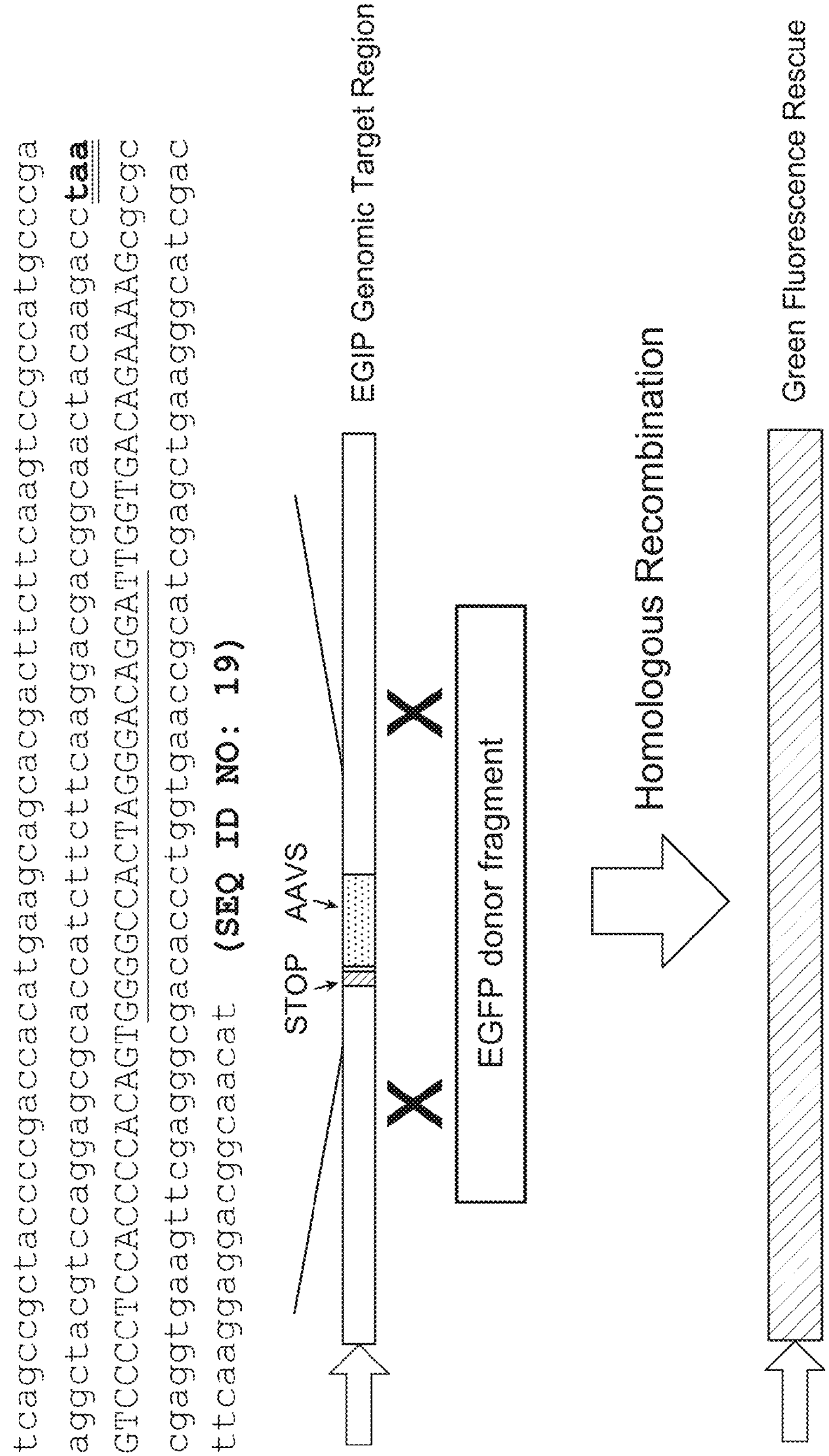
FIG. 3D provides a schematic of the recombinant genomic nucleotide sequences contained in the EGIP reporter cell line. EGFP sequence is in lowercase. The stop codon TAA is shown in lowercase. The AAVS insert is in uppercase. The portion of the AAVS insert targeted by the gRNA is underlined. The homologous recombination event with a complete EGFP donor fragment to restore the complete EGFP sequence at the genomic locus and thereby rescue green fluorescence in the cell line is illustrated.
Figure 4:
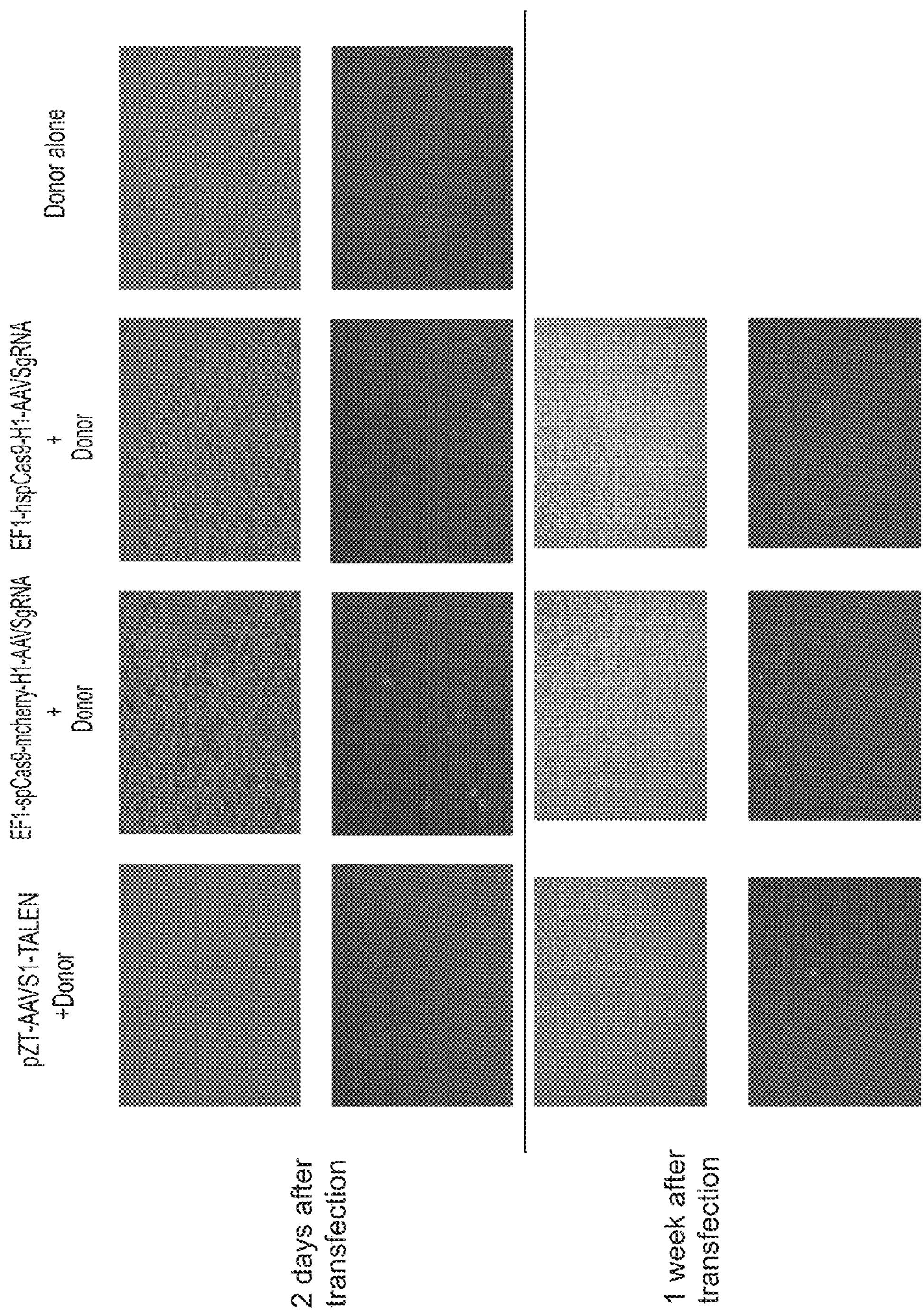
FIG. 4 provides phase contrast photomicrographs and corresponding green florescence photomicrographs of EGIP-293T cell line cultures that have been transfected with the CRISPR DNA constructs indicated and donor nucleic acid. Images taken at two days and one week post transfection are shown.

This paired guide RNA nickase approach is validated in the EGIP cell line that is described in Example 4 and FIG. 3D. Two guide nuclease target sequences were designed that target two positions in the AAVS locus that are very close to each other, and target either the top strand or bottom strand of the AAVS insert. When used simultaneously, the two Cas9 nickase events will produce a 5' overhang structure that promotes a homologous recombination event with a suitable donor fragment containing functional EGFP gene sequence.

Figure 12:
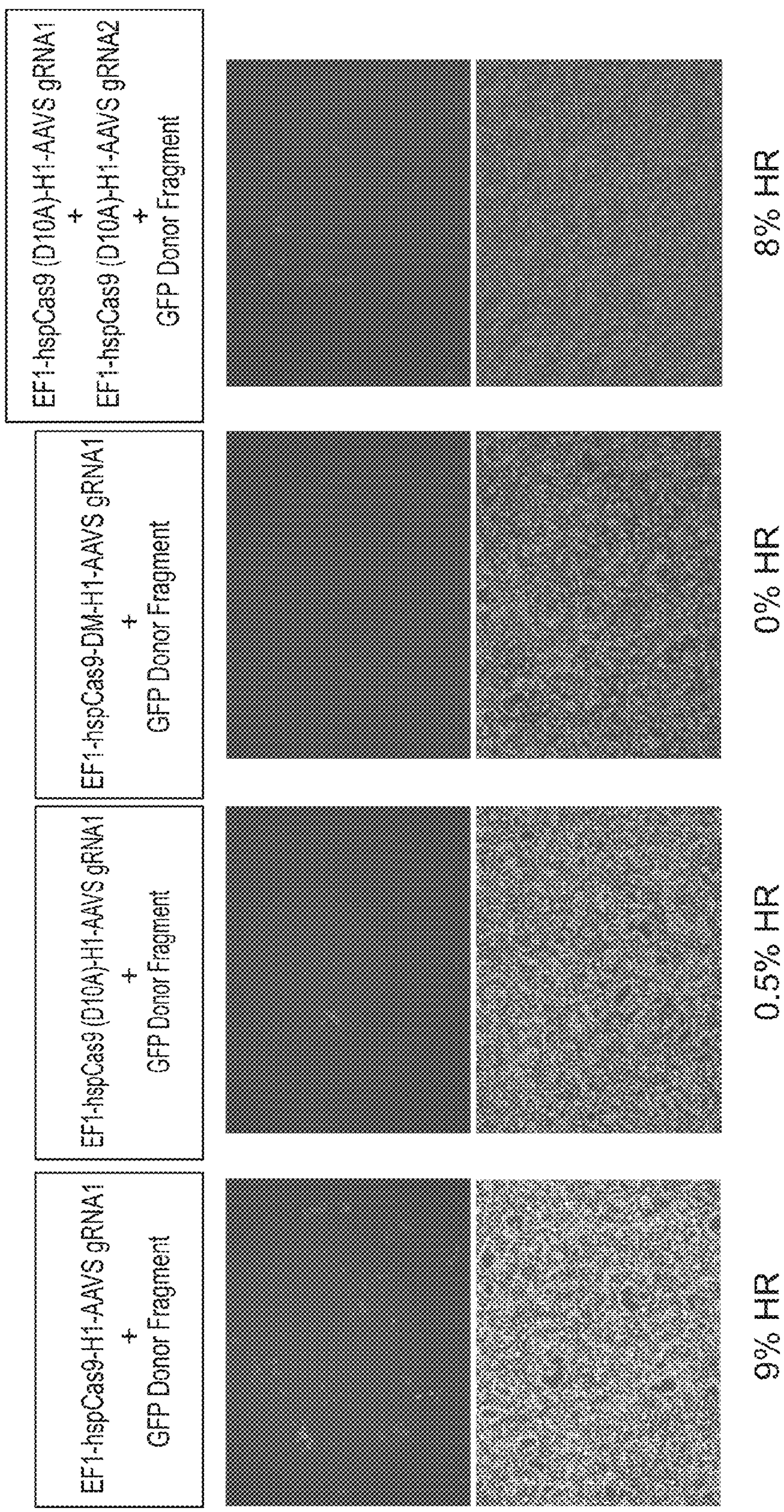
FIG. 12 provides green florescence photomicrographs and corresponding phase contrast photomicrographs of 293T cell line cultures that have been transfected with the CRISPR DNA constructs indicated and donor nucleic acid. The percentage of green fluorescent cells in the culture is indicated at the bottom.

The EGIP cell line was transfected with either one or both of a pair of AAVS guide RNA molecules (gRNA1 and gRNA2), the hspCas9 nickase (D10A) and a donor DNA containing functional EGFP sequence. Following transfection, homologous recombination efficiency was monitored by green fluorescence positive signals. As can be seen in FIGS. 108 and 12, the cells receiving only one AAVS guide RNA and Cas9 nickase showed very little recombination rescue of green fluorescence, where in contrast, cells transfected with the pair of guide RNA molecules and Cas9 nickase showed strong levels of recombination-induced green fluorescence rescue. This result validates methods using paired guide RNAs and a Cas9 nickase mutant to direct accurate homologous recombination at a target locus.

Additional experiments validating the paired guide nickase methods examined the ability of Cas9 wild type and nickase mutant enzymes to induce non-homologous end joining (NHEJ) at the same AAVS locus in the EGIP cell line, as assessed by a SURVEYOR® Nuclease assay. This assay demonstrated that no detectable NHEJ-induced mutations were detected when the Cas9 nickase is used in the targeting of this AAVS locus, where in contrast, NHEJ events are observed when using the wild type Cas9 nuclease. This validates the nickase approach for programming accurate targeted genomic editing. See Examples 8 through 10.

D) Methods for Gene Knock-Out, Gene Replacement and Gene Repair

In some aspects, the invention provides compositions and methods for in vivo gene replacement and gene repair using the CRISPR reagents described herein. The validation and proof-of-principle experiments in the present disclosure illustrate the utility of the compositions and methods described herein for engineering cell genomes in a highly targeted manner. These compositions and methods are readily adapted to generate engineered cells that can be used in biomedical research, for example, to create engineered cell lines and non-human transgenic animals. In other embodiments, engineered cell lines produced by the compositions and methods of the invention can also be used in therapeutic transplantation to treat human disease. Human diseases arising from genetic defects such as defective gene products, missing gene products or defects in gene expression can be treated with compositions and methods of the invention, or with engineered cell lines produced by the compositions and methods of the invention.

The disclosure provides proof-of-principle experiments demonstrating the effectiveness of the materials and methods of the invention to program the targeted knock out and subsequent targeted knock-in of entire gene sequences. For example, using the CRISPR reagents provided herein, an integrated functioning luciferase gene was targeted for knock out and replacement with a nucleotide sequence of a functioning red fluorescent protein. See Example 6. In that example, guide RNA targeting molecules and a codon-optimized cas9 gene (hspCas9) successfully programmed this genomic luciferase gene knockout and replacement with exogenously supplied RFP gene sequence in a human HEK293 reporter cell line. The exogenous RFP sequence was supplied to the transfection system by use of a co-transfected donor vector. See FIG. 6C. This conclusion was cross-validated using four different approaches to verify accurate gene replacement.

Similarly, the disclosure provides proof-of-principle experiments demonstrating the effectiveness of the materials and methods of the invention to program the targeted editing and repair of a genomic target locus. For example, the disclosure describes the enhanced green fluorescent inhibited protein (EGIP) reporter cell line, which contains an integrated defective EGFP sequence with a stop codon in the middle of the open reading frame that prevents the expression of a functional protein. See Examples 4 and 5, and FIG. 3D.

Using the CRISPR reagents provided herein, the defective EGIP sequence was targeted for repair by designing two guide target sequences that flank the defective region. The EGIP cell line was transfected with the pair of guide RNA molecules (gRNA1 and gRNA2), a gene encoding the hspCas9 nickase (D10A) and a donor DNA containing intact EGFP sequence. Green fluorescence was rescued in the cell line following the transfection, and a homologous recombination event was confirmed using a SURVEYOR® Nuclease assay.

V. In Vitro Transcription Systems

An important application of the Cas9/CRISPR system is the precise, site-specific genomic modification of a host cell. Targeted genomic modification includes transgene insertion (transgenesis), deletion of endogenous genes, editing of endogenous sequences. In some embodiments, the delivery, integration and expression of a transgene can result in the transcriptional regulation of another gene locus. For example, the expression of a chimeric transcription factor transgene can result in the transcriptional activation or suppression of a different gene locus. Targeted genomic modification in embryonic stem (ES) cells find particular utility with the invention. ES cells containing genomic modification can be used for injection into a blastocyst, generating a chimeric population of cells that eventually develop into an animal with the desired genetic modifications. In such applications, the use of synthesized RNA, as opposed to plasmid DNA, is preferred for efficient generation of transgenic organisms. For example, synthetic mRNA produced by in vitro transcription, owing to their smaller size, minimal immunogenicity, and lack of genomic integration, have become the modality of choice for in vivo delivery of Cas9 mRNA and targeting guide RNA. See Wang et al., "One-step generation of mice carrying mutations in multiple genes by CRISPR/Cas-mediated genome engineering," *Cell* 153(4):910-918 (May 9, 2013); Bassett et al., "Highly Efficient Targeted Mutagenesis of *Drosophila* with the CRISPR/Cas9 System," *Cell Rep.,* 4(1):220-228 (Jul. 11, 2013); Shen et al., "Generation of gene-modified mice via Cas9/RNA-mediated gene targeting," *Cell Res.,* 23(5):720-723 (May 2013).

The invention provides CRISPR/Cas reagents vectors for use in in vitro transcription to generate RNA that can be used in transfection of mammalian host cells.

Generally, in vitro transcription requires a purified linear DNA template containing a promoter, ribonucleotide triphosphates, a buffer system that includes DTT and magnesium ions, and an appropriate phage RNA polymerase. There are a variety of template options, including plasmids, PCR products, oligonucleotides and cDNA. The DNA template must contain a double-stranded promoter region where the phage polymerase binds and initiates RNA synthesis. Transcription templates include plasmid constructs engineered by cloning, cDNA templates generated by first- and second-strand synthesis from an RNA precursor, and linear templates generated by PCR or by annealing chemically synthesized oligonucleotides.

The IVT reactions can use any suitable promoter/polymerase combination, including but not limited to SP6, T7 or T3 systems. Plasmid vectors used as transcription templates should be linearized by restriction enzyme digestion. Because transcription proceeds to the end of the DNA template, linearization ensures that RNA transcripts of a defined length and sequence are generated. Restriction enzyme digestion should be followed by purification since contaminants in the digestion reaction may inhibit transcription.

In vitro transcription vectors of the invention can comprise any number and any type of regulatory elements to promote the strong and accurate generation of RNA by the bacteriophage polymerase. Similar to plasmid transfection systems, the IVT vectors, and subsequently the transcribed RNA products, can contain post-transcriptional regulatory elements. For example, expression vectors for IVT generation of Cas9 mRNA can contain 5'-UTR and 3'-UTR and a polyA tail to enhance hspCas9/hspCas9 nickase/hspCas9 DM mRNA stability and translation efficiency. See FIGS. 17A-17J. The invention also provides IVT vector backbones suitable for cloning a target sequence into a guide RNA scaffold, where an MCS or a single restriction site is engineered adjacent to the gRNA scaffold (see FIG. 17K).

A) Validation Data for the Cas9 RNA IVT System

We have tested the expression and functionality of ready-to-transfect mRNA for Cas9 nuclease and guide RNAs for their ability to cleave target sequences to induce homology directed recombination repair in an engineered cell line. The host cell line used was the HEK293T enhanced GFP inhibited protein (EGIP) cell line carrying an integrated EGFP gene containing a stop codon in the middle of the coding region of EGFP. This cell line does not produce green fluorescence signal. Suitable guide RNA and Cas9 were previously shown to direct HDR that is able to rescue the green fluorescence in the cell line following transfection of all-in-one expression vectors into the host cell in the presence of donor DNA containing functional EGFP sequence.

In vitro transcription was used to generate RNA encoding these same CRISPR guide and Cas9 components, and that RNA was used in transfection reactions into the EGIP cell line, and cotransfected with donor EGFP plasmid. These transfected cells also showed green fluorescence rescue, with an HDR efficiency comparable to that observed in the all-in-one Cas9 system. The robustness of the IVT Cas9 mRNA/gRNA system is illustrated by the fact that HDR events can be detected in transfected cells in as little as 18 hours post-transfection, whereas the Cas9 all-in-one plasmid system requires 24-48 hours before positive signals can be seen. The combination of IVT-generated Cas9 mRNA and guide RNA presents a robust alternative to plasmid-based Cas9 systems for efficient targeting and cleavage of DNA sequences, especially suitable for in vivo applications.

B) In Vitro Transcription Protocols

Figure 14B:
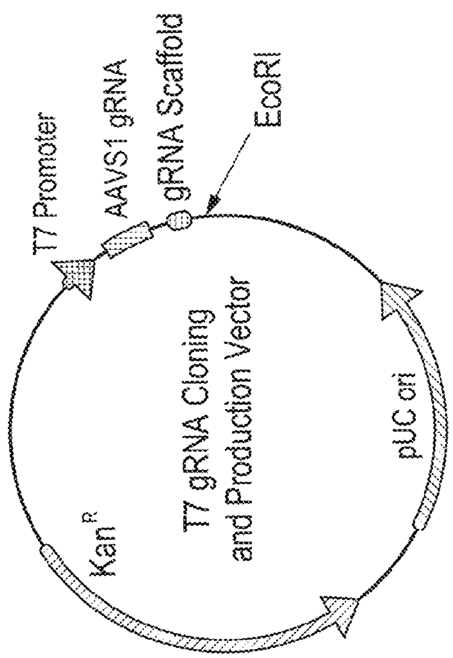
FIG. 14B provides a plasmid map of a construct used to generate in vitro transcribed RNA that is the guide RNA used in CRISPR systems. In this case, the gRNA contains a targeting sequence directed to a genomic locus containing AAVS sequence. Positions of the major features of the construct are indicated. Both of these constructs use the T7 promoter to drive mRNA production.

The general workflow of cloning the custom guide RNA target sequence into a T7 guide RNA cloning vector (an example of which is shown in FIG. 14B, and depicted more generally in FIG. 17K) is essentially the same as the procedure to prepare the all-in-one systems, where a pair synthetic oligonucleotides are annealed then cloned into the scaffold structure using two BsaI restriction sites.

The guide RNA template can be designed as follows. The two DNA oligonucleotides (a top strand and a bottom strand) can be designed according to the structure shown below.

```
                                    (SEQ ID NO: 50)
5' AGGGNNNNNNNNNNNNNNNNNNNNN 3'

                                    (SEQ ID NO: 51)
3' NNNNNNNNNNNNNNNNNNNNNCAAA 5'
```

The top strand has an AGGG overhang at its 5'-end, followed by the selected target sequence. The bottom strand has an AAAC overhang at its 5' end followed by a target sequence complementary to the top strand. For example, if the target sequence is:

AGCGAGGCTAGCGACAGCATAGG (SEQ ID NO: 47) (AGG=PAM sequence), then the top and bottom oligonucleotide sequences would be:

```
                              (SEQ ID NO: 52)
top strand:
5'-AGGGAGCGAGGCTAGCGACAGCAT-3'

                              (SEQ ID NO: 53)
bottom strand:
5'-AAACATGCTGTCGCTAGCCTCGCT-3'
```

There are two approaches to prepare DNA template for in vitro synthesis of the guide RNA. The first is PCR amplification of the guide RNA template. The template for gRNA in vitro transcription can be generated using a PCR reaction and positive gRNA construct generated using a T7 gRNA vector (e.g., FIG. 14B).

The second method is by linearization. Plasmid DNA can be linearized with EcoRI downstream of the custom gRNA to be transcribed. Circular plasmid templates will generate extremely long, heterogeneous RNA transcripts because RNA polymerases are very processive. It is recommended to examine the linearized template DNA on a gel to confirm that cleavage is complete. Since initiation of transcription is one of the limiting steps of in vitro transcription reactions, even a small amount of circular plasmid in template prep will generate a large proportion of transcript. If linearizing the template, the use of an EcoRI restriction enzyme with no star activity is recommended, such as EcoRI-HF (New England Biolabs).

C) Purification of Guide RNA Transcripts

Synthesized RNA, including guide RNA and Cas9 mRNA, can be purified by any suitable methods, commonly for example by either a spin column-based method, or by phenol:chloroform extraction followed by ethanol precipitation. Lithium Chloride (LiCl) precipitation is a convenient and effective way to remove unincorporated nucleotides and most proteins. However, the LiCl method may not efficiently precipitate RNAs smaller than 300 nucleotides. Therefore, the LiCl technique is not recommend for gRNA transcript precipitation.

Spin column-based purification will remove proteins, unincorporated nucleotides, and salts from RNA. Purify the RNA by following the spin column manufacturer's instructions. For removal of proteins and most of the free nucleotides, phenol:chloroform extraction and ethanol precipitation of RNA transcripts is a preferred method.

D) Analysis of Guide RNA Transcripts

The size of the gRNA transcripts can be analyzed by running an aliquot of the reaction on formaldehyde-based denaturing agarose gel. The concentration of the gRNA transcripts can be determined by reading the $A_{260}$ of a diluted aliquot. Typically, a 1:100 dilution will give an absorbance reading in the linear range of the spectrophotometer. For single-stranded RNA, one $A_{260}$ unit is equivalent to an RNA concentration of 40 μg/mL. The RNA concentration can be calculated as:

$$(A_{260})\times(\text{dilution factor})\times(40)=\mu\text{g/mL RNA}$$

E) Protocol for Transfection of Cas9 mRNA and Guide RNA/Transfection Conditions

Approximately 100,000 to 200,000 target cells (e.g., 293T cells) are plated into a single well of a 12-well plate in 1 mL of appropriate growth medium. A single well of cells that are untransfected, mock transfected or transfected with control nucleic acid are used as a negative control.

The next day, or when cells are 50-60% confluent, target cells are transfected with the Cas9 mRNA and gRNA (and appropriate donor vector if HDR is desired) using a suitable transfection reagent following the manufacturer's recommended protocol for 12-well plates. The use of reduced or serum-free media containing no antibiotics to dilute the vector/transfection complex is recommended.

Initially, a wide range of ratios of Cas9 mRNA to guide RNA (in this case, the AAVS1 gRNA) were tested in the transfection system. Ratios of 8:1, 16:1, 32:1 and 64:1 were tested, corresponding to 800 ng of Cas9 mRNA, and alternatively, 100 ng, 50 ng, 25 ng, and 12.5 ng of AAVS1 guide RNA. The EGIP 293T cells were cotransfected with 0.5 μg HR donor vector in cells for HDR applications. All tested ratios achieved comparable HR efficiency in comparison to a comparable all-in-one plasmid system (0.5 μg EF1-hsp-Cas9-H1-AAVS gRNA with 0.5 μg HR donor vector). For other cell lines, optimization of the amounts and ratios of Cas9 mRNA, gRNA, and donor vector is recommended.

The transfected cells are cultures for at least 12 hours before changing transfection media to complete growth media. At 48-72 hours after initial transfection, the cells can be assayed for DNA cleavage activity using the SURVEYOR® Nuclease assay, PCR genotyping analysis, or HDR activity (if using donor vector in parallel). If assaying for HDR with donor vector sequences, select cells with targeted insertion of donor vector using FACS-based sorting, for example, sorting of a fluorescent marker or culturing for antibiotic selection (e.g., Puro/Neo).

VI. Methods for Targeted Regulation of Gene Expression

In some embodiments, the invention provides CRISPR-based chimeric transcript factors that can be designed to target any genomic gene of interest, simply by engineering a suitable guide RNA molecule(s). These customizable transcription factor systems comprise two components, which are (i) the guide RNA, and (ii) a fusion protein comprising a Cas9 polypeptide and an operably linked transcriptional regulatory domain, which can be an activation domain or a suppression domain. In these systems, the guide RNA is used to tether the Cas9 with the fused regulation domain in proximity to a gene of interest. The activation or suppression domain will exert influence on the initiation of transcription of the gene of interest, thereby upregulating or downregulating expression of the encoded gene product.

A) Guide RNA Molecules for Modulating Gene Expression

A guide RNA for modulating gene expression can be designed to target any desired endogenous gene. A genomic target sequence is selected in the proximity of the endogenous gene transcription start site, or alternatively, in relation to the endogenous gene translation start site.

The target sequence is typically, but is not required to be, in a region of the DNA that is traditionally termed the "promoter proximal" region of a gene, generally in the region where transcription promoters, enhancer elements, suppressor elements, or other DNA regulatory elements are known to exert their effects on transcriptional regulation. In one aspect, the "promoter proximal" region of a gene can be defined arbitrarily as the region of genomic DNA that lies between about 1,000 base pairs upstream of the start site of transcription, and 1,000 base pairs downstream of the start site of transcription. However, it is understood by one of skill in the art that endogenous trans-acting DNA-binding regulatory proteins can exert their effects through cis-acting DNA elements that are many kilobases distant upstream or downstream from the start site of transcription of the gene. It is not intended that the invention be limited to any particular distance restraint with regard to the location of the guide RNA target sequence from the gene transcription start site, except that the target sequence lies "in proximity to" a gene of interest, where "in proximity to" refers to any distance either upstream or downstream from the gene of interest, where the Cas9-regulatory domain fusion is able to exert an effect on gene expression. In some aspects, the target sequence can lie anywhere in the first three exons of a gene.

In some aspects, as described above, the region of the gene that is considered "in proximity to" the gene is relative to the site of transcription initiation. However, as one of skill recognizes, the transcription initiation sites of some promoters are poorly defined. For that reason, the "start" site of a gene can sometimes be described using reference to a translation start site. Depending on the mammalian promoter, the distance between the start site of transcription and the start site of translation (i.e., the 5'-UTR) can range from about 100 base pairs to several thousand base pairs.

B) Cas9-Regulatory Domain Fusion Proteins

When designing the Cas9 fusion regulatory protein, generally a gene encoding a Cas9 protein that is a null nuclease is used, for example, an hspCas9 double mutant (DM) gene that encodes a Cas9 polypeptide that contains the mutations D10A and H840A.

The present disclosure provides Cas9 proteins fused to either the KRAB transcriptional repressor domain or the VP64 transcriptional activation domain. However, it is not intended that the invention be limited to the use of these two domains, as one of skill in the art recognizes that a variety of transcriptional regulatory domains can be used to construct chimeric transcription factors. For example, activation domains finding use with the invention include VP64 and the p65 activation domain. Similarly, suppression domains finding use with the invention include KRAB, the chromo shadow domain of HP1α and the WRPW (Trp-Arg-Pro-Trp) (SEQ ID NO: 54) domain of Hes1.

EXAMPLES

The following examples are offered to illustrate, but not limit, the claimed invention. It is understood that various modifications of minor nature or substitutions with substantially similar reagents or components will be recognizable to persons or ordinary skill in the art, and these modifications or substitutions are encompassed within the spirit and purview of this disclosure and within the scope of the invention.

Example 1

Design of a Codon-Optimized Polynucleotide Encoding the Cas9 Protein

A wide variety of factors regulate and influence gene expression levels. The expression of nucleotide sequences (e.g., protein open reading frames) of bacterial-origin in mammalian host cells can be technically problematic. Differences between bacterial and mammalian transcription and translation machinery often results in failed, poor or non-optimal expression of bacterial sequences when transferred to mammalian host cells. These obstacles to expression of bacterial proteins in mammalian host cells include differences in codon preference well as a wide variety of other differences in nucleic acid processing.

As a first step to creating genomic engineering tools, this example describes the design of polynucleotides that encode the bacterial Cas9 protein, and further, manipulates the bacterial sequence in order to optimize expression of the Cas9 open reading frame in mammalian host cells.

Taking into consideration as many optimization factors as possible, a polynucleotide was designed to maximize expression of Cas9 protein in both human and mouse cells. The program OptimumGene™ (Genscript) was in part used to generate the optimized sequence. The amino acid sequence of the wild type *Streptococcus pyogenes* strain SF370 CRISPR-associated nuclease Cas9 (spCas9) (National Center for Biotechnology Information, National Institutes of Health, GenBank® Accession Number AAK33936.1; SEQ ID NO: 1) was used as input for the program algorithm in order to generate a nucleotide sequence for expression of protein having the same amino acid sequence as the wild type bacterial protein, except optimized for expression in mammalian host cells.

The following parameters were used in the OptimumGene™ program in generating a first generation optimized Cas9 sequence. The program was set to generate an open reading frame that would be maximally optimized for expression in both mouse and human host systems. The program optimization parameters were set to take into account the following features: codon usage bias, GC content, CpG dinucleotide content, mRNA secondary structure, cryptic mRNA splicing sites, premature PolyA sites, internal chi sites and ribosomal bonding sites, negative CpG islands, RNA instability motif, direct repeats, reverse repeats, and Dyad repeats, restriction sites that may interfere with downstream applications (e.g., cloning), and efficiency of translational termination.

The codon usage bias was increased by upgrading the codon adaptation index (CAI) to 0.88 in both human and in mouse. The GC content was adjusted to 49.93% and unfavorable peaks were optimized to prolong the half-life of the mRNA. The native *S. pyogenes* Cas9 gene employs tandem rare codons that can reduce the efficiency of translation or even disengage the translational machinery; these codons were eliminated or minimized. Stem-loop structures, which impact ribosomal binding and stability of mRNA, were broken. In addition, the optimization process modified those negative cis-acting sites and avoided 15 of the most common restriction enzymes, as well as a BsaI site, as listed below.

| | | | |
|---|---|---|---|
| Splice (GGTAAG) | PolyA (AAAAAAA) | KpnI (GGTACC) | SacI (GAGCTC) |
| Splice (GGTGAT) | BamHI (GGATCC) | NcoI (CCATGG) | SalI (GTCGAC) |
| PolyA (AATAAA) | BglII (AGATCT) | NdeI (CATATG) | XbaI (TCTAGA) |
| PolyA (ATTAAA) | EcoRI (GAATTC) | NotI (GCGGCCGC) | XhoI (CTCGAG) |
| Destabilizing (ATTTA) | EcoRV (GATATC) | PstI (CTGCAG) | |
| PolyT (TTTTTT) | HindIII (AAGCTT) | SmaI (CCCGGG) | |

Based on these optimization criteria, a human/mouse codon-optimized polynucleotide encoding the wild type *S. pyogenes* Cas9 protein was generated by the Optimum-Gene™ program algorithm. That sequence was further edited to remove additional restriction sites and also for improving expression of the protein, while preserving the amino acid sequence of the wild type Cas9 protein. Amino acid sequences encoding N- and C-terminal nuclear localization signals and an N-terminal myc-tag were also input and optimized along with the Cas9 amino acid sequence.

Based on these program optimization criteria, the final sequence of the human/mouse codon-optimized polynucleotide encoding the *S. pyogenes* Cas9 protein open reading frame was generated. That sequence is provided in FIG. 20 and SEQ ID NO: 3. Further, the codon-optimized polynucleotide encoding the *S. pyogenes* Cas9 protein open reading frame fused with an N terminal myc-tag and two nuclear localization signals (NLS), one located in the N terminus and the other in the C-terminus, is provided in FIG. 23 and SEQ ID NO: 6. The amino acid sequence of this polypeptide is provided in FIG. 22 and SEQ ID NO: 5.

The amino acid sequences and corresponding nucleotide sequences of these N-terminus and C-terminus nuclear localization signals are also provided in FIG. 9A. In that figure, the N-terminus NLS described in this Example corresponds to NLS4, and the C-terminus NLS corresponds to NLS5. In the amino acid sequences in FIG. 9A, stop codons are indicated by an asterisk.

This human codon optimized polynucleotide encoding the spCas9 modified by the addition of the N-terminal myc-tag and two NLS (located at the N terminus and C-terminus), described in this example, is referred to herein as hspCas9 (FIG. 23 and SEQ ID NO: 6).

Example 2

Construction of an all-in-One CRISPRII System

This example describes the design and construction of vectors for the expression of CRISPR components (Cas9 and guide RNA) in mammalian cells. These engineered components are used to induce targeted cleavage of genomic DNA in mammalian cells, a first step in genomic DNA editing.

In order to achieve high efficiency cleavage of target genomic sequences of interest by Cas9, and further to provide a simple, transfection-friendly single plasmid system, an all-in-one vector was engineered for providing these sequences to a mammalian host cell. This all-in-one CRISPR system was constructed by cloning the mammalian codon optimized Cas9 sequence (hspCas9; FIG. 23) and a crRNA-tracrRNA chimeric guide molecule (gRNA scaffold) into a single mammalian expression construct. The construct engineered for this use is depicted in the maps shown in FIGS. 1A and 1B.

Figure 1E:
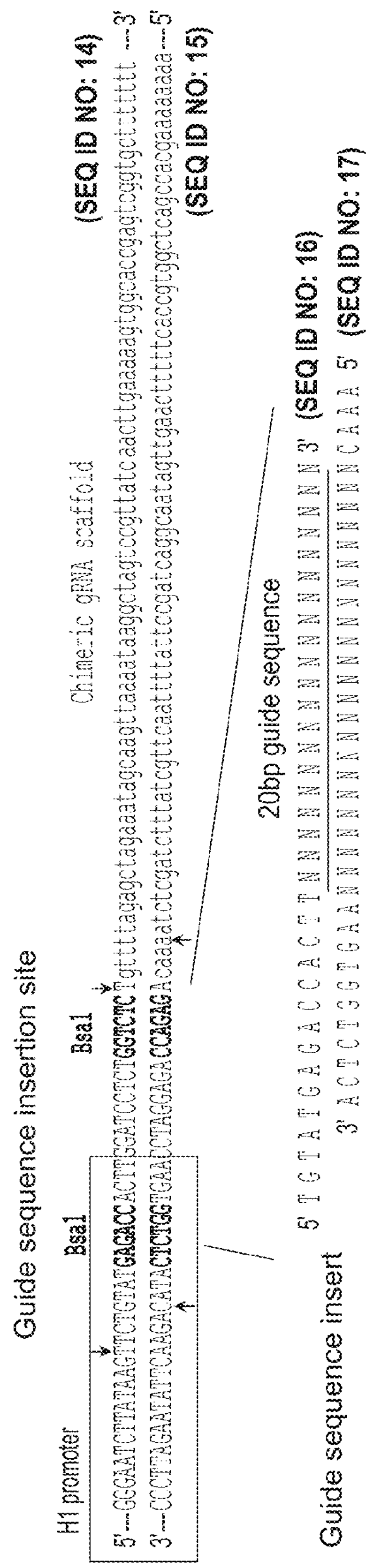
FIG. 1E provides a schematic and nucleotide sequences of the guide RNA region of the all-in-one CRISPR expression vector. The H1 promoter driving expression of the guide RNA is boxed, the BsaI restrictions sites for cloning a desired target guide sequence are in bold, and the guide RNA scaffold sequence is in lowercase. The configuration of the guide sequence insertion site is expanded below.
Figure 1F:
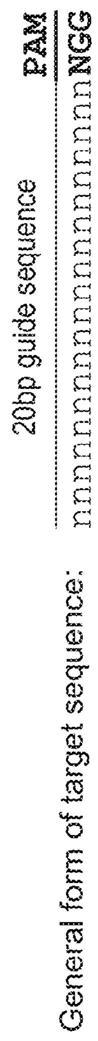
FIG. 1F provides the general form of a target guide sequence to be used in the all-in-one CRISPR system construct. The PAM motif is indicated.

As shown in FIG. 1A, expression of the human codon optimized polynucleotide encoding the spCas9 (hspCas9) is driven by the human elongation factor EF1-α hybrid promoter. The all-in-one expression construct also contains a crRNA-tracrRNA chimeric transcript cassette. The vector contains an artificial crRNA-tracrRNA fusion, where these two RNA molecules (normally expressed as two different genes in their native bacterial system) are fused into a single recombinant transcript in the all-in-one vector. This crRNA and tracrRNA fusion is termed a chimeric guide RNA scaffold. FIG. 1E.

The gRNA scaffold cassette also contains two Bsa1 restriction sites to allow any target sequence of interest to be inserted into the guide RNA scaffold. Approximately 20 base pairs of target sequence are included, and must be flanked on the upstream 3' end by the NGG protospacer-adjacent motif (PAM) sequence. In order to insert a given target sequence, the construct is digested by Bsa1, and a pair of pre-annealed synthetic oligonucleotides can be cloned into the sticky-ended all-in-one construct (FIGS. 1E and 1F). FIG. 1E provides the structure of the guide sequence insertion site comprising two Bsa1 restriction sites. The cloning of a target sequence of choice into the Bsa1 sites will allow transcription of a complete guide RNA (gRNA) that includes the required crRNA and tracrRNA motifs as well as the genomic targeting sequence. This highly flexible approach can target any genomic site in the form of $N_{20}$NGG.

Expression of this chimeric gRNA sequence is driven by an upstream H1 polymerase III promoter in conjunction with a woodchuck hepatitis virus post-transcriptional regulatory element (WPRE) sequence to increase protein stability. FIG. 1A. The H1 promoter has no constraints on the transcription initiation site, unlike the U6 promoter which requires transcription to be initiated with a G.

Example 3

Validation of Expression of Bacterial-Encoded Cas9 in Human Cells

This example describes the validation testing of the native bacterial Cas9 nucleotide sequence (written spCas9) for its ability to express in mammalian host cells. Although the vector described in Example 2 used the engineered mammalian codon-optimized Cas9 polynucleotide sequence (written hspCas9) to construct the all-in-one CRISPR system expression vector, this example addresses whether the native bacterial Cas9 nucleotide sequence can also be used in the all-in-one mammalian expression vectors.

Figure 2A:
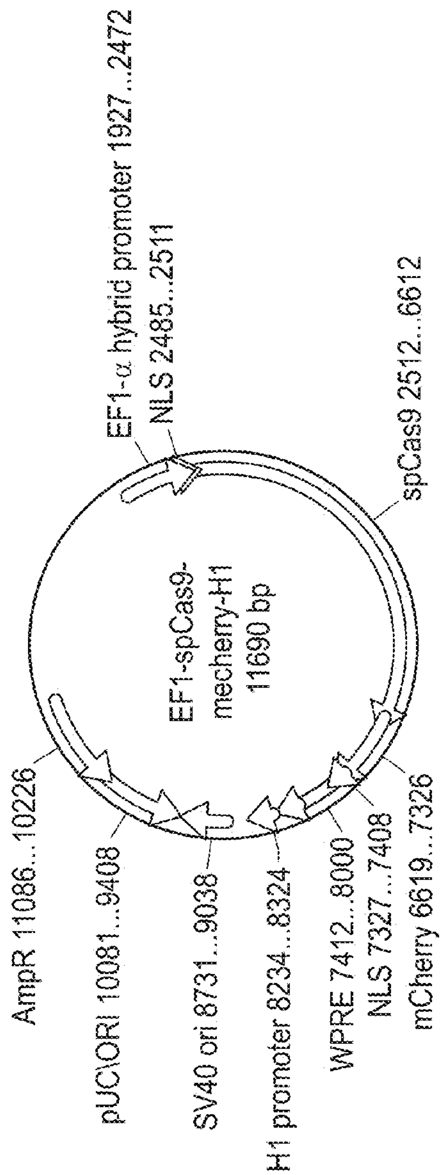
FIG. 2A provides a map of the all-in-one CRISPR expression vector EF1-spCas9-mcherry containing the *S. pyogene* encoded Cas9 gene expressed as a fusion protein with mCherry fluorescent protein.

In order to test whether the native bacterial encoded Cas9 gene was able to express in human cells, an expression vector containing the native bacterial *Streptococcus pyogenes* coded cas9 gene (referred to as spCas9) was constructed, as shown in FIG. 2A. As shown in that figure, the spCas9 was augmented with N-terminus NLS, and further fused at the C-terminus with mCherry (a red fluorescent protein) with an additional NLS downstream of mCherry. The mCherry protein is a second generation monomeric fluorophore, whose original sequence was isolated from *Discosoma* sp. mCherry matures rapidly after transcription and translation, and is highly photostable and resistant to photobleaching. The spCas9-mCherry fusion protein allows the monitoring of expression of spCas9 as well as subcellular localization of the protein. Expression of the spCas9-mCherry fusion was driven by the EF1-α hybrid promoter.

The testing was conducted in human 293T host cells. The all-in-one construct was delivered to the host cells by transient transfection of EF1-spCas9-mCherry (FIG. 2A) using Lipofectamine® 2000 (Life Technologies™) in 12 well plates. As mCherry is fused with spCas9, the mCherry signal reflects spCas9 expression and cellular localization FIG. 2B shows the red fluorescent image of a representative field of the 293T culture following transfection (far left), the same field of view with a nuclear DAPI staining (center image) and the merging of the two fields (far right image).

Figure 2B:
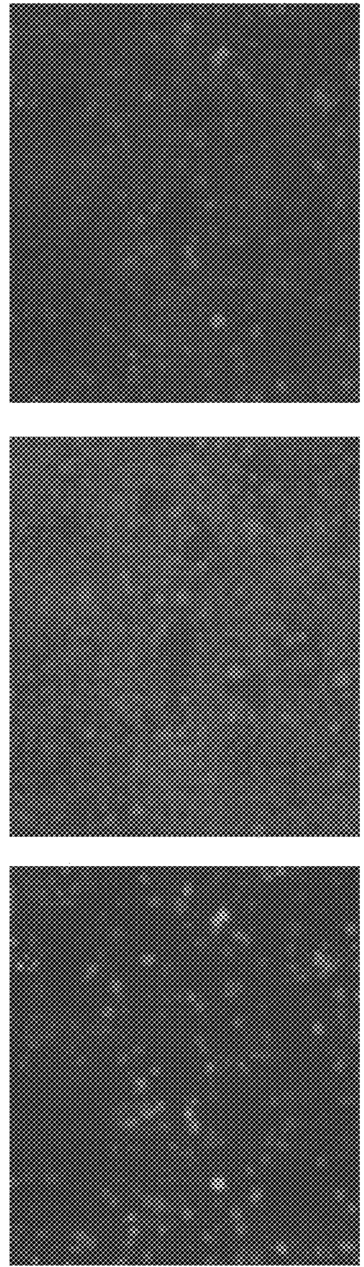
FIG. 2B provides fluorescent images, nuclear staining images and merged images of human 293T cells containing the expression construct EF1-spCas9-mcherry.

Expression of this construct, termed EF1-spCas9-mcherry, in human 293T cells revealed that bacterial encoded spCas9 express well in human 293T cells, and furthermore, localizes to the cell nucleus (FIG. 2B). The mCherry signal colocalized with nuclear staining, indicating that spCas9 protein is efficiently directed into the nucleus. This experiment indicates that the bacterial encoded Cas9 gene can also find use in the all-in-one CRISPR expression systems of the invention for use in mammalian cells, including human cells.

Example 4

Comparison of Homologous Recombination Efficiencies and Gene Repair Using CRISPR and TALEN Genomic Targeting Systems with a GFP Reporter This example describes the testing of hspCas9 and spCas9 for the target-specific DNA cleavage activity, and furthermore, also includes a previously established TAL effector nuclease heterodimer (TALEN) site-specific DNA cleavage system for comparison. This assay measured DNA cleavage activity as a function of the levels of homologous recombination at the cleaved genomic locus.

To conduct the comparison studies, a reporter cell line termed EGIP (enhanced green fluorescent inhibited protein) was genomically engineered, as shown in FIG. 3D. This stable cell line contains an integrated nucleic acid comprising EGFP sequence (lowercase nucleotides) bearing a stop codon (taa, double underlined) in the middle of the EGFP open reading frame. That stop codon is followed by a 53 base pair genomic fragment from the adeno-associated virus integration site 1 (AAVS1) (uppercase nucleotides). As a result, this cell line does not express GFP. In the presence of an uninterrupted and intact EGFP donor fragment having homology regions flanking the genomic AAVS1 insertion, the defective genomic locus can theoretically undergo a homologous recombination event that results in the excision of the AAVS and stop codon from the genomic locus, and replacement with the intact EGFP sequence from the donor fragment, thereby restoring a functional EGFP gene and inducing green fluorescence rescue.

As a result, fluorescence from EGFP can hypothetically be restored following homologous recombination (HR), as illustrated in FIG. 3D. The reappearance of EGFP positive signal is a marker for the cleavage and homologous recombination event in the cells. Thus, when AAVS sequence is targeted by either Cas9 or TALEN, and in the presence of homologous EGFP sequence, the cell line will demonstrate green fluorescence rescue.

To test the efficiency of target-sequence cleavage with the all-in-one CRISPRII system, and further, testing the ability of either codon-optimized hspCas9 or bacterial spCas9 sequence to induce genomic homologous recombination (HR), a chimeric guide RNA that targets the adeno-associated virus integration site 1 (AAVS1) fragment in the EGIP cell line was designed and constructed. The AAVS target sequence used in these systems is shown in FIG. 3C. The location of that targeted sequence within the AAVS genomic locus is underlined in FIG. 3D. The targeting sequence was cloned into the all-in-one vector using the Bsa1 restriction sites, thereby enabling the transcription of a complete guide RNA molecule, termed AAVS1 gRNA, that is able to guide the Cas9 nuclease activity to the AAVS1 locus.

Two different Cas9 open reading frames were alternatively tested in the all-in-one CRISPR systems targeting the AAVS1 locus. The two all-in-one CRISPR systems tested were the codon optimized hspCas9 gene vector and the native bacterial spCas9 gene vector. These vectors are shown schematically in FIGS. 3A and 3B.

| Vector | Expressed Sequences |
|---|---|
| EF1-hspCas9-H1-AAVSgRNA (FIG. 3A) | hspCas9 and AAVS guide RNA |
| EF1-spCas9-mcherry-H1-AAVSgRNA (FIG. 3B) | spCas9-mCherry fusion and AAVS guide RNA |

Alternatively, each of these plasmids was transfected into the EGIP 293T cells either in the presence or absence of EGFP donor fragment. The donor plasmid is a plasmid containing only wild type EGFP. A linear EGFP PCR product was also successfully used. In addition, a control transfection including only the EGFP donor fragment was also included.

In parallel, a TAL effector nuclease heterodimer (TALEN) system targeting the same AAVS1 locus was also tested, using the same host cells and EGFP donor fragment. That TALEN vector, pZT-AAVS1-TALEN, has been previously described by others as the most efficient TALEN pair targeting the AAVS1 fragment. It was previously reported that this TALEN system shows a 25% target cleavage rate and a 8.1% HR rate in 293T cells.

These plasmids were transiently transfected into 293T cells using Lipofectamine® (Life Technologies™).

FIG. 4 provides fluorescent images taken at two days and one week following transfection of the various plasmids. The observations made at both the 2 days and one week are summarized below.

| | Green Fluorescence Signal | |
|---|---|---|
| | Without Donor Fragment | With Donor Fragment |
| pZT-AAVS1-TALEN | Negative | Positive |
| EF1-hspCas9-H1-AAVSgRNA | Negative | Positive |
| EF1-spCas9-mcherry-H1-AAVSgRNA | Negative | Positive |
| Donor Fragment Only | Negative | |

As can been seen in the table, transfection of the TALEN or Cas9 constructs in the presence of EGFP donor fragment resulted in green fluorescence in a subset of the transfected cells, and further, this fluorescence was dependent on the presence of the donor fragment. The donor fragment alone did not induce the green fluorescence, indicating that the detected fluorescence was due to a homologous recombination event. It was observed that the cultures receiving the codon optimized hspCas9 and the native bacterial spCas9 both showed comparable or slightly higher percentages of green fluorescent cells (i.e., higher rates of homologous recombination) compared to the percentage of green fluorescent cells observed using the TALEN system. The GFP expression result 2 days post-transfection showed very few GFP positive cells. After one week cell propagation, GFP positive cells are more numerous.

Example 5

Comparison of Homologous Recombination Efficiencies of CRISPR and TALEN Genomic Targeting Systems Using a DNA Cleavage Activity This example provides a comparison of the relative recombination efficiencies of a guided CRISPR system and a TALEN genomic targeting system, where the two different systems target the same genomic sequences contained in a 293T cell line. This comparison of homologous recombination efficiencies used the same engineered cell line, same CRISPR components and same TALEN construct as described above in Example 4. However, in this example, the resulting homologous recombination products were assayed using a SURVEYOR® nuclease mutation detection assay (instead of by monitoring green fluorescence rescue). The recombination efficiency of the codon-optimized hspCas9 and the native prokaryotic spCas9 were directly compared to each other, as well as to the recombination efficiency of the TALEN system.

SURVEYOR® Mutation Detection Kits detect polymorphisms in double stranded DNA. The kit includes SURVEYOR® nuclease, which recognizes and cleaves mismatches arising from single nucleotide mismatch or from small insertions or deletions (indels). The SURVEYOR® assay entails amplifying a genomic region of interest by PCR, hybridizing those PCR products, digesting the annealed hybridization products with the SURVEYOR® nuclease, and resolving and visualizing the DNA products. As only hybridization products with mismatches will be digested by SURVEYOR® nuclease, the percent of digested DNA fragment vs. undigested DNA fragment can be used to calculate the indel rate of Cas9 at a particular target site in the genome.

Figure 5:
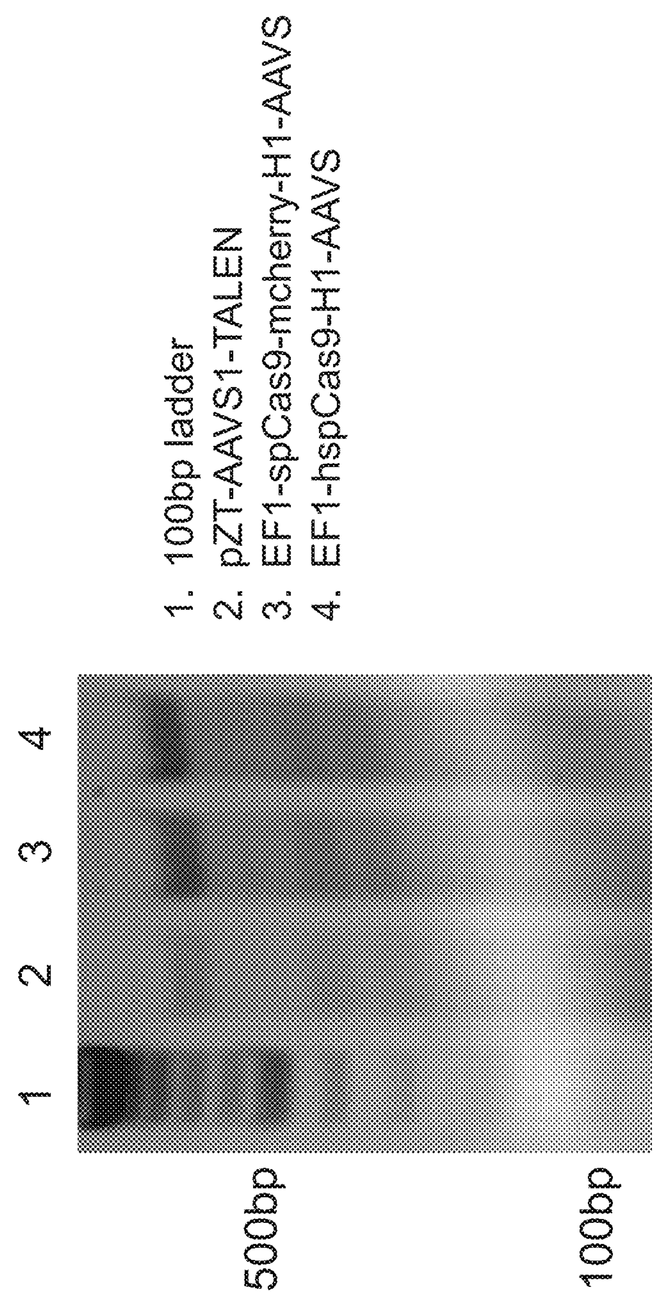
FIG. 5 provides a photograph of an agarose gel stained with ethidium bromide showing the DNA cleavage fragments generated following a SURVEYOR® Mutation Detection Kit (Transgenomic®, Inc.) assay using DNA samples derived from cell cultures transfected with the indicated CRISPR constructs.

The stable EGIP 293T cell line was transfected with the CRISPR II and TALEN constructs as described above. three days post transfection, genomic DNA from each sample was isolated, followed the SURVEYOR assay according to the manufacturer's protocol. The digestion products were resolved on an agarose gel, and visualized by ethidium boromide staining. These results of the cleavage assay are shown in FIG. 5. Upper bands represent undigested band (hybridization products without mismatch), and smaller bands represent digested bands (hybridization products with mismatch).

As seen in the gel, the SURVEYOR® Mutation Detection Kit assay detected smaller bands corresponding to hybridization products with mismatch, thereby indicating that the codon-optimized hspCas9, the native prokaryotic spCas9 and the TALEN product are all able to target and cleave the genomic AAVS target sequence in a predicted manner, generating double stranded breaks at the same position, corresponding to the AAVS sequence.

From these data, it is estimated that the homologous recombination rate of spCas9 and hspCas9 in EGIP 293T cells would be more than 8%, where 8% of the cells in the culture showed green fluorescence, and the cleavage activity would be more than 25%, where more than 25% of the cells in the culture showed a cleavage event at the AAVS locus in the EGIP 293T cells.

Therefore, both the human codon optimized Cas9 gene and the bacterial encoded Cas9 gene are able to express in human cells and achieve targeted modification at a desired genomic locus using CRISPR system reagents (a Cas9 gene and a guide RNA) supplied to the cell by transfection of an all-in-one expression vector and a donor DNA nucleic acid. By using these simple reagents, targeted site-specific DNA editing was achieved, and further, without the need to engineer a novel protein that is able to target and cleave a sequence of interest.

Example 6

Demonstration of Gene Disruption/Replacement by Homologous Recombination Using a CRISPR Genomic Targeting System with a Luciferase Reporter This example provides a description of experiments to validate the ability of CRISPR/Cas components to stimulate homologous recombination at a targeted genomic locus, resulting in knock-out of the target gene sequence, and replacement of that sequence with a different reporter. These experiments use a recombination monitoring system that has the capacity to track a single recombination event by three different cross-verification techniques. The experiments used a stably transfected cell line containing a luciferase reporter gene that is the target of the recombination event.

To further validate the all-in-one CRISPR II system, a recombinant human embryonic kidney (HEK) 293T cell line was engineered containing a genomically integrated luciferase reporter gene driven by the constitutively active CMV promoter. The stable cell line was constructed by infecting the cells with pGreenFire™ virus (System Biosciences, Inc.; Catalog No. TR010VA-1), which coexpresses the GFP and luciferase genes in a bicistronic message under the control of a single CMV promoter. The fused GFP and luciferase open reading frames are separated by a nucleotide sequence encoding the viral *Thosea asigna* 2A (T2A) peptide, which induces a co-translational ribosome "skipping", thereby producing of two separate, unfused protein products from the bicistronic mRNA. Transfected cells that were GFP positive were sorted to create the stably integrated 293T cell line, shown schematically in the top portion of FIG. 6C.

The integrated luciferase gene was targeted for disruption and replacement using all-in-one CRISPR system vectors, where the activity of the CRISPR II components induces a homologous recombination event at the luciferase locus that can be monitored by any one of three methods.

This assay system designed and tested two different gRNA sequences that target the luciferase gene. Two all-in-one CRISPR system expression vectors for the simultaneous expression of hspCas9 and a guide RNA were designed and constructed, having the general configuration shown in FIG. 6A (termed EF1-hspCas9-H1-Luc). Two guide RNAs (gRNA) which target the luciferase sequence present in the recombinant cell line were designed, having the targeting sequences shown in FIG. 6B.

```
Luc gRNA1 target sequence:
                              (SEQ ID NO: 20)
GGCATGCGAGAATCTGACGC

Luc gRNA2 target sequence:
                              (SEQ ID NO: 21)
CATGCCAGAGATCCTATTTT
```

Two all-in-one vectors were constructed by alternatively cloning these two guide sequences into the all-in-one EF1-hspCas9-H1-Luc vector, expressing the codon optimized Cas9 gene hspCas9, as shown in FIG. 6A.

The stably integrated cells expressing luciferase were alternatively transfected with either one of the two all-in-one CRISPR constructs that target the luciferase gene for cleavage. In addition, the cells were also cotransfected with a donor nucleic acid which contained flanking dsGFP, the red fluorescent protein (RFP) gene ORF, and flanking WPRE regulatory sequence (donor fragment, as shown in FIG. 6C).

These reagents target the genomic luciferase gene for replacement (knock-out) with RFP sequence from the donor fragment.

This experimental system provides a versatile and powerful assay for homologous recombination, where the presence or absence of functioning CRISPR system components and homologous recombination can be detected by any one of three assays. Testing using three assays provides strong cross verification for the genomic modification. First, cleavage activity of the targeted CRISPR II Cas9 protein can be monitored by using the SURVEYOR® Mutation Detection assay (Transgenomic®, Inc.) to detect cleavage events within the luciferase gene. Second, genomic modification can be assessed by measuring luciferase protein activity, where there would be a reduction of luciferase activity in the reporter cell line if homologous recombination was present. Third, these components are potentially sufficient to induce a homologous recombination event resulting in replacement of the genomic luciferase sequence with the RFP gene from the donor fragment. When the luciferase sequence is targeted by Cas9 protein, in the presence of the donor fragment, the 293T cells expressing luciferase cells will potentially turn RFP positive and luciferase negative by the homologous recombination event. See FIG. 6C.

A) Luciferase Assay

The luciferase stable HEK 293T cell line depicted in the top panel of FIG. 6C was transiently transfected with either EF1-hspCas9-H1-Luc gRNA1 or EF1-hspCas9-H1-Luc gRNA2 all-in-one vectors using Lipofectamine® 2000 (Life Technologies™). Three days after transfection, cells were harvested, and whole cell extracts were prepared for use in a luciferase assay (Promega), according to the manufacturer's instructions.

Figure 7A:
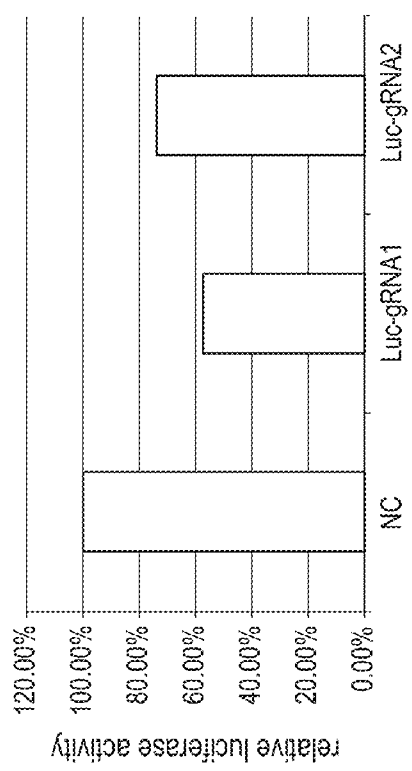
FIG. 7A provides a histogram depicting the results of a luciferase assay using cell extracts collected from cell cultures transfected with CRISPR system vectors targeting two different luciferase target sequences compared to untransfected negative control cells (NC).

It was observed that EF1-hspCas9-H1-Luc gRNA1 suppresses luciferase activity by 40% compared to untransfected negative control cells (NC). Similarly, EF1-hspCas9-H1-Luc gRNA2 reduces luciferase activity by 25% compared to untransfected negative control cells (NC). See FIG. 7A.

B) Surveyor® Nuclease Assay

The luciferase stable 293T cell line was transfected with either EF1-hspCas9-H1-Luc gRNA1 or EF1-hspCas9-H1-Luc gRNA2. Three days after transfection, cells were harvested, and genomic DNA was isolated for use in the SURVEYOR® Mutation Detection assay according to the manufacturer's protocols.

Figure 7B:
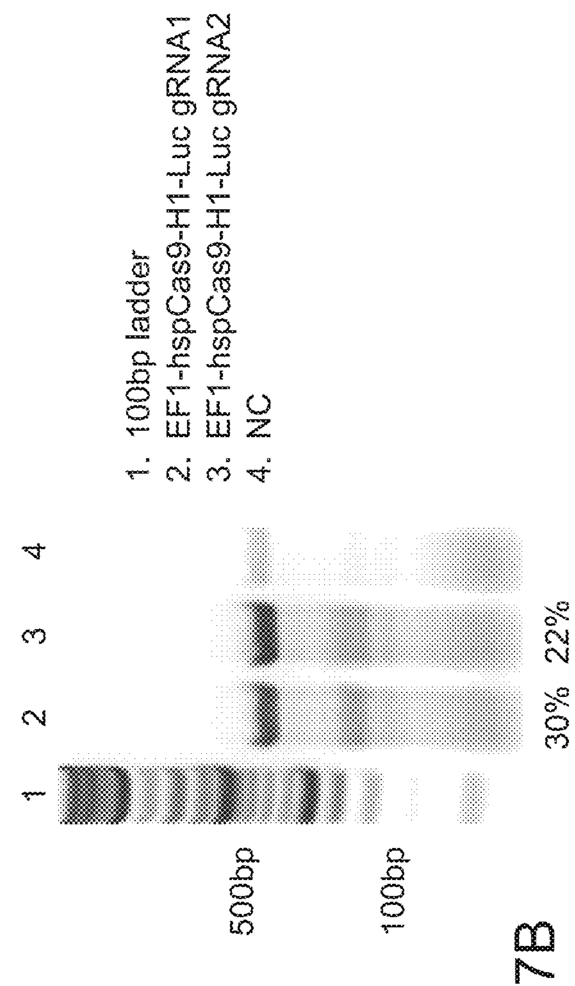
FIG. 7B provides a photograph of an agarose gel stained with ethidium bromide showing the DNA cleavage fragments generated following a SURVEYOR® Mutation Detection assay using DNA samples derived from cell cultures transfected with the same CRISPR constructs indicated in FIG. 7A, as well as DNA samples derived from untransfected negative control cells (NC).

The SURVEYOR® assay showed results consistent with the results of the luciferase assay. Cells transfected with EF1-hspCas9-H1-Luc gRNA1 showed 30% of the cleavage activity compared to untransfected negative control cells (NC), and cells transfected with the EF1-hspCas9-H1-Luc gRNA2 construct showed 22% of the cleavage activity contained in untransfected negative control cells (NC). See FIG. 7B.

C) Red Fluorescence Detection

The efficiency of the homologous recombination event in the human codon optimized all-in-one CRISPR II system was also monitored by checking RFP signal under fluorescent microscopy. The luciferase stable 293T cell line was transfected with either EF1-hspCas9-H1-Luc gRNA1 or EF1-hspCas9-H1-Luc gRNA2, and with or without the RFP donor fragment, as described above.

Figure 8:
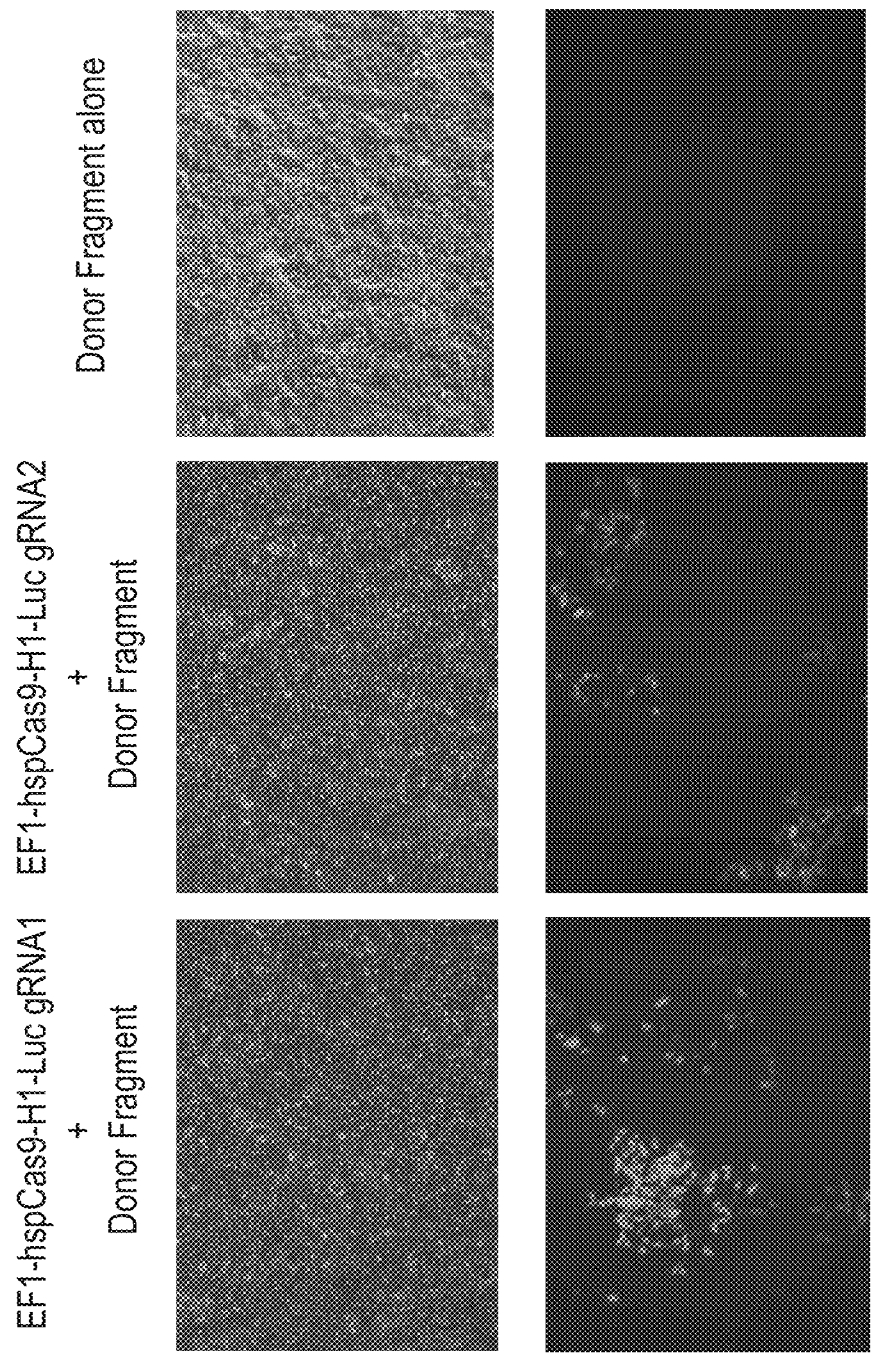
FIG. 8 provides phase contrast photomicrographs and corresponding red florescence photomicrographs of 293T cell line cultures that have been transfected with the CRISPR DNA constructs indicated and donor nucleic acid. These cell cultures were transfected with either (i) EF1-hspCas9-H1-Luc gRNA1 and donor, (ii) EF1-hspCas9-H1-Luc gRNA2 and donor, or (iii) donor alone.

Not surprisingly, RFP signal was detected in cell cultures transfected with EF1-hspCas9-H1-Luc gRNA1 and donor, as well as cultures transfected with EF1-hspCas9-H1-Luc gRNA2 and donor; further, this red fluorescence was dependent on the presence of donor fragment (see FIG. 8).

D) RFP Cell Sorting

The appearance of red fluorescence in the luciferase-stable 293T cell line is explained by a homologous recombination event involving the genomic luciferase sequence and the RFP gene contained on the donor fragment. A corollary of that explanation is that with the appearance of red fluorescence, there is a concomitant loss of luciferase activity. That hypothesis was tested using cell sorting analysis, where the transfected cell cultures described above were collected and sorted into an RFP-positive population and an RFP-negative population using FACS. Those sorted populations of cells were then used to make cell extracts for use in the luciferase assay.

It was observed that the population of RFP-positive cells displayed no luciferase activity, whereas the population of RFP-negative had detectable luciferase activity. This observation is consistent with complete replacement of the stably integrated luciferase gene from the genomic locus, where that luciferase gene has now been replaced with the RFP gene, consistent with a homologous recombination event.

Collectively, the result of each of these assays supports the assertion that the engineered all-in-one CRISPR II system using a codon-optimized Cas9 gene is a simple and robust system to achieve targeted sequence-specific genomic editing in mammalian cells.

Example 7

Nuclear Localization Signal (NLS) Optimization

This example describes the use of various nuclear localization signal (NLS) sequences in fusion proteins with the Cas9 polypeptide to test the ability of these fused NLS sequences to direct Cas9 protein to the cell nucleus, which is required for Cas9 targeting to the genomic material.

Cas9 polypeptide encoded by either the codon optimized hspCas9 (described in Example 1) or the native bacterial Cas9 open reading frame was fused with mCherry, a red fluorescent protein, in order to monitor the expression and subcellular localization of Cas9 proteins when expressed in HEK 293T host cells.

Various known NLS sequences (NLS1-NLS5) were fused at either the N terminus or C terminus of the optimized hspCas9 gene or the bacterial Cas9 gene, to direct in-frame fusions of Cas9 protein with these NLS, in various combinations. These vectors were transfected into HEK 293T host cells, and observed three days following transient transfection using Lipofectamine® 2000 (Life Technologies™). Florescence microscopy was used to assess RFP signal and effectiveness of the various NLS to drive nuclear import of the fusion proteins.

The amino acid sequences and corresponding nucleotide sequences of these various nuclear localization signals are provided in FIG. 9A. In the amino acid sequences in FIG. 9A, stop codons are indicated by an asterisk. The following fusion protein configurations were tested:

NLS1-spCas9-mcherry
NLS1-spCas9-mcherry-NLS2
NLS1-spCas9-mcherry-NLS3
NLS4-hspCas9-mcherry-NLS5

The results of the fluorescence microscopy analysis are summarized in FIG. 9B. When a single NLS was placed at the N terminus of the bacterial encoded spCas9 gene, some limited expression of fluorescent protein is observed, but import into the nucleus appears to be poor, as most of the RFP signal is observed in the cytoplasm. When NLS sequences are placed at both the N terminus and C-terminus of the bacterial encoded spCas9 gene, nuclear localization of the fusion proteins are observed, however, expression levels in the 293 cells remains weak. In contrast, when NLS4 and NLS5 sequences are placed at the N- and C-termini, respectively, robust expression of fluorescent fusion protein is detected, which is strongly localized to the nucleus.

Example 8

Methodologies for Cas9 (D10A) Mutant Target-Specific Genomic Editing

This Example describes the validation of Cas9 mutant polypeptides to direct genomic editing, including Cas9 single-stranded DNA nickases. Using the paired nickase approach described in this Example, genomic regions can be targeted for any desired deletions, insertions or substitutions.

The CRISPR/Cas9 nuclease systems for targeted genomic modification described in the present disclosure can be used in either of two ways.

A) Wild Type Cas9 Systems

The all-in-one vector systems described herein can express wild type Cas9 polypeptide (for example, the mammalian codon-optimized hspCas9 gene or the bacterial encoded spCas9 gene), which retain double-stranded nuclease activity and will produce double-stranded breaks in genomic sequences that have been targeted by the programmable and customizable guide RNAs (gRNA). This Cas9 (WT) system can be used alternatively as either (i) a targeted mutagenesis system that can induce mutations at a targeted site because of the ability of double-stranded breaks to elicit nonhomologous end joining (NHEJ), and as a result, tend to introduce insertions/deletions at the site of DNA cleavage; or (ii) used to direct homologous recombination at a targeted locus, in combination with donor nucleic acid template sequence that is also provided to the host cells.

B) Mutant Cas9 Nickase Systems

One amino acid mutation at position DMA in the Cas9 amino acid sequence results in the inactivation of the double-stranded nuclease catalytic activity and converts Cas9 to a "nickase" enzyme that makes single-stranded breaks at the target site. This Cas9 nickase can be used at a targeted site to favor homologous recombination at the site (in conjunction with suitable donor nucleic acid template sequence), and thereby, lowering the rate of undesired NHEJ events. In addition, a Cas9 protein double mutant (DM) with amino acid substitutions at amino acid positions DMA and H840A is also provided. This double mutant completely inactivates both the double-stranded cleavage activity as well as the single-stranded nickase activity, and is termed a "null nuclease."

Figure 10A:
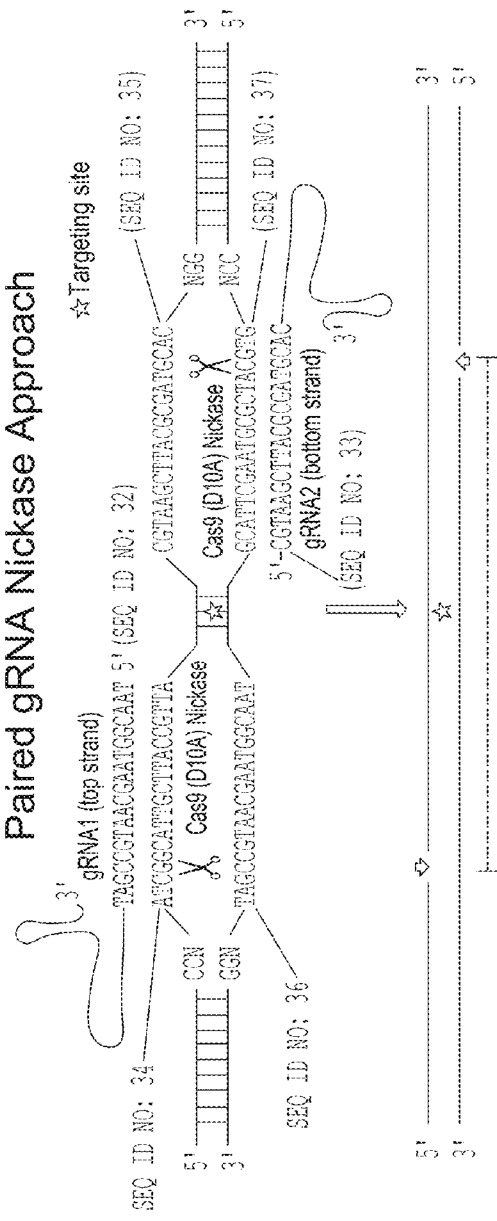
FIG. 10A provides a schematic of the cleavage step used in CRISPR-directed homologous recombination using an approach incorporating a pair of guide RNA molecules and a mutant Cas9 protein having nickase activity.

In order to enhance genome editing specificity of the Cas9(D10A) mutant, a paired guide RNA nickase approach can be used, as shown generally in FIG. 10A. As shown in the figure, two gRNA molecules (gRNA1 and gRNA2) are designed for complementarities to the top stand (sense strand, upstream of the targeting site) and bottom strand (antisense strand, downstream of the targeting site), respectively. The site where sequence editing is desired is indicated with a star. When these two guide RNA molecules are delivered to a cell in conjunction with the mutant Cas9 (D10A) nickase, the double Cas9 nicking generates a cleaved region with a 5' overhang double stranded DNA break. This configuration is highly conducive to homologous recombination when a template nucleic acid with homology to flanking sequences is present. Generally, gRNA pairs creating 5' overhangs with less than 8 base pairs of sequence overlap between the guide sequences are able to mediate detectable indel formation. Guide RNA pairs with greater than 8 base pairs of sequence overlap will tend to solicit a more advantageous homologous recombination mechanism to effectuate repair of the nicked overhang region. Generally, when designing gRNA sequences for use in paired nickase approach, it is best to first verify that each gRNA by itself is able to efficiently induce indels when coupled with wide-type Cas9 expression.

Figure 10B:
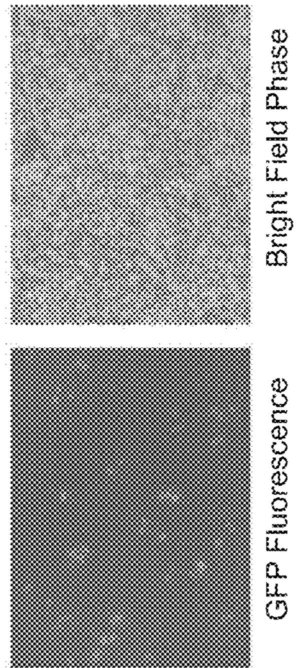
FIG. 10B provides a green florescence photomicrograph and corresponding phase contrast photomicrograph of a 293T cell culture that has been transfected with in vitro transcribed RNA expressing the mutant Cas9(D10A) nickase and two paired guide RNAs targeting an integrated AAVS genomic locus, and cotransfected with GFP donor sequence.

FIG. 10B provides sample experimental data using the paired nickase approach to site specific genomic editing. In this experiment, in vitro transcribed hspCas9 nickase mRNA and two paired guide RNA transcripts targeting the AAVS locus were transient transfected in EGIP 293 T cells using Lipofectamine® 2000 (Life Technologies™). Listed below are sequences of paired gRNA molecules:

```
AAVS gRNA1:
                              (SEQ ID NO: 18)
GGGGCCACTAGGGACAGGAT

AAVS gRNA2:
                              (SEQ ID NO: 55)
GTGGGGTGGAGGGGACTT
```

The green fluorescence photomicrograph shows restoration of green fluorescence in the EGIP cells, indicating that the paired nickase target sites created a 5' overhang that directed HR in the presence of complete EGFP nucleotide sequence donor.

Example 9

Validation of Cas9 Nickase and Cas9 Null Nuclease Using a Surveyor Cleavage Assay This Example provides validation experiments demonstrating the functionality of the Cas9 nickase mutant to direct homologous recombination using a paired nickase and template donor DNA approach as described in Example 8.

To validate the functionality of the Cas9(D10A) nickase mutant and the Cas9 double mutant null nuclease, a series of all-in-one Cas9/gRNA expression vectors were constructed, having the general structure as shown in FIG. 1A. These vectors alternatively expressed the wild type Cas9 protein, the Cas9 nickase mutant or the Cas9 null nuclease double mutant, driven by the EF1-α hybrid promoter. Each of these Cas9 proteins was encoded by the mammalian codon-optimized Cas9 gene hspCas9, containing either the wild type nucleotide sequence, or the corresponding mutant nucleotide sequences.

The cells used in the experiment was the EGIP cell line, which contains a stably integrated gene encoding the EGFP protein that is disrupted by an intervening insert containing a stop codon and the AAVS1 sequence, as described above in Example 4 and shown in FIG. 3D.

The guide RNA sequence listed below targeting the AAVS locus was cloned into hspCas9, hspCas9 (D10A) nickase and hspCas9 DM all-in-one CRISPR vector:

```
AAVS gRNA1:
                              (SEQ ID NO: 18)
GGGGCCACTAGGGACAGGAT (FIG. 3C)
```

The following all-in-one CRISPR vectors were constructed:

EF1-hspCas9-H1-AAVS gRNA1

EF1-hspCas9 (D10A)-H1-AAVS gRNA1

EF1-hspCas9 DM (null-nuclease)-H1-AAVS gRNA1

These constructs were transiently transfected into the EGIP cell line using Lipofectamine® 2000 (Life Technologies™), and EGIP untransfected cells were used as negative control (NC). Three days after transfection, genomic DNA was used for PCR template using primers that amplify EGFP region followed by a SURVEYOR Assay according to manufacturer's protocol to assess genomic double-stranded DNA cleavage efficiency.

Figure 11:
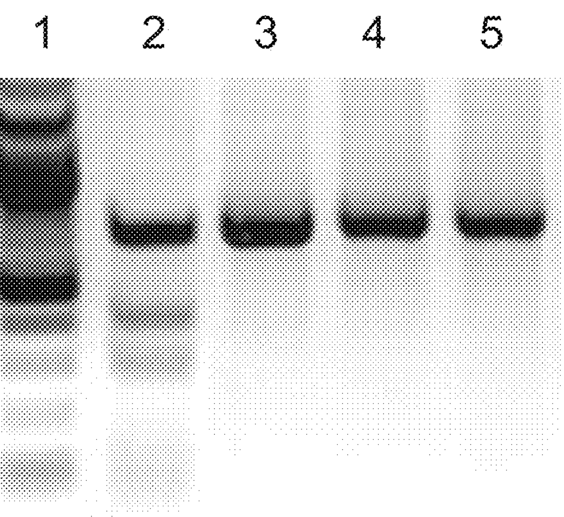
FIG. 11 provides a photograph of an agarose gel stained with ethidium bromide showing the DNA cleavage fragments generated following a SURVEYOR® Mutation Detection assay with DNA samples derived from cell cultures transfected with the indicated CRISPR constructs.

Results of the assay are shown in FIG. 11, which indicate that only the cell expressing wild type Cas9 activity showed gRNA directed double-stranded DNA cleavage, as assessed by the appearance of digested smaller bands. The Cas9 nickase mutant (D10A) and the double mutant (DM) did not show any smaller bands, indicating no double-stranded DNA cleavage activity in the host cells. Therefore, only wild type Cas9 can generate double strand breaks with the guidance of a single gRNA, while Cas9 nickase mutant (D10A) or Cas9 DM cannot mediate double strand breaks with a single gRNA.

Example 10

Validation of Cas9 Paired Nickase Method to Direct Homologous Recombination Using a GFP Rescue This Example provides further validation experiments demonstrating the functionality of the Cas9 nickase mutant to direct homologous recombination using a paired nickase and template donor DNA approach as described in Example 8.

Two guide nuclease target sequences were used that target the AAVS sequence, separated by approximately three base pairs of AAVS sequence. These target sequences were as follows:

```
AAVS gRNA1:
top strand
                    (FIG 3C; and SEQ ID NO: 18)
GGGGCCACTAGGGACAGGAT

AAVS gRNA2:
bottom strand
                                 (SEQ ID NO: 55)
GTGGGGTGGAGGGGACTT
```

These two guide RNA targeting sequences are specific for the top strand and bottom strand of the AAVS insert, respectively. These target sequences were cloned into the all-in-one vector backbone, and the complete guide RNA sequence is expressed from the H1 promoter. When used simultaneously in the same host cell, the Cas9 nickase activity will produce a 5' overhang that can promote a homologous recombination event with a suitable donor fragment. In this case, a donor fragment containing functional EGFP gene sequence was used.

The all-in-one CRISPR vectors described in Example 9 were used in transfections into the EGIP cell line in the following combinations, and also as shown in FIG. 12.

1) EF1-hspCas9(WT)-H1-AAVS gRNA1+Donor Fragment
2) EF1-hspCas9 (D10A)-H1-AAVS gRNA1+Donor Fragment
3) EF1-hspCas9 DM-H1-AAVS gRNA1+Donor Fragment
4) EF1-hspCas9 (D10A)-H1-AAVS gRNA1+EF1-hspCas9 (D10A)-H1-AAVS gRNA2+Donor Fragment Following transfection, homologous recombination efficiency was monitored by green fluorescence positive signals. See FIG. 12. It was observed that the cells receiving the hspCas9(WT) protein showed reasonable levels of homologous recombination (8-9% of the cells in the culture showed HR after transient transfection). Similarly, the cells receiving the hspCas9 nickase (D10A) in combination with the paired guide RNA molecules gRNA1 and gRNA2 also showed reasonable levels of homologous recombination (8%). In contrast, hspCas9 (D10A) that is expressed with only gRNA1 showed only 0.5% homologous recombination, and the hspCas9 DM null nuclease in combination with gRNA1 showed no detectable GFP signal.

These results indicate that the pair of AAVS guide RNA molecules were able to program the Cas9 nickase activity to two separate genomic loci, thereby creating a 5' overhang structure that can promote a homologous recombination event with an intact EGFP donor fragment.

Example 11

All-in-One hspCas9 Expression Vectors

This Example provides hspCas9 all-in-one vectors that use alternative regulatory elements and fusion protein configurations. This Example illustrates that a variety of regulatory elements and fusion protein configurations function in conjunction with the invention, and the invention is not limited to the regulatory elements and fusion protein configurations that are itemized herein.

A) Expression of Cas9 Using the CAG Promoter with an Embedded T7 Promoter

The CAG promoter is a strong synthetic promoter/enhancer construction that can be used to drive gene expression in mammalian host cells. The promoter comprises sequence elements from (i) the cytomegalovirus (CMV) immediate early enhancer element, (ii) the promoter, the first exon and the first intron of the chicken β-actin gene, and (iii) the splice acceptor of the rabbit beta-globin gene.

The T7 promoter is a bacterial promoter derived from the bacteriophage T7. In vitro T7 transcription is the synthesis of RNA using a T7 promoter and purified T7 RNA polymerase enzyme. The T7 promoter nucleotide sequence is used extensively in expression vectors that are to be used to generate in vitro transcription products due to the promoter's high affinity for the T7 RNA polymerase and robust level of expression activity.

The nucleotide sequence encoding the T2A peptide is commonly incorporated into mammalian expression vectors that generate polycistronic mRNA fusions. The viral *Thosea asigna* 2A (T2A) peptide, when placed in-frame between two ORFs in a polycistronic message induces a co-translational ribosome "skipping," thereby producing two separate, unfused protein products from the polycistronic mRNA.

Two second-generation all-in-one CRISPR vectors were designed and constructed for the expression of Cas9 polypeptides and guide RNA. Furthermore, these all-in-one vectors also contain the nucleotide sequence encoding either GFP or RFP fluorescent protein markers. These genes encoding the fluorescent proteins are transcribed in a bicistronic message with the Cas9 open reading frame, and processed co-translationally to produce separate (unfused) Cas9 and GFP/RFP proteins.

The following all-in-one constructs with the following configurations were constructed:

CAG-T7-hspCas9-T2A-GFP-H1-sgRNA (using a copGFP)

CAG-T7-hspCas9-T2A-RFP-H1-sgRNA

The T7 promoter in these constructs facilitates in vitro transcription, because the T7 promoter remains silent in mammalian host cells, but only becomes active when purified T7 RNA polymerase protein is provided in an in vitro system. This arrangement permits T7-driven in vitro transcription without the need to construct a new expression vector for use in the in vitro reaction.

In validation experiments, transient transfection of these constructs into HEK 293 cells using Lipofectamine® 2000, resulting in robust green and red fluorescence, respectively, which localized to the cell nucleus.

B) Expression of Cas9 from EBNA Vectors

Plasmid vectors based on the Epstein Barr virus (EBV) are stably maintained in multiple copy numbers extrachromosomally over long periods of time. The functional components of these vectors are the EBV latent origin of replication (oriP), which interacts with the viral transactivator protein EBNA-1 to promote episomal maintenance. Studies from others have shown the general utility of the oriP/EBNA-1 plasmid system in expressing recombinant protein sequences in mammalian cells. High transfection efficiencies using oriP/EBNA vectors is also observed due to oriP/EBNA-1 mediated nuclear import and retention of vector DNA.

An oriP/EBNA-based hspCas9 all-in-one vector was constructed having the following configuration: EF1-hspCas9-T2A-Ruby-H1-AAVS gRNA1-OriP This plasmid was cotransfected into the EGIP cell line along with EGFP rescue donor vector. The transfected cultures were viewed under green and red fluorescence microscopy two days and five days following transfection. At two days post-transfection, many red fluorescent positive cells are observed, with relatively few green fluorescent cells visible. At five days following transfection, the red fluorescent signals became faint and green fluorescent positive cells became more prominent, indicating homologous recombination events that rescue the green fluorescence in these cells.

Example 12

Targeted Transcription Suppression by Cas9 Null Nuclease

This Example describes the use of the codon-optimized hspCas9 DM null nuclease in the regulation of gene expression by targeting and occupying promoter-proximal binding sites.

In an effort to determine whether a Cas9 DM (null nuclease) targeting to genomic sequences can down-regulate gene expression (without modifying or disrupting the nucleotide sequences at the genomic DNA locus), various guide RNAs were designed that target a synthetic reporter gene, and those guide RNA were expressed in a host cell along with the hspCas9 DM gene. The activity of a luciferase reporter gene linked to the targeted promoter was monitored.

The reporter cell line used in this study was the HEK 293T cell line containing a stably integrated luciferase reporter gene driven by the constitutively active CMV promoter, as shown in the top panel of FIG. 6C. The transgene in this cell line coexpresses the luciferase and the GFP in a bicistronic message under the control of the single CMV promoter. The GFP and luciferase polypeptides are cleaved from each other during translational processing. This recombinant cell line is GFP positive and luciferase positive.

Several targeting sequences that target the integrated CMV promoter, GFP and luciferase genes, on either the sense strand or antisense strand, were designed and cloned into an all-in-one CRISPR vector, thereby producing gRNA molecules that target these various loci within the integrated transgene. These guide RNA targeting sequences are listed below. Target sequences that are located upstream of that transcription initiation site are labeled as negative, and target sequences that are located downstream of transcription initiation site are labeled as positive.

| gRNA | Targeting Sequence | Distance to transcription initiation site |
|---|---|---|
| CMV-T | CGGTAGGCGTGTACGGTGGG (SEQ ID NO: 56) | -41 bp |
| CMV-B | ACAGCGTGGATGGCGTCTCC (SEQ ID NO: 57) | +3 bp |
| GFP-T | AAGATCGAGTGCCGCATCAC (SEQ ID NO: 58) | +95 bp |
| GFP-B | CTCGATCTTCATGGCGGGCA (SEQ ID NO: 59) | +84 bp |
| Luc-T | GACGCCAAAAACATAAAGAA (SEQ ID NO: 60) | +956 bp |
| Luc-B | CGGGCCTTTCTTTATGTTTT (SEQ ID NO: 61) | +963 bp |

Figure 13A:
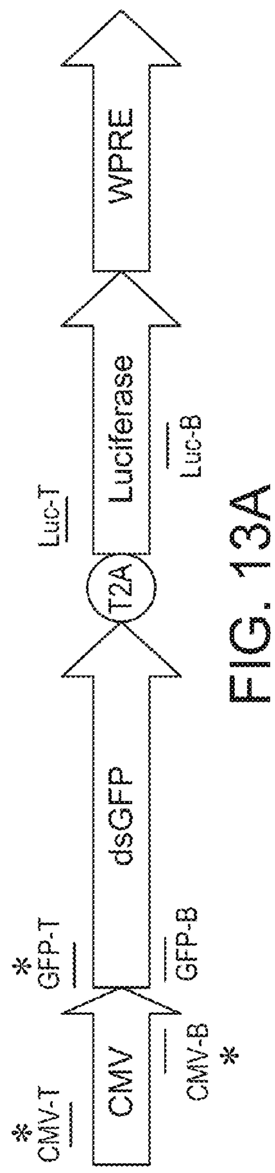
FIG. 13A provides a schematic of the recombinant genomic locus in a GFP/luciferase stable HEK 293T reporter cell line. The relative positions of six different targeting sequences are shown above and below the locus.

The approximate locations of each of these target sequences are shown schematically in FIG. 13A.

In addition to the guide RNA transcription products, the all-in-one CRISPR vector contained and expressed the codon-optimized hspCas9 DM null nuclease. The all-in-one vector was transfected into the host cell line stably expressing the integrated firefly luciferase reporter gene and GFP driven by the CMV promoter. Negative regulation of the endogenous luciferase gene was tested. The *Renilla* luciferase expression construct was cotransfected with the individual hspcas9 DM gRNA constructs, and hspCas9 DM without gRNA construct was used as a positive control. Due to their distinct evolutionary origins, firefly and *Renilla* luciferases have distinguishable enzyme structures and substrate requirements. These differences make it possible to selectively discriminate between their respective bioluminescent reactions. In this study, the *Renilla* luciferase expression is driven by a constitutive TK promoter, which reflects the transfection efficiency and cell viability to be served as an external control for normalization purposes.

Figure 13B:
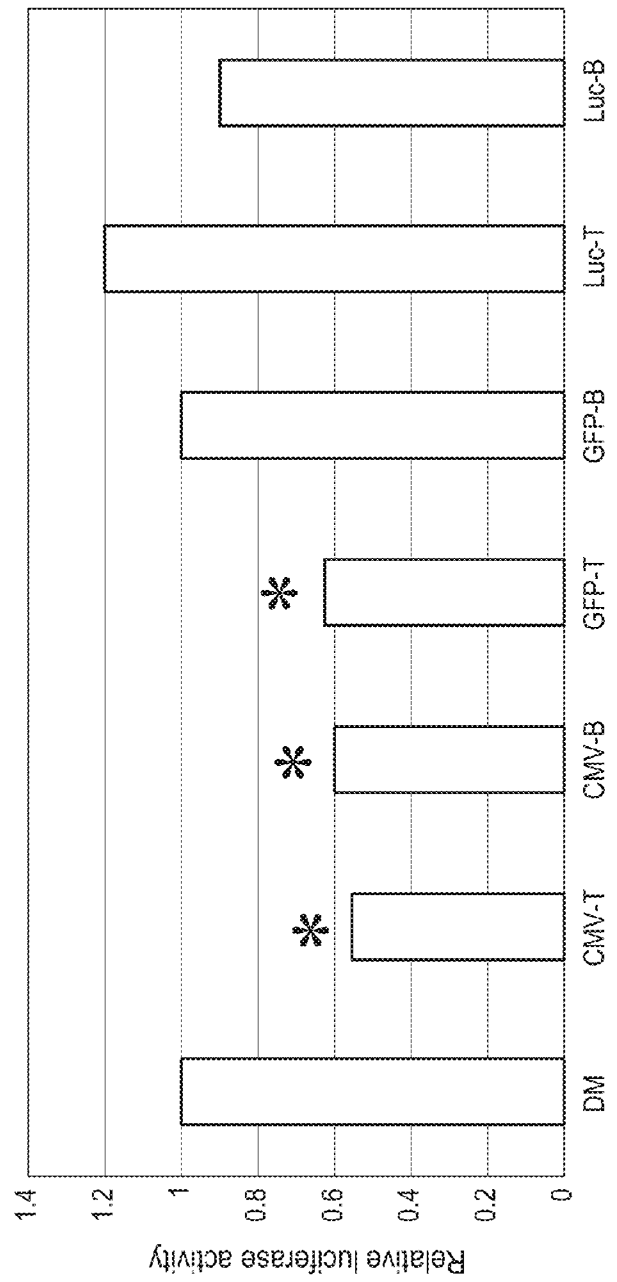
FIG. 13B provides the results of a luciferase assay using cell extracts derived from cell cultures that were transfected with Cas9 CRISPR reagents and the targeting guide RNAs as indicated. Asterisks indicate targeting sequences that showed suppression of luciferase expression.

It was observed that the all-in-one vectors expressing guide RNAs targeting CMV-T, CMV-B and GFP-T can suppress luciferase activity 40-50%. See FIG. 13B. Asterisks indicate guide RNA targets that showed transcription suppression. This finding is consistent with literature reports that the loading of spCas9 DM at promoter regions or regions close to the start codon can achieve a better suppression effect compared to more distantly located target regions.

Example 13

Targeted Transcription Suppression by Chimeric Cas9 Transcription Factors

This Example describes the use of the codon-optimized hspCas9 DM null nuclease in the regulation of gene expression by the construction of sequence-specific chimeric transcription-factor gene suppressors.

The term "transcription factors" generally refers to sequence-specific DNA-binding proteins that bind to DNA in a region usually proximal to the transcription start site, and regulate the rate of transcription initiation. Transcription factors can perform this function alone or in association with other regulatory proteins in a larger protein complex. A transcription factor can be an activator of transcription (promotes the recruitment of RNA polymerase) or act as a repressor of transcription (blocks the recruitment of RNA polymerase). The DNA sequences to which transcription factors bind are termed "enhancer elements" or "repressor elements."

A defining feature of many transcription factor proteins is the modular nature of their structure, where their DNA-binding domain is frequently distinct and functionally separable from their activation or repression domain. This modular construction in nature has allowed the construction of recombinant synthetic transcription factors that mix-and-match DNA binding domains and activation/repression domains from different naturally occurring transcription factors to form new transcription factors having novel gene-specific activities.

The validation of the CRISPR system of the invention using a mammalian codon-optimized variant of the bacterial Cas9 gene and a customizable guide RNA that programs sequence-specific DNA binding provide valuable tools for the creation of customizable transcription factors. If a suitable transcription modulation domain (e.g., an activation domain or a repressor domain) can be fused with a Cas9 polypeptide, then that fusion protein can act as a transcription fact that can be targeted to any desired genomic locus by using the programmable CRISPR guide RNA target sequence.

This system to form custom Cas9-fusion transcription factors will have numerous benefits and great utility because (i) the design of new DNA binding proteins (e.g., zinc-finger DNA binding proteins) is not required, (ii) the validation of the mammalian codon-optimized Cas9 gene hspCas9 demonstrates that this gene sequence is capable of robust expression in mammalian host cells, (iii) the preexistence of a naturally occurring DNA binding element in the promoter region of the gene of interest is not necessary, because any desired genomic DNA sequence can be targeted for protein binding by the design of a suitable Cas9 RNA guide target sequence, (iv) the all-in-one CRISPR vectors of the invention simplify transfection protocols, such that only a single vector is required to express both the Cas9 fusion protein and the guide RNA, and (v) the Cas9 moiety that is tethered to the DNA by the guide RNA can be conveniently converted from a transcription activator to a transcription repressor by swapping the transcription regulatory domain in the Cas9 fusion protein, and without the need to design a new guide RNA target sequence.

To this end, a chimeric Cas9 fusion protein was designed that can serve as a transcription repressor when expressed in conjunction with a suitable guide RNA. This Cas9 fusion contained the hspCas9 DM (null nuclease) gene fused to the KRAB transcriptional repressor domain. The KRAB domaon nucleotide and amino acid sequences are provided in FIG. 16B.

The Krüppel associated box (KRAB) is a transcriptional repression domain present in many human zinc finger transcription factors. The domain typically consists of about 75 amino acid residues, and where the minimal repression module is approximately 45 of those amino acid residues. Substitutions of the conserved amino acid residues in the domain abolish repression activity. The KRAB domain was initially identified as a periodic array of leucine residues separated by six amino acids, coined a heptad repeat (also known as a leucine zipper). This domain was later renamed after its association with the Krüppel family zinc finger transcription factors.

The KRAB domain remains one of the strongest transcriptional repressor domains identified in the human genome. A large number of independently encoded KRAB domains have been shown to be effective repressors of transcription, suggesting that this conserved amino acid sequence motif is responsible for the transcriptional repression activity, and further indicates that the KRAB repression motif will likely function across all tetrapod species (including amphibians, reptiles, birds and mammals) and will be active in many if not all cell types.

In addition to the KRAB domain, the Cas9 fusion protein also contained the Ruby red fluorescent protein sequence. The structure of the fusion was: hspCas9 DM-KRAB-RFP The fusion gene encoding this polypeptide was cloned into the all-in-one CRISPR vector under the control of the EF1-α hybrid promoter. Four different all-in-one vectors were created containing four different guide RNA target sequences. These sequences were the CMV-T and GFP-T target sequences provided in Example 12, which showed suppression of luciferase expression in the HEK 293T reporter cell line shown schematically in FIG. 13A, and Luc-B and GFP-B, which did not show any suppression of luciferase expression in that host cell line.

Each of these four all-in-one CRISPR vectors were alternatively transfected into the luciferase reporter cell line. These all-in-one vectors were cotransfected with a second plasmid expressing *Renilla* luciferase as a normalization marker. Three days following the transfection, cells were harvested and whole extracts were prepared for a dual luciferase assay (Promega) according to the manufacturer's protocol. Luciferase activity in each of the samples is provided as a relative activity compared to a control GFP-firefly luciferase stable cell line receiving only the *Renilla* luciferase expression vector (pGF), which was normalized to a value of one for reference purposes. The results of the luciferase assay are provided in the table below:

| gRNA Target | Relative Luciferase Activity |
|---|---|
| pGF | 1.00 (normalized) |
| CMV-T | 0.20 |
| Luc-B | 0.23 |
| GFP-T | 0.21 |
| GFP-B | 0.22 |

Impressively, it was observed that each of the gRNAs tested was able to suppress luciferase reporter activity by about 80% just three days post transfection.

This result validates the use of Cas9 protein, for example the hspCas9 DM-KRAB-RFP fusion protein, in the construction of chimeric Cas9 transcription factors that can be custom targeted to any gene of interest with a gRNA target sequence. In this example, that gRNA target sequence turns that targeted sequence into a transcriptional repressor element.

In the previous Example 12, it was shown that the hspCas9 DM by itself (without any fused suppressor domain) can have a suppression effect on gene expression if the Cas9 is targeted to promoter proximal DNA elements. In the present example, it is observed that the suppression effect is robustly increased by the fusion of the KRAB suppression domain to Cas9. Interestingly, it is observed in this example that the magnitude of the suppression effects of the Cas9-KRAB fusion are not limited to DNA sites in close proximity to the transcription start site or translation start site; the Luc-B and GFP-B distal target sequences showed suppression activity that was equally robust as seen when using the CMV-T and GFP-T proximal target sequences (see FIG. 13A).

Example 14

Targeted Transcription Activation by Chimeric Cas9 Transcription Factors

This Example describes the use of the codon-optimized hspCas9 DM null nuclease in the regulation of gene expression by the construction of sequence-specific chimeric transcription-factor gene activators.

The modular nature of transcription factors allows the separation of the DNA-binding domain from the activation/repression domain of the protein. Recombinant synthetic transcription factors can be constructed that mix-and-match DNA binding domains and activation/repression domains from different naturally occurring transcription factors to form novel transcription factors. The validation of the CRISPR/Cas9 system (and specifically the codon-optimized hspCas9 described herein) for designing sequence-specific tethering of a protein to DNA provides a valuable tool for the creation of customizable transcription factors.

If a suitable transcriptional activation domain can be fused with a Cas9 polypeptide, then that fusion protein can act as a transcriptional activator that can be targeted to any desired genomic locus using a guide RNA target sequence. To this end, a chimeric Cas9 fusion protein was designed that can serve as a transcription activator when expressed in conjunction with a targeting guide RNA. This Cas9 fusion contained the hspCas9 DM (null nuclease) gene fused to the VP64 transcriptional activation domain. The VP64 activation domain nucleotide and amino acid sequences are provided in FIG. 16B.

The VP64 transcriptional activation domain is tetrameric tandem repeat of the minimal activation domain (amino acids 437-447) of the herpes simplex viral protein 16 (VP16), each VP16 repeat having the sequence DALDDFDLDML (SEQ ID NO: 62). When fused to another protein moiety that provides sequence-specific DNA binding in a gene promoter region, VP64 acts as a strong transcriptional activator.

In addition to the VP64 domain, the Cas9 fusion protein also contained the red fluorescent protein Ruby sequence. The structure of the fusion was: hspCas9 DM-VP64-RFP.

The fusion gene encoding this polypeptide was cloned into the all-in-one CRISPR vector under the control of the EF1-α hybrid promoter.

Six different all-in-one vectors were constructed containing the hspCas9DM-VP64-RFP fusion gene and six different guide RNA target sequences. These sequences were designed to target the endogenous MyoD promoter region to activate MyoD gene expression. The six gRNA were derived from genomic sequences residing within 1,000 base pairs of the endogenous MyoD translation start site. These target sequences are shown below:

| gRNA | MyoD Promoter Region Target Sequence | SEQ ID NO: |
|---|---|---|
| MyoD 1 | TGAGGTCAGGTTCTCAGGCC | 63 |
| MyoD 2 | GATGGAGGGGATTCCTAACC | 64 |
| MyoD 3 | GGTGTTGGAGAGGTTTGGAA | 65 |
| MyoD 4 | CTCTGTCCCCTGATTTGTGG | 66 |
| MyoD 5 | GCTGGGGGAGGGGGAGTCCG | 67 |
| MyoD 6 | CCTCCCTCCCTGCCCGGTAG | 68 |

Based on reports of others, cotransfection of multiple gRNAs in a CRISPR system can have a synergistic effect on target gene activation. With the goal of demonstrating gene activation at the endogenous MyoD locus, all six of the all-in-one vectors were simultaneously transfected into HEK 293 cells. Five days after transfection, RNA was collected from the cells, as well as untransfected HEK 293 negative control cells. The RNA was used to generate cDNA, and then the expression level of MyoD was measured using real time quantitative PCR (qPCR) using SYBR Green. The relative abundance of MyoD transcript is indicated by cycle threshold (Ct) values. These Ct values were normalized to a negative control measurement derived from HEK 293 cells that had not received any all-in-one CRISPR vector.

Not surprisingly, this quantitation found that MyoD expression was not detectable in the HEK 293 cells. In contrast, cells transfected with the hspCas9 DM-VP64-RFP-MyoD-gRNA vector mix showed a Ct value of 29, indicating upregulation of the endogenous MyoD locus.

MyoD expression was undetectable in 293 cells, as no Ct value was detected by the qPCR system. In order to quantitate the upregulation, the Ct value was tentatively set at a value of 36, which is regarded as no expression. Thus, the fold change in expression is 2^(Ct of the negative control−Ct of the tested cells). If we take the MyoD expression in 293 cells as Ct value of 36, then the Cas9-VP64-MyoD-gRNA vector mix can enhance MyoD expression by 128 fold.

In order to confirm that endogenous MyoD transcript was generated in the HEK 293 cells, RT-PCR was used to amplify a portion of the MyoD message, and visualized on gel electrophoresis. RNA samples were collected five days post transfection from untransfected 293 cells and 293 cells that were transfected with the all-in-one hspCas9 DM-VP64-RFP gRNA vector mix expression constructs. That RNA was used to generate cDNA, and those DNA products were used in a PCR reaction with MyoD-specific primers. The PCR products were resolved on an agarose gel. There was no detectable expression of MyoD in the untransfected HEK 293 cells. In contrast, there was a robust PCR product observed having the predicted size of a MyoD PCR amplicon, indicating strong expression of that MyoD was induced by hspCas9 DM-VP64-RFP MyoD gRNA vector mix. β-actin message was used as an internal control to confirm that input cDNA amount is similar.

Example 15

Delivery of CRISPR System Components by Transfection of In Vitro Transcription Products As described in the Examples above, the all-in-one CRISPR system can be implemented in host cells in plasmid format, where plasmid DNA is transfected into the cells.

Alternatively, the components of the CRISPR system can also be delivered in an mRNA format as the products of in vitro transcription. This example describes the delivery of CRISPR system components (Cas9 nucleotide sequences and guide RNA sequences) to host cells by transfection of in vitro transcription products.

In vitro transcription (IVT) is a simple procedure that allows for cell free, template-directed synthesis of RNA molecules (e.g., synthetic mRNA molecules) using template DNA and purified biochemical reagents. Any types of RNA sequence can be produced, and in quantities large enough to use in transfections of cultured mammalian cells. It is based on the engineering of a template that includes a bacteriophage promoter sequence (e.g., the T7 promoter sequence from the bacteriophage T7, which specifically binds and initiates the phage T7 RNA polymerase) upstream of the sequence of interest followed by transcription using the corresponding purified RNA polymerase.

In view of the many advantages of using in vitro transcription products in mammalian cell transfections, including efficiency and convenience, the all-in-one CRISPR system was modified to permit the in vitro production of functionally-validated Cas9 mRNA and guide RNA molecules.

A) In Vitro Generated RNA Encoding Cas9

Figure 14A:
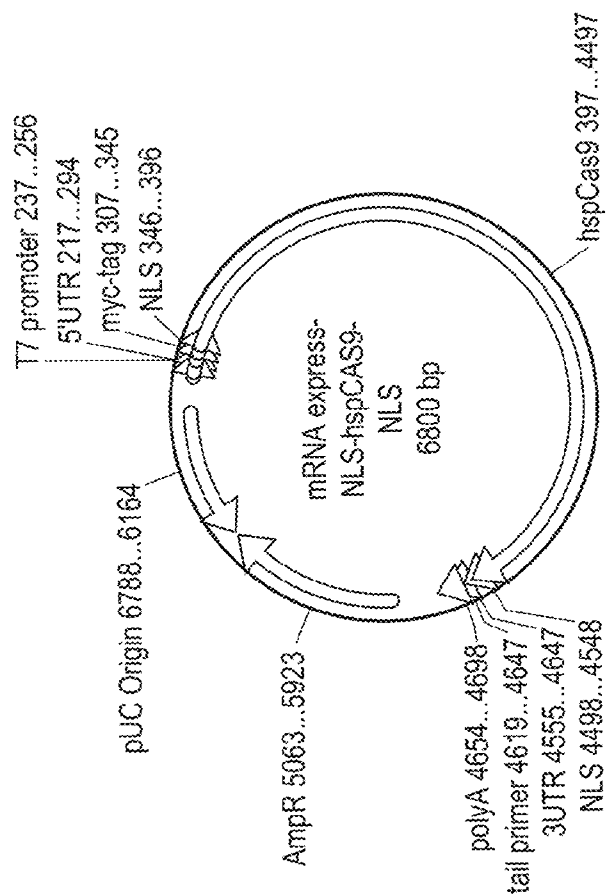
FIG. 14A provides a plasmid map of a construct used to generate in vitro transcribed mRNA product encoding a Cas9 polypeptide, in this case, encoded by the codon-optimized hspCas9 polynucleotide sequence. This mRNA is used in transfections of mammalian cells. Positions of the major features of the construct are indicated.

A vector for the in vitro expression of mRNA encoding Cas9 polypeptides was constructed. One example of this vector is shown in FIG. 14A. This vector generates an RNA molecule capable of translation in mammalian host cells. The vector expresses the Cas9 gene sequence from the T7 promoter. The vector shown in FIG. 14A expresses the codon-optimized hspCas9(WT) open reading frame that includes two NLS signals and an N-terminal myc-tag. Although the hspCas9 gene is depicted in this figure, any Cas9 open reading frame (with or without these particular NLS sequences, or with or without any other fused sequences such as tags or markers like myc-tag or fluorescent protein fusions) can be expressed from the vector.

The codon-optimized open reading frames encoding the following Cas9 polypeptides were cloned into the T7 based in vitro transcription vector shown in FIG. 14A:

hspCas9
hspCas9-GFP
hspCas9-RFP
hspCas9 D10A nickase
hspCas9 DM (null nuclease)

After the vector construction, a pair of PCR primers was used to amplify the sequence of the Cas9 polypeptides, and PCR product was used as template for in vitro transcription. Alternatively, T7-based in vitro transcription vectors containing Cas9 polypeptides can be linearized by BamHI restriction enzyme to serve as template for in vitro transcription. Robust quantities of hspCas9 mRNA were synthesized using a T7 High Yield RNA synthesis kit (New England BioLabs®, Inc.) according to the manufacturer's protocol, as assessed by resolution on a 1% denaturing agarose gel electrophoresis followed by ethidium bromide staining.

B) In Vitro Generated RNA Encoding Guide RNA Molecules

A vector for the in vitro expression of CRISPR guide RNA was also constructed, as shown in FIG. 14B. This vector also drives the in vitro expression of guide RNA from the T7 promoter. Unlike the Cas9 gene IVT product, this guide RNA product will not be translated in the host mammalian cells. Although the guide RNA depicted in this figure shows a guide RNA specific for the AAVS1 target, the vector can be used to produce a guide RNA that is specific for any desired genomic target by using the subcloning techniques described herein. Vectors for use in IVT reactions are preferentially linearized prior to the IVT reaction. As shown in FIG. 14B, this vector can be suitably linearized using the EcoRI restriction site.

The AAVS1 target sequence was cloned into the T7-based guide RNA IVT vector, as shown in FIG. 14B. Guide RNA molecules were generated by in vitro transcription. Briefly, T7-gRNA vector was linearized by EcoR1 as template for in vitro transcription using a T7 High Yield RNA synthesis kit (New England BioLabs®, Inc.) according to the manufacturer's protocol.

C) In Vitro Products Validation Experiment No. 1

This synthetic AAVS gRNA and the hspCas9(WT) synthetic mRNA produced by IVT were purified using the MEGAclear™ Kit (Life Technologies™) for purification of transcription reactions, and then co-transfected into the EGIP host cell line using Lipofectamine® 2000, along with an EGFP donor fragment capable of rescuing the defective EGFP sequence that is stably integrated into the EGIP cell line, as depicted in FIG. 3D.

The homologous recombination efficiency of the synthetic Cas9 mRNA and synthetic AAVS1 gRNA transfection system was compared with that of the EF1-hspCas9-H1-AAVS1 gRNA all-in-one vector system. Cells using the two systems were imaged for GFP fluorescence at three days following transfection. It was observed that using in vitro transcribed AAVS1 gRNA and Cas9 mRNA can efficiently induce homologous recombination as well as Cas9 all-in-one vector systems, indicated by restored GFP signal in all the vector transfections tested.

D) In Vitro Products Validation Experiment No. 2

In another validation experiment, the genes encoding hspCas9-T2A-GFP and hspCas9-T2A-RFP were alternatively cloned into the IVT vector shown in FIG. 17A. These IVT products were transfected using Lipofectamine 2000® into HEK 293 cells. One day after transfection, the cell cultures were observed under green or red fluorescence microscopy, respectively. Green fluorescence and red fluorescence were observed in these respective cultures, thereby verifying proper translation of the transfected RNA products.

E) In Vitro Products Validation Experiment No. 3

In another validation experiment, the AAVS gRNA1 and AAVS gRNA2 (as shown in FIG. 10B and described in Example 8) were cloned into the T7 gRNA cloning vector as shown in FIGS. 14B and 17K. The resulting constructs were used as template for IVT synthesis of guide RNA molecules.

IVT was also used to generate hspCas9(WT) mRNA and hspCas9 D10A nickase mRNA using the vectors shown generally in FIGS. 17B and 17C.

After purification of the hspCas9(WT) mRNA, hspCas9 nickase mRNA and the two AAVS guide RNA molecules produced from the IVT reaction, purified using the MEGAclear™ Kit (Life Technologies™). The following combinations of RNA were transfected into the EGIP cell line:

1) hspCas9(WT) mRNA+AAVS gRNA1+EGFP donor fragment DNA 2) hspCas9 D10A nickase mRNA+AAVS gRNA1+AAVS gRNA2+EGFP donor fragment DNA Homologous recombination and GFP rescue were monitored by detection of green fluorescence under fluorescence microscopy three days following transfection.

It was observed that both of these cotransfected cultures generated strong EGFP signal. It was also observed that the appearance of positive GFP signal appears significantly faster using the IVT products in the transfection compared to the analogous system that used all-in-one vector (plasmid transfection), indicating more efficient delivery and more robust expression of mRNA product using IVT system compared to the plasmid system.

F) In Vitro Products Validation Experiment No. 4

To further validate the functionality to the RNA products generated by the IVT system, the gene encoding hspCas9 (WT)-T2A-RFP was cloned into an IVT vector, and mRNA product was produced and purified as described in validation experiment number 2 above. AAVS targeting sequence as shown in FIG. 3C was used to produce guide RNA by IVT from a separate vector. EGIP host cells were transfected with the hspCas9-T2A-RFP mRNA, the AAVS gRNA and EGFP donor rescue fragment. Two days following transfection, the majority of transfected cells were red fluorescence positive, with a smaller number of cells showing GFP positive signal. The green fluorescence signals indicate homologous recombination events that rescue the green fluorescence by correcting the defective EFGP gene in the host cell genome.

Example 16

In Vitro Transcription Vectors

The in vitro transcription system vectors of the invention are modular in nature, and as such, variants can be readily produced where cassette segment are easily shuffled and replaced. The following IVT vectors are contemplated.

Figure 15A:
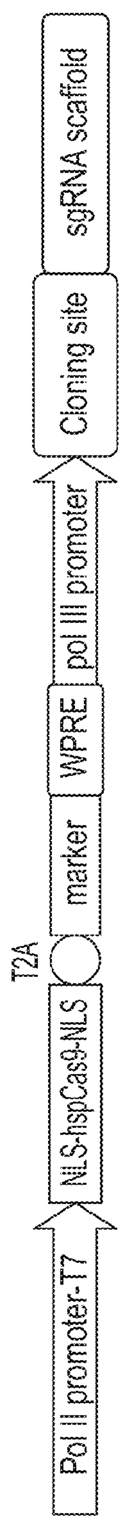
FIGS. 15A through 15C provide schematics of CRISPR/Cas9 all-in-one expression vectors that have the option to be used either as plasmids in cell transfections, or can be used for in vitro transcription reactions to generate Cas9 mRNA, including mRNA encoding hspCas9, hspCas9 nickase or hspCas9 double mutant (DM). These plasmids all generate a bicistronic mRNA encoding the Cas9 polypeptide as well as a marker of choice. The bicistronic message is translationally processed to produce two independent, unlinked proteins.
Figure 15B:
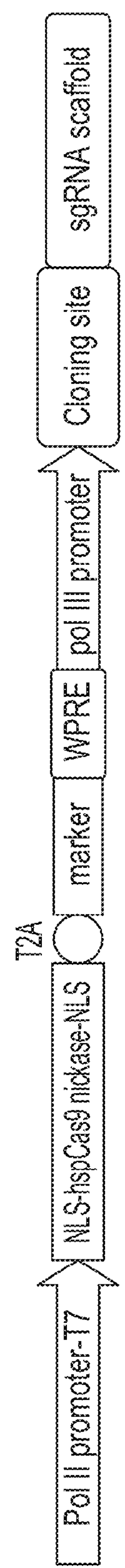
Figure 15C:
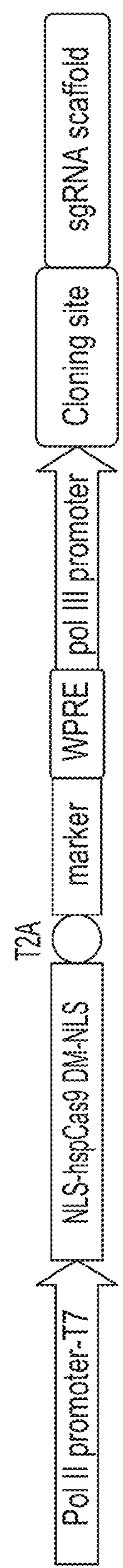

FIGS. 15A through 15C show contemplated vectors that find versatile, dual use in both CRISPR plasmid transfections as well as IVT mRNA transfections. These three vectors each contain a eukaryotic RNA polymerase II promoter that will transcribe the downstream Cas9 coding sequences when transfected into a mammalian host cell in the form of a DNA plasmid. These vectors will also transcribe the guide RNA sequences (including target sequence that is cloned into the cloning site upstream of the gRNA scaffold) using the RNA polymerase III promoter.

Significantly, each of these vectors also contains a nested phage T7 promoter immediately downstream of the mammalian pol II promoter. Thus, these same vectors can be used to generate Cas9 mRNA in an IVT reaction that uses the T7 promoter, preferentially from a linearized form of this plasmid (preferentially linearized at a site immediately following the hspCas9 genes).

These vectors can alternatively encode hspCas9 (WT) (FIG. 15A), hspCas9 nickase mutant (FIG. 15B) or hspCas9 double mutant (DM) null nuclease (FIG. 15C).

Each of these vectors can also produce a bicistronic mRNA (expressed from either the mammalian pol II promoter or the phage T7 promoter) consisting of sequence encoding Cas9 polypeptide, and further, any desired marker protein. The single mRNA encoding the Cas9 polypeptide and the marker protein will be translated in mammalian cells to produce two unlinked proteins as a consequence of the T2A peptide between the Cas9 and marker genes.

FIG. 16 shows a contemplated vector similar in configuration to the vector of FIG. 15C. The vector of FIG. 16 encodes a chimeric transcription factor consisting hspCas9 double mutant (DM) null nuclease and a fused transcriptional regulatory domain, that can be, for example, an activator domain such as VP64, or a suppressor domain such as the KRAB domain. This fusion protein can be used to modulate the transcription of any desired gene by the use of a target sequence in a guide RNA that can bring the Cas9-regulator fusion protein into proximity of the gene of interest. This vector also has dual use in IVT systems, and can also express a marker protein from a bicistronic message.

FIGS. 17A through 17K show contemplated CRISPR vectors that find use in IVT systems to produce RNA that can be used in mammalian cell transfections to program targeted genomic DNA editing. FIG. 17A provides a schematic of a CRISPR/Cas9 mRNA expression vector that can be used for in vitro transcription reactions to generate Cas9 mRNA. The vector features with 5'-UTR and 3'-UTR and a polyA tail to enhance mRNA stability and translation efficiency. FIGS. 17B through 17J provide schematics of CRISPR/Cas9 mRNA expression vectors that can be used for in vitro transcription reactions to generate Cas9 mRNA using any desired hspCas9 gene, for example, hspCas9 genes encoding Cas9-WT, Cas9-nickase and Cas9-DM null nuclease. These vectors can be configured to produce Cas9 polypeptide that is fused with a desired marker protein, or alternatively, can be configured to simultaneously produce free Cas9 polypeptide and a marker protein. FIG. 17K provides a schematic of a generalized vector that can be used for in vitro transcription reactions to generate guide RNA molecules used in CRISPR systems.

While the foregoing disclosure has been described in some detail for purposes of clarity and understanding, it will be clear to one skilled in the art from a reading of this disclosure that various changes in form and detail can be made without departing from the true scope of the invention. It is to be understood that the invention is not limited to any of the specifically recited methodologies, reagents, biological materials or instrumentation that are recited herein, where similar or equivalent methodologies, reagents, biological materials or instrumentation can be substituted and used in the construction and practice of the invention, and remain within the scope of the invention. It is understood that the description and terminology used in the present disclosure is for the purpose of describing particular embodiments of the invention only, and is not intended that the invention be limited solely to the embodiments described herein.

As used in this specification and the appended claims, singular forms such as "a", "an" and "the" include plural referents unless the content clearly dictates otherwise. For example, reference to "a plasmid" includes a plurality of plasmids; reference to "a cell" also refers to cultures or populations of cells. All industry and technical terms used herein have the same meaning as commonly understood by one of ordinary skill in the art or industry to which the invention pertains, unless defined otherwise.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A recombinant polynucleotide comprising:

(i) a nucleotide sequence selected from SEQ ID NOs: 3, 4 and 6-10, (ii) conservative variants of (i) which are at least 50% identical in nucleotide sequence compared to the nucleotide sequence of (i), and further wherein said conservative variants encode a functional Cas9 polypeptide comprising an amino acid sequence selected from:

(A) the amino acid sequence of SEQ ID NO: 1, (B) a variant of the amino acid sequence of SEQ ID NO: 1 having a D10A mutation, or (C) a variant of the amino acid sequence of SEQ ID NO: 1 having D10A and H840A mutations, or (iii) at least 100 contiguous nucleotides of SEQ ID NO: 3, 7 or 9, and further wherein said recombinant polynucleotide encodes a functional Cas9 polypeptide selected from:

(A) SEQ ID NO: 1, (B) a variant of SEQ ID NO: 1 having a D10A mutation, (C) a variant of SEQ ID NO: 1 having D10A and H840A mutations, or (D) a conservative variant of (A), (B) or (C).

2. The recombinant polynucleotide of claim 1 wherein the polynucleotide comprises the nucleotide sequence of either SEQ ID NO: 3, 7 or 9, and wherein the polynucleotide further comprises at least one operably linked nucleotide sequence encoding a nuclear localization signal.

3. An expression construct comprising the recombinant polynucleotide of claim 1.

4. An expression construct comprising the recombinant polynucleotide of claim 1, where the expression construct is a mammalian expression construct.

5. An expression construct comprising the recombinant polynucleotide of claim 1 where the expression construct is a human expression construct.

6. An mRNA expression construct comprising: (i) a recombinant polynucleotide of claim 1, and (ii) an in vitro transcription promoter element that is operably linked to the recombinant polynucleotide of claim 1.

7. An mRNA expression construct comprising: (i) a recombinant polynucleotide of claim 1, and (ii) a bacteriophage promoter element that is operably linked to the recombinant polynucleotide of claim 1.

8. A recombinant polynucleotide encoding a polypeptide comprising an amino acid sequence selected from SEQ ID NOs: 5 and 13, and conservative variants thereof.

9. An expression construct comprising:

(a) a first recombinant polynucleotide comprising:

(A) a nucleotide sequence selected from SEQ ID NOs: 3, 4 and 6-10, (B) conservative variants of (A) which are at least 50% identical in nucleotide sequence compared to the nucleotide sequence of (A), and further wherein said conservative variants encode a functional Cas9 polypeptide comprising an amino acid sequence selected from:

(i) the amino acid sequence of SEQ ID NO: 1, (ii) a variant of the amino acid sequence of SEQ ID NO: 1 having a D10A mutation, or (iii) a variant of the amino acid sequence of SEQ ID NO: 1 having D10A and H840A mutations, or (C) at least 100 contiguous nucleotides of SEQ ID NO: 3, 7 or 9, and further wherein said first recombinant polynucleotide encodes a polypeptide selected from:

(i) SEQ ID NO: 1, (ii) a variant of SEQ ID NO: 1 having a D10A mutation, (iii) a variant of SEQ ID NO: 1 having D10A and H840A mutations, or (iv) a conservative variant of (i), (ii) or (iii); and (b) a second recombinant polynucleotide encoding a guide RNA, said guide RNA comprising (i) a crRNA-tracrRNA scaffold polynucleotide, and (ii) a targeting sequence corresponding to a genomic target of interest, wherein the targeting sequence is operably linked to the crRNA-tracrRNA scaffold polynucleotide.

10. The expression construct of claim 9, wherein the expression construct is a mammalian expression construct.

11. The expression construct of claim 9, wherein the first recombinant polynucleotide comprises nucleotide sequence encoding at least one nuclear localization signal.

* * * * *

US009738908C1

(12) EX PARTE REEXAMINATION CERTIFICATE (11361st)

United States Patent

Wu

(10) Number: US 9,738,908 C1

(45) Certificate Issued: *Jul. 31, 2018

(54) CRISPR/CAS SYSTEMS FOR GENOMIC MODIFICATION AND GENE MODULATION

(71) Applicant: System Biosciences, LLC, Mountain View, CA (US)

(72) Inventor: Fangting Wu, Mountain View, CA (US)

(73) Assignee: SYSTEM BIOSCIENCES, LLC, Mountain View, CA (US)

Reexamination Request:
No. 90/014,003, Aug. 24, 2017

Reexamination Certificate for:

| | |
|---|---|
| Patent No.: | **9,738,908** |
| Issued: | **Aug. 22, 2017** |
| Appl. No.: | **14/216,655** |
| Filed: | **Mar. 17, 2014** |

( * ) Notice: This patent is subject to a terminal disclaimer.

Related U.S. Application Data

(60) Provisional application No. 61/799,586, filed on Mar. 15, 2013.

(51) Int. Cl.

| | |
|---|---|
| ***C12N 9/22*** | (2006.01) |
| ***C12N 9/14*** | (2006.01) |
| ***C12N 15/90*** | (2006.01) |
| ***C12N 15/11*** | (2006.01) |
| ***C12N 15/85*** | (2006.01) |
| ***C12N 15/10*** | (2006.01) |

(52) U.S. Cl.
CPC ............. *C12N 15/907* (2013.01); *C12N 9/22* (2013.01); *C12N 15/102* (2013.01); *C12N 15/11* (2013.01); *C12N 15/85* (2013.01); *C12N 2800/22* (2013.01)

(58) Field of Classification Search
CPC ............................ C12N 15/102; C12N 15/907
USPC ...................... 435/320.1, 325, 455; 536/23.2
See application file for complete search history.

(56) References Cited

To view the complete listing of prior art documents cited during the proceeding for Reexamination Control Number 90/014,003, please refer to the USPTO's public Patent Application Information Retrieval (PAIR) system under the Display References tab.

*Primary Examiner* — Shri Ponnaluri

(57) ABSTRACT

The invention relates to engineered CRISPR/Cas9 systems for genomic modification and regulation of gene expression in mammalian cells. The specification describes the design and validation of polynucleotides encoding the *Streptococcus pyogenes* (*S. pyogenes*) Cas9 gene and protein and variants of that protein, where the nucleotide sequence has been optimized for expression in mammalian cells, and also modified by fused sequences that enhance various aspects of the CRISPR/Cas system. The specification also describes systems for RNA-guided genome engineering and gene regulation in mammalian cells, including human cells.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-11 are cancelled.

* * * * *

SEQUENCE LISTING

<160> NUMBER OF SEQ ID NOS: 68

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

```
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200
```

```
Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 2
<211> LENGTH: 4107
<212> TYPE: DNA
<213> ORGANISM: Streptococcus pyogenes

<400> SEQUENCE: 2

```
atggataaga aatactcaat aggcttagat atcggcacaa atagcgtcgg atgggcggtg     60

atcactgatg aatataaggt tccgtctaaa aagttcaagg ttctgggaaa tacagaccgc    120

cacagtatca aaaaaaatct tataggggct cttttatttg acagtggaga gacagcggaa    180

gcgactcgtc tcaaacggac agctcgtaga aggtatacac gtcggaagaa tcgtatttgt    240

tatctacagg agattttttc aaatgagatg gcgaaagtag atgatagttt ctttcatcga    300

cttgaagagt cttttttggt ggaagaagac aagaagcatg aacgtcatcc tatttttgga    360

aatatagtag atgaagttgc ttatcatgag aaatatccaa ctatctatca tctgcgaaaa    420

aaattggtag attctactga taaagcggat ttgcgcttaa tctatttggc cttagcgcat    480

atgattaagt ttcgtggtca tttttttgatt gagggagatt taaatcctga taatagtgat    540

gtggacaaac tatttatcca gttggtacaa acctacaatc aattatttga agaaaaccct    600

attaacgcaa gtggagtaga tgctaaagcg attctttctg cacgattgag taaatcaaga    660

cgattagaaa atctcattgc tcagctcccc ggtgagaaga aaaatggctt atttgggaat    720

ctcattgctt tgtcattggg tttgacccct aattttaaat caaattttga tttggcagaa    780

gatgctaaat tacagctttc aaaagatact tacgatgatg atttagataa tttattggcg    840

caaattggag atcaatatgc tgatttgttt ttggcagcta agaatttatc agatgctatt    900

ttactttcag atatcctaag agtaaatact gaaataacta aggctcccct atcagcttca    960

atgattaaac gctacgatga acatcatcaa gacttgactc ttttaaaagc tttagttcga   1020

caacaacttc cagaaaagta taaagaaatc ttttttgatc aatcaaaaaa cggatatgca   1080

ggttatattg atgggggagc tagccaagaa gaattttata aatttatcaa accaatttta   1140
```

```
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
```

```
aaagagttac tagggatcac aattatggaa agaagttcct ttgaaaaaaa tccgattgac   3540

tttttagaag ctaaaggata taaggaagtt aaaaaagact taatcattaa actacctaaa   3600

tatagtcttt ttgagttaga aaacggtcgt aaacggatgc tggctagtgc cggagaatta   3660

caaaaaggaa atgagctggc tctgccaagc aaatatgtga atttttata tttagctagt   3720

cattatgaaa agttgaaggg tagtccagaa gataacgaac aaaaacaatt gtttgtggag   3780

cagcataagc attatttaga tgagattatt gagcaaatca gtgaattttc taagcgtgtt   3840

attttagcag atgccaattt agataaagtt cttagtgcat ataacaaaca tagagacaaa   3900

ccaatacgtg aacaagcaga aaatattatt catttattta cgttgacgaa tcttggagct   3960

cccgctgctt ttaaatattt tgatacaaca attgatcgta aacgatatac gtctacaaaa   4020

gaagttttag atgccactct tatccatcaa tccatcactg gtctttatga aacacgcatt   4080

gatttgagtc agctaggagg tgactga                                      4107
```

<210> SEQ ID NO 3
<211> LENGTH: 4104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atggacaaaa agtatagtat cggactggat attggcacta acagcgtggg atgggccgtc     60

atcaccgacg agtacaaagt gccaagcaag aagttcaagg tcctgggaaa caccgataga    120

cacagtatca agaaaaatct gattggagcc ctgctgttcg actcagggga gacagctgaa    180

gcaactaggc tgaaaagaac agctaggaga cggtatactc gccgaaagaa tcggatctgc    240

tacctccagg agattttctc caacgaaatg gccaaggtgg acgatagttt ctttcatcgc    300

ctggaggaat cattcctggt cgaggaagat aagaaacacg agaggcatcc catctttggc    360

aacattgtgg acgaggtcgc ttatcacgaa aagtacccta caatctatca tctgcggaag    420

aaactggtgg acagcactga taaggcagac ctgcgcctga tctatctggc cctggctcac    480

atgattaagt tcaggggcca ttttctgatc gagggcgatc tgaacccaga caattccgat    540

gtggacaagc tgttcatcca gctggtccag acatacaatc agctgtttga ggaaaacccc    600

attaatgcat ctggggtgga cgcaaaagcc atcctgagtg ccagactgtc taagagtagg    660

agactggaga acctgatcgc tcagctgcca ggcgaaaaga aaaacggcct gtttggaaat    720

ctgattgcac tgtcactggg actgaccccc aacttcaaga gcaattttga tctggccgag    780

gacgctaagc tccagctgag caaggacacc tacgacgatg acctggataa cctgctggct    840

cagatcggcg atcagtacgc agacctgttc ctggccgcta agaatctgtc tgacgccatc    900

ctgctgagtg atattctgag agtgaacacc gagattacaa aagcccccct gtcagctagc    960

atgatcaaga gatatgacga gcaccatcag gatctgaccc tgctgaaggc tctggtgcgg   1020

cagcagctgc ctgagaagta caaagaaatc ttctttgatc agagcaagaa tgggtacgcc   1080

ggctatattg acggcggagc ttcccaggag gagttctaca agtttatcaa acctattctg   1140

gagaagatgg acggcactga ggaactgctg gtgaaactga atcgggaaga cctgctgcgg   1200

aagcagcgca ccttcgataa cggcagcatc cctcaccaga ttcatctggg agagctgcac   1260

gcaatcctgc ggcgccagga agacttctac ccatttctga aggataaccg ggagaagatc   1320

gaaaaaattc tgactttccg catcccctac tatgtggggc ctctggcaag aggcaattcc   1380
```

```
cggtttgcct ggatgacccg caagtctgag gaaacaatca ctccctggaa cttcgaggaa   1440
gtggtcgata agggcgcttc cgcacagtct ttcattgaga ggatgacaaa ttttgacaag   1500
aacctgccaa atgaaaaagt gctgcccaag cacagcctgc tgtacgagta tttcaccgtc   1560
tataacgaac tgacaaaggt gaaatacgtc actgagggca tgagaaagcc tgccttcctg   1620
tccggagaac agaagaaagc tatcgtggac ctgctgttta aaaccaatcg gaaggtgaca   1680
gtcaagcagc tgaaagagga ctacttcaag aaaattgaat gtttcgattc tgtggagatc   1740
agtggggtcg aagacaggtt taacgcctct ctgggcacct accacgatct gctgaagatc   1800
attaaggata aagacttcct ggacaacgag gaaaatgagg acatcctgga ggacattgtg   1860
ctgaccctga cactgtttga ggatcgggaa atgatcgagg aacgcctgaa gacctacgcc   1920
catctgttcg atgacaaagt gatgaaacag ctgaagcgaa ggagatacac tgggtggggc   1980
cgactgagca ggaagctgat caatggcatt cgcgacaaac agagtggaaa gacaatcctg   2040
gactttctga agtcagatgg cttcgctaac aggaatttta tgcagctgat tcacgatgac   2100
tctctgactt tcaaagagga catccagaag gcacaggtgt ccggacaggg ggactctctg   2160
cacgagcata tcgcaaacct ggccgggagc cctgccatca agaaaggcat cctccagacc   2220
gtgaaggtgg tggacgagct ggtgaaagtc atgggaagac ataagccaga aaacatcgtg   2280
attgagatgg ccagggagaa tcagaccaca cagaaagggc agaagaactc tcgggagcgc   2340
atgaaacgca tcgaggaagg aattaaggaa ctggggagtc agatcctgaa agagcacccc   2400
gtggaaaaca cacagctcca gaatgagaag ctgtatctgt actacctcca gaatggccgc   2460
gatatgtacg tggaccagga gctggatatt aaccgactgt cagattatga cgtggatcat   2520
atcgtcccac agtcattcct gaaagatgac agcattgaca ataaggtgct gacccgcagc   2580
gacaaaaacc gaggaaagag tgataatgtc ccctcagagg aagtggtcaa gaaaatgaag   2640
aactactgga ggcagctgct gaatgccaaa ctgatcaccc agcgaaagtt tgataacctg   2700
acaaaagctg agaggggggg cctgtccgaa ctggacaaag caggcttcat caagcgacag   2760
ctggtggaga caaggcagat cacaaagcac gtcgctcaga tcctggacag caggatgaac   2820
accaagtacg atgagaatga caaactgatc cgggaagtga aggtcattac actgaagtca   2880
aaactggtga gcgactttag gaaagatttc cagttctaca aggtcagaga gatcaacaac   2940
taccaccatg ctcatgacgc atacctgaac gcagtggtcg ggactgccct gattaagaaa   3000
taccctaaac tggagtctga gttcgtgtac ggcgactata aggtgtacga tgtcagaaaa   3060
atgatcgcca agagcgagca ggaaattggc aaagccaccg ctaagtattt cttttactcc   3120
aacatcatga atttctttaa gactgagatc accctggcaa atggcgaaat ccgaaagagg   3180
ccactgattg agactaacgg agagacaggg gaaatcgtgt gggacaaagg aagagatttt   3240
gctaccgtgc ggaaggtcct gagtatgccc caagtgaata ttgtcaagaa aacagaggtg   3300
cagactggag ggttcagtaa ggaatcaatt ctgcctaaac gcaacagcga taagctgatc   3360
gcccgaaaga aagactggga ccccaagaag tatggcggat tcgactcccc aaccgtggct   3420
tactctgtcc tggtggtcgc aaaggtggag aagggaaaaa gcaagaaact gaaatccgtc   3480
aaggaactgc tggggatcac aattatggag aggagcagct tcgaaaagaa tcctatcgat   3540
tttctggagg ccaaagggta taaggaagtg aagaaagacc tgatcatcaa gctgccaaag   3600
tactctctgt ttgagctgga aaacggcaga aagcggatgc tggcaagtgc cggcgagctg   3660
caaaaaggaa atgaactggc cctgccctca aagtacgtga acttcctgta tctggctagc   3720
cactacgaga agctgaaagg ctcccctgag gataacgaac agaaacagct gtttgtggag   3780
```

```
cagcacaagc attatctgga cgagatcatt gaacagatta gcgagttctc caaacgcgtg   3840

atcctggctg acgcaaatct ggataaggtc ctgtctgcat acaacaaaca cagggacaag   3900

ccaatcagag agcaggccga aaatatcatt catctgttca ctctgaccaa cctgggagcc   3960

cccgcagcct tcaagtattt tgacactacc atcgatcgca aacgatacac aagcactaag   4020

gaggtgctgg atgctaccct gatccaccag agcattactg ggctgtacga gacaaggatc   4080

gacctgtccc agctgggggg agac                                          4104
```

<210> SEQ ID NO 4
<211> LENGTH: 4203
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atggctccca agaagaagcg aaaggtgggc atccacggcg tgcccgctgc cgacaaaaag     60

tatagtatcg gactggatat tggcactaac agcgtgggat gggccgtcat caccgacgag    120

tacaaagtgc caagcaagaa gttcaaggtc ctgggaaaca ccgatagaca cagtatcaag    180

aaaaatctga ttggagccct gctgttcgac tcaggggaga cagctgaagc aactaggctg    240

aaaagaacag ctaggagacg gtatactcgc cgaaagaatc ggatctgcta cctccaggag    300

attttctcca acgaaatggc caaggtggac gatagtttct ttcatcgcct ggaggaatca    360

ttcctggtcg aggaagataa gaaacacgag aggcatccca tctttggcaa cattgtggac    420

gaggtcgctt atcacgaaaa gtaccctaca atctatcatc tgcggaagaa actggtggac    480

agcactgata aggcagacct gcgcctgatc tatctggccc tggctcacat gattaagttc    540

agggggcatt ttctgatcga gggcgatctg aacccagaca attccgatgt ggacaagctg    600

ttcatccagc tggtccagac atacaatcag ctgtttgagg aaaaccccat taatgcatct    660

ggggtggacg caaaagccat cctgagtgcc agactgtcta agagtaggag actggagaac    720

ctgatcgctc agctgccagg cgaaaagaaa aacggcctgt ttggaaatct gattgcactg    780

tcactgggac tgacccccaa cttcaagagc aattttgatc tggccgagga cgctaagctc    840

cagctgagca aggacaccta cgacgatgac ctggataacc tgctggctca gatcggcgat    900

cagtacgcag acctgttcct ggccgctaag aatctgtctg acgccatcct gctgagtgat    960

attctgagag tgaacaccga gattacaaaa gccccccctgt cagctagcat gatcaagaga   1020

tatgacgagc accatcagga tctgaccctg ctgaaggctc tggtgcggca gcagctgcct   1080

gagaagtaca aagaaatctt ctttgatcag agcaagaatg ggtacgccgg ctatattgac   1140

ggcggagctt cccaggagga gttctacaag tttatcaaac ctattctgga gaagatggac   1200

ggcactgagg aactgctggt gaaactgaat cgggaagacc tgctgcggaa gcagcgcacc   1260

ttcgataacg gcagcatccc tcaccagatt catctgggag agctgcacgc aatcctgcgg   1320

cgccaggaag acttctaccc atttctgaag gataaccggg agaagatcga aaaaattctg   1380

actttccgca tcccctacta tgtggggcct ctggcaagag gcaattcccg gtttgcctgg   1440

atgacccgca agtctgagga aacaatcact ccctggaact tcgaggaagt ggtcgataag   1500

ggcgcttccg cacagtcttt cattgagagg atgacaaatt ttgacaagaa cctgccaaat   1560

gaaaaagtgc tgcccaagca cagcctgctg tacgagtatt tcaccgtcta taacgaactg   1620

acaaaggtga aatacgtcac tgagggcatg agaaagcctg ccttcctgtc cggagaacag   1680
```

-continued

```
aagaaagcta tcgtggacct gctgtttaaa accaatcgga aggtgacagt caagcagctg   1740
aaagaggact acttcaagaa aattgaatgt ttcgattctg tggagatcag tggggtcgaa   1800
gacaggttta acgcctctct gggcacctac cacgatctgc tgaagatcat taaggataaa   1860
gacttcctgg acaacgagga aaatgaggac atcctggagg acattgtgct gaccctgaca   1920
ctgtttgagg atcgggaaat gatcgaggaa cgcctgaaga cctacgccca tctgttcgat   1980
gacaaagtga tgaaacagct gaagcgaagg agatacactg ggtggggccg actgagcagg   2040
aagctgatca atggcattcg cgacaaacag agtggaaaga caatcctgga ctttctgaag   2100
tcagatggct tcgctaacag gaattttatg cagctgattc acgatgactc tctgactttc   2160
aaagaggaca tccagaaggc acaggtgtcc ggacaggggg actctctgca cgagcatatc   2220
gcaaacctgg ccgggagccc tgccatcaag aaaggcatcc tccagaccgt gaaggtggtg   2280
gacgagctgg tgaaagtcat gggaagacat aagccagaaa acatcgtgat tgagatggcc   2340
agggagaatc agaccacaca gaaagggcag aagaactctc gggagcgcat gaaacgcatc   2400
gaggaaggaa ttaaggaact ggggagtcag atcctgaaag agcaccccgt ggaaaacaca   2460
cagctccaga atgagaagct gtatctgtac tacctccaga atggccgcga tatgtacgtg   2520
gaccaggagc tggatattaa ccgactgtca gattatgacg tggatcatat cgtcccacag   2580
tcattcctga aagatgacag cattgacaat aaggtgctga cccgcagcga caaaaaccga   2640
ggaaagagtg ataatgtccc ctcagaggaa gtggtcaaga aaatgaagaa ctactggagg   2700
cagctgctga atgccaaact gatcacccag cgaaagtttg ataacctgac aaaagctgag   2760
aggggggggcc tgtccgaact ggacaaagca ggcttcatca agcgacagct ggtggagaca   2820
aggcagatca caaagcacgt cgctcagatc ctggacagca ggatgaacac caagtacgat   2880
gagaatgaca aactgatccg ggaagtgaag gtcattacac tgaagtcaaa actggtgagc   2940
gactttagga aagatttcca gttctacaag gtcagagaga tcaacaacta ccaccatgct   3000
catgacgcat acctgaacgc agtggtcggg actgccctga ttaagaaata ccctaaactg   3060
gagtctgagt tcgtgtacgg cgactataag gtgtacgatg tcagaaaaat gatcgccaag   3120
agcgagcagg aaattggcaa agccaccgct aagtatttct tttactccaa catcatgaat   3180
ttctttaaga ctgagatcac cctggcaaat ggcgaaatcc gaaagaggcc actgattgag   3240
actaacggag agacagggga aatcgtgtgg gacaaaggaa gagattttgc taccgtgcgg   3300
aaggtcctga gtatgcccca agtgaatatt gtcaagaaaa cagaggtgca gactggaggg   3360
ttcagtaagg aatcaattct gcctaaacgc aacagcgata agctgatcgc ccgaaagaaa   3420
gactgggacc ccaagaagta tggcggattc gactccccaa ccgtggctta ctctgtcctg   3480
gtggtcgcaa aggtggagaa gggaaaaagc aagaaactga aatccgtcaa ggaactgctg   3540
gggatcacaa ttatggagag gagcagcttc gaaaagaatc ctatcgattt tctggaggcc   3600
aaagggtata aggaagtgaa gaaagacctg atcatcaagc tgccaaagta ctctctgttt   3660
gagctggaaa acggcagaaa gcggatgctg gcaagtgccg gcgagctgca aaaaggaaat   3720
gaactggccc tgccctcaaa gtacgtgaac ttcctgtatc tggctagcca ctacgagaag   3780
ctgaaaggct cccctgagga taacgaacag aaacagctgt ttgtggagca gcacaagcat   3840
tatctggacg agatcattga acagattagc gagttctcca aacgcgtgat cctggctgac   3900
gcaaatctgg ataaggtcct gtctgcatac aacaaacaca gggacaagcc aatcagagag   3960
caggccgaaa atatcattca tctgttcact ctgaccaacc tgggagcccc cgcagccttc   4020
```

```
aagtattttg acactaccat cgatcgcaaa cgatacacaa gcactaagga ggtgctggat   4080

gctaccctga tccaccagag cattactggg ctgtacgaga caaggatcga cctgtcccag   4140

ctggggggag acaaacgccc agccgccacc aagaaagcag gacaggcaaa gaagaagaag   4200

tga                                                                4203


<210> SEQ ID NO 5
<211> LENGTH: 1413
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Ser Met Gln Lys Leu Ile Ser Glu Glu Asp Leu Met Ala Pro
1               5                   10                  15

Lys Lys Lys Arg Lys Val Gly Ile His Gly Val Pro Ala Ala Asp Lys
            20                  25                  30

Lys Tyr Ser Ile Gly Leu Asp Ile Gly Thr Asn Ser Val Gly Trp Ala
        35                  40                  45

Val Ile Thr Asp Glu Tyr Lys Val Pro Ser Lys Lys Phe Lys Val Leu
    50                  55                  60

Gly Asn Thr Asp Arg His Ser Ile Lys Lys Asn Leu Ile Gly Ala Leu
65                  70                  75                  80

Leu Phe Asp Ser Gly Glu Thr Ala Glu Ala Thr Arg Leu Lys Arg Thr
                85                  90                  95

Ala Arg Arg Arg Tyr Thr Arg Arg Lys Asn Arg Ile Cys Tyr Leu Gln
            100                 105                 110

Glu Ile Phe Ser Asn Glu Met Ala Lys Val Asp Asp Ser Phe Phe His
        115                 120                 125

Arg Leu Glu Glu Ser Phe Leu Val Glu Glu Asp Lys Lys His Glu Arg
    130                 135                 140

His Pro Ile Phe Gly Asn Ile Val Asp Glu Val Ala Tyr His Glu Lys
145                 150                 155                 160

Tyr Pro Thr Ile Tyr His Leu Arg Lys Lys Leu Val Asp Ser Thr Asp
                165                 170                 175

Lys Ala Asp Leu Arg Leu Ile Tyr Leu Ala Leu Ala His Met Ile Lys
            180                 185                 190

Phe Arg Gly His Phe Leu Ile Glu Gly Asp Leu Asn Pro Asp Asn Ser
        195                 200                 205

Asp Val Asp Lys Leu Phe Ile Gln Leu Val Gln Thr Tyr Asn Gln Leu
    210                 215                 220

Phe Glu Glu Asn Pro Ile Asn Ala Ser Gly Val Asp Ala Lys Ala Ile
225                 230                 235                 240

Leu Ser Ala Arg Leu Ser Lys Ser Arg Arg Leu Glu Asn Leu Ile Ala
                245                 250                 255

Gln Leu Pro Gly Glu Lys Lys Asn Gly Leu Phe Gly Asn Leu Ile Ala
            260                 265                 270

Leu Ser Leu Gly Leu Thr Pro Asn Phe Lys Ser Asn Phe Asp Leu Ala
        275                 280                 285

Glu Asp Ala Lys Leu Gln Leu Ser Lys Asp Thr Tyr Asp Asp Asp Leu
    290                 295                 300

Asp Asn Leu Leu Ala Gln Ile Gly Asp Gln Tyr Ala Asp Leu Phe Leu
305                 310                 315                 320
```

```
Ala Ala Lys Asn Leu Ser Asp Ala Ile Leu Leu Ser Asp Ile Leu Arg
                325                 330                 335

Val Asn Thr Glu Ile Thr Lys Ala Pro Leu Ser Ala Ser Met Ile Lys
            340                 345                 350

Arg Tyr Asp Glu His His Gln Asp Leu Thr Leu Leu Lys Ala Leu Val
        355                 360                 365

Arg Gln Gln Leu Pro Glu Lys Tyr Lys Glu Ile Phe Phe Asp Gln Ser
    370                 375                 380

Lys Asn Gly Tyr Ala Gly Tyr Ile Asp Gly Gly Ala Ser Gln Glu Glu
385                 390                 395                 400

Phe Tyr Lys Phe Ile Lys Pro Ile Leu Glu Lys Met Asp Gly Thr Glu
                405                 410                 415

Glu Leu Leu Val Lys Leu Asn Arg Glu Asp Leu Leu Arg Lys Gln Arg
            420                 425                 430

Thr Phe Asp Asn Gly Ser Ile Pro His Gln Ile His Leu Gly Glu Leu
        435                 440                 445

His Ala Ile Leu Arg Arg Gln Glu Asp Phe Tyr Pro Phe Leu Lys Asp
    450                 455                 460

Asn Arg Glu Lys Ile Glu Lys Ile Leu Thr Phe Arg Ile Pro Tyr Tyr
465                 470                 475                 480

Val Gly Pro Leu Ala Arg Gly Asn Ser Arg Phe Ala Trp Met Thr Arg
                485                 490                 495

Lys Ser Glu Glu Thr Ile Thr Pro Trp Asn Phe Glu Glu Val Val Asp
            500                 505                 510

Lys Gly Ala Ser Ala Gln Ser Phe Ile Glu Arg Met Thr Asn Phe Asp
        515                 520                 525

Lys Asn Leu Pro Asn Glu Lys Val Leu Pro Lys His Ser Leu Leu Tyr
    530                 535                 540

Glu Tyr Phe Thr Val Tyr Asn Glu Leu Thr Lys Val Lys Tyr Val Thr
545                 550                 555                 560

Glu Gly Met Arg Lys Pro Ala Phe Leu Ser Gly Glu Gln Lys Lys Ala
                565                 570                 575

Ile Val Asp Leu Leu Phe Lys Thr Asn Arg Lys Val Thr Val Lys Gln
            580                 585                 590

Leu Lys Glu Asp Tyr Phe Lys Lys Ile Glu Cys Phe Asp Ser Val Glu
        595                 600                 605

Ile Ser Gly Val Glu Asp Arg Phe Asn Ala Ser Leu Gly Thr Tyr His
    610                 615                 620

Asp Leu Leu Lys Ile Ile Lys Asp Lys Asp Phe Leu Asp Asn Glu Glu
625                 630                 635                 640

Asn Glu Asp Ile Leu Glu Asp Ile Val Leu Thr Leu Thr Leu Phe Glu
                645                 650                 655

Asp Arg Glu Met Ile Glu Glu Arg Leu Lys Thr Tyr Ala His Leu Phe
            660                 665                 670

Asp Asp Lys Val Met Lys Gln Leu Lys Arg Arg Arg Tyr Thr Gly Trp
        675                 680                 685

Gly Arg Leu Ser Arg Lys Leu Ile Asn Gly Ile Arg Asp Lys Gln Ser
    690                 695                 700

Gly Lys Thr Ile Leu Asp Phe Leu Lys Ser Asp Gly Phe Ala Asn Arg
705                 710                 715                 720

Asn Phe Met Gln Leu Ile His Asp Asp Ser Leu Thr Phe Lys Glu Asp
                725                 730                 735

Ile Gln Lys Ala Gln Val Ser Gly Gln Gly Asp Ser Leu His Glu His
```

-continued

```
            740                 745                 750

Ile Ala Asn Leu Ala Gly Ser Pro Ala Ile Lys Lys Gly Ile Leu Gln
        755                 760                 765

Thr Val Lys Val Val Asp Glu Leu Val Lys Val Met Gly Arg His Lys
    770                 775                 780

Pro Glu Asn Ile Val Ile Glu Met Ala Arg Glu Asn Gln Thr Thr Gln
785                 790                 795                 800

Lys Gly Gln Lys Asn Ser Arg Glu Arg Met Lys Arg Ile Glu Glu Gly
                805                 810                 815

Ile Lys Glu Leu Gly Ser Gln Ile Leu Lys Glu His Pro Val Glu Asn
            820                 825                 830

Thr Gln Leu Gln Asn Glu Lys Leu Tyr Leu Tyr Tyr Leu Gln Asn Gly
        835                 840                 845

Arg Asp Met Tyr Val Asp Gln Glu Leu Asp Ile Asn Arg Leu Ser Asp
    850                 855                 860

Tyr Asp Val Asp His Ile Val Pro Gln Ser Phe Leu Lys Asp Asp Ser
865                 870                 875                 880

Ile Asp Asn Lys Val Leu Thr Arg Ser Asp Lys Asn Arg Gly Lys Ser
                885                 890                 895

Asp Asn Val Pro Ser Glu Glu Val Val Lys Lys Met Lys Asn Tyr Trp
            900                 905                 910

Arg Gln Leu Leu Asn Ala Lys Leu Ile Thr Gln Arg Lys Phe Asp Asn
        915                 920                 925

Leu Thr Lys Ala Glu Arg Gly Gly Leu Ser Glu Leu Asp Lys Ala Gly
    930                 935                 940

Phe Ile Lys Arg Gln Leu Val Glu Thr Arg Gln Ile Thr Lys His Val
945                 950                 955                 960

Ala Gln Ile Leu Asp Ser Arg Met Asn Thr Lys Tyr Asp Glu Asn Asp
                965                 970                 975

Lys Leu Ile Arg Glu Val Lys Val Ile Thr Leu Lys Ser Lys Leu Val
            980                 985                 990

Ser Asp Phe Arg Lys Asp Phe Gln  Phe Tyr Lys Val Arg  Glu Ile Asn
        995                 1000                1005

Asn Tyr  His His Ala His Asp  Ala Tyr Leu Asn Ala  Val Val Gly
    1010                1015                1020

Thr Ala  Leu Ile Lys Lys Tyr  Pro Lys Leu Glu Ser  Glu Phe Val
    1025                1030                1035

Tyr Gly  Asp Tyr Lys Val Tyr  Asp Val Arg Lys Met  Ile Ala Lys
    1040                1045                1050

Ser Glu  Gln Glu Ile Gly Lys  Ala Thr Ala Lys Tyr  Phe Phe Tyr
    1055                1060                1065

Ser Asn  Ile Met Asn Phe Phe  Lys Thr Glu Ile Thr  Leu Ala Asn
    1070                1075                1080

Gly Glu  Ile Arg Lys Arg Pro  Leu Ile Glu Thr Asn  Gly Glu Thr
    1085                1090                1095

Gly Glu  Ile Val Trp Asp Lys  Gly Arg Asp Phe Ala  Thr Val Arg
    1100                1105                1110

Lys Val  Leu Ser Met Pro Gln  Val Asn Ile Val Lys  Lys Thr Glu
    1115                1120                1125

Val Gln  Thr Gly Gly Phe Ser  Lys Glu Ser Ile Leu  Pro Lys Arg
    1130                1135                1140

Asn Ser  Asp Lys Leu Ile Ala  Arg Lys Lys Asp Trp  Asp Pro Lys
    1145                1150                1155
```

```
Lys Tyr  Gly Gly Phe Asp Ser  Pro Thr Val Ala Tyr  Ser Val Leu
    1160                 1165                 1170

Val Val  Ala Lys Val Glu Lys  Gly Lys Ser Lys Lys  Leu Lys Ser
    1175                 1180                 1185

Val Lys  Glu Leu Leu Gly Ile  Thr Ile Met Glu Arg  Ser Ser Phe
    1190                 1195                 1200

Glu Lys  Asn Pro Ile Asp Phe  Leu Glu Ala Lys Gly  Tyr Lys Glu
    1205                 1210                 1215

Val Lys  Lys Asp Leu Ile Ile  Lys Leu Pro Lys Tyr  Ser Leu Phe
    1220                 1225                 1230

Glu Leu  Glu Asn Gly Arg Lys  Arg Met Leu Ala Ser  Ala Gly Glu
    1235                 1240                 1245

Leu Gln  Lys Gly Asn Glu Leu  Ala Leu Pro Ser Lys  Tyr Val Asn
    1250                 1255                 1260

Phe Leu  Tyr Leu Ala Ser His  Tyr Glu Lys Leu Lys  Gly Ser Pro
    1265                 1270                 1275

Glu Asp  Asn Glu Gln Lys Gln  Leu Phe Val Glu Gln  His Lys His
    1280                 1285                 1290

Tyr Leu  Asp Glu Ile Ile Glu  Gln Ile Ser Glu Phe  Ser Lys Arg
    1295                 1300                 1305

Val Ile  Leu Ala Asp Ala Asn  Leu Asp Lys Val Leu  Ser Ala Tyr
    1310                 1315                 1320

Asn Lys  His Arg Asp Lys Pro  Ile Arg Glu Gln Ala  Glu Asn Ile
    1325                 1330                 1335

Ile His  Leu Phe Thr Leu Thr  Asn Leu Gly Ala Pro  Ala Ala Phe
    1340                 1345                 1350

Lys Tyr  Phe Asp Thr Thr Ile  Asp Arg Lys Arg Tyr  Thr Ser Thr
    1355                 1360                 1365

Lys Glu  Val Leu Asp Ala Thr  Leu Ile His Gln Ser  Ile Thr Gly
    1370                 1375                 1380

Leu Tyr  Glu Thr Arg Ile Asp  Leu Ser Gln Leu Gly  Gly Asp Lys
    1385                 1390                 1395

Arg Pro  Ala Ala Thr Lys Lys  Ala Gly Gln Ala Lys  Lys Lys Lys
    1400                 1405                 1410
```

<210> SEQ ID NO 6
<211> LENGTH: 4242
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atggctagta tgcagaaact gattagtgaa gaggacctga tggctcccaa gaagaagcga     60

aaggtgggca tccacggcgt gcccgctgcc gacaaaaagt atagtatcgg actggatatt    120

ggcactaaca gcgtgggatg ggccgtcatc accgacgagt acaaagtgcc aagcaagaag    180

ttcaaggtcc tgggaaacac cgatagacac agtatcaaga aaaatctgat tggagccctg    240

ctgttcgact caggggagac agctgaagca actaggctga aaagaacagc taggagacgg    300

tatactcgcc gaaagaatcg gatctgctac ctccaggaga ttttctccaa cgaaatggcc    360

aaggtggacg atagtttctt tcatcgcctg gaggaatcat tcctggtcga ggaagataag    420

aaacacgaga ggcatcccat ctttggcaac attgtggacg aggtcgctta tcacgaaaag    480
```

```
taccctacaa tctatcatct gcggaagaaa ctggtggaca gcactgataa ggcagacctg    540
cgcctgatct atctggccct ggctcacatg attaagttca gggggcattt tctgatcgag    600
ggcgatctga acccagacaa ttccgatgtg gacaagctgt tcatccagct ggtccagaca    660
tacaatcagc tgtttgagga aaaccccatt aatgcatctg gggtggacgc aaaagccatc    720
ctgagtgcca gactgtctaa gagtaggaga ctggagaacc tgatcgctca gctgccaggc    780
gaaaagaaaa acggcctgtt tggaaatctg attgcactgt cactgggact gacccccaac    840
ttcaagagca attttgatct ggccgaggac gctaagctcc agctgagcaa ggacacctac    900
gacgatgacc tggataacct gctggctcag atcggcgatc agtacgcaga cctgttcctg    960
gccgctaaga atctgtctga cgccatcctg ctgagtgata ttctgagagt gaacaccgag   1020
attacaaaag cccccctgtc agctagcatg atcaagagat atgacgagca ccatcaggat   1080
ctgaccctgc tgaaggctct ggtgcggcag cagctgcctg agaagtacaa agaaatcttc   1140
tttgatcaga gcaagaatgg gtacgccggc tatattgacg gcggagcttc ccaggaggag   1200
ttctacaagt ttatcaaacc tattctggag aagatggacg gcactgagga actgctggtg   1260
aaactgaatc gggaagacct gctgcggaag cagcgcacct tcgataacgg cagcatccct   1320
caccagattc atctgggaga gctgcacgca atcctgcggc gccaggaaga cttctaccca   1380
tttctgaagg ataaccggga gaagatcgaa aaaattctga ctttccgcat cccctactat   1440
gtggggcctc tggcaagagg caattcccgg tttgcctgga tgacccgcaa gtctgaggaa   1500
acaatcactc cctggaactt cgaggaagtg gtcgataagg gcgcttccgc acagtctttc   1560
attgagagga tgacaaattt tgacaagaac ctgccaaatg aaaaagtgct gcccaagcac   1620
agcctgctgt acgagtattt caccgtctat aacgaactga caaaggtgaa atacgtcact   1680
gagggcatga gaaagcctgc cttcctgtcc ggagaacaga agaaagctat cgtggacctg   1740
ctgtttaaaa ccaatcggaa ggtgacagtc aagcagctga aagaggacta cttcaagaaa   1800
attgaatgtt tcgattctgt ggagatcagt ggggtcgaag acaggtttaa cgcctctctg   1860
ggcacctacc acgatctgct gaagatcatt aaggataaag acttcctgga caacgaggaa   1920
aatgaggaca tcctggagga cattgtgctg accctgacac tgtttgagga tcgggaaatg   1980
atcgaggaac gcctgaagac ctacgcccat ctgttcgatg acaaagtgat gaaacagctg   2040
aagcgaagga gatacactgg gtggggccga ctgagcagga agctgatcaa tggcattcgc   2100
gacaaacaga gtggaaagac aatcctggac tttctgaagt cagatggctt cgctaacagg   2160
aattttatgc agctgattca cgatgactct ctgactttca aagaggacat ccagaaggca   2220
caggtgtccg gacaggggga ctctctgcac gagcatatcg caaacctggc cgggagccct   2280
gccatcaaga aaggcatcct ccagaccgtg aaggtggtgg acgagctggt gaaagtcatg   2340
ggaagacata agccagaaaa catcgtgatt gagatggcca gggagaatca gaccacacag   2400
aaagggcaga agaactctcg ggagcgcatg aaacgcatcg aggaaggaat taaggaactg   2460
ggcagtcaga tcctgaaaga gcaccccgtg gaaaacacac agctccagaa tgagaagctg   2520
tatctgtact acctccagaa tggccgcgat atgtacgtgg accaggagct ggatattaac   2580
cgactgtcag attatgacgt ggatcatatc gtcccacagt cattcctgaa agatgacagc   2640
attgacaata aggtgctgac ccgcagcgac aaaaaccgag gaaagagtga taatgtcccc   2700
tcagaggaag tggtcaagaa aatgaagaac tactggaggc agctgctgaa tgccaaactg   2760
atcacccagc gaaagtttga taacctgaca aaagctgaga ggggggggcct gtccgaactg   2820
gacaaagcag gcttcatcaa gcgacagctg gtggagacaa ggcagatcac aaagcacgtc   2880
```

gctcagatcc tggacagcag gatgaacacc aagtacgatg agaatgacaa actgatccgg 2940
gaagtgaagg tcattacact gaagtcaaaa ctggtgagcg actttaggaa agatttccag 3000
ttctacaagg tcagagagat caacaactac caccatgctc atgacgcata cctgaacgca 3060
gtggtcggga ctgccctgat taagaaatac cctaaactgg agtctgagtt cgtgtacggc 3120
gactataagg tgtacgatgt cagaaaaatg atcgccaaga gcgagcagga aattggcaaa 3180
gccaccgcta agtatttctt ttactccaac atcatgaatt tctttaagac tgagatcacc 3240
ctggcaaatg gcgaaatccg aaagaggcca ctgattgaga ctaacggaga gacaggggaa 3300
atcgtgtggg acaaaggaag agattttgct accgtgcgga aggtcctgag tatgccccaa 3360
gtgaatattg tcaagaaaac agaggtgcag actggagggt tcagtaagga atcaattctg 3420
cctaaacgca acagcgataa gctgatcgcc cgaaagaaag actgggaccc caagaagtat 3480
ggcggattcg actccccaac cgtggcttac tctgtcctgg tggtcgcaaa ggtggagaag 3540
ggaaaaagca agaaactgaa atccgtcaag gaactgctgg ggatcacaat tatggagagg 3600
agcagcttcg aaaagaatcc tatcgatttt ctggaggcca aagggtataa ggaagtgaag 3660
aaagacctga tcatcaagct gccaaagtac tctctgtttg agctggaaaa cggcagaaag 3720
cggatgctgg caagtgccgg cgagctgcaa aaggaaatg aactggccct gccctcaaag 3780
tacgtgaact tcctgtatct ggctagccac tacgagaagc tgaaaggctc ccctgaggat 3840
aacgaacaga aacagctgtt tgtggagcag cacaagcatt atctggacga gatcattgaa 3900
cagattagcg agttctccaa acgcgtgatc ctggctgacg caaatctgga taaggtcctg 3960
tctgcataca acaaacacag ggacaagcca atcagagagc aggccgaaaa tatcattcat 4020
ctgttcactc tgaccaacct gggagccccc gcagccttca agtattttga cactaccatc 4080
gatcgcaaac gatacacaag cactaaggag gtgctggatg ctaccctgat ccaccagagc 4140
attactgggc tgtacgagac aaggatcgac ctgtcccagc tgggggggaga caaacgccca 4200 gccgccacca agaaagcagg acaggcaaag aagaagaagt ga 4242

<210> SEQ ID NO 7
<211> LENGTH: 4101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
gacaaaaagt atagtatcgg actggctatt ggcactaaca gcgtgggatg ggccgtcatc 60
accgacgagt acaaagtgcc aagcaagaag ttcaaggtcc tgggaaacac cgatagacac 120
agtatcaaga aaaatctgat tggagccctg ctgttcgact caggggagac agctgaagca 180
actaggctga aaagaacagc taggagacgg tatactcgcc gaaagaatcg gatctgctac 240
ctccaggaga ttttctccaa cgaaatggcc aaggtggacg atagtttctt tcatcgcctg 300
gaggaatcat tcctggtcga ggaagataag aaacacgaga ggcatcccat ctttggcaac 360
attgtggacg aggtcgctta tcacgaaaag taccctacaa tctatcatct gcggaagaaa 420
ctggtggaca gcactgataa ggcagacctg cgcctgatct atctggccct ggctcacatg 480
attaagttca gggggcattt tctgatcgag ggcgatctga acccagacaa ttccgatgtg 540
gacaagctgt tcatccagct ggtccagaca tacaatcagc tgtttgagga aaaccccatt 600
aatgcatctg gggtggacgc aaaagccatc ctgagtgcca gactgtctaa gagtaggaga 660

```
ctggagaacc tgatcgctca gctgccaggc gaaaagaaaa acggcctgtt tggaaatctg    720
attgcactgt cactgggact gaccccccaac ttcaagagca attttgatct ggccgaggac    780
gctaagctcc agctgagcaa ggacacctac gacgatgacc tggataacct gctggctcag    840
atcggcgatc agtacgcaga cctgttcctg gccgctaaga atctgtctga cgccatcctg    900
ctgagtgata ttctgagagt gaacaccgag attacaaaag ccccccctgtc agctagcatg    960
atcaagagat atgacgagca ccatcaggat ctgaccctgc tgaaggctct ggtgcggcag   1020
cagctgcctg agaagtacaa agaaatcttc tttgatcaga gcaagaatgg gtacgccggc   1080
tatattgacg gcggagcttc ccaggaggag ttctacaagt ttatcaaacc tattctggag   1140
aagatggacg gcactgagga actgctggtg aaactgaatc gggaagacct gctgcggaag   1200
cagcgcacct tcgataacgg cagcatccct caccagattc atctgggaga gctgcacgca   1260
atcctgcggc gccaggaaga cttctaccca tttctgaagg ataaccggga gaagatcgaa   1320
aaaattctga ctttccgcat cccctactat gtggggcctc tggcaagagg caattcccgg   1380
tttgcctgga tgacccgcaa gtctgaggaa acaatcactc cctggaactt cgaggaagtg   1440
gtcgataagg gcgcttccgc acagtctttc attgagagga tgacaaattt tgacaagaac   1500
ctgccaaatg aaaaagtgct gcccaagcac agcctgctgt acgagtattt caccgtctat   1560
aacgaactga caaaggtgaa atacgtcact gagggcatga gaaagcctgc cttcctgtcc   1620
ggagaacaga agaaagctat cgtggacctg ctgtttaaaa ccaatcggaa ggtgacagtc   1680
aagcagctga aagaggacta cttcaagaaa attgaatgtt tcgattctgt ggagatcagt   1740
ggggtcgaag acaggtttaa cgcctctctg ggcacctacc acgatctgct gaagatcatt   1800
aaggataaag acttcctgga caacgaggaa aatgaggaca tcctggagga cattgtgctg   1860
accctgacac tgtttgagga tcgggaaatg atcgaggaac gcctgaagac ctacgcccat   1920
ctgttcgatg acaaagtgat gaaacagctg aagcgaagga gatacactgg gtggggccga   1980
ctgagcagga agctgatcaa tggcattcgc gacaaacaga gtggaaagac aatcctggac   2040
tttctgaagt cagatggctt cgctaacagg aattttatgc agctgattca cgatgactct   2100
ctgactttca aagaggacat ccagaaggca caggtgtccg gacaggggga ctctctgcac   2160
gagcatatcg caaacctggc cgggagccct gccatcaaga aaggcatcct ccagaccgtg   2220
aaggtggtgg acgagctggt gaaagtcatg ggaagacata agccagaaaa catcgtgatt   2280
gagatggcca gggagaatca gaccacacag aaagggcaga agaactctcg ggagcgcatg   2340
aaacgcatcg aggaaggaat taaggaactg ggagtcaga tcctgaaaga gcacccccgtg   2400
gaaaacacac agctccagaa tgagaagctg tatctgtact acctccagaa tggccgcgat   2460
atgtacgtgg accaggagct ggatattaac cgactgtcag attatgacgt ggatcatatc   2520
gtcccacagt cattcctgaa agatgacagc attgacaata aggtgctgac ccgcagcgac   2580
aaaaaccgag gaaagagtga taatgtcccc tcagaggaag tggtcaagaa aatgaagaac   2640
tactggaggc agctgctgaa tgccaaactg atcacccagc gaaagtttga taacctgaca   2700
aaagctgaga gggggggcct gtccgaactg gacaaagcag gcttcatcaa gcgacagctg   2760
gtggagacaa ggcagatcac aaagcacgtc gctcagatcc tggacagcag gatgaacacc   2820
aagtacgatg agaatgacaa actgatccgg gaagtgaagg tcattacact gaagtcaaaa   2880
ctggtgagcg actttaggaa agatttccag ttctacaagg tcagagagat caacaactac   2940
caccatgctc atgacgcata cctgaacgca gtggtcggga ctgccctgat taagaaatac   3000
```

```
cctaaactgg agtctgagtt cgtgtacggc gactataagg tgtacgatgt cagaaaaatg   3060

atcgccaaga gcgagcagga aattggcaaa gccaccgcta agtatttctt ttactccaac   3120

atcatgaatt tctttaagac tgagatcacc ctggcaaatg gcgaaatccg aaagaggcca   3180

ctgattgaga ctaacggaga gacaggggaa atcgtgtggg acaaaggaag agattttgct   3240

accgtgcgga aggtcctgag tatgccccaa gtgaatattg tcaagaaaac agaggtgcag   3300

actggagggt tcagtaagga atcaattctg cctaaacgca acagcgataa gctgatcgcc   3360

cgaaagaaag actgggaccc caagaagtat ggcggattcg actccccaac cgtggcttac   3420

tctgtcctgg tggtcgcaaa ggtggagaag ggaaaaagca agaaactgaa atccgtcaag   3480

gaactgctgg ggatcacaat tatggagagg agcagcttcg aaaagaatcc tatcgatttt   3540

ctggaggcca aagggtataa ggaagtgaag aaagacctga tcatcaagct gccaaagtac   3600

tctctgtttg agctggaaaa cggcagaaag cggatgctgg caagtgccgg cgagctgcaa   3660

aaaggaaatg aactggccct gccctcaaag tacgtgaact tcctgtatct ggctagccac   3720

tacgagaagc tgaaaggctc ccctgaggat aacgaacaga aacagctgtt tgtggagcag   3780

cacaagcatt atctggacga gatcattgaa cagattagcg agttctccaa acgcgtgatc   3840

ctggctgacg caaatctgga taaggtcctg tctgcataca acaaacacag ggacaagcca   3900

atcagagagc aggccgaaaa tatcattcat ctgttcactc tgaccaacct gggagccccc   3960

gcagccttca agtattttga cactaccatc gatcgcaaac gatacacaag cactaaggag   4020

gtgctggatg ctaccctgat ccaccagagc attactgggc tgtacgagac aaggatcgac   4080

ctgtcccagc tgggggggaga c                                              4101
```

<210> SEQ ID NO 8
<211> LENGTH: 4242
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
atggctagta tgcagaaact gattagtgaa gaggacctga tggctcccaa gaagaagcga     60

aaggtgggca tccacggcgt gcccgctgcc gacaaaaagt atagtatcgg actggctatt    120

ggcactaaca gcgtgggatg ggccgtcatc accgacgagt acaaagtgcc aagcaagaag    180

ttcaaggtcc tgggaaacac cgatagacac agtatcaaga aaaatctgat tggagccctg    240

ctgttcgact caggggagac agctgaagca actaggctga aaagaacagc taggagacgg    300

tatactcgcc gaaagaatcg gatctgctac ctccaggaga ttttctccaa cgaaatggcc    360

aaggtggacg atagtttctt tcatcgcctg gaggaatcat tcctggtcga ggaagataag    420

aaacacgaga ggcatcccat ctttggcaac attgtggacg aggtcgctta tcacgaaaag    480

taccctacaa tctatcatct gcggaagaaa ctggtggaca gcactgataa ggcagacctg    540

cgcctgatct atctggccct ggctcacatg attaagttca gggggcattt tctgatcgag    600

ggcgatctga acccagacaa ttccgatgtg gacaagctgt tcatccagct ggtccagaca    660

tacaatcagc tgtttgagga aaaccccatt aatgcatctg gggtggacgc aaaagccatc    720

ctgagtgcca gactgtctaa gagtaggaga ctggagaacc tgatcgctca gctgccaggc    780

gaaaagaaaa acggcctgtt tggaaatctg attgcactgt cactgggact gacccccaac    840

ttcaagagca attttgatct ggccgaggac gctaagctcc agctgagcaa ggacacctac    900
```

```
gacgatgacc tggataacct gctggctcag atcggcgatc agtacgcaga cctgttcctg    960
gccgctaaga atctgtctga cgccatcctg ctgagtgata ttctgagagt gaacaccgag   1020
attacaaaag ccccccctgtc agctagcatg atcaagagat atgacgagca ccatcaggat   1080
ctgaccctgc tgaaggctct ggtgcggcag cagctgcctg agaagtacaa agaaatcttc   1140
tttgatcaga gcaagaatgg gtacgccggc tatattgacg gcggagcttc ccaggaggag   1200
ttctacaagt ttatcaaacc tattctggag aagatggacg gcactgagga actgctggtg   1260
aaactgaatc gggaagacct gctgcggaag cagcgcacct tcgataacgg cagcatccct   1320
caccagattc atctgggaga gctgcacgca atcctgcggc gccaggaaga cttctaccca   1380
tttctgaagg ataaccggga gaagatcgaa aaaattctga ctttccgcat cccctactat   1440
gtggggcctc tggcaagagg caattcccgg tttgcctgga tgacccgcaa gtctgaggaa   1500
acaatcactc cctggaactt cgaggaagtg gtcgataagg gcgcttccgc acagtctttc   1560
attgagagga tgacaaattt tgacaagaac ctgccaaatg aaaaagtgct gcccaagcac   1620
agcctgctgt acgagtattt caccgtctat aacgaactga caaaggtgaa atacgtcact   1680
gagggcatga gaaagcctgc cttcctgtcc ggagaacaga agaaagctat cgtggacctg   1740
ctgtttaaaa ccaatcggaa ggtgacagtc aagcagctga aagaggacta cttcaagaaa   1800
attgaatgtt tcgattctgt ggagatcagt ggggtcgaag acaggtttaa cgcctctctg   1860
ggcacctacc acgatctgct gaagatcatt aaggataaag acttcctgga caacgaggaa   1920
aatgaggaca tcctggagga cattgtgctg accctgacac tgtttgagga tcgggaaatg   1980
atcgaggaac gcctgaagac ctacgcccat ctgttcgatg acaaagtgat gaaacagctg   2040
aagcgaagga gatacactgg gtggggccga ctgagcagga agctgatcaa tggcattcgc   2100
gacaaacaga gtggaaagac aatcctggac tttctgaagt cagatggctt cgctaacagg   2160
aattttatgc agctgattca cgatgactct ctgactttca aagaggacat ccagaaggca   2220
caggtgtccg gacaggggga ctctctgcac gagcatatcg caaacctggc cgggagccct   2280
gccatcaaga aaggcatcct ccagaccgtg aaggtggtgg acgagctggt gaaagtcatg   2340
ggaagacata agccagaaaa catcgtgatt gagatggcca gggagaatca gaccacacag   2400
aaagggcaga agaactctcg ggagcgcatg aaacgcatcg aggaaggaat taaggaactg   2460
ggagtcaga tcctgaaaga gcaccccgtg gaaaacacac agctccagaa tgagaagctg   2520
tatctgtact acctccagaa tggccgcgat atgtacgtgg accaggagct ggatattaac   2580
cgactgtcag attatgacgt ggatcatatc gtcccacagt cattcctgaa agatgacagc   2640
attgacaata aggtgctgac ccgcagcgac aaaaaccgag gaaagagtga taatgtcccc   2700
tcagaggaag tggtcaagaa aatgaagaac tactggaggc agctgctgaa tgccaaactg   2760
atcacccagc gaaagtttga taacctgaca aaagctgaga gggggggcct gtccgaactg   2820
gacaaagcag gcttcatcaa gcgacagctg gtggagacaa ggcagatcac aaagcacgtc   2880
gctcagatcc tggacagcag gatgaacacc aagtacgatg agaatgacaa actgatccgg   2940
gaagtgaagg tcattacact gaagtcaaaa ctggtgagcg actttaggaa agatttccag   3000
ttctacaagg tcagagagat caacaactac caccatgctc atgacgcata cctgaacgca   3060
gtggtcggga ctgccctgat taagaaatac cctaaactgg agtctgagtt cgtgtacggc   3120
gactataagg tgtacgatgt cagaaaaatg atcgccaaga gcgagcagga aattggcaaa   3180
gccaccgcta agtatttctt ttactccaac atcatgaatt tctttaagac tgagatcacc   3240
ctggcaaatg gcgaaatccg aaagaggcca ctgattgaga ctaacggaga gacaggggaa   3300
```

```
atcgtgtggg acaaaggaag agattttgct accgtgcgga aggtcctgag tatgccccaa   3360

gtgaatattg tcaagaaaac agaggtgcag actggagggt tcagtaagga atcaattctg   3420

cctaaacgca acagcgataa gctgatcgcc cgaaagaaag actgggaccc caagaagtat   3480

ggcggattcg actccccaac cgtggcttac tctgtcctgg tggtcgcaaa ggtggagaag   3540

ggaaaaagca agaaactgaa atccgtcaag gaactgctgg ggatcacaat tatggagagg   3600

agcagcttcg aaaagaatcc tatcgatttt ctggaggcca aagggtataa ggaagtgaag   3660

aaagacctga tcatcaagct gccaaagtac tctctgtttg agctggaaaa cggcagaaag   3720

cggatgctgg caagtgccgg cgagctgcaa aaggaaatg aactggccct gccctcaaag   3780

tacgtgaact tcctgtatct ggctagccac tacgagaagc tgaaaggctc ccctgaggat   3840

aacgaacaga aacagctgtt tgtggagcag cacaagcatt atctggacga gatcattgaa   3900

cagattagcg agttctccaa acgcgtgatc ctggctgacg caaatctgga taaggtcctg   3960

tctgcataca acaaacacag ggacaagcca atcagagagc aggccgaaaa tatcattcat   4020

ctgttcactc tgaccaacct gggagccccc gcagccttca agtattttga cactaccatc   4080

gatcgcaaac gatacacaag cactaaggag gtgctggatg ctaccctgat ccaccagagc   4140

attactgggc tgtacgagac aaggatcgac ctgtcccagc tgggggggaga caaacgccca   4200

gccgccacca agaaagcagg acaggcaaag aagaagaagt ga                        4242
```

<210> SEQ ID NO 9
<211> LENGTH: 4104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atggacaaaa agtatagtat cggactggct attggcacta acagcgtggg atgggccgtc     60

atcaccgacg agtacaaagt gccaagcaag aagttcaagg tcctgggaaa caccgataga    120

cacagtatca agaaaaatct gattggagcc ctgctgttcg actcagggga gacagctgaa    180

gcaactaggc tgaaaagaac agctaggaga cggtatactc gccgaaagaa tcggatctgc    240

tacctccagg agattttctc caacgaaatg gccaaggtgg acgatagttt ctttcatcgc    300

ctggaggaat cattcctggt cgaggaagat aagaaacacg agaggcatcc catctttggc    360

aacattgtgg acgaggtcgc ttatcacgaa aagtacccta caatctatca tctgcggaag    420

aaactggtgg acagcactga taaggcagac ctgcgcctga tctatctggc cctggctcac    480

atgattaagt tcagggggca ttttctgatc gagggcgatc tgaacccaga caattccgat    540

gtggacaagc tgttcatcca gctggtccag acatacaatc agctgtttga ggaaaacccc    600

attaatgcat ctggggtgga cgcaaaagcc atcctgagtg ccagactgtc taagagtagg    660

agactggaga acctgatcgc tcagctgcca ggcgaaaaga aaaacggcct gtttggaaat    720

ctgattgcac tgtcactggg actgaccccc aacttcaaga gcaattttga tctggccgag    780

gacgctaagc tccagctgag caaggacacc tacgacgatg acctggataa cctgctggct    840

cagatcggcg atcagtacgc agacctgttc ctggccgcta agaatctgtc tgacgccatc    900

ctgctgagtg atattctgag agtgaacacc gagattacaa aagcccccct gtcagctagc    960

atgatcaaga gatatgacga gcaccatcag gatctgaccc tgctgaaggc tctggtgcgg   1020

cagcagctgc ctgagaagta caaagaaatc ttctttgatc agagcaagaa tgggtacgcc   1080
```

```
ggctatattg acggcggagc ttcccaggag gagttctaca agtttatcaa acctattctg   1140
gagaagatgg acggcactga ggaactgctg gtgaaactga atcgggaaga cctgctgcgg   1200
aagcagcgca ccttcgataa cggcagcatc cctcaccaga ttcatctggg agagctgcac   1260
gcaatcctgc ggcgccagga agacttctac ccatttctga aggataaccg ggagaagatc   1320
gaaaaaattc tgactttccg catcccctac tatgtggggc ctctggcaag aggcaattcc   1380
cggtttgcct ggatgacccg caagtctgag gaaacaatca ctccctggaa cttcgaggaa   1440
gtggtcgata agggcgcttc cgcacagtct ttcattgaga ggatgacaaa ttttgacaag   1500
aacctgccaa atgaaaaagt gctgcccaag cacagcctgc tgtacgagta tttcaccgtc   1560
tataacgaac tgacaaaggt gaaatacgtc actgagggca tgagaaagcc tgccttcctg   1620
tccggagaac agaagaaagc tatcgtggac ctgctgttta aaaccaatcg gaaggtgaca   1680
gtcaagcagc tgaaagagga ctacttcaag aaaattgaat gtttcgattc tgtggagatc   1740
agtggggtcg aagacaggtt taacgcctct ctgggcacct accacgatct gctgaagatc   1800
attaaggata aagacttcct ggacaacgag gaaaatgagg acatcctgga ggacattgtg   1860
ctgaccctga cactgtttga ggatcgggaa atgatcgagg aacgcctgaa gacctacgcc   1920
catctgttcg atgacaaagt gatgaaacag ctgaagcgaa ggagatacac tgggtggggc   1980
cgactgagca ggaagctgat caatggcatt cgcgacaaac agagtggaaa gacaatcctg   2040
gactttctga agtcagatgg cttcgctaac aggaatttta tgcagctgat tcacgatgac   2100
tctctgactt tcaaagagga catccagaag gcacaggtgt ccggacaggg ggactctctg   2160
cacgagcata tcgcaaacct ggccgggagc cctgccatca agaaaggcat cctccagacc   2220
gtgaaggtgg tggacgagct ggtgaaagtc atgggaagac ataagccaga aaacatcgtg   2280
attgagatgg ccagggagaa tcagaccaca cagaaagggc agaagaactc tcgggagcgc   2340
atgaaacgca tcgaggaagg aattaaggaa ctggggagtc agatcctgaa agagcacccc   2400
gtggaaaaca cacagctcca gaatgagaag ctgtatctgt actacctcca gaatggccgc   2460
gatatgtacg tggaccagga gctggatatt aaccgactgt cagattatga cgtggatgcc   2520
atcgtcccac agtcattcct gaaagatgac agcattgaca ataaggtgct gacccgcagc   2580
gacaaaaacc gaggaaagag tgataatgtc ccctcagagg aagtggtcaa gaaaatgaag   2640
aactactgga ggcagctgct gaatgccaaa ctgatcaccc agcgaaagtt tgataacctg   2700
acaaaagctg agagggggggg cctgtccgaa ctggacaaag caggcttcat caagcgacag   2760
ctggtggaga caaggcagat cacaaagcac gtcgctcaga tcctggacag caggatgaac   2820
accaagtacg atgagaatga caaactgatc cgggaagtga aggtcattac actgaagtca   2880
aaactggtga gcgactttag gaaagatttc cagttctaca aggtcagaga gatcaacaac   2940
taccaccatg ctcatgacgc atacctgaac gcagtggtcg ggactgccct gattaagaaa   3000
taccctaaac tggagtctga gttcgtgtac ggcgactata aggtgtacga tgtcagaaaa   3060
atgatcgcca agagcgagca ggaaattggc aaagccaccg ctaagtattt cttttactcc   3120
aacatcatga atttctttaa gactgagatc accctggcaa atggcgaaat ccgaaagagg   3180
ccactgattg agactaacgg agagacaggg gaaatcgtgt gggacaaagg aagagatttt   3240
gctaccgtgc ggaaggtcct gagtatgccc caagtgaata ttgtcaagaa aacagaggtg   3300
cagactggag ggttcagtaa ggaatcaatt ctgcctaaac gcaacagcga taagctgatc   3360
gcccgaaaga aagactggga ccccaagaag tatggcggat tcgactcccc aaccgtggct   3420
```

```
tactctgtcc tggtggtcgc aaaggtggag aagggaaaaa gcaagaaact gaaatccgtc   3480

aaggaactgc tggggatcac aattatggag aggagcagct tcgaaaagaa tcctatcgat   3540

tttctggagg ccaaagggta taaggaagtg aagaaagacc tgatcatcaa gctgccaaag   3600

tactctctgt ttgagctgga aaacggcaga aagcggatgc tggcaagtgc cggcgagctg   3660

caaaaaggaa atgaactggc cctgccctca aagtacgtga acttcctgta tctggctagc   3720

cactacgaga agctgaaagg ctcccctgag gataacgaac agaaacagct gtttgtggag   3780

cagcacaagc attatctgga cgagatcatt gaacagatta gcgagttctc caaacgcgtg   3840

atcctggctg acgcaaatct ggataaggtc ctgtctgcat acaacaaaca cagggacaag   3900

ccaatcagag agcaggccga aaatatcatt catctgttca ctctgaccaa cctgggagcc   3960

cccgcagcct tcaagtattt tgacactacc atcgatcgca aacgatacac aagcactaag   4020

gaggtgctgg atgctaccct gatccaccag agcattactg ggctgtacga gacaaggatc   4080

gacctgtccc agctgggggg agac                                          4104
```

<210> SEQ ID NO 10
<211> LENGTH: 4242
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atggctagta tgcagaaact gattagtgaa gaggacctga tggctcccaa gaagaagcga     60

aaggtgggca tccacggcgt gcccgctgcc gacaaaaagt atagtatcgg actggctatt    120

ggcactaaca gcgtgggatg ggccgtcatc accgacgagt acaaagtgcc aagcaagaag    180

ttcaaggtcc tgggaaacac cgatagacac agtatcaaga aaaatctgat tggagccctg    240

ctgttcgact caggggagac agctgaagca actaggctga aaagaacagc taggagacgg    300

tatactcgcc gaaagaatcg gatctgctac ctccaggaga ttttctccaa cgaaatggcc    360

aaggtggacg atagtttctt tcatcgcctg gaggaatcat tcctggtcga ggaagataag    420

aaacacgaga ggcatcccat ctttggcaac attgtggacg aggtcgctta tcacgaaaag    480

taccctacaa tctatcatct gcggaagaaa ctggtggaca gcactgataa ggcagacctg    540

cgcctgatct atctggccct ggctcacatg attaagttca gggggcattt tctgatcgag    600

ggcgatctga acccagacaa ttccgatgtg gacaagctgt tcatccagct ggtccagaca    660

tacaatcagc tgtttgagga aaaccccatt aatgcatctg ggtggacgc aaaagccatc    720

ctgagtgcca gactgtctaa gagtaggaga ctggagaacc tgatcgctca gctgccaggc    780

gaaaagaaaa acggcctgtt tggaaatctg attgcactgt cactgggact gacccccaac    840

ttcaagagca attttgatct ggccgaggac gctaagctcc agctgagcaa ggacacctac    900

gacgatgacc tggataacct gctggctcag atcggcgatc agtacgcaga cctgttcctg    960

gccgctaaga atctgtctga cgccatcctg ctgagtgata ttctgagagt gaacaccgag   1020

attacaaaag cccccctgtc agctagcatg atcaagagat atgacgagca ccatcaggat   1080

ctgaccctgc tgaaggctct ggtgcggcag cagctgcctg agaagtacaa agaaatcttc   1140

tttgatcaga gcaagaatgg gtacgccggc tatattgacg gcggagcttc ccaggaggag   1200

ttctacaagt ttatcaaacc tattctggag aagatggacg gcactgagga actgctggtg   1260

aaactgaatc gggaagacct gctgcggaag cagcgcacct tcgataacgg cagcatccct   1320
```

caccagattc atctgggaga gctgcacgca atcctgcggc gccaggaaga cttctaccca 1380
tttctgaagg ataaccggga gaagatcgaa aaaattctga ctttccgcat cccctactat 1440
gtggggcctc tggcaagagg caattcccgg tttgcctgga tgacccgcaa gtctgaggaa 1500
acaatcactc cctggaactt cgaggaagtg gtcgataagg gcgcttccgc acagtctttc 1560
attgagagga tgacaaattt tgacaagaac ctgccaaatg aaaaagtgct gcccaagcac 1620
agcctgctgt acgagtattt caccgtctat aacgaactga caaaggtgaa atacgtcact 1680
gagggcatga gaaagcctgc cttcctgtcc ggagaacaga agaaagctat cgtggacctg 1740
ctgtttaaaa ccaatcggaa ggtgacagtc aagcagctga aagaggacta cttcaagaaa 1800
attgaatgtt tcgattctgt ggagatcagt ggggtcgaag acaggtttaa cgcctctctg 1860
ggcacctacc acgatctgct gaagatcatt aaggataaag acttcctgga caacgaggaa 1920
aatgaggaca tcctggagga cattgtgctg accctgacac tgtttgagga tcgggaaatg 1980
atcgaggaac gcctgaagac ctacgcccat ctgttcgatg acaaagtgat gaaacagctg 2040
aagcgaagga gatacactgg gtggggccga ctgagcagga agctgatcaa tggcattcgc 2100
gacaaacaga gtggaaagac aatcctggac tttctgaagt cagatggctt cgctaacagg 2160
aattttatgc agctgattca cgatgactct ctgactttca aagaggacat ccagaaggca 2220
caggtgtccg gacaggggga ctctctgcac gagcatatcg caaacctggc cgggagccct 2280
gccatcaaga aaggcatcct ccagaccgtg aaggtggtgg acgagctggt gaaagtcatg 2340
ggaagacata agccagaaaa catcgtgatt gagatggcca gggagaatca gaccacacag 2400
aaagggcaga agaactctcg ggagcgcatg aaacgcatcg aggaaggaat taaggaactg 2460
gggagtcaga tcctgaaaga gcaccccgtg gaaaacacac agctccagaa tgagaagctg 2520
tatctgtact acctccagaa tggccgcgat atgtacgtgg accaggagct ggatattaac 2580
cgactgtcag attatgacgt ggatgccatc gtcccacagt cattcctgaa agatgacagc 2640
attgacaata aggtgctgac ccgcagcgac aaaaaccgag gaaagagtga taatgtcccc 2700
tcagaggaag tggtcaagaa aatgaagaac tactggaggc agctgctgaa tgccaaactg 2760
atcacccagc gaaagtttga taacctgaca aaagctgaga ggggggggct gtccgaactg 2820
gacaaagcag gcttcatcaa gcgacagctg gtggagacaa ggcagatcac aaagcacgtc 2880
gctcagatcc tggacagcag gatgaacacc aagtacgatg agaatgacaa actgatccgg 2940
gaagtgaagg tcattacact gaagtcaaaa ctggtgagcg actttaggaa agatttccag 3000
ttctacaagg tcagagagat caacaactac caccatgctc atgacgcata cctgaacgca 3060
gtggtcggga ctgccctgat taagaaatac cctaaactgg agtctgagtt cgtgtacggc 3120
gactataagg tgtacgatgt cagaaaaatg atcgccaaga gcgagcagga aattggcaaa 3180
gccaccgcta agtatttctt ttactccaac atcatgaatt tctttaagac tgagatcacc 3240
ctggcaaatg gcgaaatccg aaagaggcca ctgattgaga ctaacggaga gacaggggaa 3300
atcgtgtggg acaaaggaag agattttgct accgtgcgga aggtcctgag tatgccccaa 3360
gtgaatattg tcaagaaaac agaggtgcag actggagggt tcagtaagga atcaattctg 3420
cctaaacgca acagcgataa gctgatcgcc cgaaagaaag actgggaccc caagaagtat 3480
ggcggattcg actccccaac cgtggcttac tctgtcctgg tggtcgcaaa ggtggagaag 3540
ggaaaaagca agaaactgaa atccgtcaag gaactgctgg ggatcacaat tatggagagg 3600
agcagcttcg aaaagaatcc tatcgatttt ctggaggcca aagggtataa ggaagtgaag 3660
aaagacctga tcatcaagct gccaaagtac tctctgtttg agctggaaaa cggcagaaag 3720

```
cggatgctgg caagtgccgg cgagctgcaa aaaggaaatg aactggccct gccctcaaag   3780

tacgtgaact tcctgtatct ggctagccac tacgagaagc tgaaaggctc ccctgaggat   3840

aacgaacaga aacagctgtt tgtggagcag cacaagcatt atctggacga gatcattgaa   3900

cagattagcg agttctccaa acgcgtgatc ctggctgacg caaatctgga taaggtcctg   3960

tctgcataca acaaacacag ggacaagcca atcagagagc aggccgaaaa tatcattcat   4020

ctgttcactc tgaccaacct gggagccccc gcagccttca agtattttga cactaccatc   4080

gatcgcaaac gatacacaag cactaaggag gtgctggatg ctaccctgat ccaccagagc   4140

attactgggc tgtacgagac aaggatcgac ctgtcccagc tgggggggaga caaacgccca   4200

gccgccacca agaaagcagg acaggcaaag aagaagaagt ga                       4242
```

<210> SEQ ID NO 11
<211> LENGTH: 1400
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Ala Pro Lys Lys Lys Arg Lys Val Gly Ile His Gly Val Pro Ala
1               5                   10                  15

Ala Asp Lys Lys Tyr Ser Ile Gly Leu Asp Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
```

```
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685
```

```
Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp His Ile Val Pro Gln Ser Phe Leu Lys
    850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
        995                 1000                1005

Val Gly  Thr Ala Leu Ile Lys  Lys Tyr Pro Lys Leu  Glu Ser Glu
    1010                1015                1020

Phe Val  Tyr Gly Asp Tyr Lys  Val Tyr Asp Val Arg  Lys Met Ile
    1025                1030                1035

Ala Lys  Ser Glu Gln Glu Ile  Gly Lys Ala Thr Ala  Lys Tyr Phe
    1040                1045                1050

Phe Tyr  Ser Asn Ile Met Asn  Phe Phe Lys Thr Glu  Ile Thr Leu
    1055                1060                1065

Ala Asn  Gly Glu Ile Arg Lys  Arg Pro Leu Ile Glu  Thr Asn Gly
    1070                1075                1080

Glu Thr  Gly Glu Ile Val Trp  Asp Lys Gly Arg Asp  Phe Ala Thr
    1085                1090                1095
```

```
Val Arg  Lys Val Leu Ser Met  Pro Gln Val Asn Ile  Val Lys Lys
    1100                 1105                 1110

Thr Glu  Val Gln Thr Gly Gly  Phe Ser Lys Glu Ser  Ile Leu Pro
    1115                 1120                 1125

Lys Arg  Asn Ser Asp Lys Leu  Ile Ala Arg Lys Lys  Asp Trp Asp
    1130                 1135                 1140

Pro Lys  Lys Tyr Gly Gly Phe  Asp Ser Pro Thr Val  Ala Tyr Ser
    1145                 1150                 1155

Val Leu  Val Val Ala Lys Val  Glu Lys Gly Lys Ser  Lys Lys Leu
    1160                 1165                 1170

Lys Ser  Val Lys Glu Leu Leu  Gly Ile Thr Ile Met  Glu Arg Ser
    1175                 1180                 1185

Ser Phe  Glu Lys Asn Pro Ile  Asp Phe Leu Glu Ala  Lys Gly Tyr
    1190                 1195                 1200

Lys Glu  Val Lys Lys Asp Leu  Ile Ile Lys Leu Pro  Lys Tyr Ser
    1205                 1210                 1215

Leu Phe  Glu Leu Glu Asn Gly  Arg Lys Arg Met Leu  Ala Ser Ala
    1220                 1225                 1230

Gly Glu  Leu Gln Lys Gly Asn  Glu Leu Ala Leu Pro  Ser Lys Tyr
    1235                 1240                 1245

Val Asn  Phe Leu Tyr Leu Ala  Ser His Tyr Glu Lys  Leu Lys Gly
    1250                 1255                 1260

Ser Pro  Glu Asp Asn Glu Gln  Lys Gln Leu Phe Val  Glu Gln His
    1265                 1270                 1275

Lys His  Tyr Leu Asp Glu Ile  Ile Glu Gln Ile Ser  Glu Phe Ser
    1280                 1285                 1290

Lys Arg  Val Ile Leu Ala Asp  Ala Asn Leu Asp Lys  Val Leu Ser
    1295                 1300                 1305

Ala Tyr  Asn Lys His Arg Asp  Lys Pro Ile Arg Glu  Gln Ala Glu
    1310                 1315                 1320

Asn Ile  Ile His Leu Phe Thr  Leu Thr Asn Leu Gly  Ala Pro Ala
    1325                 1330                 1335

Ala Phe  Lys Tyr Phe Asp Thr  Thr Ile Asp Arg Lys  Arg Tyr Thr
    1340                 1345                 1350

Ser Thr  Lys Glu Val Leu Asp  Ala Thr Leu Ile His  Gln Ser Ile
    1355                 1360                 1365

Thr Gly  Leu Tyr Glu Thr Arg  Ile Asp Leu Ser Gln  Leu Gly Gly
    1370                 1375                 1380

Asp Lys  Arg Pro Ala Ala Thr  Lys Lys Ala Gly Gln  Ala Lys Lys
    1385                 1390                 1395

Lys Lys
    1400

<210> SEQ ID NO 12
<211> LENGTH: 1400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Pro Lys Lys Lys Arg Lys Val Gly Ile His Gly Val Pro Ala
1               5                   10                  15

Ala Asp Lys Lys Tyr Ser Ile Gly Leu Ala Ile Gly Thr Asn Ser Val
            20                  25                  30
```

```
Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445
```

```
Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685

Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp His Ile Val Pro Gln Ser Phe Leu Lys
    850                 855                 860

Asp Asp Ser Ile Asp Asn Lys Val Leu Thr Arg Ser Asp Lys Asn Arg
```

-continued

```
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
        995                 1000                1005

Val Gly  Thr Ala Leu Ile Lys  Lys Tyr Pro Lys Leu  Glu Ser Glu
    1010                1015                1020

Phe Val  Tyr Gly Asp Tyr Lys  Val Tyr Asp Val Arg  Lys Met Ile
    1025                1030                1035

Ala Lys  Ser Glu Gln Glu Ile  Gly Lys Ala Thr Ala  Lys Tyr Phe
    1040                1045                1050

Phe Tyr  Ser Asn Ile Met Asn  Phe Phe Lys Thr Glu  Ile Thr Leu
    1055                1060                1065

Ala Asn  Gly Glu Ile Arg Lys  Arg Pro Leu Ile Glu  Thr Asn Gly
    1070                1075                1080

Glu Thr  Gly Glu Ile Val Trp  Asp Lys Gly Arg Asp  Phe Ala Thr
    1085                1090                1095

Val Arg  Lys Val Leu Ser Met  Pro Gln Val Asn Ile  Val Lys Lys
    1100                1105                1110

Thr Glu  Val Gln Thr Gly Gly  Phe Ser Lys Glu Ser  Ile Leu Pro
    1115                1120                1125

Lys Arg  Asn Ser Asp Lys Leu  Ile Ala Arg Lys Lys  Asp Trp Asp
    1130                1135                1140

Pro Lys  Lys Tyr Gly Gly Phe  Asp Ser Pro Thr Val  Ala Tyr Ser
    1145                1150                1155

Val Leu  Val Val Ala Lys Val  Glu Lys Gly Lys Ser  Lys Lys Leu
    1160                1165                1170

Lys Ser  Val Lys Glu Leu Leu  Gly Ile Thr Ile Met  Glu Arg Ser
    1175                1180                1185

Ser Phe  Glu Lys Asn Pro Ile  Asp Phe Leu Glu Ala  Lys Gly Tyr
    1190                1195                1200

Lys Glu  Val Lys Lys Asp Leu  Ile Ile Lys Leu Pro  Lys Tyr Ser
    1205                1210                1215

Leu Phe  Glu Leu Glu Asn Gly  Arg Lys Arg Met Leu  Ala Ser Ala
    1220                1225                1230

Gly Glu  Leu Gln Lys Gly Asn  Glu Leu Ala Leu Pro  Ser Lys Tyr
    1235                1240                1245

Val Asn  Phe Leu Tyr Leu Ala  Ser His Tyr Glu Lys  Leu Lys Gly
    1250                1255                1260

Ser Pro  Glu Asp Asn Glu Gln  Lys Gln Leu Phe Val  Glu Gln His
    1265                1270                1275
```

```
Lys His  Tyr Leu Asp Glu Ile  Ile Glu Gln Ile Ser  Glu Phe Ser
    1280                 1285                 1290

Lys Arg  Val Ile Leu Ala Asp  Ala Asn Leu Asp Lys  Val Leu Ser
    1295                 1300                 1305

Ala Tyr  Asn Lys His Arg Asp  Lys Pro Ile Arg Glu  Gln Ala Glu
    1310                 1315                 1320

Asn Ile  Ile His Leu Phe Thr  Leu Thr Asn Leu Gly  Ala Pro Ala
    1325                 1330                 1335

Ala Phe  Lys Tyr Phe Asp Thr  Thr Ile Asp Arg Lys  Arg Tyr Thr
    1340                 1345                 1350

Ser Thr  Lys Glu Val Leu Asp  Ala Thr Leu Ile His  Gln Ser Ile
    1355                 1360                 1365

Thr Gly  Leu Tyr Glu Thr Arg  Ile Asp Leu Ser Gln  Leu Gly Gly
    1370                 1375                 1380

Asp Lys  Arg Pro Ala Ala Thr  Lys Lys Ala Gly Gln  Ala Lys Lys
    1385                 1390                 1395

Lys Lys
    1400


<210> SEQ ID NO 13
<211> LENGTH: 1400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Pro Lys Lys Lys Arg Lys Val Gly Ile His Gly Val Pro Ala
1               5                   10                  15

Ala Asp Lys Lys Tyr Ser Ile Gly Leu Ala Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
```

```
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640
```

```
Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685

Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp Ala Ile Val Pro Gln Ser Phe Leu Lys
    850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
        995                 1000                1005

Val Gly  Thr Ala Leu Ile Lys  Lys Tyr Pro Lys Leu  Glu Ser Glu
    1010                1015                1020

Phe Val  Tyr Gly Asp Tyr Lys  Val Tyr Asp Val Arg  Lys Met Ile
    1025                1030                1035

Ala Lys  Ser Glu Gln Glu Ile  Gly Lys Ala Thr Ala  Lys Tyr Phe
    1040                1045                1050
```

```
Phe Tyr  Ser Asn Ile Met Asn  Phe Phe Lys Thr Glu  Ile Thr Leu
    1055                 1060                 1065

Ala Asn  Gly Glu Ile Arg Lys  Arg Pro Leu Ile Glu  Thr Asn Gly
    1070                 1075                 1080

Glu Thr  Gly Glu Ile Val Trp  Asp Lys Gly Arg Asp  Phe Ala Thr
    1085                 1090                 1095

Val Arg  Lys Val Leu Ser Met  Pro Gln Val Asn Ile  Val Lys Lys
    1100                 1105                 1110

Thr Glu  Val Gln Thr Gly Gly  Phe Ser Lys Glu Ser  Ile Leu Pro
    1115                 1120                 1125

Lys Arg  Asn Ser Asp Lys Leu  Ile Ala Arg Lys Lys  Asp Trp Asp
    1130                 1135                 1140

Pro Lys  Lys Tyr Gly Gly Phe  Asp Ser Pro Thr Val  Ala Tyr Ser
    1145                 1150                 1155

Val Leu  Val Val Ala Lys Val  Glu Lys Gly Lys Ser  Lys Lys Leu
    1160                 1165                 1170

Lys Ser  Val Lys Glu Leu Leu  Gly Ile Thr Ile Met  Glu Arg Ser
    1175                 1180                 1185

Ser Phe  Glu Lys Asn Pro Ile  Asp Phe Leu Glu Ala  Lys Gly Tyr
    1190                 1195                 1200

Lys Glu  Val Lys Lys Asp Leu  Ile Ile Lys Leu Pro  Lys Tyr Ser
    1205                 1210                 1215

Leu Phe  Glu Leu Glu Asn Gly  Arg Lys Arg Met Leu  Ala Ser Ala
    1220                 1225                 1230

Gly Glu  Leu Gln Lys Gly Asn  Glu Leu Ala Leu Pro  Ser Lys Tyr
    1235                 1240                 1245

Val Asn  Phe Leu Tyr Leu Ala  Ser His Tyr Glu Lys  Leu Lys Gly
    1250                 1255                 1260

Ser Pro  Glu Asp Asn Glu Gln  Lys Gln Leu Phe Val  Glu Gln His
    1265                 1270                 1275

Lys His  Tyr Leu Asp Glu Ile  Ile Glu Gln Ile Ser  Glu Phe Ser
    1280                 1285                 1290

Lys Arg  Val Ile Leu Ala Asp  Ala Asn Leu Asp Lys  Val Leu Ser
    1295                 1300                 1305

Ala Tyr  Asn Lys His Arg Asp  Lys Pro Ile Arg Glu  Gln Ala Glu
    1310                 1315                 1320

Asn Ile  Ile His Leu Phe Thr  Leu Thr Asn Leu Gly  Ala Pro Ala
    1325                 1330                 1335

Ala Phe  Lys Tyr Phe Asp Thr  Thr Ile Asp Arg Lys  Arg Tyr Thr
    1340                 1345                 1350

Ser Thr  Lys Glu Val Leu Asp  Ala Thr Leu Ile His  Gln Ser Ile
    1355                 1360                 1365

Thr Gly  Leu Tyr Glu Thr Arg  Ile Asp Leu Ser Gln  Leu Gly Gly
    1370                 1375                 1380

Asp Lys  Arg Pro Ala Ala Thr  Lys Lys Ala Gly Gln  Ala Lys Lys
    1385                 1390                 1395

Lys Lys
    1400
```

```
<210> SEQ ID NO 14
<211> LENGTH: 131
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 14
gggaatctta taagttctgt atgagaccac ttggatcctc tggtctctgt tttagagcta 60
gaaatagcaa gttaaaataa ggctagtccg ttatcaactt gaaaaagtgg caccgagtcg 120
gtgctttttt t 131

<210> SEQ ID NO 15
<211> LENGTH: 132
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
aaaaaaaagc accgactcgg tgccactttt tcaagttgat aacggactag ccttatttta 60
acttgctatt tctagctcta aaacagagac cagaggatcc aagtggtctc atacagaact 120
tataagattc cc 132

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (16)..(35)
<223> OTHER INFORMATION: a, c, t, g, unknown or other

<400> SEQUENCE: 16
tgtatgagac cacttnnnnn nnnnnnnnnn nnnnn 35

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (5)..(27)
<223> OTHER INFORMATION: a, c, t, g, unknown or other

<400> SEQUENCE: 17
aaacnnnnnn nnnnnnnnnn nnnnnnnaag tggtctca 38

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
ggggccacta gggacaggat 20

<210> SEQ ID NO 19
<211> LENGTH: 252
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 19

tcagccgcta ccccgaccac atgaagcagc acgacttctt caagtccgcc atgcccgaag     60

gctacgtcca ggagcgcacc atcttcttca aggacgacgg caactacaag acctaagtcc    120

cctccacccc acagtggggc cactagggac aggattggtg acagaaaagc gcgccgaggt    180

gaagttcgag ggcgacaccc tggtgaaccg catcgagctg aagggcatcg acttcaagga    240

ggacggcaac at                                                        252


<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

ggcatgcgag aatctgacgc                                                 20


<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

catgccagag atcctatttt                                                 20


<210> SEQ ID NO 22
<211> LENGTH: 9
<212> TYPE: PRT
<213> ORGANISM: Unknown
<220> FEATURE:
<223> OTHER INFORMATION: Description of Unknown:
      nuclear localization signal peptide

<400> SEQUENCE: 22

Met Pro Lys Lys Lys Arg Lys Val Ala
1               5


<210> SEQ ID NO 23
<211> LENGTH: 27
<212> TYPE: DNA
<213> ORGANISM: Unknown
<220> FEATURE:
<223> OTHER INFORMATION: Description of Unknown:
      nuclear localization signal oligonucleotide

<400> SEQUENCE: 23

atgccaaaga agaagcgtaa ggtcgct                                         27


<210> SEQ ID NO 24
<211> LENGTH: 11
<212> TYPE: PRT
<213> ORGANISM: Unknown
<220> FEATURE:
<223> OTHER INFORMATION: Description of Unknown:
      nuclear localization signal peptide

<400> SEQUENCE: 24
```

Ser Arg Ala Asp Pro Lys Lys Lys Arg Lys Val
1               5                   10

<210> SEQ ID NO 25
<211> LENGTH: 36
<212> TYPE: DNA
<213> ORGANISM: Unknown
<220> FEATURE:
<223> OTHER INFORMATION: Description of Unknown:
      nuclear localization signal oligonucleotide

<400> SEQUENCE: 25
agcagagccg accccaagaa gaagcggaag gtgtag                              36

<210> SEQ ID NO 26
<211> LENGTH: 16
<212> TYPE: PRT
<213> ORGANISM: Unknown
<220> FEATURE:
<223> OTHER INFORMATION: Description of Unknown:
      nuclear localization signal peptide

<400> SEQUENCE: 26

Lys Arg Pro Ala Ala Thr Lys Lys Ala Gly Gln Ala Lys Lys Lys Lys
1               5                   10                  15

<210> SEQ ID NO 27
<211> LENGTH: 51
<212> TYPE: DNA
<213> ORGANISM: Unknown
<220> FEATURE:
<223> OTHER INFORMATION: Description of Unknown:
      nuclear localization signal oligonucleotide

<400> SEQUENCE: 27
aagcggcctg ccgccaccaa gaaggctggc caggccaaga agaagaagta g             51

<210> SEQ ID NO 28
<211> LENGTH: 17
<212> TYPE: PRT
<213> ORGANISM: Unknown
<220> FEATURE:
<223> OTHER INFORMATION: Description of Unknown:
      nuclear localization signal peptide

<400> SEQUENCE: 28

Met Ala Pro Lys Lys Lys Arg Lys Val Gly Ile His Gly Val Pro Ala
1               5                   10                  15

Ala

<210> SEQ ID NO 29
<211> LENGTH: 51
<212> TYPE: DNA
<213> ORGANISM: Unknown
<220> FEATURE:
<223> OTHER INFORMATION: Description of Unknown:
      nuclear localization signal oligonucleotide

<400> SEQUENCE: 29
atggctccca agaagaagcg aaaggtgggc atccacggcg tgcccgctgc c             51

<210> SEQ ID NO 30
<211> LENGTH: 16
<212> TYPE: PRT
<213> ORGANISM: Unknown
<220> FEATURE:

<223> OTHER INFORMATION: Description of Unknown:
      nuclear localization signal peptide

<400> SEQUENCE: 30

Lys Arg Pro Ala Ala Thr Lys Lys Ala Gly Gln Ala Lys Lys Lys Lys
1               5                   10                  15

<210> SEQ ID NO 31
<211> LENGTH: 51
<212> TYPE: DNA
<213> ORGANISM: Unknown
<220> FEATURE:
<223> OTHER INFORMATION: Description of Unknown:
      nuclear localization signal oligonucleotide

<400> SEQUENCE: 31
aaacgcccag ccgccaccaa gaaagcagga caggcaaaga agaagaagtg a 51

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
taacggtaag caatgccgat 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgtaagctta cgcgatgcac 20

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 34
ccnatcggca ttgcttaccg tta 23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 35
cgtaagctta cgcgatgcac ngg 23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 36
taacggtaag caatgccgat ngg 23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 37
ccngtgcatc gcgtaagctt acg 23

<210> SEQ ID NO 38
<211> LENGTH: 363
<212> TYPE: DNA
<213> ORGANISM: Homo sapiens

<400> SEQUENCE: 38
gacggcggtg gtgctttgtc tcctcagcac tctgctgtca ctcaaggaag tatcatcaag 60
aacaaggagg gcatggatgc taagtcacta actgcctggt cccggacact ggtgaccttc 120
aaggatgtat ttgtggactt caccagggag gagtggaagc tgctggacac tgctcagcag 180
atcgtgtaca gaaatgtgat gctggagaac tataagaacc tggtttcctt gggttatcag 240
cttactaagc cagatgtgat cctccggttg gagaagggag aagagccctg gctggtggag 300
agagaaattc accaagagac acatcctgat tcagagactg catttgaaat caaatcatca 360
gtt 363

<210> SEQ ID NO 39
<211> LENGTH: 121
<212> TYPE: PRT
<213> ORGANISM: Homo sapiens

<400> SEQUENCE: 39

Asp Gly Gly Gly Ala Leu Ser Pro Gln His Ser Ala Val Thr Gln Gly
1               5                   10                  15

Ser Ile Ile Lys Asn Lys Glu Gly Met Asp Ala Lys Ser Leu Thr Ala
            20                  25                  30

Trp Ser Arg Thr Leu Val Thr Phe Lys Asp Val Phe Val Asp Phe Thr
        35                  40                  45

Arg Glu Glu Trp Lys Leu Leu Asp Thr Ala Gln Gln Ile Val Tyr Arg
    50                  55                  60

Asn Val Met Leu Glu Asn Tyr Lys Asn Leu Val Ser Leu Gly Tyr Gln

```
65                  70                  75                  80

Leu Thr Lys Pro Asp Val Ile Leu Arg Leu Glu Lys Gly Glu Glu Pro
                85                  90                  95

Trp Leu Val Glu Arg Glu Ile His Gln Glu Thr His Pro Asp Ser Glu
            100                 105                 110

Thr Ala Phe Glu Ile Lys Ser Ser Val
        115                 120


<210> SEQ ID NO 40
<211> LENGTH: 177
<212> TYPE: DNA
<213> ORGANISM: Herpes simplex virus

<400> SEQUENCE: 40

ggttccggac gggctgacgc attggacgat tttgatctgg atatgctggg aagtgacgcc     60

ctcgatgatt ttgaccttga catgcttggt tcggatgccc ttgatgactt tgacctcgac    120

atgctcggca gtgacgccct tgatgatttc gacctggaca tgctgattaa ctctaga       177


<210> SEQ ID NO 41
<211> LENGTH: 59
<212> TYPE: PRT
<213> ORGANISM: Herpes simplex virus

<400> SEQUENCE: 41

Gly Ser Gly Arg Ala Asp Ala Leu Asp Asp Phe Asp Leu Asp Met Leu
1               5                   10                  15

Gly Ser Asp Ala Leu Asp Asp Phe Asp Leu Asp Met Leu Gly Ser Asp
            20                  25                  30

Ala Leu Asp Asp Phe Asp Leu Asp Met Leu Gly Ser Asp Ala Leu Asp
        35                  40                  45

Asp Phe Asp Leu Asp Met Leu Ile Asn Ser Arg
    50                  55


<210> SEQ ID NO 42
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

gttttagagc tagaaatagc aagttaaaat aaggctagtc cgttatcaac ttgaaaaagt     60

ggcaccgagt cggtgctttt ttt                                             83


<210> SEQ ID NO 43
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

gtttaagagc tatgctggaa acagcatagc aagttaaaat aaggctagtc cgttatcaac     60

ttgaaaaagt ggcaccgagt cggtgctttt ttt                                  93


<210> SEQ ID NO 44
<211> LENGTH: 35
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (5)..(24)
<223> OTHER INFORMATION: a, c, t, g, unknown or other

<400> SEQUENCE: 44
aaacnnnnnn nnnnnnnnnn nnnnaagtgg tctca 35

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
tgtatgagac cactt 15

<210> SEQ ID NO 46
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
aagtggtctc a 11

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
agcgaggcta gcgacagcat agg 23

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
tgtatgagac cacttagcga ggctagcgac agcat 35

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
aaacatgctg tcgctagcct cgctaagtgg tctca 35

```
<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(24)
<223> OTHER INFORMATION: a, c, t, g, unknown or other

<400> SEQUENCE: 50

agggnnnnnn nnnnnnnnnn nnnn                                            24


<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(24)
<223> OTHER INFORMATION: a, c, t, g, unknown or other

<400> SEQUENCE: 51

aaacnnnnnn nnnnnnnnnn nnnn                                            24


<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

agggagcgag gctagcgaca gcat                                            24


<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53

aaacatgctg tcgctagcct cgct                                            24


<210> SEQ ID NO 54
<211> LENGTH: 4
<212> TYPE: PRT
<213> ORGANISM: Homo sapiens

<400> SEQUENCE: 54

Trp Arg Pro Trp
1


<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 55
gtggggtgga ggggactt 18

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
cggtaggcgt gtacggtggg 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
acagcgtgga tggcgtctcc 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
aagatcgagt gccgcatcac 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
ctcgatcttc atggcgggca 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
gacgccaaaa acataaagaa 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
cgggcctttc tttatgtttt 20

<210> SEQ ID NO 62
<211> LENGTH: 11
<212> TYPE: PRT
<213> ORGANISM: Herpes simplex virus

<400> SEQUENCE: 62

Asp Ala Leu Asp Asp Phe Asp Leu Asp Met Leu
1 5 10

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
tgaggtcagg ttctcaggcc 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
gatggagggg attcctaacc 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
ggtgttggag aggtttggaa 20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
ctctgtcccc tgatttgtgg 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
gctgggggag ggggagtccg 20

-continued

```
<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68

cctccctccc tgcccggtag                                              20
```